US012016875B2

(12) United States Patent
Patel et al.

(10) Patent No.: US 12,016,875 B2
(45) **Date of Patent: *Jun. 25, 2024**

(54) METHODS FOR TREATING OR PREVENTING OPHTHALMOLOGICAL CONDITIONS

(71) Applicant: IVERIC bio, Inc., Parsippany, NJ (US)

(72) Inventors: Samir Patel, Princeton, NJ (US); Richard Everett, Randolph, NJ (US); Douglas Brooks, Durham, NC (US); Shane Xinxin Tian, Oakland, NJ (US)

(73) Assignee: IVERIC bio, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,283

(22) Filed: Apr. 7, 2023

(65) Prior Publication Data

US 2023/0364123 A1 Nov. 16, 2023

Related U.S. Application Data

(63) Continuation of application No. 17/958,710, filed on Oct. 3, 2022, now abandoned, which is a continuation of application No. 17/676,811, filed on Feb. 21, 2022, now Pat. No. 11,491,176, which is a continuation of application No. 17/346,556, filed on Jun. 14, 2021, now Pat. No. 11,273,171, which is a continuation of application No. 16/434,018, filed on Jun. 6, 2019, now abandoned, which is a continuation of application No. 15/144,429, filed on May 2, 2016, now abandoned, which is a continuation of application No. 14/329,702, filed on Jul. 11, 2014, now abandoned.

(60) Provisional application No. 61/931,125, filed on Jan. 24, 2014, provisional application No. 61/931,116, filed on Jan. 24, 2014, provisional application No. 61/931,135, filed on Jan. 24, 2014, provisional application No. 61/926,848, filed on Jan. 13, 2014, provisional application No. 61/926,825, filed on Jan. 13, 2014, provisional application No. 61/926,812, filed on Jan. 13, 2014, provisional application No. 61/911,894, filed on Dec. 4, 2013, provisional application No. 61/911,854, filed on Dec. 4, 2013, provisional application No. 61/911,860, filed on Dec. 4, 2013, provisional application No. 61/866,503, filed on Aug. 15, 2013, provisional application No. 61/866,502, filed on Aug. 15, 2013, provisional application No. 61/866,507, filed on Aug. 15, 2013, provisional application No. 61/845,938, filed on Jul. 12, 2013, provisional application No. 61/845,936, (Continued)

(51) Int. Cl.

| | |
|---|---|
| ***A61K 31/7088*** | (2006.01) |
| ***A61K 9/00*** | (2006.01) |
| ***A61K 9/14*** | (2006.01) |
| ***A61K 31/713*** | (2006.01) |
| ***A61K 39/395*** | (2006.01) |
| ***A61K 45/06*** | (2006.01) |
| ***C07K 16/22*** | (2006.01) |
| ***C12N 15/115*** | (2010.01) |

(52) U.S. Cl.

CPC ........ *A61K 31/7088* (2013.01); *A61K 9/0048* (2013.01); *A61K 9/143* (2013.01); *A61K 31/713* (2013.01); *A61K 39/3955* (2013.01); *A61K 45/06* (2013.01); *C07K 16/22* (2013.01); *C12N 15/115* (2013.01); *C07K 2317/24* (2013.01); *C07K 2317/55* (2013.01); *C07K 2317/76* (2013.01); *C12N 2310/16* (2013.01); *C12N 2310/314* (2013.01); *C12N 2310/317* (2013.01); *C12N 2310/321* (2013.01); *C12N 2310/322* (2013.01); *C12N 2310/351* (2013.01); *C12N 2320/30* (2013.01); *C12N 2320/31* (2013.01)

(58) Field of Classification Search

None

See application file for complete search history.

(56) References Cited

U.S. PATENT DOCUMENTS

| | | | |
|---|---|---|---|
| 4,601,704 | A | 7/1986 | Larkin |
| 4,914,210 | A | 4/1990 | Levenson et al. |
| 5,194,596 | A | 3/1993 | Tischer et al. |

(Continued)

FOREIGN PATENT DOCUMENTS

| | | |
|---|---|---|
| CA | 2464007 | 4/2004 |
| CN | 101443050 A | 5/2009 |

(Continued)

OTHER PUBLICATIONS

Anonymous: "NCT01089517 on Jun. 15, 2012: ClinicalTrials.gov Archive", Jun. 15, 2012 (Jun. 15, 2012), XP055341978, Retrieved from the Internet: URL:https://clinicaltrials.gov/archive/NCT01089517/2012_06_15.

(Continued)

*Primary Examiner* — Brian Whiteman

(74) *Attorney, Agent, or Firm* — Jon E. Gordon; Haug Partners LLP

(57) ABSTRACT

The present invention relates to methods for treating and preventing ophthalmological disease and disorders, comprising administering Antagonist A or another pharmaceutically acceptable salt thereof, optionally in combination with another treatment, to a subject in need thereof. The present invention also relates to methods for treating and preventing ophthalmological disease and disorders, comprising administering an anti-C5 agent (e.g., ARC1905), optionally in combination with another treatment, to a subject in need thereof.

10 Claims, 23 Drawing Sheets

Specification includes a Sequence Listing.

Related U.S. Application Data filed on Jul. 12, 2013, provisional application No. 61/845,935, filed on Jul. 12, 2013.

(56) References Cited

U.S. PATENT DOCUMENTS 5,270,163 A 12/1993 Gold et al.
5,322,691 A 6/1994 Darougar et al.
5,459,015 A 10/1995 Janjic et al.
5,475,096 A 12/1995 Gold et al.
5,496,938 A 3/1996 Gold et al.
5,668,264 A 9/1997 Janjic et al.
5,670,637 A 9/1997 Gold et al.
5,674,685 A 10/1997 Janjic et al.
5,683,867 A 11/1997 Biesecker et al.
5,696,249 A 12/1997 Gold et al.
5,723,594 A 3/1998 Janjic et al.
5,731,144 A 3/1998 Toothman et al.
5,731,424 A 3/1998 Toothman et al.
5,756,291 A 5/1998 Griffin et al.
5,811,533 A 9/1998 Gold et al.
5,814,620 A 9/1998 Robinson et al.
5,817,785 A 10/1998 Gold et al.
5,837,834 A 11/1998 Pagratis et al.
5,846,713 A 12/1998 Pagratis et al.
5,859,228 A 1/1999 Janjic et al.
5,932,462 A 8/1999 Harris et al.
5,932,602 A 8/1999 Hirth et al.
5,958,691 A 9/1999 Pieken et al.
5,990,141 A 11/1999 Hirth et al.
6,005,087 A 12/1999 Cook et al.
6,011,020 A 1/2000 Gold et al.
6,051,698 A 4/2000 Janjic et al.
6,054,297 A 4/2000 Carter et al.
6,113,906 A 9/2000 Greenwald et al.
6,147,204 A 11/2000 Gold et al.
6,168,778 B1 1/2001 Janjic et al.
6,207,816 B1 3/2001 Gold et al.
6,229,002 B1 5/2001 Janjic et al.
6,342,219 B1 1/2002 Thorpe et al.
6,342,221 B1 1/2002 Thorpe et al.
6,382,219 B1 5/2002 Jelton
6,395,888 B1 5/2002 Biesecker et al.
6,410,322 B1 6/2002 Robinson
6,416,758 B1 7/2002 Thorpe et al.
6,426,335 B1 7/2002 Janjic et al.
6,448,277 B2 9/2002 Altmann et al.
6,465,188 B1 10/2002 Gold et al.
6,537,988 B2 3/2003 Lee
6,559,126 B2 5/2003 Tournaire et al.
6,566,343 B2 5/2003 Biesecker et al.
6,582,918 B2 6/2003 Janjic et al.
6,632,926 B1 10/2003 Chen et al.
6,699,843 B2 3/2004 Pietras et al.
6,719,750 B2 4/2004 Varner et al.
6,808,719 B2 10/2004 Yaacobi
6,884,879 B1 4/2005 Baca et al.
6,897,294 B2 5/2005 Davis-Smyth et al.
7,060,269 B1 6/2006 Baca et al.
7,070,959 B1 7/2006 Papadopoulos et al.
7,141,375 B2 11/2006 Pietras et al.
7,303,041 B2 12/2007 Stuve
7,303,746 B2 12/2007 Wiegand et al.
7,303,747 B2 12/2007 Wiegand et al.
7,306,799 B2 12/2007 Wiegand et al.
7,354,581 B2 4/2008 Cedarbaum et al.
7,365,166 B2 4/2008 Baca et al.
7,374,757 B2 5/2008 Papadopoulos et al.
7,374,758 B2 5/2008 Papadopoulos et al.
7,459,436 B2 12/2008 Lehmann et al.
7,521,049 B2 4/2009 Wiegand et al.
7,531,173 B2 5/2009 Wiegand et al.
7,531,524 B2 5/2009 Rusconi
7,608,261 B2 10/2009 Furfine et al.
7,723,315 B2 5/2010 Rusconi
7,759,472 B2 7/2010 Shima et al.
7,762,988 B1 7/2010 Vitello
7,803,931 B2 * 9/2010 Benedict ................. A61P 25/00 536/24.5
7,807,164 B2 10/2010 Furfine et al.
7,879,993 B2 2/2011 Janjic et al.
7,939,654 B2 5/2011 Janjic et al.
8,039,443 B2 10/2011 Grate et al.
8,092,803 B2 1/2012 Furfine et al.
8,187,597 B2 5/2012 Shima et al.
8,206,707 B2 6/2012 Shima et al.
8,389,489 B2 3/2013 Rusconi
8,481,046 B2 7/2013 Furfine et al.
8,591,885 B2 11/2013 Chang et al.
8,685,397 B2 4/2014 Shima et al.
8,753,625 B2 6/2014 Fung et al.
8,802,107 B2 8/2014 Furfine et al.
8,859,518 B2 10/2014 Rusconi
9,046,513 B2 6/2015 Ghayur et al.
9,340,594 B2 5/2016 Furfine et al.
11,273,171 B2 * 3/2022 Patel ....................... A61P 35/00
11,491,176 B2 * 11/2022 Patel ....................... A61P 43/00
2002/0032315 A1 3/2002 Baca et al.
2002/0189705 A1 12/2002 Reihl et al.
2003/0036642 A1 2/2003 Janjic et al.
2003/0171320 A1 9/2003 Guyer
2003/0180744 A1 9/2003 Gold et al.
2004/0022727 A1 2/2004 Stanton et al.
2004/0167091 A1 8/2004 Guyer
2004/0180360 A1 9/2004 Wilson et al.
2004/0249130 A1 12/2004 Stanton et al.
2004/0253243 A1 12/2004 Epstein et al.
2004/0253679 A1 12/2004 Epstein et al.
2005/0042273 A1 2/2005 Janjic et al.
2005/0058620 A1 3/2005 Nakamoto et al.
2005/0096257 A1 5/2005 Shima et al.
2005/0124565 A1 6/2005 Diener et al.
2005/0159351 A1 7/2005 Grate et al.
2005/0244462 A1 11/2005 Farooq
2005/0244471 A1 11/2005 Shiah et al.
2005/0244500 A1 11/2005 Whitcup et al.
2005/0288490 A1 12/2005 Nakamoto et al.
2006/0018871 A1 1/2006 Benedict et al.
2006/0073113 A1 4/2006 Nakamoto et al.
2006/0079477 A1 4/2006 Biesecker et al.
2006/0088523 A1 4/2006 Andya et al.
2006/0115450 A1 6/2006 Nakamoto et al.
2006/0167435 A1 7/2006 Adamis et al.
2006/0182783 A1 8/2006 Hughes et al.
2006/0229273 A1 10/2006 Gold et al.
2006/0233860 A1 10/2006 Chang et al.
2007/0021327 A1 1/2007 Pietras et al.
2007/0027101 A1 2/2007 Guyer et al.
2007/0105809 A1 5/2007 Rusconi
2007/0184089 A1 8/2007 Howie et al.
2007/0293432 A1 12/2007 Furfine et al.
2008/0076742 A1 3/2008 Sheibani et al.
2008/0097310 A1 4/2008 Buehler et al.
2008/0145406 A1 6/2008 Asgharian et al.
2008/0152654 A1 6/2008 Reich
2008/0207883 A1 8/2008 Janjic et al.
2008/0286334 A1 11/2008 Shiah et al.
2008/0305115 A1 12/2008 Tice et al.
2009/0053138 A1 2/2009 Preiss et al.
2009/0075342 A1 3/2009 Cload et al.
2009/0269356 A1 10/2009 Epstein et al.
2010/0111942 A1 5/2010 Shima et al.
2010/0119522 A1 5/2010 Shima et al.
2010/0129364 A1 5/2010 Shima et al.
2011/0200593 A1 8/2011 Shima et al.
2012/0087858 A1 4/2012 Ghayur et al.
2012/0100136 A1 4/2012 Patel et al.
2012/0109059 A1 5/2012 Ranalletta et al.
2013/0058951 A1 3/2013 Stoller
2013/0259881 A1 10/2013 Fandl et al.
2013/0274189 A1 10/2013 Furfine et al.
2013/0295102 A1 11/2013 Johnson et al.
2013/0323242 A1 12/2013 Everett et al.
2014/0179621 A1 6/2014 Patel et al.
2014/0193402 A1 7/2014 Wiegand et al.

(56) References Cited

U.S. PATENT DOCUMENTS

| | | | |
|---|---|---|---|
| 2014/0242082 | A1 | 8/2014 | Shima et al. |
| 2014/0294816 | A1 | 10/2014 | Shima et al. |
| 2014/0335078 | A1 | 11/2014 | Fung et al. |
| 2015/0017163 | A1 | 1/2015 | Patel et al. |
| 2015/0157709 | A1 | 6/2015 | Everett et al. |
| 2015/0182623 | A1 | 7/2015 | Everett et al. |
| 2015/0202288 | A1 | 7/2015 | Shima et al. |
| 2015/0202289 | A1 | 7/2015 | Shima et al. |
| 2016/0038589 | A1 | 2/2016 | Patel |
| 2016/0264969 | A1 | 9/2016 | Patel et al. |

FOREIGN PATENT DOCUMENTS

| | | | |
|---|---|---|---|
| EP | 1660057 | | 5/2012 |
| JP | 2009-529058 | | 8/2009 |
| JP | 2012-525415 | A | 10/2012 |
| WO | WO 95/16032 | | 6/1995 |
| WO | WO 96/27006 | | 9/1996 |
| WO | WO 96/30046 | | 10/1996 |
| WO | WO 96/38579 | | 12/1996 |
| WO | WO 98/18480 | | 5/1998 |
| WO | WO 98/45331 | A2 | 10/1998 |
| WO | WO 98/45331 | A3 | 12/1998 |
| WO | WO 99/31119 | | 6/1999 |
| WO | WO 99/41271 | | 8/1999 |
| WO | WO 00/64946 | | 11/2000 |
| WO | WO 2001/027264 | | 4/2001 |
| WO | WO 2001/087351 | | 11/2001 |
| WO | WO 2003/013541 | | 2/2003 |
| WO | WO 2003/020276 | | 3/2003 |
| WO | WO 2003/025019 | | 3/2003 |
| WO | WO 2003/039404 | | 5/2003 |
| WO | WO 2004/005282 | | 1/2004 |
| WO | WO 2004/050899 | | 6/2004 |
| WO | WO 2004/094614 | | 11/2004 |
| WO | WO 2005/000890 | | 1/2005 |
| WO | WO 2005/000895 | | 1/2005 |
| WO | WO 2005/014814 | | 2/2005 |
| WO | WO 2005/020972 | | 3/2005 |
| WO | WO 2006/050498 | | 5/2006 |
| WO | WO 2007/035621 | | 3/2007 |
| WO | WO 2007/056227 | | 5/2007 |
| WO | WO 2007/103549 | | 9/2007 |
| WO | WO 2007/149334 | | 12/2007 |
| WO | WO 2010/127029 | | 11/2010 |
| WO | WO 2013/093762 | | 6/2013 |
| WO | WO 2013/149086 | | 10/2013 |
| WO | WO 2013/181495 | | 12/2013 |
| WO | WO 2013/181495 | A2 | 12/2013 |
| WO | WO 2014/109999 | | 7/2014 |
| WO | WO 2015/006734 | | 1/2015 |
| WO | WO 2016/025313 | | 2/2016 |
| WO | WO 2019/040397 | A1 | 2/2019 |

OTHER PUBLICATIONS

Carla Lucia Esposito et al.: "New Insight into Clinical Development of Nucleic Acid Aptamers", Discovery Medicine, vol. 11, No. 61, Jun. 30, 2011 (Jun. 30, 2011), pp. 487-496, XP055341843.

Laura Cerchia et al.: "Coupling Aptamers to Short Interfering RNAs as Therapeutics", Pharmaceuticals, vol. 4, No. 12, Dec. 27, 2011 (Dec. 27, 2011), pp. 1434-1449, XP055082625.

Jaffe Glenn J. et al.: "A Phase 1 Study of Intravitreous E10030 in Combination with Ranibizumab in Neovascular Age-Related Macular Degeneration", Ophthalmology, vol. 123, No. 1, 2016, pp. 78-85, XP029364125.

Kanji Takahashi et al., Treatment Guidelines for Age-Related Macular Degeneration, Nippon Ganka Gakkai Zasshi, Dec. 10, 2012, vol. 116, No. 12, p. 1150-1155.

Miho Nozaki et al., Drusen Complement Components C3a and C5a Promote Choroidal Neovascularization, PNAS, Feb. 14, 2006, vol. 103, No. 7, p. 2328-2333.

Office Action for U.S. Appl. No. 14/598,365, mailed Sep. 15, 2016, 27 pages.

Office Action for U.S. Appl. No. 14/610,332, mailed Sep. 15, 2016, 23 pages.

Abdollahi, A. et al., "Inhibition of platelet-derived growth factor signaling attenuates pulmonary fibrosis," The Journal of Experimental Medicine, vol. 201, No. 6, Mar. 21, 2005, 925-935.

Arevalo, J. F. et al., "Tractional retinal detachment following intravitreal bevacizumab (Avastin) in patients with severe proliferative diabetic retinopathy," Br. J. Ophthalmol. 2008;92:213-216.

Armulik, A. et al., "Endothelial/Pericyte Interactions," Circ. Res. 2005;97(6):512-523.

Arnold, J. J. et al., "Age related macular degeneration," BMJ 2000; 321(7263):741-744.

Barikian, A. et al., "Induction With Intravitreal Bevacizumab Every Two Weeks in the Management of Neovascular Age-Related Macular Degeneration," Am J Ophthalmol 2015;159:131-137.

Boor, P. et al., "PDGF and the progression of renal disease," Nephrol Dial Transplant (2014) 29:(1)i45-i54.

Busbee, B. G. et al., "Twelve-Month Efficacy and Safety of 0.5 mg or 2.0 mg Ranibizumab in Patients with Subfoveal Neovascular Age-related Macular Degeneration," Ophthalmology 2013; 120(5):1046-1056.

Caballero, S. et al., "Anti-sphingosine-1-phosphate monoclonal antibodies inhibit angiogenesis and sub-retinal fibrosis in a murine model of laserinduced choroidal neovascularization," Exp Eye Res. Mar. 2009 ; 88(3):367-377. doi:10.1016/j.exer.2008.07.012.

Campochiaro, P. A. et al., "Platelet-Derived Growth Factor is Chemotactic for Human Retinal Pigment Epithelial Cells," Arch. Ophthalmol., 103(4):576-579 (Apr. 1985).

Day, J. C., "Population Projections of the United States, by Age, Sex, Race, and Hispanic Orgin: 1993-2050," U.S. Bureau of the Census, Current Population Reports, P25-1104, U.S. Department of Commerce, U.S. Government Printing Office, Washington, DC (Nov. 1993), 133 pages.

DeLuca, C. et al., "Imatinib mesylate (gleevec) induced unilateral optic disc edema," Optom Vis Sci., 89(10):e16-e22 (Oct. 2012).

Dvorak, H. F. et al., "Vascular Permeability Factor/Vascular Endothelial Growth Factor, Microvascular Hyperpermeability, and Angiogenesis," American Journal of Pathology, vol. 146, No. 5, 1029-1039 (May 1995).

Green, W. R. et al., "Age related macular degeneration histopathologic studies. The 1992 Lorenz E. Zimmerman Lecture," Ophthalmology 1993; 100:1519-1535.

Grossniklaus, H. E. et al., "Histopathologic and Ultrastructural Features of Surgically Excised Subfoveal Choroidal Neovascular Lesions," Arch Ophthalmol. 2005;123(7):914-921.

Grunwald, J. E. et al., "Risk of Geographic Atrophy in the Comparison of Age-related Macular Degeneration Treatments Trials," Ophthalmology 2014; 121(1):150-161.

Hellerbrand, C., "Hepatic stellate cells—the pericytes in the liver," Pflugers Arch—Eur J Physiol (2013) 465(6):775-778.

Hinton, D. R. et al., "Apoptosis in surgically excised choroidal neovascular membranes in age-related macular degeneration," Arch. Ophthalmol., 116(2):203-209 (1998).

Hwang, J. C. et al., "Development of Subretinal Fibrosis After Anti-VEGF Treatment in Neovascular Age-Related Macular Degeneration," Ophthalmic Surgery, Lasers & Imaging (Oct. 2009), 6 pages, doi: 10.3928/15428877-20100924-01.

Ishikawa, K. et al., "Molecular mechanisms of subretinal fibrosis in age-related macular degeneration," Experimental Eye Research, 142:19-25 (2016).

Iwayama, T. et al., "Involvement of PDGF in Fibrosis and Scleroderma: Recent Insights from Animal Models and Potential Therapeutic Opportunities," Curr Rheumatol Rep (2013) 15(2):304, 6 pages.

Jain, R. K., "Normalizing tumor vasculature with anti-angiogenic therapy: A new paradigm for combination therapy," Nature Medicine, 7(9):987-989 (Sep. 2001).

Jo, Y-J et al., "Establishment of a New Animal Model of Focal Subretinal Fibrosis That Resembles Disciform Lesion in Advanced Age-Related Macular Degeneration," Invest Ophthalmol Vis Sci. 2011;52:6089-6095. DOI:10.1167/iovs.10-5189.

(56) References Cited

OTHER PUBLICATIONS

Kang, H. M. et al., "Subfoveal Choroidal Thickness as a Potential Predictor of Visual Outcome and Treatment Response After Intravitreal Ranibizumab Injections for Typical Exudative Age-Related Macular Degeneration," Am J Ophthalmol 2014;157:1013-1021.
Keck, P. J. et al., "Vascular permeability factor, an endothelial cell mitogen related to PDGF," Science, 1989; 246(4935):1309-1312.
Kent, D. et al., "Choroidal neovascularization: a wound healing perspective," Molecular Vision 2003; 9:747-755.
LeBleu, V. S. et al., "Blockade of PDGF receptor signaling reduces myofibroblast number and attenuates renal fibrosis," Kidney International (2011) 80(11):1119-1121.
Leibowitz, H. M. et al., "The Framingham Eye Study monograph: An ophthalmological and epidemiological study of cataract, glaucoma, diabetic retinopathy, macular degeneration, and visual acuity in a general population of 2631 adults, 1973-1975," Surv Ophthalmol, 1980;24(Suppl), 335-610.
Lim, L. S. et al., "Age-related macular degeneration," Lancet, 2012; 379:1728-1738.
Liu, Y. et al., "Inhibition of PDGF, TGF-b, and Abl signaling and reduction of liver fibrosis by the small molecule Bcr-Abl tyrosine kinase antagonist Nilotinib," Journal of Hepatology, 2011; 55(3):612-625.
Nishioka, Y. et al., "Targeting platelet-derived growth factor as a therapeutic approach in pulmonary fibrosis," J. Med. Invest. 60(3-4):175-183 (Aug. 2013).
Pauleikhoff, D., "Neovascular age-related macular degeneration," Retina, 25:1065-1084 (2005).
Savage, D. G. et al., "Imatinib mesylate—a new oral targeted therapy," N. Engl. J. Med. Feb. 2002;346(9):683-693.
Seppa, H. et al., "Platelet-derived Growth Factor is Chemotactic for Fibroblasts," The Journal of Cell Biology, 92(2):584-588 (Feb. 1982).
Sjoblom, T. et al., "Growth inhibition of dermatofibrosarcoma protuberans tumors by the platelet-derived growth factor receptor antagonist STI571 through induction of apoptosis," Cancer Res 61(15):5778-5783 (2001).
Van Geest, R. J. et al., "A shift in the balance of vascular endothelial growth factor and connective tissue growth factor by bevacizumab causes the angiofibrotic switch in proliferative diabetic retinopathy," Br J Ophthalmol 2012;96:587e590. doi: 10.1136/bjophthalmol-2011-301005.
Wieman, T. J. et al., "Efficacy and Safely of a Topical Gel Formulation of Recombinant Human Platelet-Derived Growth Factor-BB (Becaplermin) in Patients With Chronic Neuropathic Diabetic Ulcers," Diabetes Care, 21(5):822-827 (May 1998).
Woodcock, H. V. et al., "Reducing lung function decline in patients with idiopathic pulmonary fibrosis: potential of nintedanib," Drug Design, Development and Therapy, 2013; 7:503-510.
Dugel, P. U. et al., "Anti-VEGF resistance in neovascular AMD: Role of PDGF antagonism," Investigative Ophthalmology & Visual Science, 56(7):2826 (Jun. 2015), ARVO Annual Meeting Abstract.
Singh, R. P. et al., "A single-arm, investigator-initiated study of the efficacy, safety and tolerability of intravitreal aflibercept injection in subjects with exudative age-related macular degeneration, previously treated with ranibizumab or bevacizumab: 6-month interim analysis," Br. J. Ophthalmol. 98:i22-i27 (2014).
Supplementary European Search Report for European Application No. 13796692.5, mailed Oct. 26, 2016, 16 pages.
Office Action for U.S. Appl. No. 14/522,360, mailed Dec. 9, 2016, 23 pages.
Supplementary European Search Report for European Application No. 14823713.4, mailed Feb. 13, 2017, 9 pages.
ClinicalTrials.gov Archive [online], "View of NCT01089517 on Jun. 15, 2012," A Phase 2, Randomized, Double-Masked, Controlled Trial to Establish the Safety and Efficacy of Intravitreous Injections of E10030 (Anti-PDGF Pegylated Aptamer) Given in Combination With Lucentis in Subjects with Neovascular Age-Related Macular Degeneration, Retrieved from the Internet: URL: <https://clinicaltrials.gov/archive/NCT01089517/2012_06_15,> [Retrieved on Feb. 3, 2017], 3 pages.
Burgess, W. H. et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 111(5):2129-2138 (1990).
Cerchia, L. et al., "Coupling aptamers to short interfering RNAs as therapeutics," Pharmaceuticals, 4(12):1434-1449 (Dec. 2011).
Esposito, C. L. et al., "New insight into clinical development of nucleic acid aptamers," Discovery Medicine, 11(61):487-496 (Jun. 2011).
Greer, S. et al., "Studies on depurination of DNA by heat," J. Mol. Biol. 1962, 4:123-141.
Guiotto, A. et al., "Anchimeric assistance effect on regioselective hydrolysis of branched PEGs: a mechanistic investigation," Bioorganic & Medicinal Chemistry, 12:5031-5037 (2004).
Heier, J. S. et al., "The 1-year results of CLEAR-IT 2, a phase 2 study of vascular endothelial growth factor trap-eye dosed as-needed after 12-week fixed dosing," Ophthalmology, 118(6):1098-1106 (Mar. 2011).
Jaffe, G. J. et al., "Dual Antagonism of PDGF and VEGF in Neovascular Age-Related Macular Degeneration. A Phase IIb, Multicenter, Randomized Controlled Trial," Ophthalmology, pp. 1-11, 2016.
Jaffe, G. J. et al., "A Phase 1 study of intravitreous E10030 in combination with ranibizumab in neovascular age-related macular degeneration," Ophthalmology, 123(1):78-85 (2016).
Krotz, A. H. et al., "Synthesis of Antisense Oligonucleotides with Minimum Depurination," Nucleosides, Nucleotides and Nucleic Acids, 22(2):129-134 (2003).
Lazar, E. et al., "Transforming growth factor alpha: mutation of aspartic acid 47 and leucine 48 results in different biological activities," Molecular and Cellular Biology, 8(3):1247-1252 (1988).
Lindahl, T. et al., "Rate of depurination of native deoxyribonucleic acid," Biochemistry, 11(19):3610-3618 (1972).
Macugen (pegaptanib sodium injection) package insert (Dec. 2011), 2 pages.
Marguet, E. et al., "DNA stability at temperatures typical for hyperthermophiles," Nucleic Acids Research, 22(9):1681-1686 (1994).
Marguet, E. et al., "Protection of DNA by salts against thermodegradation at temperatures typical for hyperthermophiles," Extremophiles 1998, 2:115-122.
Ophthotech, "Ophthotech announces results from pivotal phase 3 trials of Fovista in wet age-related macular degeneration," Conference call and webcast, Dec. 12, 2016, 3 pages.
Perez-Santonja, J. J. et al., "Inhibition of corneal neovascularization by topical bevacizumab (Anti-VEGF) and sunitinib (Anti-VEGF and Anti-PDGF) in an animal model," American Journal of Ophthalmology, 150(4):519-528.e1 (Oct. 2010).
Roger, M. et al., "Selective heat inactivation of pneumococcal transforming deoxyribonucleate," Biochemistry, vol. 47:653-669 (1961).
Stewart, M. W. et al., "Aflibercept (VEGF trap-eye): the newest anti-VEGF drug," British Journal of Ophthalmology, 96(9):1157-1158 (Sep. 2012).
Suzuki, T. et al., "Mechanistic studies on depurination and apurinic site chain breakage in oligodeoxyribonucleotides," Nucleic Acids Research, 22(23):4997-5003 (1994).
Wells, J. A. et al., "Aflibercept, bevacizumab, or ranibizumab for diabetic macular edema. Two-year results from a comparative effectiveness randomized clinical trial," Ophthalmology, 123(6):1351-1359 (Jun. 2016).
Office Action for U.S. Appl. No. 10/926,806, mailed Oct. 1, 2009, 13 pages.
Office Action for U.S. Appl. No. 10/926,806, mailed May 27, 2009, 19 pages.
Office Action for U.S. Appl. No. 10/926,806, mailed Sep. 30, 2008, 37 pages.
Office Action for U.S. Appl. No. 10/926,806, mailed Jan. 24, 2008, 30 pages.
Office Action for U.S. Appl. No. 10/926,806, mailed May 7, 2007, 18 pages.

(56) References Cited

OTHER PUBLICATIONS

International Search Report and Written Opinion for International Application No. PCT/US2004/027612, mailed Sep. 19, 2005, 23 pages.
International Preliminary Report on Patentability for International Application No. PCT/US2004/027612, dated Aug. 27, 2006, 10 pages.
European Search Report for European U.S. Appl. No. 10/013,061, mailed Dec. 7, 2010, 8 pages.
Office Action for U.S. Appl. No. 12/465,051, mailed Sep. 28, 2011, 19 pages.
Office Action for U.S. Appl. No. 12/465,051, mailed Jan. 19, 2011, 16 pages.
Office Action for U.S. Appl. No. 12/564,863, mailed Jul. 13, 2011, 19 pages.
Office Action for U.S. Appl. No. 12/641,270, mailed Sep. 6, 2011, 29 pages.
Office Action for U.S. Appl. No. 12/641,270, mailed Jan. 31, 2011, 28 pages.
Office Action for U.S. Appl. No. 12/987,508, mailed Aug. 16, 2011, 26 pages.
Office Action for U.S. Appl. No. 12/987,508, mailed Dec. 13, 2011, 18 pages.
Office Action for U.S. Appl. No. 14/186,149, mailed Aug. 1, 2014, 20 pages.
Office Action for U.S. Appl. No. 14/303,973, mailed Jul. 24, 2014, 27 pages.
Supplementary European Search Report and Opinion for European Application No. 10770279.7, mailed Feb. 19, 2013, 6 pages.
Office Action for U.S. Appl. No. 13/284,221, mailed Jun. 15, 2012, 16 pages.
Office Action for U.S. Appl. No. 13/284,221, mailed Feb. 11, 2013, 12 pages.
International Search Report and Written Opinion for International Application No. PCT/US2010/032816, mailed Sep. 17, 2010, 11 pages.
International Preliminary Report on Patentability for International Application No. PCT/US2010/032816, dated Nov. 1, 2011, 7 pages.
Supplementary European Search Report for European Application No. 16150606.8, mailed May 11, 2016, 9 pages.
Office Action for U.S. Appl. No. 13/963,872, mailed Apr. 21, 2015, 17 pages.
Supplementary Partial European Search Report for European Application No. 13796692.5, mailed Feb. 23, 2016, 8 pages.
Office Action for U.S. Appl. No. 13/797,821, mailed Apr. 23, 2014, 17 pages.
International Search Report and Written Opinion for International Application No. PCT/US2013/043536, mailed Dec. 20, 2013, 15 pages.
International Preliminary Report on Patentability for International Application No. PCT/US2013/043536, dated Dec. 2, 2014, 11 pages.
Office Action for U.S. Appl. No. 14/554,894, mailed Apr. 21, 2016, 15 pages.
International Search Report and Written Opinion for International Application No. PCT/US2014/046416, mailed Dec. 10, 2014, 10 pages.
International Search Report and Written Opinion for International Application No. PCT/US2014/052400, mailed Feb. 6, 2015, 10 pages.
International Search Report and Written Opinion for International Application No. PCT/US2015/044196, mailed Nov. 3, 2015, 10 pages.
A Phase 1, Safety, Tolerability and Pharmacokinetic Profile of Intravitreous Injections of E10030 (Anti-PDGF Pegylated Aptamer) in Subjects With Neovascular Age-Related Macular Degeneration, First Received on Dec. 4, 2007, ClinicalTrials.gov [online], [Retrieved on Jan. 18, 2012]. Retrieved from the Internet: <URL: http://clinicaltrials.gov/ct2/show/NCT00569140>, 5 pages.
A Safety and Efficacy Study of E10030 (Anti-PDGF Pegylated Aptamer) Plus Lucentis for Neovascular Age-Related Macular Degeneration, First Received on Mar. 12, 2010, ClinicalTrials.gov [online], [Retrieved on Jan. 18, 2012]. Retrieved from the Internet: <URL: http://clinicaltrials.gov/show/NCT01089517>, 6 pages.
Abrams, T. J. et al., "SU11248 inhibits KIT and platelet-derived growth factor receptor β in preclinical models of human small cell lung cancer," Molecular Cancer Therapeutics, 2(5):471-478 (2003).
Abramsson, A. et al., "Analysis of mural cell recruitment to tumor vessels," Circulation, 105:112-117 (2002).
Adamis, A. P. et al., "Inhibition of vascular endothelial growth factor prevents retinal ischemia-associated iris neovascularization in a nonhuman primate," Arch. Ophthalmol., 114:66-71 (1996).
Adamis, A. P. et al., "The role of vascular endothelial growth factor in ocular health and disease," Retina, 25:111-118 (2005).
Akiyama, H. et al., "Intraocular injection of an aptamer that binds PDGF-B: a potential treatment for proliferative retinopathies," Journal of Cellular Physiology, 207:407-412 (2006).
Amano, S. et al., "Requirement for vascular endothelial growth factor in wound- and inflammation related corneal neovascularization," Invest. Ophthalmol. Vis. Sci., 39:18-22 (1998).
Andrae, J. et al., "Role of platelet-derived growth factors in physiology and medicine," Genes & Development, 22(10):1276-1312 (2008).
Arakelyan, L. et al., "A computer algorithm describing the process of vessel formation and maturation, and its use for predicting the effects of anti-angiogenic and anti-maturation therapy on vascular tumor growth," Angiogenesis, 5(3):203-214 (2002).
Avastin (Bevacizumab), Labeling Text, Genentech, Inc. (Feb. 26, 2004), 27 pages.
Balasubramaniam, V. et al., "Role of platelet-derived growth factor in vascular remodeling during pulmonary hypertension in the ovine fetus," Am J Physiol Lung Cell Mol Physiol., 284(5):L826-L833 (2003).
Battegay, E. J., "Angiogenesis: mechanistic insights, neovascular diseases, and therapeutic prospects," J. Mol. Med., 73:333-346 (1995).
Benelli, U. et al., "Trapidil inhibits endothelial cell proliferation and angiogenesis in the chick chorioallantoic membrane and in the rat cornea," Journal of Ocular Pharmacology and Therapeutics, 11(2):157-166 (1995).
Benjamin, L. E. et al., "A plasticity window for blood vessel remodelling is defined by pericyte coverage of the preformed endothelial network and is regulated by PDGF-B and VEGF," Development, 125(9):1591-1598 (1998).
Benjamin, L. E. et al., "Selective ablation of immature blood vessels in established human tumors follows vascular endothelial growth factor withdrawal," J. Clin. Invest., 103:159-165 (1999).
Bergers, G. et al., "Benefits of targeting both pericytes and endothelial cells in the tumor vasculature with kinase inhibitors," Journal of Clinical Investigation, 111(9):1287-1295 (2003).
Bergers, G. et al., "Tumorigenesis and the angiogenic switch," Nature Reviews Cancer, 3:401-410 (Jun. 2003).
Biesecker, G. et al., "Derivation of RNA aptamer inhibitors of human complement C5," Immunopharmacology, 42(1-3):219-230 (1999).
Biswas, P. et al., "Comparative role of intravitreal ranibizumab versus bevacizumab in choroidal neovascular membrance in age-related macular degeneration," Indian J. Opthalmol., 59(3):191-196 (2011).
Bloch, S. B. et al., "Subfoveal fibrosis in eyes with neovascular age-related macular degeneration treated with intravitreal ranibizumab," Am. J. Ophthalmol., 156:116-124 (2013).
Boyer, D. S., "Combined Inhibition of Platelet Derived (PDGF) and Vascular Endothelial (VEGF) Growth Factors for the Treatment of Neovascular Age-Related Macular Degeneration (NV-AMD)—Results of a Phase 1 Study," [online], Presentation Abstract, May 4, 2009, 2 pages. [Retrieved from the Internet on Mar. 26, 2009.] URL: <http://arvo.abstractsonline.com/Plan/AbstractPrintView.aspx?mID=2281&sKey=f6e4ae6c-. . . >.
Boyer, D. S., A phase 2b study of Fovista, a platelet derived growth factor (PDGF) inhibitor in combination with a vascular endothelial growth factor (VEGF) inhibitor for neovascular age-related macular

(56) References Cited

OTHER PUBLICATIONS degeneratoin (AMD), ARVO 2013 Annual Meeting Abstracts, 280 AMD and Drugs, 618-620 Paper Session, Program No. 2175 (May 6, 2013), 1 page.
Bradley, J. et al., "Combination therapy for the treatment of ocular neovascularization," Angiogenesis, 10(2):141-148 (2007).
Brody, E. N. et al., "Aptamers as therapeutic and diagnostic agents," Reviews in Molecular Biotechnology, 74(1):5-13 (2000).
Brown, D. M. et al., "Ranibizumab versus Verteporfin for Neovascular Age-Related Macular Degeneration," The New England Journal of Medicine, 355(14):1432-1444 (2006).
Brown, L. F. et al., "Vascular permeability factor/vascular endothelial growth factor: a multifunctional angiogenic cytokine," EXS. 79:233-69 (1997).
Brown, E. B. et al., "In vivo measurement of gene expression, angiogenesis and physiological function in tumors using multiphoton laser scanning microscopy," Nat. Med., 7:864-868 (2001).
Burcovich, B. et al., "Branched polyethylene glycol (bPEG) conjugated antisense oligonucleotides," Nucleosides and Nucleotides, 17(9-11):1567-1570 (1998).
Burke, D. H. et al., "Recombination, RNA evolution, and bifunctional RNA molecules isolated through chimeric SELEX," RNA, 4(9):1165-1175 (1998).
Campochiaro, P. A., "Retinal and choroidal neovascularization," Journal of Cellular Physiology, 184(3):301-310 (2000).
Campochiaro, P. A. et al., "The pathogenesis of choroidal neovascularization in patients with age-related macular degeneration," Molecular Vision, 5:34-38 (1999).
Campochiaro, P. A., "Pathogenic mechanisms in proliferative vitreoretinopathy," Archives of Ophthalmology, 115(2):237-241 (1997).
Cao, R. et al., "Angiogenesis stimulated by PDGF-CC, a novel member in the PDGF family, involves activation of PDGFR-$\alpha\alpha$ and -$\alpha\beta$ receptors," FASEB J, 16(12):1575-1583 (2002).
Cao, R. et al., "VEGFR1-mediated pericyte ablation links VEGF and PIGF to cancer-associated retinopathy," PNAS, 107(2):856-861 (2010).
Carmeliet, P., "Angiogenesis in health and disease," Nature Medicine, 9(6):653-660 (2003).
Carmeliet, P. et al., "Review Article: Angiogenesis in cancer and other diseases," Nature, 407:249-257 (2000).
Carmeliet, P. et al., "Molecular mechanisms and clinical applications of angiogenesis," Nature, 473(7347):298-307 (2011).
Castellon, R. et al., "Effects of angiogenic growth factor combinations on retinal endothelial cells," Exp. Eye Res., 74(4):523-535 (2002).
Cerchia, L. et al., "Nucleic acid aptamers in cancer medicine," FEBS Letters, 528(1-3):12-16 (2002).
Chalam, K. V. et al., "Anti platelet derived growth factor antibody inhibits retinal pigment epithelial cell induced collagen contraction," IOVS, 39(4):S864 (1998).
Chaudhary, V. et al., "The effect of triamcinolone acetonide as an adjunctive treatment to verteporfin therapy in neovascular age-related macular degeneration: A prospective, randomized, placebo controlled pilot clinical trial," Invest. Ophthalmol. Vis. Sci., 46:E-Abstract 2308 (2005).
Chekenya, M. et al., "The glial precursor proteoglycan, NG2, is expressed on tumour neovasculature by vascular pericytes in human malignant brain tumours," Neuropathol. Appl. Neurobiol., 28:367-380 (2002).
Cochran, J. R. et al., "Domain-level antibody epitope mapping through yeast surface display of epidermal growth factor receptor fragments," Journal of Immunological Methods, 287:147-158 (2004).
Cogburn, L. A. et al, "Growth, metabolic and endocrine responses of broiler cockerels given a daily subcutaneous injection of natural or biosynthetic chicken growth hormone," The Journal of Nutrition, 119(8):1213-1222 (1989).
Cousins, S. W. et al., Patterns of CNV Fluorescein and Indocyanine Green Angiographic Regression Responses After Anti-VEGF Monotherapy or Anti-VEGF Plus Anti-PDGF Combotherapy, [online], Presentation Abstract, May 4, 2009, 2 pages. [Retrieved from the Internet on Mar. 26, 2009.] URL: <http://arvo.abstractsonline.com/Plan/AbstractPrintView.aspx?mID=2281&sKey=f6e4ae6c-. . . >.
Cullinan-Bove, K. et al., "Vascular endothelial growth factor/Vascular permeability factor expression in the rat uterus: rapid stimulation by estrogen correlates with estrogen-induced increases in uterine capillary permeability and growth," Endocrinology, 133(2):829-837 (1993).
Daniel, E. et al., "Risk of scar in the comparison of age-related macular degeneration treatments trials," Ophthalmology, pp. 1-11 (2013).
Darland, D. C. et al., "Pericyte production of cell-associated VEGF is differentiation-dependent and is associated with endothelial survival," Dev. Biol., 264:275-288 (2003).
Darland, D. C. et al., "Blood vessel maturation: vascular development comes of age," J. Clin. Invest., 103:157-158 (1999).
Database BIOSIS DN PREV200300143652 & ARVO Annual Meeting Abstract Search and Program Planner, 2002, vol. 2002, pp. Abstract No. 1931, 2 pages.
Davies, D. R. et al., "Unique motifs and hydrophobic interactions shape the binding of modified DNA ligands to protein targets," PNAS, 109(49):19971-19976 (2012).
Davuluri, G. et al., "Activated VEGF receptor shed into the vitreous in eyes with wet AMD: a new class of biomarkers in the vitreous with potential for predicting the treatment timing and monitoring response," Arch. Ophthalmol., 127(5):613-621 (2009).
Dixon, J. A. et al., "VEGF Trap-Eye for the treatment of neovascular age-related macular degeneration," Expert Opinion Investig. Drugs., 18(10):1573-1580 (2009).
Do, D. V. et al., "An exploratory study of the safety, tolerability and bioactivity of a single intravitreal injection of vascular endothelial growth factor Trap-Eye in patients with diabetic macular oedema," British Journal of Ophthalmology, 93(2):144-149 (2009).
Do, D. V. et al., "Neovascular Age-Related Macular Degeneration," FocalPoints, Clinical Modules for Ophthalmologists, vol. XXVIII, No. 12 (Module 3 of 3), pp. 1-14 (2010).
Dong, A. et al., "Antagonism of PDGF-BB suppresses subretinal neovascularization and enhances the effects of blocking VEGF-A," Angiogenesis, 17(3):553-562 (2013).
Doggrell, S. A., "Pegaptanib: the first antiangiogenic agent approved for neovascular macular degeneration," Expert Opinion Pharmacotherapy, 6(8):1421-1423 (2005).
Drolet et al., "Pharmacokinetics and safety of an anti-vascular endothelial growth factor aptamer (NX1838) following injection into the vitreous humor of rhesus monkeys," Pharm. Res., 17(12):1503-1510 (2000).
Dugel, P. U., "Anti-PDGF combination therapy in neovascular age-related macular degeneration: Results of a phase 2b study," Retina Today, pp. 65-67 and 71 (Mar. 2013).
Dugel, P. U., "Anti-PDGF therapy offers new approach to AMD treatment," Retina Times (2012), 8 pages.
Ebos, J. M. L. et al., "Imatinib mesylate (STI-571) reduces Bcr-Abl-mediated vascular endothelial growth factor secretion in chronic myelogenous leukemia," Molecular Cancer Research, 1(2):89-95 (2002).
Enge, M. et al., "Endothelium-specific platelet-derived growth factor-B ablation mimics diabetic retinopathy," The EMBO Journal, 21(16):4307-4316 (2002).
Erber, R. et al., "Combined inhibition of VEGF- and PDGF-signaling enforces tumor vessel regression by interfering with pericyte-mediated endothelial cell survival mechanisms," The FASEB Journal, 18(2):338-340 (2004).
Ergun, E. et al., "Photodynamic therapy with verteporfin and intravitreal triamcinolone acetonide in the treatment of neovascular age-related macular degeneration," Am. J. Ophthalmol., 142: 10-16 (2006).
Everett, R., "Aptamers in Age Related Macular Degeneration: Above and Beyond Anti-VEGF," AAPS Presentation, Jun. 23, 2009, 2 pages.
Everett, R., "E10030, A Pegylated Aptamer Targeting Pericytes: Therapeutic Application for Age-Related Macular Degeneration (AMD)," DIA Presentation, Sep. 23, 2008, 25 pages.

(56) References Cited

OTHER PUBLICATIONS

Eyetech Study Group: Preclinical and phase 1A clinical evaluation of an anti-VEGF pegylated aptamer (EYE001) for the treatment of exudative age-related macular degeneration, Retina, 22:143-152 (2002).
EYLEA (Aflibercept) Injection, Highlights of Prescribing Information, Regeneron Pharmaceuticals, Inc. (Nov. 18, 2011), 15 pages.
Falcon, B. L. et al., "Aptamers Specifically Targeting PDGF-B Decrease Blood Vessels and Pericytes in Tumors," Presented at the FASEB Experimental Biology, San Diego, CA (2005).
Falk, M. K. et al., "Four-year treatment results of neovascular age-related macular degeneration with ranibizumab and causes for discontinuation of treatment," Am. J. Ophthalmol., 155(1):89-95.e3 (2013).
Fan, T-P. D. et al., "Controlling the vasculature: angiogenesis, anti-angiogenesis and vascular targeting of gene therapy," Trends Pharmacol. Sci., 16(2):57-66 (1995).
Ferrara, N., "Vascular endothelial growth factor: basic science and clinical progress," Endocr. Rev., 25:581-611 (2004).
Ferris, F. L. et al., "Age-related macular degeneration and blindness due to neovascular maculopathy," Arch. Ophthalmol., 102:1640-1642 (1984).
Floege, J. et al., "Novel approach to specific growth factor inhibition in vivo. Antagonism of platelet-derived growth factor in glomerulonephritis by aptamers," Am J Pathol., 154(1):169-179 (1999).
Folkman, J., "Angiogenesis in cancer, vascular, rheumatoid and other disease," Nature Medicine, 1(1):27-31 (1995).
Foss, A. J. E. et al., "Microvessel count predicts survival in uveal melanoma", Cancer Research, 56(13):2900-2903 (1996).
Friedlander, M., "Fibrosis and diseases of the eye," Journal of Clinical Investigation, 117(3):576-586 (2007).
Fukumura, D. et al., "Tumor induction of VEGF promoter activity in stromal cells," Cell, 94:715-725 (1998).
Gee, M. S. et al., "Tumor vessel development and maturation impose limits on the effectiveness of anti-vascular therapy," Am. J. Pathol., 162:183-193 (2003).
George, D., "Platelet-derived growth factor receptors: a therapeutic target in solid tumors," Seminars in Oncology, 28(5):27-33 (2001).
Gomi, F. et al., "Pharmacological therapy for age-related macular degeneration," Ophthalmology, 46(12):1709-1716 (2004).
Gragoudas, E. S. et al., "Pegaptanib for neovascular age-related macular degeneration," N. Engl. J. Med., 351:2805-2816 (2004).
Green, L. S. et al., "Nuclease-resistant nucleic acid ligands to vascular permeability factor/vascular endothelial growth factor," Chemistry & Biology, 2(10):683-695 (1995).
Greenberg, J. I. et al., "A role for VEGF as a negative regulator of pericyte function and vessel maturation," Nature, 456(7223):809-813 (2008).
Guyer, D. R. et al, "Preclinical and phase 1A clinical evaluation of an anti-VEGF pegylated aptamer (EYE001) for the treatment of exudative age-related macular degeneration," Retina, 22(2):143-152 (2002).
Harris, J. M. et al., "Effect of pegylation on pharmaceuticals," Nature Reviews, 2:214-221 (2003).
Heier, J. S. et al., "Intravitreal aflibercept (VEGF Trap-Eye) in wet age-related macular degeneration," Ophthalmology, 119(12):2537-2548 (2012).
Hellstrom, M. et al., "Role of PDGF-B and PDGFR-beta in recruitment of vascular smooth muscle cells and pericytes during embryonic blood vessel formation in the mouse," Development, 126:3047-3055 (1999).
Hellstrom, M. et al., "Lack of pericytes leads to endothelial hyperplasia and abnormal vascular morphogenesis," J. Cell. Biol., 153:543-553 (2001).
Ishida, S. et al., "VEGF164-mediated inflammation is required for pathological, but not physiological, ischemia-induced retinal neovascularization," J. Exp. Med., 198:483-489 (2003).
Jain, R. K., "Molecular regulation of vessel maturation," Nature Medicine, 9(6):685-693 (2003).
Jain, R. K. et al., "What brings pericytes to tumor vessels?", The Journal of Clinical Investigation, 112(8):1134-1136 (2003).
Jo, N. et al., "Inhibition of platelet-derived growth factor B signaling enhances the efficacy of anti-vascular endothelial growth factor therapy in multiple models of ocular neovascularization," American Journal of Pathology, 168(6):2036-2053 (2006).
Joussen, A. M. et al., "VEGF-dependent conjunctivalization of the corneal surface," Invest. Ophthalmol. Vis. Sci., 44:117-123 (2003).
Kaempf, S. et al., "Effects of bevacizumab (Avastin) on retinal cells in organotypic culture," Invest. Ophthalmol. Vis. Sci., 49(7):3164-3171 (2008).
Kaiser, P. K. et al., "Integrin peptide therapy: The first wet AMD experience," ARVO 2013 Annual Meeting Abstracts, 280 AMD and Drugs, 618-620 Paper Session, Program No. 2177 (May 6, 2013), 2 pages.
Kawada, H. et al., "Multifunctional antioxidants protect cells from mitochondrial dysfunction and ABETA neurotoxicity," ARVO 2013 Annual Meeting Abstracts, 280 AMD and Drugs, 618-620 Paper Session, Program No. 2176 (May 6, 2013), 1 page.
Ke, L. D. et al., "A novel approach to glioma gene therapy: down-regulation of the vascular endothelial growth factor in glioma cells using ribozymes," International Journal of Oncology, 12(6): 1391-1396 (1998).
Keane, P. A. et al., "Evaluation of age-related macular degeneration with optical coherence tomography," Survey of Ophthalmology, 57(5):389-414 (2012).
Kinose, F. et al, "Inhibition of retinal and choroidal neovascularization by a novel KDR kinase inhibitor," Molecular Vision, 11:366-373 (2005).
Klein, R. et al., The relationship of age-related maculopathy, cataract, and glaucoma to visual acuity, Invest. Ophthalmol. Vis. Sci., 36:182-191 (1995).
Kliffen, M. et al., "Increased expression of angiogenic growth factors in age-related maculopathy," British Journal of Ophthalmology, 81:154-162 (1997).
Kohno, R. et al., "Histopathology of neovascular tissue from eyes with proliferative diabetic retinopathy after intravitreal bevacizumab injection," Am. J. Ophthalmol., 150(2):223-229.e1 (2010).
Kompella, U. B. et al., "Drug Product Development for the Back of the Eye," Advances in the Pharmaceutical Sciences Series, AAPSPress, Springer (2011), 595 pages.
Koyama, N. et al., "Migratory and proliferative effect of platelet-derived growth factor in rabbit retinal endothelial cells: evidence of an autocrine pathway of platelet-derived growth factor," J. Cell Physiol., 158(1):1-6 (1994).
Krzystolik, M. G. et al., "Prevention of experimental choroidal neovascularization with intravitreal anti-vascular endothelial growth factor antibody fragment," Arch. Ophthalmol., 120:338-346 (2002).
Kudelka, M. R. et al., "Emergence of dual VEGF and PDGF antagonists in the treatment of exudative age-related macular degeneration," Expert Rev. Ophthalmology, 8(5):475-484 (2013).
Kwak, N. et al., "VEGF is major stimulator in model of choroidal neovascularization," Invest. Ophthalmol. Vis. Sci., 41:3158-3164 (2000).
Lai, C-M et al., "Inhibition of corneal neovascularization by recombinant adenovirus mediated antisense VEGF RNA," Exp. Eye Res., 75(6):625-634 (2002).
Lei, H. et al., "Recent developments in our understanding of how platelet-derived growth factor (PDGF) and its receptors contribute to proliferative vitreoretinopathy," Exp. Eye Res., 90(3):376-381 (2010).
Leppanen, O. et al., "Intimal hyperplasia recurs after removal of PDGF-AB and -BB inhibition in the rat carotid artery injury model," Arterioscler Thromb Vasc Biol., 20(11):e89-e95 (2000).
Li, V. W. et al., "Microvessel count and cerebrospinal fluid basic fibroblast growth factor in children with brain tumours," The Lancet, 344(8915):82-86 (1994).
Li, Q. et al., "IKK2 inhibition using TPCA-1/PLGA microspheres attenuates the laser induced choroidal neovascularization," ARVO 2013 Annual Meeting Abstracts, 280 AMD and Drugs, 618-620 Paper Session, Program No. 2179 (May 6, 2013), 2 pages.
Lindahl, P. et al., "Pericyte loss and microaneurysm formation in PDGF-B-deficient mice," Science, 277:242-245 (1997).

(56) References Cited

OTHER PUBLICATIONS

Lindheimer, M. D., "Unraveling the mysteries of preeclampsia," Am. J. Obstet. Gynecol., 193:3-4 (2005).
Livak, K. J. et al., "Analysis of relative gene expression data using real-time quantitative PCR and the 2(-Delta Delta C(T)) Method," Methods, 25:402-408 (2001).
Lu, C. et al., "Targeting pericytes with a PDGF-B aptamer in human ovarian carcinoma models," Cancer Biol. Ther., 9(3):176-182 (2010).
Lucentis (ranibizumab injection), Highlights of Prescribing Information, Genentech, Inc. (Jun. 30, 2006), 7 pages.
Magno, A. L. et al., "Development and implementation of an ELISA to detect 'anti-Ranibizumab' immunity in age-related macular degeneration patients," ARVO 2013 Annual Meeting Abstracts, 280 AMD and Drugs, 618-620 Paper Session, Program No. 2181 (May 6, 2013), 2 pages.
Martin, D. F. et al., "Ranibizumab and bevacizumab for treatment of neovascular age-related macular degeneration: two-year results: Comparison of Age-related Macular Degeneration Treatments Trials (CATT) Research Group," Ophthalmology, 119(7):1388-1398 (2012).
Capelle, M. A. H. et al., "High throughput screening of protein formulation stability: Practical considerations," European Journal of Pharmaceutics and Biopharmaceutics, 65:131-148 (2007).
Mayer, G. et al., "Aptamers in Research and Drug Development," Biodrugs, 18(6):351-359 (2004).
McCarty, M. F. et al, "Promises and pitfalls of anti-angiogenic therapy in clinical trials," Trends in Molecular Medicine, 9(2):53-58 (2003).
Monfardini, C. et al., "A Branched Monomethoxypoly(ethylene glycol) for Protein Modification," Bioconjugate Chem., 6:62-69 (1995).
Morescalchi, F. et al., "Proliferative Vitreoretinopathy after Eye Injuries: An Overexpression of Growth Factors and Cytokines Leading to a Retinal Keloid," Mediators of Inflammation, vol. 2013, Article ID 269787, Aug. 26, 2013, 12 pages.
Mori, K. et al., "Inhibition of choroidal neovascularization by intravenous injection of adenoviral vectors expressing secretable endostatin," Am. J. Pathol., 159:313-320 (2001).
Morikawa, S. et al., "Abnormalities in pericytes on blood vessels and endothelial sprouts in tumors," Am. J. Pathol., 160:985-1000 (2002).
Moromizato, Y. et al., "CD18 and ICAM-1-dependent corneal neovascularization and inflammation alter limbal injury," Am. J. Pathol., 157:1277-1281 (2000).
Nakabayashi, M. et al., "HGF/NK4 inhibited VEGF-induced angiogenesis in in vitro cultured endothelial cells and in vivo rabbit model," Diabetologia, 46(1):115-123 (2003).
Ng, E. W. M. et al., "Anti-VEGF aptamer (pegaptanib) therapy for ocular vascular disease," Ann. NY Acad. Sci., 1082:151-171 (2006).
Ng, E. W. M. et al., "Pegaptanib, a targeted anit-VEGF aptamer for ocular vascular disease," Nat. Rev. Drug. Discov., 5(2):123-132 (2006).
Ngo, J. T. et al., "Computational complexity, protein structure prediction, and the levinthal paradox," In The Protein Folding Problem and Tertiary Structure Prediction, Merz, Jr. et al. (eds.), Brikhauser Boston, pp. 492-495 (1994).
Nguyen, Q. D. et al., "A phase I trial of an IV-administered vascular endothelial growth factor trap for treatment in patients with choroidal neovascularization due to age-related macular degeneration," Ophthalmology, 113(9):1522-1532 (2006).
Ostendorf, T. et al., "Specific antagonism of PDGF prevents renal scarring in experimental glomerulonephritis," J. Am. Soc. Nephrol., 12(5):909-918 (2001).
Ozaki, H. et al., "Blockade of vascular endothelial cell growth factor receptor signaling is sufficient to completely prevent retinal neovascularization," American Journal of Pathology, 156(2):697-707 (2000).
Patel, S., "New innovations in AMD technology may be promising," Retina Today, pp. 24-25 (2008).
Patel, S., "Combination therapy for age-related macular degeneration," Retina, 29:S45-S48 (2009).
Pechan, P. et al., "Novel anti-VEGF chimeric molecules delivered by AAV vectors for inhibition of retinal neovascularization," Gene Therapy, 16(1):10-16 (2009).
Pegaptanib: New drug. In macular degeneration: too many risks for too little benefit, Prescire Int., 15(84):127-129 (abstract, no authors listed) (2006).
Petrukhin, K., "New therapeutic targets in atrophic age-related macular degeneration," Expert Opin. Ther. Targets, 11(5):625-630 (2007).
"Particulate matter in ophthalmic solutions," USP789, U.S. Pharmacopeia, Pharmacopeial Forum, 28(5):1496 (Sep. 2002), 3 pages.
"Particulate matter in injections," USP788, Revision Bulletin, The United States Pharmacopeial Convention (Oct. 1, 2011), 3 pages.
Pierce, E. A. et al., "Vascular endothelial growth factor/vascular permeability factor expression in a mouse model of retinal neovascularization," Proc Natl Acad Sci. USA, 92(3):905-909 (1995).
Pietras, K. et al., "Inhibition of PDGF receptor signaling in tumor stroma enhances antitumor effect of chemotherapy," Cancer Research, 62(19):5476-5484 (2002).
Pietras, K. et al, "Inhibition of platelet-derived growth factor receptors reduces interstitial hypertension and increases transcapillary transport in tumors," Cancer Research, 61(7):2929-2934 (2001).
Pontes de Carvalho, R. A. et al., "Delivery from episcleral exoplants," Invest Ophthalmol Vis Sci., 47(1):4532-4539 (2006).
Rao, L. J. et al., "Neovascular AMD: Treatment beyond anti-VEGF," Mar. 1, 2014, 10 pages.
Rasmussen, A. et al., "A 4-year longitudinal study of 555 patients treated with ranibizumab for neovascular age-related macular degeneration," Ophthalmology, 120(12):2630-2636 (2013).
Riemer, A. B. et al., "Matching of trastuzumab (Herceptin) epitope mimics onto the surface of Her-2/neu—a new method of epitope definition," Molecular Immunology, 42(9):1121-1124 (2005).
Rimmele, M., "Nucleic acid aptamers as tools and drugs: recent developments," ChemBioChem., 4:963-971 (2003).
Ritter, M. R. et al., "Three-dimensional in vivo imaging of the mouse intraocular vasculature during development and disease," Invest Ophthalmol Vis Sci., 46(9):3021-3026 (2005).
Robinson, G. S. et al., "Oligodeoxynucleotides inhibit retinal neovascularization in a murine model of proliferative retinopathy," Proc. Natl. Acad. Sci. USA, 93:4851-4856 (1996).
Rodrigues, E. B. et al., "Therapeutic monoclonal antibodies in ophthalmology," Progress in Retinal and Eye Research, 28(2):117-144 (2009).
Rofagha, S. et al., "Seven-year outcomes in ranibizumab-treated patients in anchor, marina, and horizon," Ophthalmology, pp. 1-8 (2013).
Rofagha, S. et al., "Seven-year outcomes in ranibizumab-treated patients in Anchor, Marina, and Horizon: a multicenter cohort study (Seven-Up)," Ophthalmology, 120(11):2292-2299 (2013).
Rosenfeld, P. J. et al., "Ranibizumab for Neovascular Age-Related Macular Degeneration," The New England Journal of Medicine, 355(14):1419-1431 (2006).
Ruckman, J. et al., "2'-Fluoropyrimidine RNA-based aptamers to the 165-amino acid form of vascular endothelial growth factor ($VEGF_{165}$). Inhibition of receptor binding and VEGF-induced vascular permeability through interactions requiring the exon 7-encoded domain," J. Biol. Chem., 273(32):20556-20567 (1998).
Ruhrberg, C. et al., "Spatially restricted patterning cues provided by heparin-binding VEGF-A control blood vessel branching morphogenesis," Genes Dev., 16:2684-2698 (2002).
Ruiz-Ederra, J. et al., "Aquaporin-1 independent microvessel proliferation in a neonatal mouse model of oxygen-induced retinopathy," Invest Ophthalmol Vis Sci., 48(10):4802-4810 (2007).
Saishin, Y. et al, "The kinase inhibitor PKC412 suppresses epiretinal membrane formation and retinal detachment in mice with proliferative retinopathies," Invest Ophthalmol Vis Sci, 44(8):3656-3662 (2003).
Sano, H. et al., "Study on PDGF receptor β pathway in glomerular formation in neonate mice," Annals New York Acad. Sci., 947:303-305 (2001).

(56) References Cited

OTHER PUBLICATIONS

Schmidt-Erfurth, U. et al., "Intravitreal aflibercept injection for neovascular age-related macular degeneration," Ophthalmology, p. 1-9 (2013).
Schraermeyer, U. et al., "Effects of intravitreally injected ranibizumab and aflibercept on retina and choroid of monkey eyes," ARVO 2013 Annual Meeting Abstracts, 280 AMD and Drugs, 618-620 Paper Session, Program No. 2180 (May 6, 2013), 1 page.
Semeraro, F. et al., "Aflibercept in wetAMD: specific role and optimal use," Drug Design, Development and Therapy, 7:711-722 (2013).
Senger, D. R. et al., "Vascular permeability factor (VPF, VEGF) in tumor biology," Cancer and Metastasis Reviews, 12(3-4):303-324 (1993).
Sennino, B. et al., "Sequential loss of tumor vessel pericytes and endothelial cells after inhibition of platelet-derived growth factor B by selective aptamer AX102," Cancer Research, 67(15):7358-7367 (2007).
Shami, M. et al., "The use of antisense DNA against the receptors for platelet derived growth factor, fibroblast growth factor, and phosphoinositol-3-kinase in vitro and to block PVR in a rabbit model using human pigment epithelial cells," IOVS, 39(4):S580 (1998).
Shawver, L. K. et al., "Smart drugs: tyrosine kinase inhibitors in cancer therapy," Cancer Cell, 1(2):117-123 (2002).
Silva, R. et al., "The SECURE study: long-term safety of ranibizumab 0.5 mg in neovascular age-related macular degeneration," Ophthalmology, 120(1):130-139 (2013).
Sims, D. E., "The pericyte—a review," Tissue Cell, 18:153-174 (1986).
Singer, M. A. et al., "HORIZON: An open-label extension trial of ranibizumab for choroidal neovascularization secondary to age-related macular degeneration," Ophthalmology, pp. 1-9 (2012).
Singh, R. et al., "Topical Pazopanib for the treatment of previously untreated choroidal neovascularization due to age-related macular degeneration," ARVO 2013 Annual Meeting Abstracts, 280 AMD and Drugs, 618-620 Paper Session, Program No. 2178 (May 6, 2013), 1 page.
Skolnick, J. et al, "From genes to protein structure and function: novel applications of computational approaches in the genomic era," Trends in Biotechnol., 18(1):34-39 (2000).
SOMAmer Technical Note, SomaLogic, Inc., SSM017, Rev. 1, DCN 13-084 (2013), 2 pages.
Sorbera, L. A. et al., "Pegaptanib Sodium," Drugs of the Future, 27(9):841 (2002).
Stahl, A. et al., "The mouse retina as an angiogenesis model," Invest. Ophthalmol. Vis. Sci., 51(6):2813-2826 (2010).
Steffensmeier, A. C. G. et al., "Vitreous injections of pegaptanib sodium triggering allergic reactions," Am J Ophthalmology, 143(3):512-513 (2007).
Stewart, M. W., "PDGF: Ophthalmology's next great target," Expert Review of Ophthalmology, 8(6):527-537 (2013).
Stockmann, C. et al., "Deletion of vascular endothelial growth factor in myeloid cells accelerates tumorigenesis," Nature, 456:814-819 (2008).
Stryer et al., In: Biochemistry, pp. 86 and 92, Third Edition, W. H. Freeman and Company, New York (1988).
Submacular Surgery Trials Research Group, "Histopathologic and ultrastructural features of surgically excised subfoveal choroidal neovascular lesions. Submacular Surgery Trials Report No. 7," Arch. Ophthalmol., 123:914-921 (2005).
Sundberg, C. et al., "Stable expression of angiopoietin-1 and other markers by cultured pericytes: phenotypic similarities to a subpopulation of cells in maturing vessels during later stages of angiogenesis in vivo," Lab. Invest., 82:387-401 (2002).
Tahiri-Alaoui, A. et al., "High affinity nucleic acid aptamers for streptavidin incorporated into bi-specific capture ligands," Nucleic Acids Research, 30(10):e45 (2002), 9 pages.
Thomas, K. A., "Vascular endothelial growth factor, a potent and selective angiogenic agent," The Journal of Biological Chemistry, 271(2):603-606 (1996).
Tobe, T. et al., "Targeted disruption of the FGF2 gene does not prevent choroidal neovascularization in a murine model," American Journal of Pathology, 153(5):1641-1646 (1998).
Tol, J. et al., "Chemotherapy, bevacizumab, and cetuximab in metastatic colorectal cancer," New England Journal of Medicine, 360(6):563-572 (2009).
Uemura, A. et al., "Recombinant angiopoietin-1 restores higher-order architecture of growing blood vessels in mice in the absence of mural cells," J. Clin. Invest., 110:1619-1628 (2002).
Wallace, R. B. et al, "Oligonucleotide probes for the screening of recombinant DNA libraries," Methods in Enzymology, 152:432-439 (1987).
Warne, N. W., "Development of high concentration protein biopharmaceuticals: The use of platform approaches in formulation development," European Journal of Pharmaceutics and Biopharmaceutics, 78(2):208-212 (2011).
Weidner, N. et al., "Tumor angiogenesis correlates with metastasis in invasive prostate carcinoma", Am J Pathol., 143(2):401-409 (1993).
Weidner, N. et al., "Tumor angiogenesis: a new significant and independent prognostic indicator in early-stage breast carcinoma," J. Natl Cancer Inst., 84(24):1875-1887 (1992).
West, H. et al., "Stabilization of the retinal vascular network by reciprocal feedback between blood vessels and astrocytes," Development, 132:1855-1862 (2005).
Wilkinson-Berka, J. L. et al., "Inhibition of platelet-derived growth factor promotes pericyte loss and angiogenesis in ischemic retinopathy," American Journal of Pathology, 164(4):1263-1273 (2004).
Willett, C. G. et al., "Direct evidence that the VEGF-specific antibody bevacizumab has antivascular effects in human rectal cancer," Nat Med., 10(2):145-147 (2004).
Winkler, F. et al., "Kinetics of vascular normalization by VEGFR2 blockade governs brain tumor response to radiation: Role of oxygenation, angiopoietin-1, and matrix metalloproteinases," Cancer Cell, 6(6):553-563 (2004).
Witte, L. et al., "Monoclonal antibodies targeting the VEGF receptor-2 (Flk1/KDR) as an anti-angiogenic therapeutic strategy," Cancer and Metastasis Reviews, 17:155-161 (1998).
Wood, J. M., "Inhibition of vascular endothelial growth factor (VEGF) as a novel approach for cancer therapy," Medicina (Buenos Aires), 60(2):41-47 (2000).
Writing Committee for the UK Age-Related Macular Degeneration EMR Users Group, "The neovascular age-related macular degeneration database: multicenter study of 92 976 ranibizumab injections: report 1: visual acuity," Ophthalmology, 121(5):1092-1101 (2014).
Yoshida, S. et al., "Involvement of interleukin-8, vascular endothelial growth factor, and basic fibroblast growth factor in tumor necrosis factor alpha-dependent angiogenesis," Molecular and Cellular Biology, 17(7):4015-4023 (1997).
Younes, C. K. et al., "Labelled oligonucleotides as radiopharmaceuticals: pitfalls, problems and perspectives," Current Pharmaceutical Design, 8(16):1451-1466 (2002).
Yu, L. et al., "Interaction between bevacizumab and murine VEGF-A: a reassessment," Investigative Ophthalmology & Visual Science, 49(2):522-527 (2008).
Zhang, M. et al., "Recombinant anti-vascular endothelial growth factor fusion protein efficiently suppresses choridal neovasularization in monkeys," Molecular Vision, 14:37-49 (2008).
Zhang, L. et al., "Vector-based RNAi, a novel tool for isoform-specific knock-down of VEGF and anti-angiogenesis gene therapy of cancer," Biochemical and Biophysical Research Communications, 303(4):1169-1178 (2003).
Zhang, W. et al., "A monoclonal antibody that blocks VEGF binding to VEGFR2 (KDR/Flk-1) inhibits vascular expression of Flk-1 and tumor growth in an orthotopic human breast cancer model," Angiogenesis, 5(1-2):35-44 (2002).
Zhang, Y. et al., "Tissue oxygen levels control astrocyte movement and differentiation in developing retina," Brain Res. Dev. Brain Res., 118:135-145 (1999).

(56) References Cited

OTHER PUBLICATIONS

Zhu, Z. et al., "Inhibition of Tumor Growth and Metastasis by Targeting Tumor-Associated Angiogenesis with Antagonists to the Receptors of Vascular Endothelial Growth Factor," Investigational New Drugs, 17:195-212 (1999.
Zondor, S. D. et al., "Bevacizumab: an angiogenesis inhibitor with efficacy in colorectal and other malignancies," Ann. Pharmacother., 38:1258-1264 (2004).
Folkman, J. et al., "Angiogenesis," Minireview, The Journal of Biological Chemistry, 267(16): 10931-10934 (Jun. 1992).
Office Action issued in corresponding Israel Application No. 243485 dated Jul. 29, 2019.
Supplementary European Search Report issued in corresponding European Application No. 14823713.4 dated Feb. 13, 2017.
Office Action issued in corresponding Japanese Application No. 2016-525821 dated Mar. 29, 2018.
Office Action issued in corresponding Chinese Application No. 201480039516.5 dated Apr. 9, 2018.
Examination Report issued in corresponding Australian Application No. 2014286996 dated Mar. 12, 2019.
Office Action issued in corresponding Japanese Application No. 2018-124310 dated May 9, 2019.
Office Action issued in corresponding Israeli Application No. 243485 dated Jul. 29, 2019.
A Phase I Study of ARC1905 (Anti-C5 Aptamer) in Subjects with Dry Age-Related Macular Degeneration, NCT00950638, published on clinicaltrials. gov URL://clinicaltrials.gov/ct2/show/study/NCT00950638 and https://clinicaltrials.gov/ct2/history/NCT009540638?, Last retrieved Feb. 24, 2021, first published on Aug. 3, 2009 according to ClinicalTrials.Gov.
Anonymous: "History of Changes for Study: NCT00950638," Sep. 4, 2012 (Sep. 4, 2012), XP055668318, Retrieved from the Internet: URL:https://clinicaltrials.gov/ct2/history/NCT00950638?V5=View#StudyPageTop [retrieved on Feb. 23, 2020].
R.S. Apte, "Targeting Complement Factor 5 in Neovascular Age-Related Macular Degeneration (NV-AMD)—Results of a Phase I Study," Apr. 1, 2009 (Apr. 1, 2009), XP55668326, *Investigative Ophthalmology & Visual*, vol. 50, No. 13, Retrieved from the Internet: URL:https://iovs.arvojournals.org/article.aspx?articleid=2367197 [retrieved on Feb. 13, 2020].
Office Action dated May 25, 2021 issued in corresponding Japanese Application No. 2020-106892.
Matt Hasson: Combined complement inhibitor, anti-VEGF may be safe for treatment of wet AMD, Jul. 10, 2010 (Jul. 10, 2010), XP55668328, Retrieved from the Internet: URL:https://www.healio.com/ophthalmology/retina-vitreous/news/print/ocular-surgery-news/19e987b6a-24cl-4099-8d8b-0b3e32266956}/combined-complement-inhibitor-anti-vegf-may-be-safe-for-treatment-of-wet-amd [retrieved on Feb. 13, 2020].
Ella Leung et al: "Update on current and future novel therapies for dry age-related macular degeneration," Expert Review of Clinical Pharmacology Nov. 1, 2014 Expert Reviews Ltd. GBR, vol. 6, No. 5, Sep. 10, 2013 (Sep. 10, 2013), pp. 565-579, XP055331168, UK.
Ni Zhang et al: "Emerging Pharmacologic Therapies for Wet Age-Related Macular Degeneration," Ophthalmologica, Karger, Basel, CH, vol. 223, No. 6, Jan. 1, 2009 (Jan. 1, 2009), pp. 401-410, XP009164747.
"An Animal Model of Age-related Macular Degeneration in Senescent Macrophage Recruitment Impaired Mice," Investigative Ophthalmology & Visual Science, May 2001, vol. 44, Issue 13, No. 1718.
European Search Report mailed Feb. 21, 2020 in corresponding European Application No. EP 19192389.5.
Examination Report No. 1 dated Mar. 1, 2021 issued in corresponding Australian Application No. 2020201824.
First Examiner's Report dated Sep. 24, 2020 issued in corresponding Canadian Application No. 2,915,255.
First Office Action issued Dec. 28, 2020 in corresponding Chinese Application No. 201910114391.2.
Retina Today, pp. 52-55, Oct. 2010.
Vaz et al., Geographic Atrophy, amdbook.org 2017 [online], [retrieved on Nov. 15, 2021]. Retrieved from the Internet, URL:https://amdbook.org/content/geographic-atrophy-0, 21 pages.
Rosenfeld, P. J. et al., Emixustat Hydrochloride for Geographic Atrophy Secondary to Age-Related Macular Degeneration. Ophthalmology. Oct. 2018, Epub Apr. 30, 2018, vol. 125, No. 10; pp. 1556-1567; abstract; p. 1558, first column, second paragraph; DOI:10.1016/j.ophtha.2018.03.059.
F. Hoffman-La Roche Ltd., A Phase III, Multicenter, Randomized, Double-Masked, Sham-Contyrolled Study to Assess the Efficacy and Safety of Lampalizumab Administered Intravitreally to Patients with Geographic Atrophy Secondary to Age-Related Macular Degeneration. Sep. 24, 2015 [retrieved on Jan. 14, 2021]. Retrieved from the Internet [URL:https://jamanetwork.com/journals/ophth/articlepdf/2680577/eoi180031suppl_prod.pdf]; p. 173, fifth paragraph; p. 174, first paragraph; p. 175, first paragraph.
International Search Report and Written Opinion mailed on Feb. 9, 2021 in the corresponding International Application No. PCT/US2020/057422.
Corrected International Search Report and Written Opinion mailed on Feb. 25, 2021 in the corresponding International Application No. PCT/US2020/057422.
Jaffe Glenn J. et al., "C5 Inhibitor A vacincaptad Pegol for Geographic Atrophy Due to Age-Related Macular Degeneration", Ophthalmology, vol. 128, No. 4, Sep. 1, 2020, pp. 576-586, XP093092863.
Search Report issued in corresponding European patent application No. 20883760.9 dated Oct. 30, 2023.

* cited by examiner where R represents the following structure:

and n is about 450.

5

5

Increased Efficacy Independent of Baseline Lesion Size

Increased Efficacy Independent of Baseline Vision

Antagonist A Combination Group had Greater Proportion of Patients With Significant Visual Gain Intent to Treat population using Last Observation Carried Forward (ITT LOCF)

Antagonist A Combination Group had Fewer Patients With Visual Loss 1.5mg Antagonist A + Lucentis® 0.5mg Lucentis®

Intent to Treat population using Last Observation Carried Forward (ITT LOCF)

Improved Final Visual Acuity Outcome in Antagonist A 1.5 mg Combination Arm: 20/40 or Better Improved Final Visual Acuity Outcome in Antagonist A 1.5 mg Combination Arm: 20/25 or Better Improved Final Visual Acuity Outcome in Antagonist A 1.5 mg Combination Arm: 20/200 or Worse Increased Reduction in CNV Size in Small and Large Baseline CNV in Antaognist A (1.5 mg) Combination Arm Decrease in Neovascular Size Increased Reduction in CNV Size in Small and Large Baseline CNV in Antaognist A (1.5 mg) Combination Arm Decrease in Neovascular Size

ARC1905 Phase 2a Dry AMD (GA) Trial

- No adverse events considered to be related to ARC1905

ARC1905 Phase 2a Dry AMD (GA) Trial

SEQUENCE LISTING

```
Sequence total quantity: 98
SEQ ID NO: 1            moltype = DNA  length = 30
FEATURE                 Location/Qualifiers
misc_feature            1..30
                        note = Synthetic anti-PDGF aptamer
misc_difference         1
                        note = misc_feature - May be modified with two 20 kD
                         polyethylene glycol polymer chains that are covalently
                         attached to the two amino groups of a lysine residue via
                         carbamate linkages
misc_difference         1
                        note = misc_feature - May be modified with a bifunctional
                         alpha-hydroxy-omega-amino linker covalently attached to
                         the polyethylene glycol polymer chains via an amide bond
misc_difference         6
                        note = misc_feature - May be 2'-fluoro-2'-deoxyuridine
misc_difference         8
                        note = misc_feature - May be 2'-fluoro-2'-deoxycytidine
misc_difference         9
                        note = misc_feature - May be 2'-O-Methyl-2'-deoxyguanosine
misc_difference         9..10
                        note = misc_feature - May be linked via hexaethylene glycol
                         moieties via phosphodiester linkages
misc_difference         14
                        note = misc_feature - May be 2'-O-Methyl-2'-deoxyguanosine
misc_difference         16
                        note = misc_feature - May be 2'-O-Methyl-2'-deoxyguanosine
misc_difference         19
                        note = misc_feature - May be 2'-fluoro-2'-deoxyuridine
misc_difference         20
                        note = misc_feature - May be 2'-fluoro-2'-deoxycytidine
misc_difference         21
                        note = misc_feature - May be 2'-O-Methyl-2'-deoxyadenosine
misc_difference         21..22
                        note = misc_feature - May be linked via hexaethylene glycol
```

```
                        moieties via phosphodiester linkages
misc_difference         26..27
                        note = misc_feature - May be 2'-fluoro-2'-deoxycytidine
misc_difference         28
                        note = misc_feature - May be 2'-fluoro-2'-deoxyuridine
misc_difference         29
                        note = misc_feature - May be 2'-O-Methyl-2'-deoxyguanosine
misc_difference         30
                        note = misc_feature - May be an inverted orientation T
                        (3'-3'-linked)
source                  1..30
                        mol_type = other DNA
                        organism = synthetic construct
misc_feature            1..5
                        note = DNA
misc_feature            6
                        note = RNA
misc_feature            7
                        note = DNA
misc_feature            8..9
                        note = RNA
misc_feature            10..13
                        note = DNA
misc_feature            14
                        note = RNA
misc_feature            15
                        note = DNA
misc_feature            16
                        note = RNA
misc_feature            17..18
                        note = DNA
misc_feature            19..21
                        note = RNA
misc_feature            22..25
                        note = DNA
misc_feature            26..29
                        note = RNA
misc_feature            30
                        note = DNA
SEQUENCE: 1
caggctacgc gtagagcatc atgatcctgt                                     30

SEQ ID NO: 2            moltype = DNA  length = 2137
FEATURE                 Location/Qualifiers
source                  1..2137
                        mol_type = unassigned DNA
                        organism = Homo sapiens
SEQUENCE: 2
ccctgcctgc ctccctgcgc acccgcagcc tcccccgctg cctccctagg gctcccctcc  60
ggccgccagc gcccattttt cattccctag atagagatac tttgcgcgca cacacataca  120
tacgcgcgca aaaaggaaaa aaaaaaaaaa aagcccaccc tccagcctcg ctgcaaagag  180
aaaaccggag cagccgcagc tcgcagctcg cagcccgcag cccgcagagg acgcccagag  240
cggcgagcgg gcgggcagac ggaccgacgg actcgcgccg cgtccacctg tcggccgggc  300
ccagccgagc gcgcagcggg cacgccgcgc gcgcggagca gccgtgcccg ccgcccgggc  360
ccgccgccag ggcgcacacg ctcccgcccc cctacccggc ccgggcggga gtttgcacct  420
ctccctgccc gggtgctcga gctgccgttg caaagccaac tttggaaaaa gtttttttggg  480
ggagacttgg gccttgaggt gcccagctcc gcgctttccg attttggggg cctttccaga  540
aaatgttgca aaaaagctaa gccggcgggc agaggaaaac gcctgtagcc ggcgagtgaa  600
gacgaaccat cgactgccgt gttccttttc ctcttggagg ttggagtccc ctgggcgccc  660
ccacacggct agacgcctcg gctggttcgc gacgcagccc cccggccgtg gatgctgcac  720
tcgggctcgg gatccgccca ggtagcggcc tcggacccag gtcctgcgcc caggtcctcc  780
cctgcccccc agcgacggag ccggggccgg gggcggcggc gccgggggca tgcgggtgag  840
ccgcggctgc agaggcctga gcgcctgatc gccgcggacc cgagccgagc ccaccccccct  900
ccccagcccc ccaccctggc cgcgggggcg gcgcgctcga tctacgcgtt cggggccccg  960
cggggccggg cccggagtcg gcatgaatcg ctgctgggcg ctcttcctgt ctctctgctg  1020
ctacctgcgt ctggtcagcg ccgaggggga ccccattccc gaggagcttt atgagatgct  1080
gagtgaccac tcgatccgct cctttgatga tctccaacgc ctgctgcacg gagaccccgg  1140
agaggaagat ggggccgagt tggacctgaa catgacccgc tcccactctg gaggcgagct  1200
ggagagcttg gctcgtggaa gaaggagcct gggttccctg accattgctg agccggccat  1260
gatcgccgag tgcaagacgc gcaccgaggt gttcgagatc tcccggcgcc tcatagaccg  1320
caccaacgcc aacttcctgg tgtggccgcc ctgtgtggag gtgcagcgct gctccggctg  1380
ctgcaacaac cgcaacgtgc agtgccgccc cacccaggtg cagctgcgac ctgtccaggt  1440
gagaaagatc gagattgtgc ggaagaagcc aatctttaag aaggccacgg tgacgctgga  1500
agaccacctg gcatgcaagt gtgagacagt ggcagctgca cggcctgtga cccgaagccc  1560
ggggggttcc caggagcagc gagccaaaac gccccaaact cgggtgacca ttcggacggt  1620
gcgagtccgc cggcccccca agggcaagca ccggaaattc aagcacacgc atgacaagac  1680
ggcactgaag gagacccttg gagcctaggg gcatcggcag gagagtgtgt gggcagggtt  1740
atttaatatg gtatttgctg tattgccccc atggggcctt ggagtagata atattgtttc  1800
cctcgtccgt ctgtctcgat gcctgattcg gacggccaat ggtgcctccc ccacccctcc  1860
```

-continued

```
acgtgtccgt ccacccttcc atcagcgggt ctcctcccag cggcctccgg ctcttgccca  1920
gcagctcaag aagaaaaaga aggactgaac tccatcgcca tcttcttccc ttaactccaa  1980
gaacttggga taagagtgtg agagagactg atggggtcgc tctttggggg aaacgggttc  2040
cttcccctgc acctggcctg ggccacacct gagcgctgtg gactgtcctg aggagccctg  2100
aggacctctc agcatagcct gcctgatccc tgaaccc                           2137

SEQ ID NO: 3            moltype = AA  length = 241
FEATURE                 Location/Qualifiers
source                  1..241
                        mol_type = protein
                        organism = Homo sapiens
SEQUENCE: 3
MNRCWALFLS LCCYLRLVSA EGDPIPEELY EMLSDHSIRS FDDLQRLLHG DPGEEDGAEL  60
DLNMTRSHSG GELESLARGR RSLGSLTIAE PAMIAECKTR TEVFEISRRL IDRTNANFLV  120
WPPCVEVQRC SGCCNNRNVQ CRPTQVQLRP VQVRKIEIVR KKPIFKKATV TLEDHLACKC  180
ETVAAARPVT RSPGGSQEQR AKTPQTRVTI RTVRVRRPPK GKHRKFKHTH DKTALKETLG  240
A                                                                  241

SEQ ID NO: 4            moltype = DNA  length = 2305
FEATURE                 Location/Qualifiers
source                  1..2305
                        mol_type = unassigned DNA
                        organism = Homo sapiens
SEQUENCE: 4
ttcttggggc tgatgtccgc aaatatgcag aattaccggc cgggtcgctc ctgaagccag  60
cgcggggagc gagcgcggcg gcggccagca ccgggaacgc accgaggaag aagcccagcc  120
cccgccctcc gcccccttccg tccccacccc ctacccggcg gcccaggagg ctccccggct  180
gcggcgcgca ctccctgttt ctcctcctcc tggctggcgc tgcctgcctc tccgcactca  240
ctgctcgccg ggcgccgtcc gccagctccg tgctccccgc gccaccctcc tccgggccgc  300
gctccctaag ggatggtact gaatttcgcc gccacaggag accggctgga gcgcccgccc  360
cgcgcctcgc ctctcctccg agcagccagc gcctcgggac gcgatgagga ccttggcttg  420
cctgctgctc ctcggctgcg gatacctcgc ccatgttctg gccgaggaag ccgagatccc  480
ccgcgaggtg atcgagaggc tggcccgcag tcagatccac agcatccggg acctccagcg  540
actcctggag atagactccg tagggagtga ggattctttg gacaccagcc tgagagctca  600
cggggtccac gccactaagc atgtgcccga gaagcggccc ctgcccattc ggaggaagag  660
aagcatcgag gaagctgtcc ccgctgtctg caagaccagg acggtcattt acgagattcc  720
tcggagtcag gtcgacccca cgtccgccaa cttcctgatc tggcccccgt gcgtggaggt  780
gaaacgctgc accggctgct gcaacacgag cagtgtcaag tgccagccct cccgcgtcca  840
ccaccgcagc gtcaaggtgg ccaaggtgga atacgtcagg aagaagccaa aattaaaaga  900
agtccaggtg aggttagagg agcatttgga gtgcgcctgc gcgaccacaa gcctgaatcc  960
ggattatcgg gaagaggaca cggatgtgag gtgaggatga gccgcagccc tttcctggga  1020
catggatgta catggcgtgt tacattcctg aacctactat gtacggtgct ttattgccag  1080
tgtgcggtct ttgttctcct ccgtgaaaaa ctgtgtccga gaacactcgg gagaacaaag  1140
agacagtgca catttgttta atgtgacatc aaagcaagta ttgtagcact cggtgaagca  1200
gtaagaagct tccttgtcaa aaagagagag agagagagag agagagaaaa caaaaccaca  1260
aatgacaaaa acaaaacgga ctcacaaaaa tatctaaact cgatgagatg gagggtcgcc  1320
ccgtgggatg gaagtgcaga ggtctcagca gactggattt ctgtccgggt ggtcacaggt  1380
gctttttgc cgaggatgca gagcctgctt tgggaacgac tccagagggg tgctggtggg  1440
ctctgcaggg cccgcaggaa gcaggaatgt cttggaaacc gccacgcgaa ctttagaaac  1500
cacacctcct cgctgtagta tttaagccca tacagaaacc ttcctgagag ccttaagtgg  1560
ttttttttt tgtttttgtt ttgttttttt tttttttgtt ttttttttt ttttttttt  1620
ttacaccata aagtgattat taagcttcct tttactcttt ggctagcttt ttttttttt  1680
ttttttttt tttttttaa ttatctcttg gatgacattt acaccgataa cacacaggct  1740
gctgtaactg tcaggacagt gcgacggtat ttttcctagc aagatgcaaa ctaatgagat  1800
gtattaaaat aaacatggta tacctaccta tgcatcattt cctaaatgtt tctggctttg  1860
tgtttctccc ttaccctgct ttatttgtta atttaagcca ttttgaaaga actatgcgtc  1920
aaccaatcgt acgccgtccc tgcggcacct gccccagagc ccgtttgtgg ctgagtgaca  1980
acttgttccc cgcagtgcac acctagaatg ctgtgttccc acgcggcacg tgagatgcat  2040
tgccgcttct gtctgtgttg ttggtgtgcc ctggtgccgt ggtggcggtc actccctctg  2100
ctgccagtgt ttggacagaa cccaaattct ttatttttgg taagatattg tgctttacct  2160
gtattaacag aaatgtgtgt gtgtggtttg ttttttgta aaggtgaagt ttgtatgttt  2220
acctaatatt acctgttttg tatacctgag agcctgctat gttcttcttt tgttgatcca  2280
aaattaaaaa aaaaatacca ccaac                                        2305

SEQ ID NO: 5            moltype = AA  length = 196
FEATURE                 Location/Qualifiers
source                  1..196
                        mol_type = protein
                        organism = Homo sapiens
SEQUENCE: 5
MRTLACLLLL GCGYLAHVLA EEAEIPREVI ERLARSQIHS IRDLQRLLEI DSVGSEDSLD  60
TSLRAHGVHA TKHVPEKRPL PIRRKRSIEE AVPAVCKTRT VIYEIPRSQV DPTSANFLIW  120
PPCVEVKRCT GCCNTSSVKC QPSRVHHRSV KVAKVEYVRK KPKLKEVQVR LEEHLECACA  180
TTSLNPDYRE EDTDVR                                                  196

SEQ ID NO: 6            moltype = DNA  length = 3018
FEATURE                 Location/Qualifiers
source                  1..3018
                        mol_type = unassigned DNA
```

```
                         organism = Homo sapiens
SEQUENCE: 6
gcccggagag ccgcatctat tggcagcttt gttattgatc agaaactgct cgccgccgac  60
ttggcttcca gtctggctgc gggcaaccct tgagttttcg cctctgtcct gtcccccgaa  120
ctgacaggtg ctcccagcaa cttgctgggg acttctcgcc gctcccccgc gtccccaccc  180
cctcattcct ccctcgcctt cacccccacc cccaccactt cgccacagct caggatttgt  240
ttaaaccttg ggaaactggt tcaggtccag gttttgcttt gatccttttc aaaaactgga  300
gacacagaag agggctctag gaaaaagttt tggatgggat tatgtggaaa ctaccctgcg  360
attctctgct gccagagcag gctcggcgct tccaccccag tgcagccttc cctggcggt  420
ggtgaaagag actcgggagt cgctgcttcc aaagtgcccg ccgtgagtga gctctcaccc  480
cagtcagcca aatgagcctc ttcgggcttc tcctgctgac atctgccctg gccggccaga  540
gacaggggac tcaggcggaa tccaacctga gtagtaaatt ccagttttcc agcaacaagg  600
aacagaacgg agtacaagat cctcagcatg agagaattat tactgtgtct actaatggaa  660
gtattcacag cccaaggttt cctcatactt atccaagaaa tacggtcttg gtatggagat  720
tagtagcagt agaggaaaat gtatggatac aacttacgtt tgatgaaaga tttgggcttg  780
aagacccaga agatgacata tgcaagtatg attttgtaga agttgaggaa cccagtgatg  840
gaactatatt agggcgctgg tgtggttctg gtactgtacc aggaaaacag atttctaaag  900
gaaatcaaat taggataaga tttgtatctg atgaatattt tccttctgaa ccagggttct  960
gcatccacta caacattgtc atgccacaat tcacagaagc tgtgagtcct tcagtgctac  1020
ccccttcagc tttgccactg gacctgctta ataatgctat aactgccttt agtaccttgg  1080
aagaccttat tcgatatctt gaaccagaga gatggcagtt ggacttagaa gatctatata  1140
ggccaacttg gcaacttctt ggcaaggctt ttgtttttgg aagaaaatcc agagtggtgg  1200
atctgaacct tctaacagag gaggtaagat tatacagctg cacacctcgt aacttctcag  1260
tgtccataag ggaagaacta aagagaaccg ataccatttt ctggccaggt tgtctcctgg  1320
ttaaacgctg tggtgggaac tgtgcctgtt gtctccacaa ttgcaatgaa tgtcaatgtg  1380
tcccaagcaa agttactaaa aaataccacg aggtccttca gttgagacca aagaccggtg  1440
tcaggggatt gcacaaatca ctcaccgacg tggccctgga gcaccatgag gagtgtgact  1500
gtgtgtgcag agggagcaca ggaggatagc cgcatcacca ccagcagctc ttgcccagag  1560
ctgtgcagtg cagtggctga ttctattaga gaacgtatgc gttatctcca tccttaatct  1620
cagttgtttg cttcaaggac ctttcatctt caggatttac agtgcattct gaaagaggag  1680
acatcaaaca gaattaggag ttgtgcaaca gctcttttga gaggaggcct aaaggacagg  1740
agaaaaggtc ttcaatcgtg gaaagaaaat taaatgttgt attaaataga tcaccagcta  1800
gtttcagagt taccatgtac gtattccact agctgggttc tgtatttcag ttctttcgat  1860
acggcttagg gtaatgtcag tacaggaaaa aaactgtgca agtgagcacc tgattccgtt  1920
gccttgctta actctaaagc tccatgtcct gggcctaaaa tcgtataaaa tctggatttt  1980
ttttttttt tttgctcata ttcacatatg taaaccagaa cattctatgt actacaaacc  2040
tggtttttaa aaaggaacta tgttgctatg aattaaactt gtgtcgtgct gataggacag  2100
actggatttt tcatatttct tattaaaatt tctgccattt agaagaagag aactacattc  2160
atggtttgga agagataaac ctgaaaagaa gagtggcctt atcttcactt tatcgataag  2220
tcagtttatt tgtttcattg tgtacatttt tatattctcc ttttgacatt ataactgttg  2280
gcttttctaa tcttgttaaa tatatctatt tttaccaaag gtatttaata ttctttttta  2340
tgacaactta gatcaactat ttttagcttg gtaaattttt ctaaacacaa ttgttatagc  2400
cagaggaaca aagatgatat aaaatattgt tgctctgaca aaaatacatg tatttcattc  2460
tcgtatggtg ctagagttag attaatctgc attttaaaaa actgaattgg aatagaattg  2520
gtaagttgca aagacttttt gaaaataatt aaattatcat atcttccatt cctgttattg  2580
gagatgaaaa taaaaagcaa cttatgaaag tagacattca gatccagcca ttactaacct  2640
attccttttt tggggaaatc tgagcctagc tcagaaaaac ataaagcacc ttgaaaaaga  2700
cttggcagct tcctgataaa gcgtgctgtg ctgtgcagta ggaacacatc ctatttattg  2760
tgatgttgtg gttttattat cttaaactct gttccataca cttgtataaa tacatggata  2820
tttttatgta cagaagtatg tctcttaacc agttcactta ttgtactctg gcaatttaaa  2880
agaaaatcag taaaatattt tgcttgtaaa atgcttaata tcgtgcctag gttatgtggt  2940
gactatttga atcaaaaatg tattgaatca tcaaataaaa gaatgtggct attttgggga  3000
gaaaattaaa aaaaaaaa                                                3018

SEQ ID NO: 7             moltype = AA  length = 345
FEATURE                  Location/Qualifiers
source                   1..345
                         mol_type = protein
                         organism = Homo sapiens
SEQUENCE: 7
MSLFGLLLLT SALAGQRQGT QAESNLSSKF QFSSNKEQNG VQDPQHERII TVSTNGSIHS  60
PRFPHTYPRN TVLVWRLVAV EENVWIQLTF DERFGLEDPE DDICKYDFVE VEEPSDGTIL  120
GRWCGSGTVP GKQISKGNQI RIRFVSDEYF PSEPGFCIHY NIVMPQFTEA VSPSVLPPSA  180
LPLDLLNNAI TAFSTLEDLI RYLEPERWQL DLEDLYRPTW QLLGKAFVFG RKSRVVDLNL  240
LTEEVRLYSC TPRNFSVSIR EELKRTDTIF WPGCLLVKRC GGNCACCLHN CNECQCVPSK  300
VTKKYHEVLQ LRPKTGVRGL HKSLTDVALE HHEECDCVCR GSTGG                  345

SEQ ID NO: 8             moltype = DNA  length = 3997
FEATURE                  Location/Qualifiers
source                   1..3997
                         mol_type = unassigned DNA
                         organism = Homo sapiens
SEQUENCE: 8
tctcaggggc cgcggccggg gctggagaac gctgctgctc cgctcgcctg ccccgctaga  60
ttcggcgctg cccgccccct gcagcctgtg ctgcagctgc cggccaccgg agggggcgaa  120
caaacaaacg tcaacctgtt gtttgtcccg tcaccattta tcagctcagc accacaagga  180
agtgcggcac ccacacgcgc tcggaaagtt cagcatgcag gaagtttggg gagagctcgg  240
cgattagcac agcgacccgg gccagcgcag ggcgagcgca ggcggcgaga gcgcagggcg  300
gcgcggcgtc ggtcccggga gcagaacccg gctttttctt ggagcgacgc tgtctctagt  360
```

-continued

```
cgctgatccc aaatgcaccg gctcatcttt gtctacactc taatctgcgc aaacttttgc  420
agctgtcggg acacttctgc aacccgcag agcgcatcca tcaaagcttt gcgcaacgcc  480
aacctcaggc gagatgagag caatcacctc acagacttgt accgaagaga tgagaccatc  540
caggtgaaag gaaacggcta cgtgcagagt cctagattcc cgaacagcta ccccaggaac  600
ctgctcctga catggcggct tcactctcag gagaatacac ggatacagct agtgtttgac  660
aatcagtttg gattagagga agcagaaaat gatatctgta ggtatgattt tgtggaagtt  720
gaagatatat ccgaaaccag taccattatt agaggacgat ggtgtggaca caaggaagtt  780
cctccaagga taaaatcaag aacgaaccaa attaaaatca cattcaagtc cgatgactac  840
tttgtggcta aacctggatt caagatttat tattctttgc tggaagattt ccaacccgca  900
gcagcttcag agaccaactg ggaatctgtc acaagctcta tttcaggggt atcctataac  960
tctccatcag taacggatcc cactctgatt gcggatgctc tggacaaaaa aattgcagaa  1020
tttgatacag tggaagatct gctcaagtac ttcaatccag agtcatggca agaagatctt  1080
gagaatatgt atctggacac ccctcggtat cgaggcaggt cataccatga ccggaagtca  1140
aaagttgacc tggataggct caatgatgat gccaagcgtt acagttgcac tcccaggaat  1200
tactcggtca atataagaga agagctgaag ttggccaatg tggtcttctt tccacgttgc  1260
ctcctcgtgc agcgctgtgg aggaaattgt ggctgtggaa ctgtcaactg gaggtcctgc  1320
acatgcaatt cagggaaaac cgtgaaaaag tatcatgagg tattacagtt tgagcctggc  1380
cacatcaaga ggaggggtag agctaagacc atggctctag ttgacatcca gttggatcac  1440
catgaacgat gtgattgtat ctgcagctca agaccacctc gataagagaa tgtgcacatc  1500
cttacattaa gcctgaaaga acctttagtt taaggagggt gagataagag accctttttcc  1560
taccagcaac caaacttact actagcctgc aatgcaatga acacaagtgg ttgctgagtc  1620
tcagccttgc tttgttaatg ccatggcaag tagaaaggta tatcatcaac ttctatacct  1680
aagaatatag gattgcattt aataatagtg tttgaggtta tatatgcaca aacacacaca  1740
gaaatatatt catgtctatg tgtatataga tcaaatgttt tttttggtat atataaccag  1800
gtacaccaga gcttacatat gtttgagtta gactcttaaa atcctttgcc aaaataaggg  1860
atggtcaaat atatgaaaca tgtctttaga aaatttagga gataaattta tttttaaatt  1920
ttgaaacaca aaacaatttt gaatcttgct ctcttaaaga aagcatcttg tatattaaaa  1980
atcaaaagat gaggctttct tacatataca tcttagttga ttattaaaaa aggaaaaata  2040
tggtttccag agaaaaggcc aatacctaag catttttttcc atgagaagca ctgcatactt  2100
acctatgtgg actataataa cctgtctcca aaaccatgcc ataataatat aagtgcttta  2160
gaaattaaat cattgtgttt tttatgcatt ttgctgaggc atgcttattc atttaacacc  2220
tatctcaaaa acttacttag aaggtttttt attatagtcc tacaaaagac aatgtataag  2280
ctgtaacaga attttgaatt gtttttcttt gcaaaacccc tccacaaaag caaatccttt  2340
caagaatggc atgggcattc tgtatgaacc tttccagatg gtgttcagtg aaagatgtgg  2400
gtagttgaga acttaaaaag tgaacattga aacatcgacg taactggaaa ttaggtggga  2460
tatttgatag gatccatatc taataatgga ttcgaactct ccaaactaca ccaattaatt  2520
taatgtatct tgcttttgtg ttcccgtctt tttgaaatat agacatggat ttataatggc  2580
attttatatt tggcaggcca tcatagatta tttacaacct aaaagctttt gtgtatcaaa  2640
aaaatcacat tttattaatg taaatttcta atcgtatact tgctcactgt tctgatttcc  2700
tgtttctgaa ccaagtaaaa tcagtcctag aggctatggt tcttaatcta tggagcttgc  2760
tttaagaagc cagttgtcaa ttgtggtaac acaagtttgg ccctgctgtc ctactgttta  2820
atagaaaact gttttacatt ggttaatggt atttagagta attttttctc tctgcctcct  2880
ttgtgtctgt tttaaaggag actaactcca ggagtaggaa atgattcatc atcctccaaa  2940
gcaagaggct taagagagaa acaccgaaat tcagatagct cagggactgc taacagagaa  3000
ctacattttt cttattgcct tgaaagttaa aaggaaagca gatttcttca gtgactttgt  3060
ggtcctacta actacaacca gtttgggtga cagggctggt aaagtcccag tgttagatga  3120
gtgacctaaa tatacttaga tttctaagta tggtgctctc aggtccaagt tcaactattc  3180
ttaagcagtg caattcttcc cagttatttg agatgaaaga tctctgctta ttgaagatgt  3240
accttctaaa actttcctaa aagtgtctga tgtttttact caagaggggga gtggtaaaat  3300
taaatactct attgttcaat tctctaaaat cccagaacac aatcagaaat agctcaggca  3360
gacactaata attaagaacg ctcttcctct tcataactgc tttgcaagtt tcctgtgaaa  3420
acatcagttt cctgtaccaa agtcaaaatg aacgttacat cactctaacc tgaacagctc  3480
acaatgtagc tgtaaatata aaaaatgaga gtgttctacc cagttttcaa taaaccttcc  3540
aggctgcaat aaccagcaag gttttcagtt aaagccctat ctgcactttt tatttattag  3600
ctgaaatgta agcaggcata ttcactcact tttctttgcc tttcctgaga gttttattaa  3660
aacttctccc ttggttacct gttatctttt gcacttctaa catgtagcca ataaatctat  3720
ttgatagcca tcaaaggaat aaaaagctgg ccgtacaaat tacatttcaa aacaaaccct  3780
aataaatcca catttccgca tggctcattc acctggaata atgcctttta ttgaatatgt  3840
tcttataggg caaaacactt tcataagtag agtttttat gtttttgtc atatcggtaa  3900
catgcagctt tttcctctca tagcatttc tatagcgaat gtaatatgcc tcttatcttc  3960
atgaaaaata aatattgctt ttgaacaaaa ctaaaaa                         3997
```

SEQ ID NO: 9 moltype = AA length = 370
FEATURE Location/Qualifiers
source 1..370
mol_type = protein
organism = Homo sapiens

SEQUENCE: 9

```
MHRLIFVYTL ICANFCSCRD TSATPQSASI KALRNANLRR DESNHLTDLY RRDETIQVKG  60
NGYVQSPRFP NSYPRNLLLT WRLHSQENTR IQLVFDNQFG LEEAENDICR YDFVEVEDIS  120
ETSTIIRGRW CGHKEVPPRI KSRTNQIKIT FKSDDYFVAK PGFKIYYSLL EDFQPAAASE  180
TNWESVTSSI SGVSYNSPSV TDPTLIADAL DKKIAEFDTV EDLLKYFNPE SWQEDLENMY  240
LDTPRYRGRS YHDRKSKVDL DRLNDDAKRY SCTPRNYSVN IREELKLANV VFFPRCLLVQ  300
RCGGNCGCGT VNWRSCTCNS GKTVKKYHEV LQFEPGHIKR RGRAKTMALV DIQLDHHERC  360
DCICSSRPPR                                                       370
```

SEQ ID NO: 10 moltype = DNA length = 3979
FEATURE Location/Qualifiers
source 1..3979

-continued

```
                      mol_type = unassigned DNA
                      organism = Homo sapiens
SEQUENCE: 10
tctcaggggc cgcggccggg gctggagaac gctgctgctc cgctcgcctg ccccgctaga  60
ttcggcgctg cccgcccccct gcagcctgtg ctgcagctgc cggccaccgg agggggcgaa  120
caaacaaacg tcaacctgtt gtttgtcccg tcaccattta tcagctcagc accacaagga  180
agtgcggcac ccacacgcgc tcggaaagtt cagcatgcag gaagtttggg gagagctcgg  240
cgattagcac agcgacccgg gccagcgcag ggcgagcgca ggcggcgaga gcgcagggcg  300
gcgcggcgtc ggtcccggga gcagaacccg gctttttctt ggagcgacgc tgtctctagt  360
cgctgatccc aaatgcaccg gctcatcttt gtctacactc taatctgcgc aaacttttgc  420
agctgtcggg acacttctgc aacccccgcag agcgcatcca tcaaagcttt gcgcaacgcc  480
aacctcaggc gagatgactt gtaccgaaga gatgagacca tccaggtgaa aggaaacggc  540
tacgtgcaga gtcctagatt cccgaacagc taccccagga acctgctcct gacatggcgg  600
cttcactctc aggagaatac acggatacag ctagtgtttg acaatcagtt tggattagag  660
gaagcagaaa atgatatctg taggtatgat tttgtggaag ttgaagatat atccgaaacc  720
agtaccatta ttagaggacg atggtgtgga cacaaggaag ttcctccaag gataaaatca  780
agaacgaacc aaattaaaat cacattcaag tccgatgact actttgtggc taaacctgga  840
ttcaagattt attattcttt gctggaagat ttccaacccg cagcagcttc agagaccaac  900
tgggaatctg tcacaagctc tatttcaggg gtatcctata actctccatc agtaacggat  960
cccactctga ttgcggatgc tctggacaaa aaaattgcag aatttgatac agtggaagat  1020
ctgctcaagt acttcaatcc agagtcatgg caagaagatc ttgagaatat gtatctggac  1080
acccctcggt atcgaggcag gtcataccat gaccggaagt caaaagttga cctggatagg  1140
ctcaatgatg atgccaagcg ttacagttgc actcccagga attactcggt caatataaga  1200
gaagagctga agttggccaa tgtggtcttc tttccacgtt gcctcctcgt gcagcgctgt  1260
ggaggaaatt gtggctgtgg aactgtcaac tggaggtcct gcacatgcaa ttcagggaaa  1320
accgtgaaaa agtatcatga ggtattacag tttgagcctg gccacatcaa gaggaggggt  1380
agagctaaga ccatggctct agttgacatc cagttggatc accatgaacg atgtgattgt  1440
atctgcagct caagaccacc tcgataagag aatgtgcaca tccttacatt aagcctgaaa  1500
gaacctttag tttaaggagg gtgagataag agaccctttt cctaccagca accaaactta  1560
ctactagcct gcaatgcaat gaacacaagt ggttgctgag tctcagcctt gctttgttaa  1620
tgccatggca agtagaaagg tatatcatca acttctatac ctaagaatat aggattgcat  1680
ttaataatag tgtttgaggt tatatatgca caaacacaca cagaaatata ttcatgtcta  1740
tgtgtatata gatcaaatgt ttttttggt atatataacc aggtacacca gagcttacat  1800
atgtttgagt tagactctta aaatcctttg ccaaaataag ggatggtcaa atatatgaaa  1860
catgtcttta gaaaatttag gagataaatt tatttttaaa ttttgaaaca caaaacaatt  1920
ttgaatcttg ctctcttaaa gaaagcatct tgtatattaa aaatcaaaag atgaggcttt  1980
cttacatata catcttagtt gattattaaa aaaggaaaaa tatggtttcc agagaaaagg  2040
ccaataccta agcatttttt ccatgagaag cactgcatac ttacctatgt ggactataat  2100
aacctgtctc caaaaccatg ccataataat ataagtgctt tagaaattaa atcattgtgt  2160
tttttatgca ttttgctgag gcatgcttat tcatttaaca cctatctcaa aaacttactt  2220
agaaggtttt ttattatagt cctacaaaag acaatgtata agctgtaaca gaattttgaa  2280
ttgtttttct ttgcaaaacc cctccacaaa agcaaatcct ttcaagaatg gcatgggcat  2340
tctgtatgaa cctttccaga tggtgttcag tgaaagatgt gggtagttga gaacttaaaa  2400
agtgaacatt gaaacatcga cgtaactgga aattaggtgg gatatttgat aggatccata  2460
tctaataatg gattcgaact ctccaaacta caccaattaa tttaatgtat cttgcttttg  2520
tgttcccgtc tttttgaaat atagacatgg atttataatg gcattttata tttggcaggc  2580
catcatagat tatttacaac ctaaaagctt ttgtgtatca aaaaaatcac attttattaa  2640
tgtaaatttc taatcgtata cttgctcact gttctgattt cctgtttctg aaccaagtaa  2700
aatcagtcct agaggctatg gttcttaatc tatggagctt gctttaagaa gccagttgtc  2760
aattgtggta acacaagttt ggccctgctg tcctactgtt taatagaaaa ctgttttaca  2820
ttggttaatg gtatttagag taattttttc tctctgcctc ctttgtgtct gttttaaagg  2880
agactaactc caggagtagg aaatgattca tcatcctcca aagcaagagg cttaagagag  2940
aaacaccgaa attcagatag ctcagggact gctaacagag aactacattt ttcttattgc  3000
cttgaaagtt aaaaggaaag cagatttctt cagtgacttt gtggtcctac taactacaac  3060
cagtttgggt gacagggctg gtaaagtccc agtgttagat gagtgaccta aatatactta  3120
gatttctaag tatggtgctc tcaggtccaa gttcaactat tcttaagcag tgcaattctt  3180
cccagttatt tgagatgaaa gatctctgct tattgaagat gtaccttcta aaactttcct  3240
aaaagtgtct gatgttttta ctcaagaggg gagtggtaaa attaaatact ctattgttca  3300
attctctaaa atcccagaac acaatcagaa atagctcagg cagacactaa taattaagaa  3360
cgctcttcct cttcataact gctttgcaag tttcctgtga aaacatcagt ttcctgtacc  3420
aaagtcaaaa tgaacgttac atcactctaa cctgaacagc tcacaatgta gctgtaaata  3480
taaaaaatga gagtgttcta cccagttttc aataaacctt ccaggctgca ataaccagca  3540
aggttttcag ttaaagccct atctgcactt tttatttatt agctgaaatg taagcaggca  3600
tattcactca cttttctttg cctttcctga gagttttatt aaaacttctc ccttggttac  3660
ctgttatctt ttgcacttct aacatgtagc caataaatct atttgatagc catcaaagga  3720
ataaaaagct ggccgtacaa attacatttc aaaacaaacc ctaataaatc cacatttccg  3780
catggctcat tcacctggaa taatgccttt tattgaatat gttcttatag ggcaaaacac  3840
tttcataagt agagtttttt atgtttttg tcatatcggt aacatgcagc tttttcctct  3900
catagcattt tctatagcga atgtaatatg cctcttatct tcatgaaaaa taaatattgc  3960
ttttgaacaa aactaaaaa                                               3979

SEQ ID NO: 11         moltype = AA  length = 364
FEATURE               Location/Qualifiers
source                1..364
                      mol_type = protein
                      organism = Homo sapiens
SEQUENCE: 11
MHRLIFVYTL ICANFCSCRD TSATPQSASI KALRNANLRR DDLYRRDETI QVKGNGYVQS  60
PRFPNSYPRN LLLTWRLHSQ ENTRIQLVFD NQFGLEEAEN DICRYDFVEV EDISETSTII  120
```

-continued

```
RGRWCGHKEV PPRIKSRTNQ IKITFKSDDY FVAKPGFKIY YSLLEDFQPA AASETNWESV  180
TSSISGVSYN SPSVTDPTLI ADALDKKIAE FDTVEDLLKY FNPESWQEDL ENMYLDTPRY  240
RGRSYHDRKS KVDLDRLNDD AKRYSCTPRN YSVNIREELK LANVVFFPRC LLVQRCGGNC  300
GCGTVNWRSC TCNSGKTVKK YHEVLQFEPG HIKRRGRAKT MALVDIQLDH HERCDCICSS  360
RPPR                                                              364

SEQ ID NO: 12           moltype = DNA  length = 6574
FEATURE                 Location/Qualifiers
source                  1..6574
                        mol_type = unassigned DNA
                        organism = Homo sapiens
SEQUENCE: 12
aagagcaaaa agcgaaggcg caatctggac actgggagat tcggagcgca gggagtttga  60
gagaaacttt tattttgaag agaccaaggt tgaggggggg cttatttcct gacagctatt  120
tacttagagc aaatgattag ttttagaagg atggactata acattgaatc aattacaaaa  180
cgcggttttt gagcccatta ctgttggagc tacagggaga gaaacagagg aggagactgc  240
aagagatcat tggaggccgt gggcacgctc tttactccat gtgtgggaca ttcattgcgg  300
aataacatcg gaggagaagt ttcccagagc tatggggact tcccatccgg cgttcctggt  360
cttaggctgt cttctcacag ggctgagcct aatcctctgc cagctttcat taccctctat  420
ccttccaaat gaaaatgaaa aggttgtgca gctgaattca tccttttctc tgagatgctt  480
tggggagagt gaagtgagct ggcagtaccc catgtctgaa gaagagagct ccgatgtgga  540
aatcagaaat gaagaaaaca acagcggcct ttttgtgacg gtcttggaag tgagcagtgc  600
ctcggcggcc cacacagggt tgtacacttg ctattacaac cacactcaga cagaagagaa  660
tgagcttgaa ggcaggcaca tttacatcta tgtgccagac ccagatgtag cctttgtacc  720
tctaggaatg acggattatt tagtcatcgt ggaggatgat gattctgcca ttataccttg  780
tcgcacaact gatcccgaga ctcctgtaac cttacacaac agtgaggggg tggtacctgc  840
ctcctacgac agcagacagg gctttaatgg gaccttcact gtagggccct atatctgtga  900
ggccaccgtc aaaggaaaga agttccagac catcccattt aatgtttatg ctttaaaagc  960
aacatcagag ctggatctag aaatggaagc tcttaaaacc gtgtataagt caggggaaac  1020
gattgtggtc acctgtgctg tttttaacaa tgaggtggtt gaccttcaat ggacttaccc  1080
tggagaagtg aaaggcaaag gcatcacaat gctggaagaa atcaaagtcc catccatcaa  1140
attggtgtac actttgacgg tccccgaggc cacggtgaaa gacagtggag attacgaatg  1200
tgctgcccgc caggctacca gggaggtcaa agaaatgaag aaagtcacta tttctgtcca  1260
tgagaaaggt ttcattgaaa tcaaacccac cttcagccag ttggaagctg tcaacctgca  1320
tgaagtcaaa cattttgttg tagaggtgcg ggcctaccca cctcccagga tatcctggct  1380
gaaaaacaat ctgactctga ttgaaaatct cactgagatc accactgatg tggaaaagat  1440
tcaggaaata aggtatcgaa gcaaattaaa gctgatccgt gctaaggaag aagacagtgg  1500
ccattatact attgtagctc aaaatgaaga tgctgtgaag agctatactt ttgaactgtt  1560
aactcaagtt ccttcatcca ttctggactt ggtcgatgat caccatggct caactggggg  1620
acagacggtg aggtgcacag ctgaaggcac gccgcttcct gatattgagt ggatgatatg  1680
caaagatatt aagaaatgta ataatgaaac ttcctggact attttggcca acaatgtctc  1740
aaacatcatc acggagatcc actcccgaga caggagtacc gtggagggcc gtgtgacttt  1800
cgccaaagtg gaggagacca tcgccgtgcg atgcctggct aagaatctcc ttggagctga  1860
gaaccgagag ctgaagctgg tggctcccac cctgcgttct gaactcacgg tggctgctgc  1920
agtcctggtg ctgttggtga ttgtgatcat ctcacttatt gtcctggttg tcatttggaa  1980
acagaaaccg aggtatgaaa ttcgctggag ggtcattgaa tcaatcagcc cagatggaca  2040
tgaatatatt tatgtggacc cgatgcagct gccttatgac tcaagatggg agtttccaag  2100
agatggacta gtgcttggtc gggtcttggg gtctggagcg tttgggaagg tggttgaagg  2160
aacagcctat ggattaagcc ggtcccaacc tgtcatgaaa gttgcagtga agatgctaaa  2220
acccacggcc agatccagtg aaaaacaagc tctcatgtct gaactgaaga taatgactca  2280
cctggggcca catttgaaca ttgtaaactt gctgggagcc tgcaccaagt caggccccat  2340
ttacatcatc acagagtatt gcttctatgg agatttggtc aactatttgc ataagaatag  2400
ggatagcttc ctgagccacc acccagagaa gccaaagaaa gagctggata tctttggatt  2460
gaaccctgct gatgaaagca cacggagcta tgttatttta tcttttgaaa acaatggtga  2520
ctacatggac atgaagcagg ctgatactac acagtatgtc cccatgctag aaaggaaaga  2580
ggtttctaaa tattccgaca tccagagatc actctatgat cgtccagcct catataagaa  2640
gaaatctatg ttagactcag aagtcaaaaa cctcctttca gatgataact cagaaggcct  2700
tactttattg gatttgttga gcttcaccta tcaagttgcc cgaggaatgg agtttttggc  2760
ttcaaaaaat tgtgtccacc gtgatctggc tgctcgcaac gtcctcctgg cacaaggaaa  2820
aattgtgaag atctgtgact ttggcctggc cagagacatc atgcatgatt cgaactatgt  2880
gtcgaaaggc agtacctttc tgcccgtgaa gtggatggct cctgagagca tctttgacaa  2940
cctctacacc acactgagtg atgtctggtc ttatggcatt ctgctctggg agatcttttc  3000
ccttggtggc accccttacc ccggcatgat ggtggattct actttctaca ataagatcaa  3060
gagtgggtac cggatggcca agcctgacca cgctaccagt gaagtctacg agatcatggt  3120
gaaatgctgg aacagtgagc cggagaagag accctccttt taccacctga gtgagattgt  3180
ggagaatctg ctgcctggac aatataaaaa gagttatgaa aaaattcacc tggacttcct  3240
gaagagtgac catcctgctg tggcacgcat gcgtgtggac tcagacaatg catacattgg  3300
tgtcacctac aaaaacgagg aagacaagct gaaggactgg gagggtggtc tggatgagca  3360
gagactgagc gctgacagtg gctacatcat tcctctgcct gacattgacc ctgtccctga  3420
ggaggaggac ctgggcaaga ggaacagaca cagctcgcag acctctgaag agagtgccat  3480
tgagacgggt tccagcagtt ccaccttcat caagagagag gacgagacca ttgaagacat  3540
cgacatgatg gatgacatcg gcatagactc ttcagacctg gtggaagaca gcttcctgta  3600
actggcggat tcgaggggtt ccttccactt ctggggccac ctctggatcc cgttcagaaa  3660
accactttat tgcaatgcag aggttgagag gaggacttgg ttgatgttta aagagaagtt  3720
cccagccaag ggcctcgggg agcgttctaa atatgaatga atgggatatt ttgaaatgaa  3780
ctttgtcagt gttgcctctt gcaatgcctc agtagcatct cagtggtgtg tgaagtttgg  3840
agatagatgg ataagggaat aataggccac agaaggtgaa ctttgtgctt caaggacatt  3900
ggtgagagtc caacagacac aatttatact gcgacagaac ttcagcattg taattatgta  3960
aataactcta accaaggctg tgtttagatt gtattaacta tcttctttgg acttctgaag  4020
```

```
agaccactca atccatccat gtacttccct cttgaaacct gatgtcagct gctgttgaac  4080
tttttaaaga agtgcatgaa aaaccatttt tgaaccttaa aaggtactgg tactatagca  4140
ttttgctatc ttttttagtg ttaaagagat aaagaataat aattaaccaa ccttgtttaa  4200
tagatttggg tcatttagaa gcctgacaac tcattttcat attgtaatct atgtttataa  4260
tactactact gttatcagta atgctaaatg tgtaataatg taacatgatt tccctccaga  4320
gaaagcacaa tttaaaacaa tccttactaa gtaggtgatg agtttgacag tttttgacat  4380
ttatattaaa taacatgttt ctctataaag tatggtaata gctttagtga attaaattta  4440
gttgagcata gagaacaaag taaaagtagt gttgtccagg aagtcagaat ttttaactgt  4500
actgaatagg ttccccaatc catcgtatta aaaaacaatt aactgccctc tgaaataatg  4560
ggattagaaa caaacaaaac tcttaagtcc taaaagttct caatgtagag gcataaacct  4620
gtgctgaaca taacttctca tgtatattac ccaatggaaa atataatgat cagcaaaaag  4680
actggatttg cagaagtttt tttttttttt ttcttcatgc ctgatgaaag ctttggcgac  4740
cccaatatat gtatttttttg aatctatgaa cctgaaaagg gtcagaagga tgcccagaca  4800
tcagcctcct tctttcaccc cttaccccaa agagaaagag tttgaaactc gagaccataa  4860
agatattctt tagtggaggc tggatgtgca ttagcctgga tcctcagttc tcaaatgtgt  4920
gtggcagcca ggatgactag atcctgggtt tccatccttg agattctgaa gtatgaagtc  4980
tgagggaaac cagagtctgt atttttctaa actccctggc tgttctgatc ggccagtttt  5040
cggaaacact gacttaggtt tcaggaagtt gccatgggaa acaaataatt tgaactttgg  5100
aacagggttg gcattcaacc acgcaggaag cctactattt aaatccttgg cttcaggtta  5160
gtgacattta atgccatcta gctagcaatt gcgaccttaa tttaactttc cagtcttagc  5220
tgaggctgag aaagctaaag tttggttttg acaggttttc caaaagtaaa gatgctactt  5280
cccactgtat gggggagatt gaactttccc cgtctcccgt cttctgcctc ccactccata  5340
ccccgccaag gaaaggcatg tacaaaaatt atgcaattca gtgttccaag tctctgtgta  5400
accagctcag tgttttggtg gaaaaaacat tttaagtttt actgataatt tgaggttaga  5460
tgggaggatg aattgtcaca tctatccaca ctgtcaaaca ggttggtgtg ggttcattgg  5520
cattctttgc aatactgctt aattgctgat accatatgaa tgaaacatgg gctgtgatta  5580
ctgcaatcac tgtgctatcg gcagatgatg ctttggaaga tgcagaagca ataataaagt  5640
acttgactac ctactggtgt aatctcaatg caagccccaa ctttcttatc caacttttttc  5700
atagtaagtg cgaagactga gccagattgg ccaattaaaa acgaaaacct gactaggttc  5760
tgtagagcca attagacttg aaatacgttt gtgtttctag aatcacagct caagcattct  5820
gtttatcgct cactctccct tgtacagcct tattttgttg gtgctttgca ttttgatatt  5880
gctgtgagcc ttgcatgaca tcatgaggcc ggatgaaact tctcagtcca gcagtttcca  5940
gtcctaacaa atgctcccac ctgaatttgt atatgactgc atttgtgtgt gtgtgtgtgt  6000
tttcagcaaa ttccagattt gtttcctttt ggcctcctgc aaagtctcca gaagaaaatt  6060
tgccaatctt tcctactttc tatttttatg atgacaatca aagccggcct gagaaacact  6120
atttgtgact ttttaaacga ttagtgatgt ccttaaaatg tggtctgcca atctgtacaa  6180
aatggtccta tttttgtgaa gagggacata agataaaatg atgttataca tcaatatgta  6240
tatatgtatt tctatataga cttggagaat actgccaaaa catttatgac aagctgtatc  6300
actgccttcg tttatatttt tttaactgtg ataatcccca caggcacatt aactgttgca  6360
cttttgaatg tccaaaattt atattttaga aataataaaa agaaagatac ttacatgttc  6420
ccaaaacaat ggtgtggtga atgtgtgaga aaaactaact tgatagggtc taccaataca  6480
aaatgtatta cgaatgcccc tgttcatgtt tttgttttaa aacgtgtaaa tgaagatctt  6540
tatatttcaa taaatgatat ataatttaaa gtta                            6574

SEQ ID NO: 13          moltype = AA  length = 1089
FEATURE                Location/Qualifiers
source                 1..1089
                       mol_type = protein
                       organism = Homo sapiens
SEQUENCE: 13
MGTSHPAFLV LGCLLTGLSL ILCQLSLPSI LPNENEKVVQ LNSSFSLRCF GESEVSWQYP  60
MSEEESSDVE IRNEENNSGL FVTVLEVSSA SAAHTGLYTC YYNHTQTEEN ELEGRHIYIY  120
VPDPDVAFVP LGMTDYLVIV EDDDSAIIPC RTTDPETPVT LHNSEGVVPA SYDSRQGFNG  180
TFTVGPYICE ATVKGKKFQT IPFNVYALKA TSELDLEMEA LKTVYKSGET IVVTCAVFNN  240
EVVDLQWTYP GEVKGKGITM LEEIKVPSIK LVYTLTVPEA TVKDSGDYEC AARQATREVK  300
EMKKVTISVH EKGFIEIKPT FSQLEAVNLH EVKHFVVEVR AYPPPRISWL KNNLTLIENL  360
TEITTDVEKI QEIRYRSKLK LIRAKEEDSG HYTIVAQNED AVKSYTFELL TQVPSSILDL  420
VDDHHGSTGG QTVRCTAEGT PLPDIEWMIC KDIKKCNNET SWTILANNVS NIITEIHSRD  480
RSTVEGRVTF AKVEETIAVR CLAKNLLGAE NRELKLVAPT LRSELTVAAA VLVLLVIVII  540
SLIVLVVIWK QKPRYEIRWR VIESISPDGH EYIYVDPMQL PYDSRWEFPR DGLVLGRVLG  600
SGAFGKVVEG TAYGLSRSQP VMKVAVKMLK PTARSSEKQA LMSELKIMTH LGPHLNIVNL  660
LGACTKSGPI YIITEYCFYG DLVNYLHKNR DSFLSHHPEK PKKELDIFGL NPADESTRSY  720
VILSFENNGD YMDMKQADTT QYVPMLERKE VSKYSDIQRS LYDRPASYKK KSMLDSEVKN  780
LLSDDNSEGL TLLDLLSFTY QVARGMEFLA SKNCVHRDLA ARNVLLAQGK IVKICDFGLA  840
RDIMHDSNYV SKGSTFLPVK WMAPESIFDN LYTTLSDVWS YGILLWEIFS LGGTPYPGMM  900
VDSTFYNKIK SGYRMAKPDH ATSEVYEIMV KCWNSEPEKR PSFYHLSEIV ENLLPGQYKK  960
SYEKIHLDFL KSDHPAVARM RVDSDNAYIG VTYKNEEDKL KDWEGGLDEQ RLSADSGYII  1020
PLPDIDPVPE EEDLGKRNRH SSQTSEESAI ETGSSSSTFI KREDETIEDI DMMDDIGIDS  1080
SDLVEDSFL                                                         1089

SEQ ID NO: 14          moltype = DNA  length = 5718
FEATURE                Location/Qualifiers
source                 1..5718
                       mol_type = unassigned DNA
                       organism = Homo sapiens
SEQUENCE: 14
ctcctgaggc tgccagcagc cagcagtgac tgcccgccct atctgggacc caggatcgct  60
ctgtgagcaa cttggagcca gagaggagat caacaaggag gaggagagag ccggcccctc  120
agccctgctg cccagcagca gcctgtgctc gccctgccca acgcagacag ccagacccag  180
```

-continued

```
ggcggcccct ctggcggctc tgctcctccc gaaggatgct tggggagtga ggcgaagctg  240
ggccgctcct ctcccctaca gcagcccccct tcctccatcc ctctgttctc ctgagccttc  300
aggagcctgc accagtcctg cctgtccttc tactcagctg ttacccactc tgggaccagc  360
agtctttctg ataactggga gagggcagta aggaggactt cctggagggg gtgactgtcc  420
agagcctgga actgtgccca caccagaagc catcagcagc aaggacacca tgcggcttcc  480
gggtgcgatg ccagctctgg ccctcaaagg cgagctgctg ttgctgtctc tcctgttact  540
tctggaacca cagatctctc agggcctggt cgtcacaccc ccggggccag agcttgtcct  600
caatgtctcc agcaccttcg ttctgacctg ctcgggttca gctccggtgg tgtgggaacg  660
gatgtcccag gagcccccac aggaaatggc caaggcccag gatggcacct tctccagcgt  720
gctcacactg accaacctca ctgggctaga cacgggagaa tacttttgca cccacaatga  780
ctcccgtgga ctggagaccg atgagcggaa acggctctac atctttgtgc cagatcccac  840
cgtgggcttc ctccctaatg atgccgagga actattcatc tttctcacgg aaataactga  900
gatcaccatt ccatgccgag taacagaccc acagctggtg gtgacactgc acgagaagaa  960
aggggacgtt gcactgcctg tcccctatga tcaccaacgt ggcttttctg gtatctttga  1020
ggacagaagc tacatctgca aaaccaccat tggggacagg gaggtggatt ctgatgccta  1080
ctatgtctac agactccagg tgtcatccat caacgtctct gtgaacgcag tgcagactgt  1140
ggtccgccag ggtgagaaca tcaccctcat gtgcattgtg atcgggaatg aggtggtcaa  1200
cttcgagtgg acatacccccc gcaaagaaag tgggcggctg gtggagccgg tgactgactt  1260
cctcttggat atgccttacc acatccgctc catcctgcac atccccagtg ccgagttaga  1320
agactcgggg acctacacct gcaatgtgac ggagagtgtg aatgaccatc aggatgaaaa  1380
ggccatcaac atcaccgtgg ttgagagcgg ctacgtgcgg ctcctgggag aggtgggcac  1440
actacaattt gctgagctgc atcggagccg gacactgcag gtagtgttcg aggcctaccc  1500
accgcccact gtcctgtggt tcaaagacaa ccgcaccctg ggcgactcca gcgctggcga  1560
aatcgccctg tccacgcgca acgtgtcgga gacccggtat gtgtcagagc tgacactggt  1620
tcgcgtgaag gtggcagagg ctggccacta caccatgcgg gccttccatg aggatgctga  1680
ggtccagctc tccttccagc tacagatcaa tgtccctgtc cgagtgctgg agctaagtga  1740
gagccaccct gacagtgggg aacagacagt ccgctgtcgt ggccggggca tgccccagcc  1800
gaacatcatc tggtctgcct gcagagacct caaaaggtgt ccacgtgagc tgccgcccac  1860
gctgctgggg aacagttccg aagaggagag ccagctggag actaacgtga cgtactggga  1920
ggaggagcag gagtttgagg tggtgagcac actgcgtctg cagcacgtgg atcggccact  1980
gtcggtgcgc tgcacgctgc gcaacgctgt gggccaggac acgcaggagg tcatcgtggt  2040
gccacactcc ttgcccttta aggtggtggt gatctcagcc atcctggccc tggtggtgct  2100
caccatcatc tcccttatca tcctcatcat gctttggcag aagaagccac gttacgagat  2160
ccgatggaag gtgattgagt ctgtgagctc tgacggccat gagtacatct acgtggaccc  2220
catgcagctg ccctatgact ccacgtggga gctgccgcgg gaccagcttg tgctgggacg  2280
caccctcggc tctggggcct ttgggcaggt ggtggaggcc acggctcatg gcctgagcca  2340
ttctcaggcc acgatgaaag tggccgtcaa gatgcttaaa tccacagccc gcagcagtga  2400
gaagcaagcc cttatgtcgg agctgaagat catgagtcac cttgggcccc acctgaacgt  2460
ggtcaacctg ttgggggcct gcaccaaagg aggacccatc tatatcatca ctgagtactg  2520
ccgctacgga gacctggtgg actacctgca ccgcaacaaa cacaccttcc tgcagcacca  2580
ctccgacaag cgccgcccgc ccagcgcgga gctctacagc aatgctctgc ccgttgggct  2640
cccccctgccc agccatgtgt ccttgaccgg ggagagcgac ggtggctaca tggacatgag  2700
caaggacgag tcggtggact atgtgcccat gctggacatg aaaggagacg tcaaatatgc  2760
agacatcgag tcctccaact acatggcccc ttacgataac tacgttccct ctgcccctga  2820
gaggacctgc cgagcaactt tgatcaacga gtctccagtg ctaagctaca tggacctcgt  2880
gggcttcagc taccaggtgg ccaatggcat ggagtttctg gcctccaaga actgcgtcca  2940
cagagacctg gcggctagga acgtgctcat ctgtgaaggc aagctggtca agatctgtga  3000
ctttggcctg gctcgagaca tcatgcggga ctcgaattac atctccaaag gcagcacctt  3060
tttgccttta aagtggatgg ctccggagag catcttcaac agcctctaca ccaccctgag  3120
cgacgtgtgg tccttcggga tcctgctctg ggagatcttc accttgggtg gcacccctta  3180
cccagagctg cccatgaacg agcagttcta caatgccatc aaacggggtt accgcatggc  3240
ccagcctgcc catgcctccg acgagatcta tgagatcatg cagaagtgct gggaagagaa  3300
gtttgagatt cggcccccct tctcccagct ggtgctgctt ctcgagagac tgttgggcga  3360
aggttacaaa aagaagtacc agcaggtgga tgaggagttt ctgaggagtg accacccagc  3420
catccttcgg tcccaggccc gcttgcctgg gttccatggc ctccgatctc cctggacac  3480
cagctccgtc ctctatactg ccgtgcagcc caatgagggt gacaacgact atatcatccc  3540
cctgcctgac cccaaacccg aggttgctga cgagggccca ctggagggtt cccccagcct  3600
agccagctcc accctgaatg aagtcaacac ctcctcaacc atctcctgtg acagccccct  3660
ggagccccag gacgaaccag agccagagcc ccagcttgag ctccaggtgg agccggagcc  3720
agagctggaa cagttgccgg attcggggtg ccctgcgcct cgggcggaag cagaggatag  3780
cttcctgtag gggctggcc cctaccctgc cctgcctgaa gctccccccc tgccagcacc  3840
cagcatctcc tggcctggcc tgaccgggct tcctgtcagc caggctgccc ttatcagctg  3900
tccccttctg gaagctttct gctcctgacg tgttgtgccc caaaccctgg ggctggctta  3960
ggaggcaaga aaactgcagg ggccgtgacc agccctctgc ctccagggag gccaactgac  4020
tctgagccag ggttccccca gggaactcag ttttcccata tgtaagatgg gaaagttagg  4080
cttgatgacc cagaatctag gattctctcc ctggctgaca ggtggggaga ccgaatccct  4140
ccctgggaag attcttggag ttactgaggt ggtaaattaa cttttttctg ttcagccagc  4200
tacccctcaa ggaatcatag ctctctcctc gcacttttat ccacccagga gctagggaag  4260
agaccctagc ctccctggct gctggctgag ctagggccta gccttgagca gtgttgcctc  4320
atccagaaga aagccagtct cctccctatg atgccagtcc ctgcgttccc tggcccgagc  4380
tggtctgggg ccattaggca gcctaattaa tgctggaggc tgagccaagt acaggacacc  4440
cccagcctgc agcccttgcc cagggcactt ggagcacacg cagccatagc aagtgcctgt  4500
gtccctgtcc ttcaggccca tcagtcctgg ggcttttttct ttatcaccct cagtcttaat  4560
ccatccacca gagtctagaa ggccagacgg gccccgcatc tgtgatgaga atgtaaatgt  4620
gccagtgtgg agtggccacg tgtgtgtgcc agtatatggc cctggctctg cattggacct  4680
gctatgaggc tttggaggaa tccctcaccc tctctgggcc tcagtttccc cttcaaaaaa  4740
tgaataagtc ggacttatta actctgagtg ccttgccagc actaacattc tagagtattc  4800
caggtggttg cacatttgtc cagatgaagc aaggccatat accctaaact tccatcctgg  4860
gggtcagctg ggctcctggg agattccaga tcacacatca cactctgggg actcaggaac  4920
```

-continued

```
catgcccctt ccccaggccc ccagcaagtc tcaagaacac agctgcacag gccttgactt  4980
agagtgacag ccggtgtcct ggaaagcccc cagcagctgc cccagggaca tgggaagacc  5040
acgggacctc tttcactacc cacgatgacc tccgggggta tcctgggcaa aagggacaaa  5100
gagggcaaat gagatcacct cctgcagccc accactccag cacctgtgcc gaggtctgcg  5160
tcgaagacag aatggacagt gaggacagtt atgtcttgta aaagacaaga agcttcagat  5220
gggtacccca agaaggatgt gagaggtggg cgctttggag gtttgcccct cacccaccag  5280
ctgccccatc cctgaggcag cgctccatgg gggtatggtt ttgtcactgc ccagacctag  5340
cagtgacatc tcattgtccc cagcccagtg ggcattggag gtgccagggg agtcagggtt  5400
gtagccaaga cgcccccgca cggggagggt tgggaagggg gtgcaggaag ctcaacccct  5460
ctgggcacca accctgcatt gcaggttggc accttacttc cctgggatcc ccagagttgg  5520
tccaaggagg gagagtgggt tctcaatacg gtaccaaaga tataatcacc taggtttaca  5580
aatattttta ggactcacgt taactcacat ttatacagca gaaatgctat tttgtatgct  5640
gttaagtttt tctatctgtg tacttttttt taagggaaag attttaatat taaacctggt  5700
gcttctcact cacaaaaa                                                5718

SEQ ID NO: 15          moltype = AA  length = 1106
FEATURE                Location/Qualifiers
source                 1..1106
                       mol_type = protein
                       organism = Homo sapiens
SEQUENCE: 15
MRLPGAMPAL ALKGELLLLS LLLLLEPQIS QGLVVTPPGP ELVLNVSSTF VLTCSGSAPV  60
VWERMSQEPP QEMAKAQDGT FSSVLTLTNL TGLDTGEYFC THNDSRGLET DERKRLYIFV  120
PDPTVGFLPN DAEELFIFLT EITEITIPCR VTDPQLVVTL HEKKGDVALP VPYDHQRGFS  180
GIFEDRSYIC KTTIGDREVD SDAYYVYRLQ VSSINVSVNA VQTVVRQGEN ITLMCIVIGN  240
EVVNFEWTYP RKESGRLVEP VTDFLLDMPY HIRSILHIPS AELEDSGTYT CNVTESVNDH  300
QDEKAINITV VESGYVRLLG EVGTLQFAEL HRSRTLQVVF EAYPPPTVLW FKDNRTLGDS  360
SAGEIALSTR NVSETRYVSE LTLVRVKVAE AGHYTMRAFH EDAEVQLSFQ LQINVPVRVL  420
ELSESHPDSG EQTVRCRGRG MPQPNIIWSA CRDLKRCPRE LPPTLLGNSS EEESQLETNV  480
TYWEEEQEFE VVSTLRLQHV DRPLSVRCTL RNAVGQDTQE VIVVPHSLPF KVVVISAILA  540
LVVLTIISLI ILIMLWQKKP RYEIRWKVIE SVSSDGHEYI YVDPMQLPYD STWELPRDQL  600
VLGRTLGSGA FGQVVEATAH GLSHSQATMK VAVKMLKSTA RSSEKQALMS ELKIMSHLGP  660
HLNVVNLLGA CTKGGPIYII TEYCRYGDLV DYLHRNKHTF LQHHSDKRRP PSAELYSNAL  720
PVGLPLPSHV SLTGESDGGY MDMSKDESVD YVPMLDMKGD VKYADIESSN YMAPYDNYVP  780
SAPERTCRAT LINESPVLSY MDLVGFSYQV ANGMEFLASK NCVHRDLAAR NVLICEGKLV  840
KICDFGLARD IMRDSNYISK GSTFLPLKWM APESIFNSLY TTLSDVWSFG ILLWEIFTLG  900
GTPYPELPMN EQFYNAIKRG YRMAQPAHAS DEIYEIMQKC WEEKFEIRPP FSQLVLLLER  960
LLGEGYKKKY QQVDEEFLRS DHPAILRSQA RLPGFHGLRS PLDTSSVLYT AVQPNEGDND  1020
YIIPLPDPKP EVADEGPLEG SPSLASSTLN EVNTSSTISC DSPLEPQDEP EPEPQLELQV  1080
EPEPELEQLP DSGCPAPRAE AEDSFL                                       1106

SEQ ID NO: 16          moltype = DNA  length = 3626
FEATURE                Location/Qualifiers
source                 1..3626
                       mol_type = unassigned DNA
                       organism = Homo sapiens
SEQUENCE: 16
tcgcggaggc ttggggcagc cggtagctc ggaggtcgtg gcgctggggg ctagcaccag  60
cgctctgtcg ggaggcgcag cggttaggtg gaccggtcag cggactcacc ggccagggcg  120
ctcggtgctg gaatttgata ttcattgatc cgggttttat ccctcttctt ttttcttaaa  180
catttttttt taaaactgta ttgtttctcg ttttaattta tttttgcttg ccattcccca  240
cttgaatcgg gccgacggct tggggagatt gctctacttc cccaaatcac tgtggatttt  300
ggaaaccagc agaaagagga aagaggtagc aagagctcca gagagaagtc gaggaagaga  360
gagacggggt cagagagagc gcgcgggcgt gcgagcagcg aaagcgacag gggcaaagtg  420
agtgacctgc ttttgggggt gaccgccgga gcgcggcgtg agccctcccc cttgggatcc  480
cgcagctgac cagtcgcgct gacggacaga cagacagaca ccgcccccag ccccagctac  540
cacctcctcc ccggccggcg gcggacagtg gacgcggcgg cgagccgcgg gcaggggccg  600
gagcccgcgc ccggaggcgg ggtggagggg gtcggggctc gcggcgtcgc actgaaactt  660
ttcgtccaac ttctgggctg ttctcgcttc ggaggagccg tggtccgcgc gggggaagcc  720
gagccgagcg gagccgcgag aagtgctagc tcgggccggg aggagccgca gccggaggag  780
ggggaggagg aagaagagaa ggaagaggag agggggccgc agtggcgact cggcgctcgg  840
aagccgggct catggacggg tgaggcggcg gtgtgcgcag acagtgctcc agccgcgcgc  900
gctccccagg ccctggcccg ggcctcgggc cggggaggaa gagtagctcg ccgaggcgcc  960
gaggagagcg ggccgcccca cagcccgagc cggagaggga gcgcgagccg cgccggcccc  1020
ggtcgggcct ccgaaaccat gaactttctg ctgtcttggg tgcattggag ccttgccttg  1080
ctgctctacc tccaccatgc caagtggtcc caggctgcac ccatggcaga aggaggaggg  1140
cagaatcatc acgaagtggt gaagttcatg gatgtctatc agcgcagcta ctgccatcca  1200
atcgagaccc tggtggacat cttccaggag taccctgatg agatcgagta catcttcaag  1260
ccatcctgtg tgcccctgat gcgatgcggg ggctgctgca atgacgaggg cctggagtgt  1320
gtgcccactg aggagtccaa catcaccatg cagattatgc ggatcaaacc tcaccaaggc  1380
cagcacatag gagagatgag cttcctacag cacaacaaat gtgaatgcag accaaagaaa  1440
gatagagcaa gacaagaaaa aaaatcagtt cgaggaaagg gaaaggggca aaaacgaaag  1500
cgcaagaaat cccggtataa gtcctggagc gttccctgtg ggccttgctc agagcggaga  1560
aagcatttgt ttgtacaaga tccgcagacg tgtaaatgtt cctgcaaaaa cacagactcg  1620
cgttgcaagg cgaggcagct tgagttaaac gaacgtactt gcagatgtga caagccgagg  1680
cggtgagccg ggcaggagga aggagcctcc ctcagggttt cgggaaccag atctctcacc  1740
aggaaagact gatacagaac gatcgataca gaaaccacgc tgccgccacc acaccatcac  1800
catcgacaga acagtcctta atccagaaac ctgaaatgaa ggaagaggag actctgcgca  1860
gagcactttg ggtccggagg gcgagactcc ggcggaagca ttcccgggcg ggtgacccag  1920
```

-continued

```
cacggtccct cttggaattg gattcgccat tttattttc ttgctgctaa atcaccgagc  1980
ccggaagatt agagagtttt atttctggga ttcctgtaga cacacccacc cacatacata  2040
catttatata tatatatatt atatatatat aaaaataaat atctctattt tatatatata  2100
aaatatatat attcttttt taaattaaca gtgctaatgt tattggtgtc ttcactggat  2160
gtatttgact gctgtggact tgagttggga ggggaatgtt cccactcaga tcctgacagg  2220
gaagaggagg agatgagaga ctctggcatg atcttttttt tgtcccactt ggtggggcca  2280
gggtcctctc ccctgcccag gaatgtgcaa ggccagggca tgggggcaaa tatgacccag  2340
ttttgggaac accgacaaac ccagccctgg cgctgagcct ctctacccca ggtcagacgg  2400
acagaaagac agatcacagg tacagggatg aggacaccgg ctctgaccag gagtttgggg  2460
agcttcagga cattgctgtg ctttggggat tccctccaca tgctgcacgc gcatctcgcc  2520
cccaggggca ctgcctggaa gattcaggag cctgggcggc cttcgcttac tctcacctgc  2580
ttctgagttg cccaggagac cactggcaga tgtcccggcg aagagaagag acacattgtt  2640
ggaagaagca gcccatgaca gctccccttc ctgggactcg ccctcatcct cttcctgctc  2700
cccttcctgg ggtgcagcct aaaaggacct atgtcctcac accattgaaa ccactagttc  2760
tgtcccccca ggagacctgg ttgtgtgtgt gtgagtggtt gaccttcctc catcccctgg  2820
tccttccctt cccttcccga ggcacagaga gacagggcag gatccacgtg cccattgtgg  2880
aggcagagaa aagagaaagt gttttatata cggtacttat ttaatatccc tttttaatta  2940
gaaattaaaa cagttaattt aattaaagag tagggttttt tttcagtatt cttggttaat  3000
atttaatttc aactatttat gagatgtatc ttttgctctc tcttgctctc ttatttgtac  3060
cggtttttgt atataaaatt catgtttcca atctctctct ccctgatcgg tgacagtcac  3120
tagcttatct tgaacagata tttaattttg ctaacactca gctctgccct ccccgatccc  3180
ctggctcccc agcacacatt cctttgaaat aaggtttcaa tatacatcta catactatat  3240
atatatttgg caacttgtat ttgtgtgtat atatatatat atatgtttat gtatatatgt  3300
gattctgata aaatagacat tgctattctg ttttttatat gtaaaaacaa aacaagaaaa  3360
aatagagaat tctacatact aaatctctct cctttttaa ttttaatatt tgttatcatt  3420
tatttattgg tgctactgtt tatccgtaat aattgtgggg aaaagatatt aacatcacgt  3480
ctttgtctct agtgcagttt ttcgagatat tccgtagtac atatttattt ttaaacaacg  3540
acaaagaaat acagatatat cttaaaaaaa aaaaagcatt ttgtattaaa gaatttaatt  3600
ctgatctcaa aaaaaaaaaa aaaaaa                                      3626
```

```
SEQ ID NO: 17          moltype = AA  length = 395
FEATURE                Location/Qualifiers
source                 1..395
                       mol_type = protein
                       organism = Homo sapiens
SEQUENCE: 17
MTDRQTDTAP SPSYHLLPGR RRTVDAAASR GQGPEPAPGG GVEGVGARGV ALKLFVQLLG  60
CSRFGGAVVR AGEAEPSGAA RSASSGREEP QPEEGEEEEE KEEERGPQWR LGARKPGSWT  120
GEAAVCADSA PAARAPQALA RASGRGGRVA RRGAEESGPP HSPSRRGSAS RAGPGRASET  180
MNFLLSWVHW SLALLLYLHH AKWSQAAPMA EGGGQNHHEV VKFMDVYQRS YCHPIETLVD  240
IFQEYPDEIE YIFKPSCVPL MRCGGCCNDE GLECVPTEES NITMQIMRIK PHQGQHIGEM  300
SFLQHNKCEC RPKKDRARQE KKSVRGKGKG QKRKRKKSRY KSWSVPCGPC SERRKHLFVQ  360
DPQTCKCSCK NTDSRCKARQ LELNERTCRC DKPRR                            395
```

```
SEQ ID NO: 18          moltype = DNA  length = 4017
FEATURE                Location/Qualifiers
source                 1..4017
                       mol_type = unassigned DNA
                       organism = Homo sapiens
SEQUENCE: 18
atggtcagct actgggacac cggggtcctg ctgtgcgcgc tgctcagctg tctgcttctc  60
acaggatcta gttcaggttc aaaattaaaa gatcctgaac tgagtttaaa aggcacccag  120
cacatcatgc aagcaggcca gacactgcat ctccaatgca ggggggaagc agcccataaa  180
tggtctttgc ctgaaatggt gagtaaggaa agcgaaaggc tgagcataac taaatctgcc  240
tgtggaagaa atggcaaaca attctgcagt actttaacct tgaacacagc tcaagcaaac  300
cacactggct tctacagctg caaatatcta gctgtaccta cttcaaagaa gaaggaaaca  360
gaatctgcaa tctatatatt tattagtgat acaggtagac ctttcgtaga gatgtacagt  420
gaaatccccg aaattataca catgactgaa ggaagggagc tcgtcattcc ctgccgggtt  480
acgtcaccta acatcactgt tactttaaaa aagtttccac ttgacacttt gatccctgat  540
ggaaaacgca taatctggga cagtagaaag ggcttcatca tatcaaatgc aacgtacaaa  600
gaaatagggc ttctgacctg tgaagcaaca gtcaatgggc atttgtataa gacaaactat  660
ctcacacatc gacaaaccaa tacaatcata gatgtccaaa taagcacacc acgcccagtc  720
aaattactta gaggccatac tcttgtcctc aattgtactg ctaccactcc cttgaacacg  780
agagttcaaa tgacctggag ttaccctgat gaaaaaaata agagagcttc cgtaaggcga  840
cgaattgacc aaagcaattc ccatgccaac atattctaca gtgttcttac tattgacaaa  900
atgcagaaca aagacaaagg actttatact tgtcgtgtaa ggagtggacc atcattcaaa  960
tctgttaaca cctcagtgca tatatatgat aaagcattca tcactgtgaa acatcgaaaa  1020
cagcaggtgc ttgaaaccgt agctggcaag cggtcttacc ggctctctat gaaagtgaag  1080
gcatttccct cgccggaagt tgtatggtta aaagatgggt tacctgcgac tgagaaatct  1140
gctcgctatt tgactcgtgg ctactcgtta attatcaagg acgtaactga agaggatgca  1200
gggaattata caatcttgct gagcataaaa cagtcaaatg tgtttaaaaa cctcactgcc  1260
actctaattg tcaatgtgaa accccagatt tacgaaaagg ccgtgtcatc gtttccagac  1320
ccggctctct acccactggg cagcagacaa atcctgactt gtaccgcata tggtatccct  1380
caacctacaa tcaagtggtt ctggcacccc tgtaaccata atcattccga agcaaggtgt  1440
gacttttgtt ccaataatga agagtcctct atcctggatg ctgacagcaa catgggaaac  1500
agaattgaga gcatcactca gcgcatggca ataatagaag gaaagaataa gatggctagc  1560
accttggttg tggctgactc tagaatttct ggaatctaca tttgcatagc ttccaataaa  1620
gttgggactg tgggaagaaa cataagcttt tatatcacag atgtgccaaa tgggtttcat  1680
gttaacttgg aaaaaatgcc gacggaagga gaggacctga aactgtcttg cacagttaac  1740
```

-continued

```
aagttcttat acagagacgt tacttggatt ttactgcgga cagttaataa cagaacaatg  1800
cactacagta ttagcaagca aaaaatggcc atcactaagg agcactccat cactcttaat  1860
cttaccatca tgaatgtttc cctgcaagat tcaggcacct atgcctgcag agccaggaat  1920
gtatacacag ggaagaaat cctccagaag aaagaaatta caatcagaga tcaggaagca  1980
ccatacctcc tgcgaaacct cagtgatcac acagtggcca tcagcagttc caccacttta  2040
gactgtcatg ctaatggtgt ccccgagcct cagatcactt ggtttaaaaa caaccacaaa  2100
atacaacaag agcctggaat tattttagga ccaggaagca gcacgctgtt tattgaaaga  2160
gtcacagaag aggatgaagg tgtctatcac tgcaaagcca ccaaccagaa gggctctgtg  2220
gaaagttcag catacctcac tgttcaagga acctcggaca agtctaatct ggagctgatc  2280
actctaacat gcacctgtgt ggctgcgact ctcttctggc tcctattaac cctctttatc  2340
cgaaaaatga aaaggtcttc ttctgaaata aagactgact acctatcaat tataatggac  2400
ccagatgaag ttcctttgga tgagcagtgt gagcggctcc cttatgatgc cagcaagtgg  2460
gagtttgccc gggagagact taaactgggc aaatcacttg gaagaggggc ttttggaaaa  2520
gtggttcaag catcagcatt tggcattaag aaatcaccta cgtgccggac tgtggctgtg  2580
aaaatgctga aagaggggc cacggccagc gagtacaaag ctctgatgac tgagctaaaa  2640
atcttgaccc acattggcca ccatctgaac gtggttaacc tgctgggagc ctgcaccaag  2700
caaggagggc ctctgatggt gattgttgaa tactgcaaat atggaaatct ctccaactac  2760
ctcaagagca aacgtgactt attttttctc aacaaggatg cagcactaca catggagcct  2820
aagaaagaaa aaatggagcc aggcctggaa caaggcaaga aaccaagact agatagcgtc  2880
accagcagcg aaagctttgc gagctccggc tttcaggaag ataaaagtct gagtgatgtt  2940
gaggaagagg aggattctga cggtttctac aaggagccca tcactatgga agatctgatt  3000
tcttacagtt ttcaagtggc cagaggcatg gagttcctgt cttccagaaa gtgcattcat  3060
cgggacctgg cagcgagaaa cattctttta tctgagaaca acgtggtgaa gatttgtgat  3120
tttggccttg cccgggatat ttataagaac cccgattatg tgagaaaagg agatactcga  3180
cttcctctga aatggatggc tcctgaatct atctttgaca aaatctacag caccaagagc  3240
gacgtgtggt cttacggagt attgctgtgg gaaatcttct ccttaggtgg gtctccatac  3300
ccaggagtac aaatggatga ggacttttgc agtcgcctga gggaaggcat gaggatgaga  3360
gctcctgagt actctactcc tgaaatctat cagatcatgc tggactgctg gcacagagac  3420
ccaaaagaaa ggccaagatt tgcagaactt gtggaaaaac taggtgattt gcttcaagca  3480
aatgtacaac aggatggtaa agactacatc ccaatcaatg ccatactgac aggaaatagt  3540
gggtttacat actcaactcc tgccttctct gaggacttct tcaaggaaag tatttcagct  3600
ccgaagttta attcaggaag ctctgatgat gtcagatatg taaatgcttt caagttcatg  3660
agcctggaaa gaatcaaaac ctttgaagaa cttttaccga atgccacctc catgtttgat  3720
gactaccagg gcgacagcag cactctgttg gcctctccca tgctgaagcg cttcacctgg  3780
actgacagca aacccaaggc ctcgctcaag attgacttga gagtaaccag taaaagtaag  3840
gagtcggggc tgtctgatgt cagcaggccc agtttctgcc attccagctg tgggcacgtc  3900
agcgaaggca agcgcaggtt cacctacgac cacgctgagc tggaaaggaa aatcgcgtgc  3960
tgctccccgc ccccagacta caactcggtg gtcctgtact ccaccccacc catctag     4017

SEQ ID NO: 19           moltype = AA  length = 1338
FEATURE                 Location/Qualifiers
source                  1..1338
                        mol_type = protein
                        organism = Homo sapiens
SEQUENCE: 19
MVSYWDTGVL LCALLSCLLL TGSSSGSKLK DPELSLKGTQ HIMQAGQTLH LQCRGEAAHK  60
WSLPEMVSKE SERLSITKSA CGRNGKQFCS TLTLNTAQAN HTGFYSCKYL AVPTSKKKET  120
ESAIYIFISD TGRPFVEMYS EIPEIIHMTE GRELVIPCRV TSPNITVTLK KFPLDTLIPD  180
GKRIIWDSRK GFIISNATYK EIGLLTCEAT VNGHLYKTNY LTHRQTNTII DVQISTPRPV  240
KLLRGHTLVL NCTATTPLNT RVQMTWSYPD EKNKRASVRR RIDQSNSHAN IFYSVLTIDK  300
MQNKDKGLYT CRVRSGPSFK SVNTSVHIYD KAFITVKHRK QQVLETVAGK RSYRLSMKVK  360
AFPSPEVVWL KDGLPATEKS ARYLTRGYSL IIKDVTEEDA GNYTILLSIK QSNVFKNLTA  420
TLIVNVKPQI YEKAVSSFPD PALYPLGSRQ ILTCTAYGIP QPTIKWFWHP CNHNHSEARC  480
DFCSNNEESS ILDADSNMGN RIESITQRMA IIEGKNKMAS TLVVADSRIS GIYICIASNK  540
VGTVGRNISF YITDVPNGFH VNLEKMPTEG EDLKLSCTVN KFLYRDVTWI LLRTVNNRTM  600
HYSISKQKMA ITKEHSITLN LTIMNVSLQD SGTYACRARN VYTGEEILQK KEITIRDQEA  660
PYLLRNLSDH TVAISSSTTL DCHANGVPEP QITWFKNNHK IQQEPGIILG PGSSTLFIER  720
VTEEDEGVYH CKATNQKGSV ESSAYLTVQG TSDKSNLELI TLTCTCVAAT LFWLLLTLFI  780
RKMKRSSSEI KTDYLSIIMD PDEVPLDEQC ERLPYDASKW EFARERLKLG KSLGRGAFGK  840
VVQASAFGIK KSPTCRTVAV KMLKEGATAS EYKALMTELK ILTHIGHHLN VVNLLGACTK  900
QGGPLMVIVE YCKYGNLSNY LKSKRDLFFL NKDAALHMEP KKEKMEPGLE QGKKPRLDSV  960
TSSESFASSG FQEDKSLSDV EEEEDSDGFY KEPITMEDLI SYSFQVARGM EFLSSRKCIH  1020
RDLAARNILL SENNVVKICD FGLARDIYKN PDYVRKGDTR LPLKWMAPES IFDKIYSTKS  1080
DVWSYGVLLW EIFSLGGSPY PGVQMDEDFC SRLREGMRMR APEYSTPEIY QIMLDCWHRD  1140
PKERPRFAEL VEKLGDLLQA NVQQDGKDYI PINAILTGNS GFTYSTPAFS EDFFKESISA  1200
PKFNSGSSDD VRYVNAFKFM SLERIKTFEE LLPNATSMFD DYQGDSSTLL ASPMLKRFTW  1260
TDSKPKASLK IDLRVTSKSK ESGLSDVSRP SFCHSSCGHV SEGKRRFTYD HAELERKIAC  1320
CSPPPDYNSV VLYSTPPI                                                1338

SEQ ID NO: 20           moltype = DNA  length = 5830
FEATURE                 Location/Qualifiers
source                  1..5830
                        mol_type = unassigned DNA
                        organism = Homo sapiens
SEQUENCE: 20
actgagtccc gggaccccgg gagagcggtc agtgtgtggt cgctgcgttt cctctgcctg  60
cgccgggcat cacttgcgcg ccgcagaaag tccgtctggc agcctggata tcctctccta  120
ccggcacccg cagacgcccc tgcagccgcc ggtcggcgcc cgggctccct agccctgtgc  180
gctcaactgt cctgcgctgc ggggtgccgc gagttccacc tccgcgcctc cttctctaga  240
```

-continued

```
caggcgctgg gagaaagaac cggctcccga gttctgggca tttcgcccgg ctcgaggtgc  300
aggatgcaga gcaaggtgct gctggccgtc gccctgtggc tctgcgtgga gacccgggcc  360
gcctctgtgg gtttgcctag tgtttctctt gatctgccca ggctcagcat acaaaaagac  420
atacttacaa ttaaggctaa tacaactctt caaattactt gcaggggaca gagggacttg  480
gactggcttt ggcccaataa tcagagtggc agtgagcaaa gggtggaggt gactgagtgc  540
agcgatggcc tcttctgtaa gacactcaca attccaaaag tgatcggaaa tgacactgga  600
gcctacaagt gcttctaccg ggaaactgac ttggcctcgg tcatttatgt ctatgttcaa  660
gattacagat ctccatttat tgcttctgtt agtgaccaac atggagtcgt gtacattact  720
gagaacaaaa acaaaactgt ggtgattcca tgtctcgggt ccatttcaaa tctcaacgtg  780
tcactttgtg caagataccc agaaaagaga tttgttcctg atggtaacag aatttcctgg  840
gacagcaaga agggctttac tattcccagc tacatgatca gctatgctgg catggtcttc  900
tgtgaagcaa aaattaatga tgaaagttac cagtctatta tgtacatagt tgtcgttgta  960
gggtatagga tttatgatgt ggttctgagt ccgtctcatg gaattgaact atctgttgga  1020
gaaaagcttg tcttaaattg tacagcaaga actgaactaa atgtggggat tgacttcaac  1080
tgggaatacc cttcttcgaa gcatcagcat aagaaacttg taaaccgaga cctaaaaacc  1140
cagtctggga gtgagatgaa gaaatttttg agcaccttaa ctatagatgg tgtaacccgg  1200
agtgaccaag gattgtacac ctgtgcagca tccagtgggc tgatgaccaa gaagaacagc  1260
acatttgtca gggtccatga aaaacctttt gttgcttttg gaagtggcat ggaatctctg  1320
gtggaagcca cggtggggga gcgtgtcaga atccctgcga agtaccttgg ttacccaccc  1380
ccagaaataa aatggtataa aaatggaata ccccttgagt ccaatcacac aattaaagcg  1440
gggcatgtac tgacgattat ggaagtgagt gaaagagaca caggaaatta cactgtcatc  1500
cttaccaatc ccatttcaaa ggagaagcag agccatgtgg tctctctggt tgtgtatgtc  1560
ccaccccaga ttggtgagaa atctctaatc tctcctgtgg attcctacca gtacggcacc  1620
actcaaacgc tgacatgtac ggtctatgcc attcctcccc cgcatcacat ccactggtat  1680
tggcagttgg aggaagagtg cgccaacgag cccagccaag ctgtctcagt gacaaaccca  1740
tacccttgtg aagaatggag aagtgtggag gacttccagg gaggaaataa aattgaagtt  1800
aataaaaatc aatttgctct aattgaagga aaaaacaaaa ctgtaagtac ccttgttatc  1860
caagcggcaa atgtgtcagc tttgtacaaa tgtgaagcgg tcaacaaagt cgggagagga  1920
gagagggtga tctccttcca cgtgaccagg ggtcctgaaa ttactttgca acctgacatg  1980
cagcccactg agcaggagag cgtgtctttg tggtgcactg cagacagatc tacgtttgag  2040
aacctcacat ggtacaagct tggcccacag cctctgccaa tccatgtggg agagttgccc  2100
acacctgttt gcaagaactt ggatactctt tggaaattga atgccaccat gttctctaat  2160
agcacaaatg acattttgat catggagctt aagaatgcat ccttgcagga ccaaggagac  2220
tatgtctgcc ttgctcaaga caggaagacc aagaaaagac attgcgtggt caggcagctc  2280
acagtcctag agcgtgtggc acccacgatc acaggaaacc tggagaatca gacgacaagt  2340
attggggaaa gcatcgaagt ctcatgcacg gcatctggga atccccctcc acagatcatg  2400
tggtttaaag ataatgagac ccttgtagaa gactcaggca ttgtattgaa ggatgggaac  2460
cggaacctca ctatccgcag agtgaggaag gaggacgaag gcctctacac ctgccaggca  2520
tgcagtgttc ttggctgtgc aaaagtggag gcatttttca taatagaagg tgcccaggaa  2580
aagacgaact tggaaatcat tattctagta ggcacggcgg tgattgccat gttcttctgg  2640
ctacttcttg tcatcatcct acggaccgtt aagcgggcca atggagggga actgaagaca  2700
ggctacttgt ccatcgtcat ggatccagat gaactcccat tggatgaaca ttgtgaacga  2760
ctgccttatg atgccagcaa atgggaattc cccagagacc ggctgaagct aggtaagcct  2820
cttggccgtg gtgcctttgg ccaagtgatt gaagcagatg cctttggaat tgacaagaca  2880
gcaacttgca ggacagtagc agtcaaaatg ttgaaagaag gagcaacaca cagtgagcat  2940
cgagctctca tgtctgaact caagatcctc attcatattg gtcaccatct caatgtggtc  3000
aaccttctag gtgcctgtac caagccagga gggccactca tggtgattgt ggaattctgc  3060
aaatttggaa acctgtccac ttacctgagg agcaagagaa atgaatttgt cccctacaag  3120
accaaagggg cacgattccg tcaagggaaa gactacgttg gagcaatccc tgtggatctg  3180
aaacggcgct tggacagcat caccagtagc cagagctcag ccagctctgg atttgtggag  3240
gagaagtccc tcagtgatgt agaagaagag gaagctcctg aagatctgta taaggacttc  3300
ctgaccttgg agcatctcat ctgttacagc ttccaagtgg ctaagggcat ggagttcttg  3360
gcatcgcgaa agtgtatcca cagggacctg gcggcacgaa atatcctctt atcggagaag  3420
aacgtggtta aaatctgtga ctttggcttg gcccgggata tttataaaga tccagattat  3480
gtcagaaaag gagatgctcg cctccctttg aaatggatgg ccccagaaac aatttttgac  3540
agagtgtaca caatccagag tgacgtctgg tcttttggtg ttttgctgtg ggaaatattt  3600
tccttaggtg cttctccata tcctggggta aagattgatg aagaattttg taggcgattg  3660
aaagaaggaa ctagaatgag ggcccctgat tatactacac cagaaatgta ccagaccatg  3720
ctggactgct ggcacgggga gcccagtcag agacccacgt tttcagagtt ggtggaacat  3780
ttgggaaatc tcttgcaagc taatgctcag caggatggca aagactacat tgttcttccg  3840
atatcagaga ctttgagcat ggaagaggat tctggactct ctctgcctac ctcacctgtt  3900
tcctgtatgg aggaggagga agtatgtgac cccaaattcc attatgacaa cacagcagga  3960
atcagtcagt atctgcagaa cagtaagcga aagagccggc ctgtgagtgt aaaaacattt  4020
gaagatatcc cgttagaaga accagaagta aaagtaatcc cagatgacaa ccagacggac  4080
agtggtatgg ttcttgcctc agaagagctg aaaactttgg aagacagaac caaattatct  4140
ccatcttttg gtggaatggt gcccagcaaa agcagggagt ctgtggcatc tgaaggctca  4200
aaccagacaa gcggctacca gtccggatat cactccgatg acacagacac caccgtgtac  4260
tccagtgagg aagcagaact tttaaagctg atagagattg gagtgcaaac cggtagcaca  4320
gcccagattc tccagcctga ctcggggacc acactgagct ctcctcctgt ttaaaaggaa  4380
gcatccacac cccaactccc ggacatcaca tgagaggtct gctcagattt tgaagtgttg  4440
ttctttccac cagcaggaag tagccgcatt tgattttcat ttcgacaaca gaaaaaggac  4500
ctcggactgc agggagccag tcttctaggc atatcctgga agaggcttgt gacccaagaa  4560
tgtgtctgtg tcttctccca gtgttgacct gatcctcttt tttcattcat ttaaaaagca  4620
ttatcatgcc cctgctgcgg gtctcaccat gggtttagaa caaagagctt caagcaatgg  4680
ccccatcctc aaagaagtag cagtacctgg ggagctgaca cttctgtaaa actagaagat  4740
aaaccaggca acgtaagtgt tcgaggtgtt gaagatggga aggatttgca gggctgagtc  4800
tatccaagag gctttgttta ggacgtgggt cccaagccaa gccttaagtg tggaattcgg  4860
attgatagaa aggaagacta acgttacctt gctttggaga gtactggagc ctgcaaatgc  4920
attgtgtttg ctctggtgga ggtgggcatg ggtctgttc tgaaatgtaa agggttcaga  4980
```

-continued

```
cggggtttct ggttttagaa ggttgcgtgt tcttcgagtt gggctaaagt agagttcgtt  5040
gtgctgtttc tgactcctaa tgagagttcc ttccagaccg ttagctgtct ccttgccaag  5100
ccccaggaag aaaatgatgc agctctggct ccttgtctcc caggctgatc ctttattcag  5160
aataccacaa agaaaggaca ttcagctcaa ggctccctgc cgtgttgaag agttctgact  5220
gcacaaacca gcttctggtt tcttctggaa tgaataccct catatctgtc ctgatgtgat  5280
atgtctgaga ctgaatgcgg gaggttcaat gtgaagctgt gtgtggtgtc aaagtttcag  5340
gaaggatttt accccttttgt tcttcccccct gtccccaacc cactctcacc ccgcaaccca  5400
tcagtatttt agttatttgg cctctactcc agtaaacctg attgggtttg ttcactctct  5460
gaatgattat tagccagact tcaaaattat tttatagccc aaattataac atctattgta  5520
ttatttagac ttttaacata tagagctatt tctactgatt tttgcccttg ttctgtcctt  5580
tttttcaaaa aagaaaatgt gttttttgtt tggtaccata gtgtgaaatg ctgggaacaa  5640
tgactataag acatgctatg gcacatatat ttatagtctg tttatgtaga aacaaatgta  5700
atatattaaa gccttatata taatgaactt tgtactattc acattttgta tcagtattat  5760
gtagcataac aaaggtcata atgctttcag caattgatgt cattttatta aagaacattg  5820
aaaaacttga                                                          5830

SEQ ID NO: 21          moltype = AA  length = 1356
FEATURE                Location/Qualifiers
source                 1..1356
                       mol_type = protein
                       organism = Homo sapiens
SEQUENCE: 21
MQSKVLLAVA LWLCVETRAA SVGLPSVSLD LPRLSIQKDI LTIKANTTLQ ITCRGQRDLD  60
WLWPNNQSGS EQRVEVTECS DGLFCKTLTI PKVIGNDTGA YKCFYRETDL ASVIYVYVQD  120
YRSPFIASVS DQHGVVYITE NKNKTVVIPC LGSISNLNVS LCARYPEKRF VPDGNRISWD  180
SKKGFTIPSY MISYAGMVFC EAKINDESYQ SIMYIVVVVG YRIYDVVLSP SHGIELSVGE  240
KLVLNCTART ELNVGIDFNW EYPSSKHQHK KLVNRDLKTQ SGSEMKKFLS TLTIDGVTRS  300
DQGLYTCAAS SGLMTKKNST FVRVHEKPFV AFGSGMESLV EATVGERVRI PAKYLGYPPP  360
EIKWYKNGIP LESNHTIKAG HVLTIMEVSE RDTGNYTVIL TNPISKEKQS HVVSLVVYVP  420
PQIGEKSLIS PVDSYQYGTT QTLTCTVYAI PPPHHIHWYW QLEEECANEP SQAVSVTNPY  480
PCEEWRSVED FQGGNKIEVN KNQFALIEGK NKTVSTLVIQ AANVSALYKC EAVNKVGRGE  540
RVISFHVTRG PEITLQPDMQ PTEQESVSLW CTADRSTFEN LTWYKLGPQP LPIHVGELPT  600
PVCKNLDTLW KLNATMFSNS TNDILIMELK NASLQDQGDY VCLAQDRKTK KRHCVVRQLT  660
VLERVAPTIT GNLENQTTSI GESIEVSCTA SGNPPPQIMW FKDNETLVED SGIVLKDGNR  720
NLTIRRVRKE DEGLYTCQAC SVLGCAKVEA FFIIEGAQEK TNLEIIILVG TAVIAMFFWL  780
LLVIILRTVK RANGGELKTG YLSIVMDPDE LPLDEHCERL PYDASKWEFP RDRLKLGKPL  840
GRGAFGQVIE ADAFGIDKTA TCRTVAVKML KEGATHSEHR ALMSELKILI HIGHHLNVVN  900
LLGACTKPGG PLMVIVEFCK FGNLSTYLRS KRNEFVPYKT KGARFRQGKD YVGAIPVDLK  960
RRLDSITSSQ SSASSGFVEE KSLSDVEEEE APEDLYKDFL TLEHLICYSF QVAKGMEFLA  1020
SRKCIHRDLA ARNILLSEKN VVKICDFGLA RDIYKDPDYV RKGDARLPLK WMAPETIFDR  1080
VYTIQSDVWS FGVLLWEIFS LGASPYPGVK IDEEFCRRLK EGTRMRAPDY TTPEMYQTML  1140
DCWHGEPSQR PTFSELVEHL GNLLQANAQQ DGKDYIVLPI SETLSMEEDS GLSLPTSPVS  1200
CMEEEEVCDP KFHYDNTAGI SQYLQNSKRK SRPVSVKTFE DIPLEEPEVK VIPDDNQTDS  1260
GMVLASEELK TLEDRTKLSP SFGGMVPSKS RESVASEGSN QTSGYQSGYH SDDTDTTVYS  1320
SEEAELLKLI EIGVQTGSTA QILQPDSGTT LSSPPV                            1356

SEQ ID NO: 22          moltype = AA  length = 16
FEATURE                Location/Qualifiers
source                 1..16
                       mol_type = protein
                       organism = Homo sapiens
SEQUENCE: 22
CNDEGLECVP TEESNI                                                   16

SEQ ID NO: 23          moltype = AA  length = 16
FEATURE                Location/Qualifiers
source                 1..16
                       mol_type = protein
                       organism = Homo sapiens
SEQUENCE: 23
CPDDGLECVP TGQHQV                                                   16

SEQ ID NO: 24          moltype = AA  length = 1676
FEATURE                Location/Qualifiers
source                 1..1676
                       mol_type = protein
                       organism = Homo sapiens
SEQUENCE: 24
MGLLGILCFL IFLGKTWGQE QTYVISAPKI FRVGASENIV IQVYGYTEAF DATISIKSYP  60
DKKFSYSSGH VHLSSENKFQ NSAILTIQPK QLPGGQNPVS YVYLEVVSKH FSKSKRMPIT  120
YDNGFLFIHT DKPVYTPDQS VKVRVYSLND DLKPAKRETV LTFIDPEGSE VDMVEEIDHI  180
GIISFPDFKI PSNPRYGMWT IKAKYKEDFS TTGTAYFEVK EYVLPHFSVS IEPEYNFIGY  240
KNFKNFEITI KARYFYNKVV TEADVYITFG IREDLKDDQK EMMQTAMQNT MLINGIAQVT  300
FDSETAVKEL SYYSLEDLNN KYLYIAVTVI ESTGGFSEEA EIPGIKYVLS PYKLNLVATP  360
LFLKPGIPYP IKVQVKDSLD QLVGGVPVTL NAQTIDVNQE TSDLDPSKSV TRVDDGVASF  420
VLNLPSGVTV LEFNVKTDAP DLPEENQARE GYRAIAYSSL SQSYLYIDWT DNHKALLVGE  480
HLNIIVTPKS PYIDKITHYN YLILSKGKII HFGTREKFSD ASYQSINIPV TQNMVPSSRL  540
LVYYIVTGEQ TAELVSDSVW LNIEEKCGNQ LQVHLSPDAD AYSPGQTVSL NMATGMDSWV  600
ALAAVDSAVY GVQRGAKKPL ERVFQFLEKS DLGCGAGGGL NNANVFHLAG LTFLTNANAD  660
```

-continued

```
DSQENDEPCK EILRPRRTLQ KKIEEIAAKY KHSVVKKCCY DGACVNNDET CEQRAARISL  720
GPRCIKAFTE CCVVASQLRA NISHKDMQLG RLHMKTLLPV SKPEIRSYFP ESWLWEVHLV  780
PRRKQLQFAL PDSLTTWEIQ GVGISNTGIC VADTVKAKVF KDVFLEMNIP YSVVRGEQIQ  840
LKGTVYNYRT SGMQFCVKMS AVEGICTSES PVIDHQGTKS SKCVRQKVEG SSSHLVTFTV  900
LPLEIGLHNI NFSLETWFGK EILVKTLRVV PEGVKRESYS GVTLDPRGIY GTISRRKEFP  960
YRIPLDLVPK TEIKRILSVK GLLVGEILSA VLSQEGINIL THLPKGSAEA ELMSVVPVFY  1020
VFHYLETGNH WNIFHSDPLI EKQKLKKKLK EGMLSIMSYR NADYSYSVWK GGSASTWLTA  1080
FALRVLGQVN KYVEQNQNSI CNSLLWLVEN YQLDNGSFKE NSQYQPIKLQ GTLPVEAREN  1140
SLYLTAFTVI GIRKAFDICP LVKIDTALIK ADNFLLENTL PAQSTFTLAI SAYALSLGDK  1200
THPQFRSIVS ALKREALVKG NPPIYRFWKD NLQHKDSSVP NTGTARMVET TAYALLTSLN  1260
LKDINYVNPV IKWLSEEQRY GGGFYSTQDT INAIEGLTEY SLLVKQLRLS MDIDVSYKHK  1320
GALHNYKMTD KNFLGRPVEV LLNDDLIVST GFGSGLATVH VTTVVHKTST SEEVCSFYLK  1380
IDTQDIEASH YRGYGNSDYK RIVACASYKP SREESSSGSS HAVMDISLPT GISANEEDLK  1440
ALVEGVDQLF TDYQIKDGHV ILQLNSIPSS DFLCVRFRIF ELFEVGFLSP ATFTVYEYHR  1500
PDKQCTMFYS TSNIKIQKVC EGAACKCVEA DCGQMQEELD LTISAETRKQ TACKPEIAYA  1560
YKVSITSITV ENVFVKYKAT LLDIYKTGEA VAEKDSEITF IKKVTCTNAE LVKGRQYLIM  1620
GKEALQIKYN FSFRYIYPLD SLTWIEYWPR DTTCSSCQAF LANLDEFAED IFLNGC      1676

SEQ ID NO: 25          moltype = RNA  length = 42
FEATURE                Location/Qualifiers
misc_feature           1..42
                       note = Synthetic C5 specific aptamer
misc_difference        1
                       note = misc_feature - May be 2'OH-guanosine
misc_difference        2
                       note = misc_feature - May be 2'OH-adenosine
misc_difference        3
                       note = misc_feature - May be 2'-fluoro-2'-deoxycytidine
misc_difference        4
                       note = misc_feature - May be 2'OH-guanosine
misc_difference        5
                       note = misc_feature - May be 2'OH-adenosine
misc_difference        6
                       note = misc_feature - May be 2'-fluoro-2'-deoxyuridine
misc_difference        7
                       note = misc_feature - May be 2'OH-guanosine
misc_difference        8
                       note = misc_feature - May be 2'-fluoro-2'-deoxycytidine
misc_difference        9
                       note = misc_feature - May be 2'OH-guanosine
misc_difference        10
                       note = misc_feature - May be 2'OH-guanosine
misc_difference        11
                       note = misc_feature - May be 2'-fluoro-2'-deoxyuridine
misc_difference        12
                       note = misc_feature - May be 2'-fluoro-2'-deoxycytidine
misc_difference        13
                       note = misc_feature - May be 2'-fluoro-2'-deoxyuridine
misc_difference        14
                       note = misc_feature - May be 2'-fluoro-2'-deoxycytidine
misc_difference        15
                       note = misc_feature - May be 2'OH-adenosine
misc_difference        16
                       note = misc_feature - May be 2'-fluoro-2'-deoxyuridine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'OH-guanosine
misc_difference        20
                       note = misc_feature - May be 2'-fluoro-2'-deoxyuridine
misc_difference        21
                       note = misc_feature - May be 2'-fluoro-2'-deoxycytidine
misc_difference        22
                       note = misc_feature - May be 2'OH-guanosine
misc_difference        23
                       note = misc_feature - May be 2'OH-adenosine
misc_difference        24
                       note = misc_feature - May be 2'OH-guanosine
misc_difference        25
                       note = misc_feature - May be 2'-fluoro-2'-deoxyuridine
misc_difference        26
                       note = misc_feature - May be 2'OH-guanosine
misc_difference        27
                       note = misc_feature - May be 2'-fluoro-2'-deoxyuridine
misc_difference        28
                       note = misc_feature - May be 2'OH-guanosine
misc_difference        29
```

-continued

```
                        note = misc_feature - May be 2'OH-adenosine
misc_difference         30
                        note = misc_feature - May be 2'OH-guanosine
misc_difference         31
                        note = misc_feature - May be 2'-fluoro-2'-deoxyuridine
misc_difference         32
                        note = misc_feature - May be 2'-fluoro-2'-deoxyuridine
misc_difference         33
                        note = misc_feature - May be 2'-fluoro-2'-deoxyuridine
misc_difference         34
                        note = misc_feature - May be 2'OH-adenosine
misc_difference         35
                        note = misc_feature - May be 2'-fluoro-2'-deoxycytidine
misc_difference         36
                        note = misc_feature - May be 2'-fluoro-2'-deoxycytidine
misc_difference         37
                        note = misc_feature - May be 2'-fluoro-2'-deoxyuridine
misc_difference         38
                        note = misc_feature - May be 2'-fluoro-2'-deoxyuridine
misc_difference         39
                        note = misc_feature - May be 2'-fluoro-2'-deoxycytidine
misc_difference         40
                        note = misc_feature - May be 2'OH-guanosine
misc_difference         41
                        note = misc_feature - May be 2'-fluoro-2'-deoxyuridine
misc_difference         42
                        note = misc_feature - May be 2'-fluoro-2'-deoxycytidine
source                  1..42
                        mol_type = other RNA
                        organism = synthetic construct
SEQUENCE: 25
gacgatgcgg tctcatgcgt cgagtgtgag tttaccttcg tc                      42

SEQ ID NO: 26           moltype = DNA  length = 39
FEATURE                 Location/Qualifiers
misc_feature            1..39
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be 2'-fluoro-2'-deoxycytidine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be 2'-fluoro-2'-deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
```

```
misc_difference        22
                       note = misc_feature - May be 2'-O-Methyl-2'-deoxyguanosine
misc_difference        23
                       note = misc_feature - May be 2'-fluoro-2'-deoxyuridine
misc_difference        24
                       note = misc_feature - May be 2'-fluoro-2'-deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'OH-adenosine
misc_difference        32
                       note = misc_feature - May be 2'-fluoro-2'-deoxycytidine
misc_difference        33
                       note = misc_feature - May be 2'-fluoro-2'-deoxycytidine
misc_difference        34
                       note = misc_feature - May be 2'-fluoro-2'-deoxyuridine
misc_difference        35
                       note = misc_feature - May be 2'-O-Methyl-2'-deoxyguanosine
misc_difference        36
                       note = misc_feature - May be 2'-fluoro-2'-deoxycytidine
misc_difference        37
                       note = misc_feature - May be 2'-O-Methyl-2'-deoxyguanosine
misc_difference        38
                       note = misc_feature - May be an inverted orientation T
                        (3'-3'-linked)
source                 1..39
                       mol_type = other DNA
                       organism = synthetic construct
misc_feature           1..38
                       note = RNA
misc_feature           39
                       note = DNA
SEQUENCE: 26
cgccgcggtc tcaggcgctg agtctgagtt tacctgcgt                         39

SEQ ID NO: 27          moltype = RNA  length = 44
FEATURE                Location/Qualifiers
misc_feature           1..44
                       note = Synthetic C5 specific aptamer
misc_difference        1
                       note = misc_feature - May be 2'OH-adenosine
misc_difference        2
                       note = misc_feature - May be 2'OH-guanosine
misc_difference        3
                       note = misc_feature - May be 2'OH-guanosine
misc_difference        4
                       note = misc_feature - May be 2'OH-adenosine
misc_difference        5
                       note = misc_feature - May be 2'-fluoro-2'-deoxycytidine
misc_difference        6
                       note = misc_feature - May be 2'OH-guanosine
misc_difference        7
                       note = misc_feature - May be 2'OH-adenosine
misc_difference        8
                       note = misc_feature - May be 2'-fluoro-2'-deoxyuridine
misc_difference        9
                       note = misc_feature - May be 2'OH-guanosine
misc_difference        10
                       note = misc_feature - May be 2'-fluoro-2'-deoxycytidine
misc_difference        11
                       note = misc_feature - May be 2'OH-guanosine
misc_difference        12
                       note = misc_feature - May be 2'OH-guanosine
misc_difference        13
                       note = misc_feature - May be 2'-fluoro-2'-deoxyuridine
misc_difference        14
                       note = misc_feature - May be 2'-fluoro-2'-deoxycytidine
misc_difference        15
                       note = misc_feature - May be 2'-fluoro-2'-deoxyuridine
```

```
misc_difference        16
                       note = misc_feature - May be 2'-fluoro-2'-deoxycytidine
misc_difference        17
                       note = misc_feature - May be 2'OH-adenosine
misc_difference        18
                       note = misc_feature - May be 2'-fluoro-2'-deoxyuridine
misc_difference        19
                       note = misc_feature - May be 2'OH-guanosine
misc_difference        20
                       note = misc_feature - May be 2'-fluoro-2'-deoxycytidine
misc_difference        21
                       note = misc_feature - May be 2'OH-guanosine
misc_difference        22
                       note = misc_feature - May be 2'-fluoro-2'-deoxyuridine
misc_difference        23
                       note = misc_feature - May be 2'-fluoro-2'-deoxycytidine
misc_difference        24
                       note = misc_feature - May be 2'OH-guanosine
misc_difference        25
                       note = misc_feature - May be 2'OH-adenosine
misc_difference        26
                       note = misc_feature - May be 2'OH-guanosine
misc_difference        27
                       note = misc_feature - May be 2'-fluoro-2'-deoxyuridine
misc_difference        28
                       note = misc_feature - May be 2'OH-guanosine
misc_difference        29
                       note = misc_feature - May be 2'-fluoro-2'-deoxyuridine
misc_difference        30
                       note = misc_feature - May be 2'OH-guanosine
misc_difference        31
                       note = misc_feature - May be 2'OH-adenosine
misc_difference        32
                       note = misc_feature - May be 2'OH-guanosine
misc_difference        33
                       note = misc_feature - May be 2'-fluoro-2'-deoxyuridine
misc_difference        34
                       note = misc_feature - May be 2'-fluoro-2'-deoxyuridine
misc_difference        35
                       note = misc_feature - May be 2'-fluoro-2'-deoxyuridine
misc_difference        36
                       note = misc_feature - May be 2'OH-adenosine
misc_difference        37
                       note = misc_feature - May be 2'-fluoro-2'-deoxycytidine
misc_difference        38
                       note = misc_feature - May be 2'-fluoro-2'-deoxycytidine
misc_difference        39
                       note = misc_feature - May be 2'-fluoro-2'-deoxyuridine
misc_difference        40
                       note = misc_feature - May be 2'-fluoro-2'-deoxyuridine
misc_difference        41
                       note = misc_feature - May be 2'-fluoro-2'-deoxycytidine
misc_difference        42
                       note = misc_feature - May be 2'OH-guanosine
misc_difference        43
                       note = misc_feature - May be 2'-fluoro-2'-deoxyuridine
misc_difference        44
                       note = misc_feature - May be 2'-fluoro-2'-deoxycytidine
source                 1..44
                       mol_type = other RNA
                       organism = synthetic construct
SEQUENCE: 27
aggacgatgc ggtctcatgc gtcgagtgtg agtttacctt cgtc                   44

SEQ ID NO: 28          moltype = RNA  length = 40
FEATURE                Location/Qualifiers
misc_feature           1..40
                       note = Synthetic C5 specific aptamer
misc_difference        1
                       note = misc_feature - May be 2'OH-adenosine
misc_difference        2
                       note = misc_feature - May be 2'OH-guanosine
misc_difference        3
                       note = misc_feature - May be 2'-fluoro-2'-deoxycytidine
misc_difference        4
                       note = misc_feature - May be 2'-O-Methyl-2'-deoxyguanosine
misc_difference        5
                       note = misc_feature - May be 2'-fluoro-2'-deoxycytidine
misc_difference        6
```

```
                        note = misc_feature - May be 2'-fluoro-2'-deoxycytidine
misc_difference         7
                        note = misc_feature - May be 2'OH-guanosine
misc_difference         8
                        note = misc_feature - May be 2'-fluoro-2'-deoxycytidine
misc_difference         9
                        note = misc_feature - May be 2'-O-Methyl-2'-deoxyguanosine
misc_difference         10
                        note = misc_feature - May be 2'-O-Methyl-2'-deoxyguanosine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-fluoro-2'-deoxyuridine
misc_difference         14
                        note = misc_feature - May be 2'-fluoro-2'-deoxycytidine
misc_difference         15
                        note = misc_feature - May be 2'-O-Methyl-2'-deoxyadenosine
misc_difference         16
                        note = misc_feature - May be 2'-O-Methyl-2'-deoxyguanosine
misc_difference         17
                        note = misc_feature - May be 2'-O-Methyl-2'-deoxyguanosine
misc_difference         18
                        note = misc_feature - May be 2'-fluoro-2'-deoxycytidine
misc_difference         19
                        note = misc_feature - May be 2'OH-guanosine
misc_difference         20
                        note = misc_feature - May be 2'-fluoro-2'-deoxycytidine
misc_difference         21
                        note = misc_feature - May be 2'-fluoro-2'-deoxyuridine
misc_difference         22
                        note = misc_feature - May be 2'-O-Methyl-2'-deoxyguanosine
misc_difference         23
                        note = misc_feature - May be 2'-O-Methyl-2'-deoxyadenosine
misc_difference         24
                        note = misc_feature - May be 2'-O-Methyl-2'-deoxyguanosine
misc_difference         25
                        note = misc_feature - May be 2'-fluoro-2'-deoxyuridine
misc_difference         26
                        note = misc_feature - May be 2'-fluoro-2'-deoxycytidine
misc_difference         27
                        note = misc_feature - May be 2'-fluoro-2'-deoxyuridine
misc_difference         28
                        note = misc_feature - May be 2'-O-Methyl-2'-deoxyguanosine
misc_difference         29
                        note = misc_feature - May be 2'-O-Methyl-2'-deoxyadenosine
misc_difference         30
                        note = misc_feature - May be 2'-O-Methyl-2'-deoxyguanosine
misc_difference         31
                        note = misc_feature - May be 2'-fluoro-2'-deoxyuridine
misc_difference         32
                        note = misc_feature - May be 2'-fluoro-2'-deoxyuridine
misc_difference         33
                        note = misc_feature - May be 2'-fluoro-2'-deoxyuridine
misc_difference         34
                        note = misc_feature - May be 2'OH-adenosine
misc_difference         35
                        note = misc_feature - May be 2'-fluoro-2'-deoxycytidine
misc_difference         36
                        note = misc_feature - May be 2'-fluoro-2'-deoxycytidine
misc_difference         37
                        note = misc_feature - May be 2'-fluoro-2'-deoxyuridine
misc_difference         38
                        note = misc_feature - May be 2'-O-Methyl-2'-deoxyguanosine
misc_difference         39
                        note = misc_feature - May be 2'-fluoro-2'-deoxycytidine
misc_difference         40
                        note = misc_feature - May be 2'-O-Methyl-2'-deoxyguanosine
source                  1..40
                        mol_type = other RNA
                        organism = synthetic construct
SEQUENCE: 28
agcgccgcgg tctcaggcgc tgagtctgag tttacctgcg                        40

SEQ ID NO: 29           moltype = RNA  length = 46
FEATURE                 Location/Qualifiers
misc_feature            1..46
                        note = Synthetic C5 specific aptamer
```

```
misc_difference        1
                       note = misc_feature - May be 2'OH-guanosine
misc_difference        2
                       note = misc_feature - May be 2'OH-guanosine
misc_difference        3
                       note = misc_feature - May be 2'-fluoro-2'-deoxycytidine
misc_difference        4
                       note = misc_feature - May be 2'OH-guanosine
misc_difference        5
                       note = misc_feature - May be 2'OH-adenosine
misc_difference        6
                       note = misc_feature - May be 2'-fluoro-2'-deoxyuridine
misc_difference        7
                       note = misc_feature - May be 2'-fluoro-2'-deoxyuridine
misc_difference        8
                       note = misc_feature - May be 2'OH-adenosine
misc_difference        9
                       note = misc_feature - May be 2'-fluoro-2'-deoxycytidine
misc_difference        10
                       note = misc_feature - May be 2'-fluoro-2'-deoxyuridine
misc_difference        11
                       note = misc_feature - May be 2'OH-guanosine
misc_difference        12
                       note = misc_feature - May be 2'OH-guanosine
misc_difference        13
                       note = misc_feature - May be 2'OH-guanosine
misc_difference        14
                       note = misc_feature - May be 2'OH-adenosine
misc_difference        15
                       note = misc_feature - May be 2'-fluoro-2'-deoxycytidine
misc_difference        16
                       note = misc_feature - May be 2'OH-guanosine
misc_difference        17
                       note = misc_feature - May be 2'OH-guanosine
misc_difference        18
                       note = misc_feature - May be 2'OH-adenosine
misc_difference        19
                       note = misc_feature - May be 2'-fluoro-2'-deoxycytidine
misc_difference        20
                       note = misc_feature - May be 2'-fluoro-2'-deoxyuridine
misc_difference        21
                       note = misc_feature - May be 2'-fluoro-2'-deoxycytidine
misc_difference        22
                       note = misc_feature - May be 2'OH-guanosine
misc_difference        23
                       note = misc_feature - May be 2'-fluoro-2'-deoxycytidine
misc_difference        24
                       note = misc_feature - May be 2'OH-guanosine
misc_difference        25
                       note = misc_feature - May be 2'OH-adenosine
misc_difference        26
                       note = misc_feature - May be 2'-fluoro-2'-deoxyuridine
misc_difference        27
                       note = misc_feature - May be 2'OH-guanosine
misc_difference        28
                       note = misc_feature - May be 2'-fluoro-2'-deoxyuridine
misc_difference        29
                       note = misc_feature - May be 2'OH-guanosine
misc_difference        30
                       note = misc_feature - May be 2'OH-adenosine
misc_difference        31
                       note = misc_feature - May be 2'OH-guanosine
misc_difference        32
                       note = misc_feature - May be 2'-fluoro-2'-deoxycytidine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'OH-adenosine
misc_difference        36
                       note = misc_feature - May be 2'OH-guanosine
misc_difference        37
                       note = misc_feature - May be 2'OH-adenosine
misc_difference        38
                       note = misc_feature - May be 2'-fluoro-2'-deoxycytidine
misc_difference        39
                       note = misc_feature - May be 2'OH-guanosine
misc_difference        40
```

-continued

```
                        note = misc_feature - May be 2'OH-adenosine
misc_difference         41
                        note = misc_feature - May be 2'-fluoro-2'-deoxycytidine
misc_difference         42
                        note = misc_feature - May be 2'-fluoro-2'-deoxyuridine
misc_difference         43
                        note = misc_feature - May be 2'-fluoro-2'-deoxycytidine
misc_difference         44
                        note = misc_feature - May be 2'OH-guanosine
misc_difference         45
                        note = misc_feature - May be 2'-fluoro-2'-deoxycytidine
misc_difference         46
                        note = misc_feature - May be 2'-fluoro-2'-deoxycytidine
source                  1..46
                        mol_type = other RNA
                        organism = synthetic construct
SEQUENCE: 29
ggcgattact gggacggact cgcgatgtga gcccagacga ctcgcc                  46

SEQ ID NO: 30           moltype = RNA  length = 40
FEATURE                 Location/Qualifiers
misc_feature            1..40
                        note = Synthetic C5 specific aptamer
misc_difference         1
                        note = misc_feature - May be 2'OH-guanosine
misc_difference         2
                        note = misc_feature - May be 2'OH-guanosine
misc_difference         3
                        note = misc_feature - May be 2'-fluoro-2'-deoxycytidine
misc_difference         4
                        note = misc_feature - May be 2'-fluoro-2'-deoxyuridine
misc_difference         5
                        note = misc_feature - May be 2'-fluoro-2'-deoxyuridine
misc_difference         6
                        note = misc_feature - May be 2'-fluoro-2'-deoxycytidine
misc_difference         7
                        note = misc_feature - May be 2'-fluoro-2'-deoxyuridine
misc_difference         8
                        note = misc_feature - May be 2'OH-guanosine
misc_difference         9
                        note = misc_feature - May be 2'OH-adenosine
misc_difference         10
                        note = misc_feature - May be 2'OH-adenosine
misc_difference         11
                        note = misc_feature - May be 2'OH-guanosine
misc_difference         12
                        note = misc_feature - May be 2'OH-adenosine
misc_difference         13
                        note = misc_feature - May be 2'-fluoro-2'-deoxyuridine
misc_difference         14
                        note = misc_feature - May be 2'-fluoro-2'-deoxyuridine
misc_difference         15
                        note = misc_feature - May be 2'OH-adenosine
misc_difference         16
                        note = misc_feature - May be 2'-fluoro-2'-deoxyuridine
misc_difference         17
                        note = misc_feature - May be 2'-fluoro-2'-deoxyuridine
misc_difference         18
                        note = misc_feature - May be 2'-fluoro-2'-deoxyuridine
misc_difference         19
                        note = misc_feature - May be 2'-fluoro-2'-deoxycytidine
misc_difference         20
                        note = misc_feature - May be 2'OH-guanosine
misc_difference         21
                        note = misc_feature - May be 2'-fluoro-2'-deoxycytidine
misc_difference         22
                        note = misc_feature - May be 2'OH-guanosine
misc_difference         23
                        note = misc_feature - May be 2'OH-adenosine
misc_difference         24
                        note = misc_feature - May be 2'-fluoro-2'-deoxyuridine
misc_difference         25
                        note = misc_feature - May be 2'OH-guanosine
misc_difference         26
                        note = misc_feature - May be 2'-fluoro-2'-deoxyuridine
misc_difference         27
                        note = misc_feature - May be 2'OH-guanosine
misc_difference         28
                        note = misc_feature - May be 2'OH-adenosine
```

```
misc_difference        29
                       note = misc_feature - May be 2'OH-adenosine
misc_difference        30
                       note = misc_feature - May be 2'-fluoro-2'-deoxycytidine
misc_difference        31
                       note = misc_feature - May be 2'-fluoro-2'-deoxyuridine
misc_difference        32
                       note = misc_feature - May be 2'-fluoro-2'-deoxycytidine
misc_difference        33
                       note = misc_feature - May be 2'-fluoro-2'-deoxycytidine
misc_difference        34
                       note = misc_feature - May be 2'OH-adenosine
misc_difference        35
                       note = misc_feature - May be 2'OH-guanosine
misc_difference        36
                       note = misc_feature - May be 2'OH-adenosine
misc_difference        37
                       note = misc_feature - May be 2'-fluoro-2'-deoxycytidine
misc_difference        38
                       note = misc_feature - May be 2'-fluoro-2'-deoxycytidine
misc_difference        39
                       note = misc_feature - May be 2'-fluoro-2'-deoxycytidine
misc_difference        40
                       note = misc_feature - May be 2'-fluoro-2'-deoxycytidine
source                 1..40
                       mol_type = other RNA
                       organism = synthetic construct
SEQUENCE: 30
ggcttctgaa gattatttcg cgatgtgaac tccagacccc                        40

SEQ ID NO: 31          moltype = RNA  length = 40
FEATURE                Location/Qualifiers
misc_feature           1..40
                       note = Synthetic C5 specific aptamer
misc_difference        1
                       note = misc_feature - May be 2'OH-guanosine
misc_difference        2
                       note = misc_feature - May be 2'OH-guanosine
misc_difference        3
                       note = misc_feature - May be 2'-fluoro-2'-deoxycytidine
misc_difference        4
                       note = misc_feature - May be 2'OH-guanosine
misc_difference        5
                       note = misc_feature - May be 2'-fluoro-2'-deoxycytidine
misc_difference        6
                       note = misc_feature - May be 2'-fluoro-2'-deoxycytidine
misc_difference        7
                       note = misc_feature - May be 2'OH-guanosine
misc_difference        8
                       note = misc_feature - May be 2'-fluoro-2'-deoxycytidine
misc_difference        9
                       note = misc_feature - May be 2'OH-guanosine
misc_difference        10
                       note = misc_feature - May be 2'OH-guanosine
misc_difference        11
                       note = misc_feature - May be 2'-fluoro-2'-deoxyuridine
misc_difference        12
                       note = misc_feature - May be 2'-fluoro-2'-deoxycytidine
misc_difference        13
                       note = misc_feature - May be 2'-fluoro-2'-deoxyuridine
misc_difference        14
                       note = misc_feature - May be 2'-fluoro-2'-deoxycytidine
misc_difference        15
                       note = misc_feature - May be 2'OH-adenosine
misc_difference        16
                       note = misc_feature - May be 2'OH-guanosine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'OH-guanosine
misc_difference        20
                       note = misc_feature - May be 2'-fluoro-2'-deoxycytidine
misc_difference        21
                       note = misc_feature - May be 2'-fluoro-2'-deoxyuridine
misc_difference        22
                       note = misc_feature - May be 2'OH-guanosine
misc_difference        23
```

```
                         note = misc_feature - May be 2'OH-adenosine
misc_difference          24
                         note = misc_feature - May be 2'OH-guanosine
misc_difference          25
                         note = misc_feature - May be 2'-fluoro-2'-deoxyuridine
misc_difference          26
                         note = misc_feature - May be 2'-fluoro-2'-deoxycytidine
misc_difference          27
                         note = misc_feature - May be 2'-fluoro-2'-deoxyuridine
misc_difference          28
                         note = misc_feature - May be 2'OH-guanosine
misc_difference          29
                         note = misc_feature - May be 2'OH-adenosine
misc_difference          30
                         note = misc_feature - May be 2'OH-guanosine
misc_difference          31
                         note = misc_feature - May be 2'-fluoro-2'-deoxyuridine
misc_difference          32
                         note = misc_feature - May be 2'-fluoro-2'-deoxyuridine
misc_difference          33
                         note = misc_feature - May be 2'-fluoro-2'-deoxyuridine
misc_difference          34
                         note = misc_feature - May be 2'OH-adenosine
misc_difference          35
                         note = misc_feature - May be 2'-fluoro-2'-deoxycytidine
misc_difference          36
                         note = misc_feature - May be 2'-fluoro-2'-deoxycytidine
misc_difference          37
                         note = misc_feature - May be 2'-fluoro-2'-deoxyuridine
misc_difference          38
                         note = misc_feature - May be 2'OH-guanosine
misc_difference          39
                         note = misc_feature - May be 2'-fluoro-2'-deoxycytidine
misc_difference          40
                         note = misc_feature - May be 2'OH-guanosine
source                   1..40
                         mol_type = other RNA
                         organism = synthetic construct
SEQUENCE: 31
ggcgccgcgg tctcaggcgc tgagtctgag tttacctgcg                        40

SEQ ID NO: 32            moltype = DNA  length = 39
FEATURE                  Location/Qualifiers
misc_feature             1..39
                         note = Synthetic C5 specific aptamer
misc_difference          1
                         note = misc_feature - May be 2'-fluoro-2'-deoxycytidine
misc_difference          2
                         note = misc_feature - May be 2'-O-Methyl-2'-deoxyguanosine
misc_difference          3
                         note = misc_feature - May be 2'-fluoro-2'-deoxycytidine
misc_difference          4
                         note = misc_feature - May be 2'-fluoro-2'-deoxycytidine
misc_difference          5
                         note = misc_feature - May be 2'OH-guanosine
misc_difference          6
                         note = misc_feature - May be 2'-fluoro-2'-deoxycytidine
misc_difference          7
                         note = misc_feature - May be 2'-O-Methyl-2'-deoxyguanosine
misc_difference          8
                         note = misc_feature - May be 2'-O-Methyl-2'-deoxyguanosine
misc_difference          9
                         note = misc_feature - May be 2'-fluoro-2'-deoxyuridine
misc_difference          10
                         note = misc_feature - May be deoxycytidine
misc_difference          11
                         note = misc_feature - May be 2'OH-thymidine
misc_difference          12
                         note = misc_feature - May be deoxycytidine
misc_difference          13
                         note = misc_feature - May be 2'-O-Methyl-2'-deoxyadenosine
misc_difference          14
                         note = misc_feature - May be 2'-O-Methyl-2'-deoxyguanosine
misc_difference          15
                         note = misc_feature - May be 2'-O-Methyl-2'-deoxyguanosine
misc_difference          16
                         note = misc_feature - May be deoxycytidine
misc_difference          17
                         note = misc_feature - May be 2'OH-guanosine
```

-continued

```
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be deoxycytidine
misc_difference        34
                       note = misc_feature - May be deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
misc_difference        39
                       note = misc_feature - May be an inverted orientation T
                        (3'-3'-linked)
source                 1..39
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
misc_feature           39
                       note = DNA
SEQUENCE: 32
cgccgcggtc tcaggcgctg agtctgagtt tacctgcgt                         39

SEQ ID NO: 33          moltype = DNA  length = 39
FEATURE                Location/Qualifiers
misc_feature           1..39
                       note = Synthetic C5 specific aptamer
misc_difference        1
                       note = misc_feature - May be 2'-O-Methyl-2'-deoxycytidine
misc_difference        2
                       note = misc_feature - May be 2'-O-Methyl-2'-deoxyguanosine
misc_difference        3
                       note = misc_feature - May be 2'-O-Methyl-2'-deoxycytidine
misc_difference        4
                       note = misc_feature - May be 2'-fluoro-2'-deoxycytidine
```

-continued

```
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be deoxycytidine
misc_difference         34
                        note = misc_feature - May be deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-O-Methyl-2'-deoxycytidine
misc_difference         38
                        note = misc_feature - May be 2'-O-Methyl-2'-deoxyguanosine
misc_difference         39
                        note = misc_feature - May be an inverted orientation T
                         (3'-3'-linked)
source                  1..39
                        mol_type = other DNA
                        organism = synthetic construct
misc_feature            1..10
                        note = RNA
misc_feature            11
                        note = DNA
misc_feature            12..22
```

-continued

```
                        note = RNA
misc_feature            23
                        note = DNA
misc_feature            24
                        note = RNA
misc_feature            25
                        note = DNA
misc_feature            26..38
                        note = RNA
misc_feature            39
                        note = DNA
SEQUENCE: 33
cgccgcggtc tcaggcgctg agtctgagtt tacctgcgt                        39

SEQ ID NO: 34           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
```

```
                        note = misc_feature - May be 2'-fluoro-2'-deoxyuridine
misc_difference         32
                        note = misc_feature - May be 2'OH-adenosine
misc_difference         33
                        note = misc_feature - May be 2'OH-cytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 34
cgccgcggtc tcaggcgctg agtctgagtt tacctgcg                          38

SEQ ID NO: 35           moltype = DNA  length = 38
FEATURE                 Location/Qualifiers
misc_feature            1..38
                        note = Synthetic C5 specific aptamer
misc_difference         1
                        note = misc_feature - May be deoxycytidine
misc_difference         2
                        note = misc_feature - May be 2'-O-Methyl-2'-deoxyguanosine
misc_difference         3
                        note = misc_feature - May be deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
```

-continued

```
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 35
cgccgcggtc tcaggcgctg agtctgagtt tacctgcg                          38

SEQ ID NO: 36          moltype = DNA  length = 38
FEATURE                Location/Qualifiers
misc_feature           1..38
                       note = Synthetic C5 specific aptamer
misc_difference        1
                       note = misc_feature - May be deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
```

```
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 36
cgccgcggtc tcaggcgctg agtctgagtt tacctgcg                        38

SEQ ID NO: 37           moltype = DNA  length = 38
FEATURE                 Location/Qualifiers
```

-continued

| | |
|---|---|
| misc_feature | 1..38<br>note = Synthetic C5 specific aptamer |
| misc_difference | 1<br>note = misc_feature - May be 2′-fluoro-2′-deoxycytidine |
| misc_difference | 2<br>note = misc_feature - May be 2′-O-Methyl-2′-deoxyguanosine |
| misc_difference | 3<br>note = misc_feature - May be deoxycytidine |
| misc_difference | 4<br>note = misc_feature - May be 2′-fluoro-2′-deoxycytidine |
| misc_difference | 5<br>note = misc_feature - May be 2′OH-guanosine |
| misc_difference | 6<br>note = misc_feature - May be 2′-fluoro-2′-deoxycytidine |
| misc_difference | 7<br>note = misc_feature - May be 2′-O-Methyl-2′-deoxyguanosine |
| misc_difference | 8<br>note = misc_feature - May be 2′-O-Methyl-2′-deoxyguanosine |
| misc_difference | 9<br>note = misc_feature - May be 2′-fluoro-2′-deoxyuridine |
| misc_difference | 10<br>note = misc_feature - May be deoxycytidine |
| misc_difference | 11<br>note = misc_feature - May be 2′OH-thymidine |
| misc_difference | 12<br>note = misc_feature - May be deoxycytidine |
| misc_difference | 13<br>note = misc_feature - May be 2′-O-Methyl-2′-deoxyadenosine |
| misc_difference | 14<br>note = misc_feature - May be 2′-O-Methyl-2′-deoxyguanosine |
| misc_difference | 15<br>note = misc_feature - May be 2′-O-Methyl-2′-deoxyguanosine |
| misc_difference | 16<br>note = misc_feature - May be deoxycytidine |
| misc_difference | 17<br>note = misc_feature - May be 2′OH-guanosine |
| misc_difference | 18<br>note = misc_feature - May be 2′-fluoro-2′-deoxycytidine |
| misc_difference | 19<br>note = misc_feature - May be 2′-fluoro-2′-deoxyuridine |
| misc_difference | 20<br>note = misc_feature - May be 2′-O-Methyl-2′-deoxyguanosine |
| misc_difference | 21<br>note = misc_feature - May be 2′-O-Methyl-2′-deoxyadenosine |
| misc_difference | 22<br>note = misc_feature - May be 2′-O-Methyl-2′-deoxyguanosine |
| misc_difference | 23<br>note = misc_feature - May be 2′OH-thymidine |
| misc_difference | 24<br>note = misc_feature - May be deoxycytidine |
| misc_difference | 25<br>note = misc_feature - May be 2′OH-thymidine |
| misc_difference | 26<br>note = misc_feature - May be 2′-O-Methyl-2′-deoxyguanosine |
| misc_difference | 27<br>note = misc_feature - May be 2′-O-Methyl-2′-deoxyadenosine |
| misc_difference | 28<br>note = misc_feature - May be 2′-O-Methyl-2′-deoxyguanosine |
| misc_difference | 29<br>note = misc_feature - May be 2′-fluoro-2′-deoxyuridine |
| misc_difference | 30<br>note = misc_feature - May be 2′-fluoro-2′-deoxyuridine |
| misc_difference | 31<br>note = misc_feature - May be 2′-fluoro-2′-deoxyuridine |
| misc_difference | 32<br>note = misc_feature - May be 2′OH-adenosine |
| misc_difference | 33<br>note = misc_feature - May be 2′-fluoro-2′-deoxycytidine |
| misc_difference | 34<br>note = misc_feature - May be 2′-fluoro-2′-deoxycytidine |
| misc_difference | 35<br>note = misc_feature - May be 2′-fluoro-2′-deoxyuridine |
| misc_difference | 36<br>note = misc_feature - May be 2′-O-Methyl-2′-deoxyguanosine |
| misc_difference | 37<br>note = misc_feature - May be 2′-fluoro-2′-deoxycytidine |
| misc_difference | 38<br>note = misc_feature - May be 2′-O-Methyl-2′-deoxyguanosine |
| source | 1..38 |

```
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 37
cgccgcggtc tcaggcgctg agtctgagtt tacctgcg                            38

SEQ ID NO: 38           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
```

```
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 38
cgccgcggtc tcaggcgctg agtctgagtt tacctgcg                          38

SEQ ID NO: 39          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-O-Methyl-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
```

-continued

```
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 39
cgccgcggtc tcaggcgctg agtctgagtt tacctgcg                          38

SEQ ID NO: 40           moltype = DNA  length = 37
FEATURE                 Location/Qualifiers
misc_feature            1..37
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
```

```
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxyuridine
misc_difference        35
                       note = misc_feature - May be 2'-O-Methyl-2'-deoxyguanosine
misc_difference        36
                       note = misc_feature - May be 2'-O-Methyl-2'-deoxycytidine
misc_difference        37
                       note = misc_feature - May be 2'-O-Methyl-2'-deoxyguanosine
source                 1..37
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..37
                       note = RNA
SEQUENCE: 40
cgccgcggtc tcaggcgctg agtctgagtt tactgcg                          37
```

-continued

```
SEQ ID NO: 41            moltype = DNA  length = 38
FEATURE                  Location/Qualifiers
misc_feature             1..38
                         note = Synthetic C5 specific aptamer
misc_difference          1
                         note = misc_feature - May be 2'-O-Methyl-2'-deoxycytidine
misc_difference          2
                         note = misc_feature - May be 2'-O-Methyl-2'-deoxyguanosine
misc_difference          3
                         note = misc_feature - May be 2'-fluoro-2'-deoxycytidine
misc_difference          4
                         note = misc_feature - May be 2'-fluoro-2'-deoxycytidine
misc_difference          5
                         note = misc_feature - May be 2'OH-guanosine
misc_difference          6
                         note = misc_feature - May be 2'-fluoro-2'-deoxycytidine
misc_difference          7
                         note = misc_feature - May be 2'-O-Methyl-2'-deoxyguanosine
misc_difference          8
                         note = misc_feature - May be 2'-O-Methyl-2'-deoxyguanosine
misc_difference          9
                         note = misc_feature - May be 2'-fluoro-2'-deoxyuridine
misc_difference          10
                         note = misc_feature - May be deoxycytidine
misc_difference          11
                         note = misc_feature - May be 2'OH-thymidine
misc_difference          12
                         note = misc_feature - May be deoxycytidine
misc_difference          13
                         note = misc_feature - May be 2'-O-Methyl-2'-deoxyadenosine
misc_difference          14
                         note = misc_feature - May be 2'-O-Methyl-2'-deoxyguanosine
misc_difference          15
                         note = misc_feature - May be 2'-O-Methyl-2'-deoxyguanosine
misc_difference          16
                         note = misc_feature - May be deoxycytidine
misc_difference          17
                         note = misc_feature - May be 2'OH-guanosine
misc_difference          18
                         note = misc_feature - May be 2'-fluoro-2'-deoxycytidine
misc_difference          19
                         note = misc_feature - May be 2'-fluoro-2'-deoxyuridine
misc_difference          20
                         note = misc_feature - May be 2'-O-Methyl-2'-deoxyguanosine
misc_difference          21
                         note = misc_feature - May be 2'-O-Methyl-2'-deoxyadenosine
misc_difference          22
                         note = misc_feature - May be 2'-O-Methyl-2'-deoxyguanosine
misc_difference          23
                         note = misc_feature - May be 2'OH-thymidine
misc_difference          24
                         note = misc_feature - May be deoxycytidine
misc_difference          25
                         note = misc_feature - May be 2'OH-thymidine
misc_difference          26
                         note = misc_feature - May be 2'-O-Methyl-2'-deoxyguanosine
misc_difference          27
                         note = misc_feature - May be 2'-O-Methyl-2'-deoxyadenosine
misc_difference          28
                         note = misc_feature - May be 2'-O-Methyl-2'-deoxyguanosine
misc_difference          29
                         note = misc_feature - May be 2'-fluoro-2'-deoxyuridine
misc_difference          30
                         note = misc_feature - May be 2'-fluoro-2'-deoxyuridine
misc_difference          31
                         note = misc_feature - May be 2'-fluoro-2'-deoxyuridine
misc_difference          32
                         note = misc_feature - May be 2'OH-adenosine
misc_difference          33
                         note = misc_feature - May be 2'-fluoro-2'-deoxycytidine
misc_difference          34
                         note = misc_feature - May be 2'-fluoro-2'-deoxycytidine
misc_difference          35
                         note = misc_feature - May be 2'-fluoro-2'-deoxyuridine
misc_difference          36
                         note = misc_feature - May be 2'-O-Methyl-2'-deoxyguanosine
misc_difference          37
                         note = misc_feature - May be 2'-fluoro-2'-deoxycytidine
```

```
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 41
cgccgcggtc tcaggcgctg agtctgagtt tacctgcg                          38

SEQ ID NO: 42          moltype = DNA  length = 37
FEATURE                Location/Qualifiers
misc_feature           1..37
                       note = Synthetic C5 specific aptamer
misc_difference        1
                       note = misc_feature - May be 2'-O-Methyl-2'-deoxycytidine
misc_difference        2
                       note = misc_feature - May be 2'-O-Methyl-2'-deoxyguanosine
misc_difference        3
                       note = misc_feature - May be 2'-O-Methyl-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
```

-continued

```
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxyuridine
misc_difference         35
                        note = misc_feature - May be 2'-O-Methyl-2'-deoxyguanosine
misc_difference         36
                        note = misc_feature - May be 2'-O-Methyl-2'-deoxycytidine
misc_difference         37
                        note = misc_feature - May be 2'-O-Methyl-2'-deoxyguanosine
source                  1..37
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..37
                        note = RNA
SEQUENCE: 42
cgccgcggtc tcaggcgctg agtctgagtt tactgcg                          37

SEQ ID NO: 43           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
```

```
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'OH-cytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 43
cgccgcggtc tcaggcgctg agtctgagtt tacctgcg                          38

SEQ ID NO: 44          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be deoxycytidine
misc_difference        7
```

-continued

```
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
```

```
                         note = RNA
SEQUENCE: 44
cgccgcggtc tcaggcgctg agtctgagtt tacctgcg                          38

SEQ ID NO: 45            moltype = DNA  length = 38
FEATURE                  Location/Qualifiers
misc_feature             1..38
                         note = Synthetic C5 specific aptamer
misc_difference          1
                         note = misc_feature - May be 2'-fluoro-2'-deoxycytidine
misc_difference          2
                         note = misc_feature - May be 2'-O-Methyl-2'-deoxyguanosine
misc_difference          3
                         note = misc_feature - May be 2'-fluoro-2'-deoxycytidine
misc_difference          4
                         note = misc_feature - May be deoxycytidine
misc_difference          5
                         note = misc_feature - May be 2'OH-guanosine
misc_difference          6
                         note = misc_feature - May be deoxycytidine
misc_difference          7
                         note = misc_feature - May be 2'-O-Methyl-2'-deoxyguanosine
misc_difference          8
                         note = misc_feature - May be 2'-O-Methyl-2'-deoxyguanosine
misc_difference          9
                         note = misc_feature - May be 2'-fluoro-2'-deoxyuridine
misc_difference          10
                         note = misc_feature - May be deoxycytidine
misc_difference          11
                         note = misc_feature - May be 2'OH-thymidine
misc_difference          12
                         note = misc_feature - May be deoxycytidine
misc_difference          13
                         note = misc_feature - May be 2'-O-Methyl-2'-deoxyadenosine
misc_difference          14
                         note = misc_feature - May be 2'-O-Methyl-2'-deoxyguanosine
misc_difference          15
                         note = misc_feature - May be 2'-O-Methyl-2'-deoxyguanosine
misc_difference          16
                         note = misc_feature - May be deoxycytidine
misc_difference          17
                         note = misc_feature - May be 2'OH-guanosine
misc_difference          18
                         note = misc_feature - May be 2'-fluoro-2'-deoxycytidine
misc_difference          19
                         note = misc_feature - May be 2'-fluoro-2'-deoxyuridine
misc_difference          20
                         note = misc_feature - May be 2'-O-Methyl-2'-deoxyguanosine
misc_difference          21
                         note = misc_feature - May be 2'-O-Methyl-2'-deoxyadenosine
misc_difference          22
                         note = misc_feature - May be 2'-O-Methyl-2'-deoxyguanosine
misc_difference          23
                         note = misc_feature - May be 2'OH-thymidine
misc_difference          24
                         note = misc_feature - May be deoxycytidine
misc_difference          25
                         note = misc_feature - May be 2'OH-thymidine
misc_difference          26
                         note = misc_feature - May be 2'-O-Methyl-2'-deoxyguanosine
misc_difference          27
                         note = misc_feature - May be 2'-O-Methyl-2'-deoxyadenosine
misc_difference          28
                         note = misc_feature - May be 2'-O-Methyl-2'-deoxyguanosine
misc_difference          29
                         note = misc_feature - May be 2'-fluoro-2'-deoxyuridine
misc_difference          30
                         note = misc_feature - May be 2'-fluoro-2'-deoxyuridine
misc_difference          31
                         note = misc_feature - May be 2'-fluoro-2'-deoxyuridine
misc_difference          32
                         note = misc_feature - May be 2'OH-adenosine
misc_difference          33
                         note = misc_feature - May be 2'-fluoro-2'-deoxycytidine
misc_difference          34
                         note = misc_feature - May be 2'-fluoro-2'-deoxycytidine
misc_difference          35
                         note = misc_feature - May be 2'-fluoro-2'-deoxyuridine
misc_difference          36
```

-continued

```
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 45
cgccgcggtc tcaggcgctg agtctgagtt tacctgcg                          38

SEQ ID NO: 46           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
```

-continued

```
misc_difference       26
                      note = misc_feature - May be 2'-O-Methyl-2'-deoxyguanosine
misc_difference       27
                      note = misc_feature - May be 2'-O-Methyl-2'-deoxyadenosine
misc_difference       28
                      note = misc_feature - May be 2'-O-Methyl-2'-deoxyguanosine
misc_difference       29
                      note = misc_feature - May be 2'-fluoro-2'-deoxyuridine
misc_difference       30
                      note = misc_feature - May be 2'-fluoro-2'-deoxyuridine
misc_difference       31
                      note = misc_feature - May be 2'-fluoro-2'-deoxyuridine
misc_difference       32
                      note = misc_feature - May be 2'OH-adenosine
misc_difference       33
                      note = misc_feature - May be 2'-fluoro-2'-deoxycytidine
misc_difference       34
                      note = misc_feature - May be 2'-fluoro-2'-deoxycytidine
misc_difference       35
                      note = misc_feature - May be 2'-fluoro-2'-deoxyuridine
misc_difference       36
                      note = misc_feature - May be 2'-O-Methyl-2'-deoxyguanosine
misc_difference       37
                      note = misc_feature - May be 2'-fluoro-2'-deoxycytidine
misc_difference       38
                      note = misc_feature - May be 2'-O-Methyl-2'-deoxyguanosine
source                1..38
                      mol_type = other DNA
                      organism = synthetic construct
misc_feature          1..10
                      note = RNA
misc_feature          11
                      note = DNA
misc_feature          12..22
                      note = RNA
misc_feature          23
                      note = DNA
misc_feature          24
                      note = RNA
misc_feature          25
                      note = DNA
misc_feature          26..38
                      note = RNA
SEQUENCE: 46
cgccgcggtc tcaggcgctg agtctgagtt tacctgcg                          38

SEQ ID NO: 47         moltype = DNA  length = 38
FEATURE               Location/Qualifiers
misc_feature          1..38
                      note = Synthetic C5 specific aptamer
misc_difference       1
                      note = misc_feature - May be 2'-fluoro-2'-deoxycytidine
misc_difference       2
                      note = misc_feature - May be 2'-O-Methyl-2'-deoxyguanosine
misc_difference       3
                      note = misc_feature - May be 2'-fluoro-2'-deoxycytidine
misc_difference       4
                      note = misc_feature - May be 2'-fluoro-2'-deoxycytidine
misc_difference       5
                      note = misc_feature - May be 2'OH-guanosine
misc_difference       6
                      note = misc_feature - May be 2'-fluoro-2'-deoxycytidine
misc_difference       7
                      note = misc_feature - May be 2'-O-Methyl-2'-deoxyguanosine
misc_difference       8
                      note = misc_feature - May be 2'-O-Methyl-2'-deoxyguanosine
misc_difference       9
                      note = misc_feature - May be 2'-fluoro-2'-deoxyuridine
misc_difference       10
                      note = misc_feature - May be deoxycytidine
misc_difference       11
                      note = misc_feature - May be 2'OH-thymidine
misc_difference       12
                      note = misc_feature - May be deoxycytidine
misc_difference       13
                      note = misc_feature - May be 2'-O-Methyl-2'-deoxyadenosine
misc_difference       14
                      note = misc_feature - May be 2'-O-Methyl-2'-deoxyguanosine
misc_difference       15
```

-continued

```
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be deoxycytidine
misc_difference         19
                        note = misc_feature - May be 2'OH-thymidine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..18
                        note = RNA
misc_feature            19
                        note = DNA
misc_feature            20..22
                        note = RNA
misc_feature            23
                        note = DNA
misc_feature            24
                        note = RNA
misc_feature            25
                        note = DNA
misc_feature            26..38
                        note = RNA
SEQUENCE: 47
cgccgcggtc tcaggcgctg agtctgagtt tacctgcg                          38

SEQ ID NO: 48           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
```

-continued

| | |
|---|---|
| misc_difference | 3<br>note = misc_feature - May be 2'-fluoro-2'-deoxycytidine |
| misc_difference | 4<br>note = misc_feature - May be 2'-fluoro-2'-deoxycytidine |
| misc_difference | 5<br>note = misc_feature - May be 2'OH-guanosine |
| misc_difference | 6<br>note = misc_feature - May be 2'-fluoro-2'-deoxycytidine |
| misc_difference | 7<br>note = misc_feature - May be 2'-O-Methyl-2'-deoxyguanosine |
| misc_difference | 8<br>note = misc_feature - May be 2'-O-Methyl-2'-deoxyguanosine |
| misc_difference | 9<br>note = misc_feature - May be 2'-fluoro-2'-deoxyuridine |
| misc_difference | 10<br>note = misc_feature - May be deoxycytidine |
| misc_difference | 11<br>note = misc_feature - May be 2'OH-thymidine |
| misc_difference | 12<br>note = misc_feature - May be deoxycytidine |
| misc_difference | 13<br>note = misc_feature - May be 2'-O-Methyl-2'-deoxyadenosine |
| misc_difference | 14<br>note = misc_feature - May be 2'-O-Methyl-2'-deoxyguanosine |
| misc_difference | 15<br>note = misc_feature - May be 2'-O-Methyl-2'-deoxyguanosine |
| misc_difference | 16<br>note = misc_feature - May be deoxycytidine |
| misc_difference | 17<br>note = misc_feature - May be 2'OH-guanosine |
| misc_difference | 18<br>note = misc_feature - May be deoxycytidine |
| misc_difference | 19<br>note = misc_feature - May be 2'OH-thymidine |
| misc_difference | 20<br>note = misc_feature - May be 2'-O-Methyl-2'-deoxyguanosine |
| misc_difference | 21<br>note = misc_feature - May be 2'-O-Methyl-2'-deoxyadenosine |
| misc_difference | 22<br>note = misc_feature - May be 2'-O-Methyl-2'-deoxyguanosine |
| misc_difference | 23<br>note = misc_feature - May be 2'OH-thymidine |
| misc_difference | 24<br>note = misc_feature - May be deoxycytidine |
| misc_difference | 25<br>note = misc_feature - May be 2'OH-thymidine |
| misc_difference | 26<br>note = misc_feature - May be 2'-O-Methyl-2'-deoxyguanosine |
| misc_difference | 27<br>note = misc_feature - May be 2'-O-Methyl-2'-deoxyadenosine |
| misc_difference | 28<br>note = misc_feature - May be 2'-O-Methyl-2'-deoxyguanosine |
| misc_difference | 29<br>note = misc_feature - May be 2'-fluoro-2'-deoxyuridine |
| misc_difference | 30<br>note = misc_feature - May be 2'-fluoro-2'-deoxyuridine |
| misc_difference | 31<br>note = misc_feature - May be 2'-fluoro-2'-deoxyuridine |
| misc_difference | 32<br>note = misc_feature - May be 2'OH-adenosine |
| misc_difference | 33<br>note = misc_feature - May be 2'-fluoro-2'-deoxycytidine |
| misc_difference | 34<br>note = misc_feature - May be 2'-fluoro-2'-deoxycytidine |
| misc_difference | 35<br>note = misc_feature - May be 2'-fluoro-2'-deoxyuridine |
| misc_difference | 36<br>note = misc_feature - May be 2'-O-Methyl-2'-deoxyguanosine |
| misc_difference | 37<br>note = misc_feature - May be 2'-fluoro-2'-deoxycytidine |
| misc_difference | 38<br>note = misc_feature - May be 2'-O-Methyl-2'-deoxyguanosine |
| source | 1..38<br>mol_type = other DNA<br>organism = synthetic construct |
| misc_feature | 1..10<br>note = RNA |
| misc_feature | 11<br>note = DNA |

-continued

```
misc_feature          12..18
                      note = RNA
misc_feature          19
                      note = DNA
misc_feature          20..22
                      note = RNA
misc_feature          23
                      note = DNA
misc_feature          24
                      note = RNA
misc_feature          25
                      note = DNA
misc_feature          26..38
                      note = RNA
SEQUENCE: 48
cgccgcggtc tcaggcgctg agtctgagtt tacctgcg                          38

SEQ ID NO: 49         moltype = DNA  length = 38
FEATURE               Location/Qualifiers
misc_feature          1..38
                      note = Synthetic C5 specific aptamer
misc_difference       1
                      note = misc_feature - May be 2'-fluoro-2'-deoxycytidine
misc_difference       2
                      note = misc_feature - May be 2'-O-Methyl-2'-deoxyguanosine
misc_difference       3
                      note = misc_feature - May be 2'-fluoro-2'-deoxycytidine
misc_difference       4
                      note = misc_feature - May be 2'-fluoro-2'-deoxycytidine
misc_difference       5
                      note = misc_feature - May be 2'OH-guanosine
misc_difference       6
                      note = misc_feature - May be 2'-fluoro-2'-deoxycytidine
misc_difference       7
                      note = misc_feature - May be 2'-O-Methyl-2'-deoxyguanosine
misc_difference       8
                      note = misc_feature - May be 2'-O-Methyl-2'-deoxyguanosine
misc_difference       9
                      note = misc_feature - May be 2'-fluoro-2'-deoxyuridine
misc_difference       10
                      note = misc_feature - May be deoxycytidine
misc_difference       11
                      note = misc_feature - May be 2'OH-thymidine
misc_difference       12
                      note = misc_feature - May be deoxycytidine
misc_difference       13
                      note = misc_feature - May be 2'-O-Methyl-2'-deoxyadenosine
misc_difference       14
                      note = misc_feature - May be 2'-O-Methyl-2'-deoxyguanosine
misc_difference       15
                      note = misc_feature - May be 2'-O-Methyl-2'-deoxyguanosine
misc_difference       16
                      note = misc_feature - May be deoxycytidine
misc_difference       17
                      note = misc_feature - May be 2'OH-guanosine
misc_difference       18
                      note = misc_feature - May be 2'-fluoro-2'-deoxycytidine
misc_difference       19
                      note = misc_feature - May be 2'-fluoro-2'-deoxyuridine
misc_difference       20
                      note = misc_feature - May be 2'-O-Methyl-2'-deoxyguanosine
misc_difference       21
                      note = misc_feature - May be 2'-O-Methyl-2'-deoxyadenosine
misc_difference       22
                      note = misc_feature - May be 2'-O-Methyl-2'-deoxyguanosine
misc_difference       23
                      note = misc_feature - May be 2'OH-thymidine
misc_difference       24
                      note = misc_feature - May be deoxycytidine
misc_difference       25
                      note = misc_feature - May be 2'OH-thymidine
misc_difference       26
                      note = misc_feature - May be 2'-O-Methyl-2'-deoxyguanosine
misc_difference       27
                      note = misc_feature - May be 2'-O-Methyl-2'-deoxyadenosine
misc_difference       28
                      note = misc_feature - May be 2'-O-Methyl-2'-deoxyguanosine
misc_difference       29
                      note = misc_feature - May be 2'OH-thymidine
```

```
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..28
                       note = RNA
misc_feature           29
                       note = DNA
misc_feature           30..38
                       note = RNA
SEQUENCE: 49
cgccgcggtc tcaggcgctg agtctgagtt tacctgcg                          38

SEQ ID NO: 50          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
```

-continued

```
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'OH-thymidine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..29
                        note = RNA
misc_feature            30
                        note = DNA
misc_feature            31..38
                        note = RNA
SEQUENCE: 50
cgccgcggtc tcaggcgctg agtctgagtt tacctgcg                          38

SEQ ID NO: 51           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
```

```
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'OH-thymidine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
```

```
misc_feature          24
                      note = RNA
misc_feature          25
                      note = DNA
misc_feature          26..30
                      note = RNA
misc_feature          31
                      note = DNA
misc_feature          32..38
                      note = RNA
SEQUENCE: 51
cgccgcggtc tcaggcgctg agtctgagtt tacctgcg                          38

SEQ ID NO: 52         moltype = DNA  length = 38
FEATURE               Location/Qualifiers
misc_feature          1..38
                      note = Synthetic C5 specific aptamer
misc_difference       1
                      note = misc_feature - May be 2'-fluoro-2'-deoxycytidine
misc_difference       2
                      note = misc_feature - May be 2'-O-Methyl-2'-deoxyguanosine
misc_difference       3
                      note = misc_feature - May be 2'-fluoro-2'-deoxycytidine
misc_difference       4
                      note = misc_feature - May be 2'-fluoro-2'-deoxycytidine
misc_difference       5
                      note = misc_feature - May be 2'OH-guanosine
misc_difference       6
                      note = misc_feature - May be 2'-fluoro-2'-deoxycytidine
misc_difference       7
                      note = misc_feature - May be 2'-O-Methyl-2'-deoxyguanosine
misc_difference       8
                      note = misc_feature - May be 2'-O-Methyl-2'-deoxyguanosine
misc_difference       9
                      note = misc_feature - May be 2'-fluoro-2'-deoxyuridine
misc_difference       10
                      note = misc_feature - May be deoxycytidine
misc_difference       11
                      note = misc_feature - May be 2'OH-thymidine
misc_difference       12
                      note = misc_feature - May be deoxycytidine
misc_difference       13
                      note = misc_feature - May be 2'-O-Methyl-2'-deoxyadenosine
misc_difference       14
                      note = misc_feature - May be 2'-O-Methyl-2'-deoxyguanosine
misc_difference       15
                      note = misc_feature - May be 2'-O-Methyl-2'-deoxyguanosine
misc_difference       16
                      note = misc_feature - May be deoxycytidine
misc_difference       17
                      note = misc_feature - May be 2'OH-guanosine
misc_difference       18
                      note = misc_feature - May be 2'-fluoro-2'-deoxycytidine
misc_difference       19
                      note = misc_feature - May be 2'-fluoro-2'-deoxyuridine
misc_difference       20
                      note = misc_feature - May be 2'-O-Methyl-2'-deoxyguanosine
misc_difference       21
                      note = misc_feature - May be 2'-O-Methyl-2'-deoxyadenosine
misc_difference       22
                      note = misc_feature - May be 2'-O-Methyl-2'-deoxyguanosine
misc_difference       23
                      note = misc_feature - May be 2'OH-thymidine
misc_difference       24
                      note = misc_feature - May be deoxycytidine
misc_difference       25
                      note = misc_feature - May be 2'OH-thymidine
misc_difference       26
                      note = misc_feature - May be 2'-O-Methyl-2'-deoxyguanosine
misc_difference       27
                      note = misc_feature - May be 2'-O-Methyl-2'-deoxyadenosine
misc_difference       28
                      note = misc_feature - May be 2'-O-Methyl-2'-deoxyguanosine
misc_difference       29
                      note = misc_feature - May be 2'OH-thymidine
misc_difference       30
                      note = misc_feature - May be 2'OH-thymidine
misc_difference       31
                      note = misc_feature - May be 2'OH-thymidine
```

-continued

```
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..28
                       note = RNA
misc_feature           29..31
                       note = DNA
misc_feature           32..38
                       note = RNA
SEQUENCE: 52
cgccgcggtc tcaggcgctg agtctgagtt tacctgcg                          38

SEQ ID NO: 53          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
```

```
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'OH-thymidine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..34
                        note = RNA
misc_feature            35
                        note = DNA
misc_feature            36..38
                        note = RNA
SEQUENCE: 53
cgccgcggtc tcaggcgctg agtctgagtt tacctgcg                          38

SEQ ID NO: 54           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
```

-continued

```
misc_difference      7
                     note = misc_feature - May be 2'-O-Methyl-2'-deoxyguanosine
misc_difference      8
                     note = misc_feature - May be 2'-O-Methyl-2'-deoxyguanosine
misc_difference      9
                     note = misc_feature - May be 2'-O-Methyl-2'-deoxyuridine
misc_difference      10
                     note = misc_feature - May be deoxycytidine
misc_difference      11
                     note = misc_feature - May be 2'OH-thymidine
misc_difference      12
                     note = misc_feature - May be deoxycytidine
misc_difference      13
                     note = misc_feature - May be 2'-O-Methyl-2'-deoxyadenosine
misc_difference      14
                     note = misc_feature - May be 2'-O-Methyl-2'-deoxyguanosine
misc_difference      15
                     note = misc_feature - May be 2'-O-Methyl-2'-deoxyguanosine
misc_difference      16
                     note = misc_feature - May be deoxycytidine
misc_difference      17
                     note = misc_feature - May be 2'OH-guanosine
misc_difference      18
                     note = misc_feature - May be 2'-fluoro-2'-deoxycytidine
misc_difference      19
                     note = misc_feature - May be 2'-fluoro-2'-deoxyuridine
misc_difference      20
                     note = misc_feature - May be 2'-O-Methyl-2'-deoxyguanosine
misc_difference      21
                     note = misc_feature - May be 2'-O-Methyl-2'-deoxyadenosine
misc_difference      22
                     note = misc_feature - May be 2'-O-Methyl-2'-deoxyguanosine
misc_difference      23
                     note = misc_feature - May be 2'OH-thymidine
misc_difference      24
                     note = misc_feature - May be deoxycytidine
misc_difference      25
                     note = misc_feature - May be 2'OH-thymidine
misc_difference      26
                     note = misc_feature - May be 2'-O-Methyl-2'-deoxyguanosine
misc_difference      27
                     note = misc_feature - May be 2'-O-Methyl-2'-deoxyadenosine
misc_difference      28
                     note = misc_feature - May be 2'-O-Methyl-2'-deoxyguanosine
misc_difference      29
                     note = misc_feature - May be 2'-fluoro-2'-deoxyuridine
misc_difference      30
                     note = misc_feature - May be 2'-fluoro-2'-deoxyuridine
misc_difference      31
                     note = misc_feature - May be 2'-fluoro-2'-deoxyuridine
misc_difference      32
                     note = misc_feature - May be 2'OH-adenosine
misc_difference      33
                     note = misc_feature - May be deoxycytidine
misc_difference      34
                     note = misc_feature - May be deoxycytidine
misc_difference      35
                     note = misc_feature - May be 2'-fluoro-2'-deoxyuridine
misc_difference      36
                     note = misc_feature - May be 2'-O-Methyl-2'-deoxyguanosine
misc_difference      37
                     note = misc_feature - May be 2'-fluoro-2'-deoxycytidine
misc_difference      38
                     note = misc_feature - May be 2'-O-Methyl-2'-deoxyguanosine
source               1..38
                     mol_type = other DNA
                     organism = synthetic construct
misc_feature         1..10
                     note = RNA
misc_feature         11
                     note = DNA
misc_feature         12..22
                     note = RNA
misc_feature         23
                     note = DNA
misc_feature         24
                     note = RNA
misc_feature         25
                     note = DNA
```

```
misc_feature            26..38
                        note = RNA
SEQUENCE: 54
cgccgcggtc tcaggcgctg agtctgagtt tacctgcg                           38

SEQ ID NO: 55           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-O-Methyl-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
```

```
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 55
cgccgcggtc tcaggcgctg agtctgagtt tacctgcg                          38

SEQ ID NO: 56          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-O-Methyl-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
```

```
                          note = misc_feature - May be 2'OH-thymidine
misc_difference           26
                          note = misc_feature - May be 2'-O-Methyl-2'-deoxyguanosine
misc_difference           27
                          note = misc_feature - May be 2'-O-Methyl-2'-deoxyadenosine
misc_difference           28
                          note = misc_feature - May be 2'-O-Methyl-2'-deoxyguanosine
misc_difference           29
                          note = misc_feature - May be 2'-fluoro-2'-deoxyuridine
misc_difference           30
                          note = misc_feature - May be 2'-fluoro-2'-deoxyuridine
misc_difference           31
                          note = misc_feature - May be 2'-fluoro-2'-deoxyuridine
misc_difference           32
                          note = misc_feature - May be 2'OH-adenosine
misc_difference           33
                          note = misc_feature - May be 2'-fluoro-2'-deoxycytidine
misc_difference           34
                          note = misc_feature - May be 2'-fluoro-2'-deoxycytidine
misc_difference           35
                          note = misc_feature - May be 2'-fluoro-2'-deoxyuridine
misc_difference           36
                          note = misc_feature - May be 2'-O-Methyl-2'-deoxyguanosine
misc_difference           37
                          note = misc_feature - May be 2'-fluoro-2'-deoxycytidine
misc_difference           38
                          note = misc_feature - May be 2'-O-Methyl-2'-deoxyguanosine
source                    1..38
                          mol_type = other DNA
                          organism = synthetic construct
misc_feature              1..10
                          note = RNA
misc_feature              11
                          note = DNA
misc_feature              12..22
                          note = RNA
misc_feature              23
                          note = DNA
misc_feature              24
                          note = RNA
misc_feature              25
                          note = DNA
misc_feature              26..38
                          note = RNA
SEQUENCE: 56
cgccgcggtc tcaggcgctg agtctgagtt tacctgcg                          38

SEQ ID NO: 57             moltype = DNA  length = 38
FEATURE                   Location/Qualifiers
misc_feature              1..38
                          note = Synthetic C5 specific aptamer
misc_difference           1
                          note = misc_feature - May be 2'-fluoro-2'-deoxycytidine
misc_difference           2
                          note = misc_feature - May be 2'-O-Methyl-2'-deoxyguanosine
misc_difference           3
                          note = misc_feature - May be 2'-fluoro-2'-deoxycytidine
misc_difference           4
                          note = misc_feature - May be 2'-O-Methyl-2'-deoxycytidine
misc_difference           5
                          note = misc_feature - May be 2'OH-guanosine
misc_difference           6
                          note = misc_feature - May be 2'-O-Methyl-2'-deoxycytidine
misc_difference           7
                          note = misc_feature - May be 2'-O-Methyl-2'-deoxyguanosine
misc_difference           8
                          note = misc_feature - May be 2'-O-Methyl-2'-deoxyguanosine
misc_difference           9
                          note = misc_feature - May be 2'-fluoro-2'-deoxyuridine
misc_difference           10
                          note = misc_feature - May be deoxycytidine
misc_difference           11
                          note = misc_feature - May be 2'OH-thymidine
misc_difference           12
                          note = misc_feature - May be deoxycytidine
misc_difference           13
                          note = misc_feature - May be 2'-O-Methyl-2'-deoxyadenosine
misc_difference           14
                          note = misc_feature - May be 2'-O-Methyl-2'-deoxyguanosine
```

```
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 57
cgccgcggtc tcaggcgctg agtctgagtt tacctgcg                          38

SEQ ID NO: 58          moltype = RNA  length = 37
FEATURE                Location/Qualifiers
misc_feature           1..37
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
```

-continued

```
                        note = misc_feature - May be 2'OH-guanosine
misc_difference         5
                        note = misc_feature - May be 2'-fluoro-2'-deoxycytidine
misc_difference         6
                        note = misc_feature - May be 2'-O-Methyl-2'-deoxyguanosine
misc_difference         7
                        note = misc_feature - May be 2'-O-Methyl-2'-deoxyguanosine
misc_difference         8
                        note = misc_feature - May be 2'-fluoro-2'-deoxyuridine
misc_difference         9
                        note = misc_feature - May be deoxycytidine
misc_difference         10
                        note = misc_feature - May be 2'-fluoro-2'-deoxyuridine
misc_difference         11
                        note = misc_feature - May be deoxycytidine
misc_difference         12
                        note = misc_feature - May be 2'-O-Methyl-2'-deoxyadenosine
misc_difference         13
                        note = misc_feature - May be 2'-O-Methyl-2'-deoxyguanosine
misc_difference         14
                        note = misc_feature - May be 2'-O-Methyl-2'-deoxyguanosine
misc_difference         15
                        note = misc_feature - May be deoxycytidine
misc_difference         16
                        note = misc_feature - May be 2'OH-guanosine
misc_difference         17
                        note = misc_feature - May be 2'-O-Methyl-2'-deoxycytidine
misc_difference         18
                        note = misc_feature - May be 2'-fluoro-2'-deoxyuridine
misc_difference         19
                        note = misc_feature - May be 2'-O-Methyl-2'-deoxyguanosine
misc_difference         20
                        note = misc_feature - May be 2'-O-Methyl-2'-deoxyadenosine
misc_difference         21
                        note = misc_feature - May be 2'-O-Methyl-2'-deoxyguanosine
misc_difference         22
                        note = misc_feature - May be 2'-fluoro-2'-deoxyuridine
misc_difference         23
                        note = misc_feature - May be deoxycytidine
misc_difference         24
                        note = misc_feature - May be 2'-fluoro-2'-deoxyuridine
misc_difference         25
                        note = misc_feature - May be 2'-O-Methyl-2'-deoxyguanosine
misc_difference         26
                        note = misc_feature - May be 2'-O-Methyl-2'-deoxyadenosine
misc_difference         27
                        note = misc_feature - May be 2'-O-Methyl-2'-deoxyguanosine
misc_difference         28
                        note = misc_feature - May be 2'-fluoro-2'-deoxyuridine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'OH-adenosine
misc_difference         32
                        note = misc_feature - May be 2'-fluoro-2'-deoxycytidine
misc_difference         33
                        note = misc_feature - May be 2'-fluoro-2'-deoxycytidine
misc_difference         34
                        note = misc_feature - May be 2'-fluoro-2'-deoxyuridine
misc_difference         35
                        note = misc_feature - May be 2'-O-Methyl-2'-deoxyguanosine
misc_difference         36
                        note = misc_feature - May be 2'-fluoro-2'-deoxycytidine
misc_difference         37
                        note = misc_feature - May be 2'-O-Methyl-2'-deoxyguanosine
source                  1..37
                        mol_type = other RNA
                        organism = synthetic construct
SEQUENCE: 58
cgcgcggtct caggcgctga gtctgagttt acctgcg                          37

SEQ ID NO: 59           moltype = RNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
```

-continued

```
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'-fluoro-2'-deoxyuridine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-O-Methyl-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'-fluoro-2'-deoxyuridine
misc_difference        24
                       note = misc_feature - May be deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other RNA
                       organism = synthetic construct
SEQUENCE: 59
cgccgcggtc tcaggcgctg agtctgagtt tacctgcg                     38
```

```
SEQ ID NO: 60          moltype = RNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'-fluoro-2'-deoxyuridine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-O-Methyl-2'-deoxycytidine
misc_difference        19
                       note = misc_feature - May be 2'-O-Methyl-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'-fluoro-2'-deoxyuridine
misc_difference        24
                       note = misc_feature - May be deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
```

-continued

```
misc_difference        38
                       note = misc_feature - May be 2'-O-Methyl-2'-deoxyguanosine
source                 1..38
                       mol_type = other RNA
                       organism = synthetic construct
SEQUENCE: 60
cgccgcggtc tcaggcgctg agtctgagtt tacctgcg                          38

SEQ ID NO: 61          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-O-Methyl-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
```

```
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 61
cgccgcggtc tcaggcgctg agtctgagtt tacctgcg                          38

SEQ ID NO: 62           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
```

-continued

```
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-O-Methyl-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 62
cgccgcggtc tcaggcgctg agtctgagtt tacctgcg                          38

SEQ ID NO: 63          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
```

-continued

```
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-O-Methyl-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 63
cgccgcggtc tcaggcgctg agtctgagtt tacctgcg                          38

SEQ ID NO: 64           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
```

-continued

```
misc_difference      3
                     note = misc_feature - May be 2'-fluoro-2'-deoxycytidine
misc_difference      4
                     note = misc_feature - May be 2'-fluoro-2'-deoxycytidine
misc_difference      5
                     note = misc_feature - May be 2'OH-guanosine
misc_difference      6
                     note = misc_feature - May be 2'-fluoro-2'-deoxycytidine
misc_difference      7
                     note = misc_feature - May be 2'-O-Methyl-2'-deoxyguanosine
misc_difference      8
                     note = misc_feature - May be 2'-O-Methyl-2'-deoxyguanosine
misc_difference      9
                     note = misc_feature - May be 2'-fluoro-2'-deoxyuridine
misc_difference      10
                     note = misc_feature - May be deoxycytidine
misc_difference      11
                     note = misc_feature - May be 2'OH-thymidine
misc_difference      12
                     note = misc_feature - May be deoxycytidine
misc_difference      13
                     note = misc_feature - May be 2'-O-Methyl-2'-deoxyadenosine
misc_difference      14
                     note = misc_feature - May be 2'-O-Methyl-2'-deoxyguanosine
misc_difference      15
                     note = misc_feature - May be 2'-O-Methyl-2'-deoxyguanosine
misc_difference      16
                     note = misc_feature - May be deoxycytidine
misc_difference      17
                     note = misc_feature - May be 2'OH-guanosine
misc_difference      18
                     note = misc_feature - May be 2'-fluoro-2'-deoxycytidine
misc_difference      19
                     note = misc_feature - May be 2'-fluoro-2'-deoxyuridine
misc_difference      20
                     note = misc_feature - May be 2'-O-Methyl-2'-deoxyguanosine
misc_difference      21
                     note = misc_feature - May be 2'-O-Methyl-2'-deoxyadenosine
misc_difference      22
                     note = misc_feature - May be 2'-O-Methyl-2'-deoxyguanosine
misc_difference      23
                     note = misc_feature - May be 2'OH-thymidine
misc_difference      24
                     note = misc_feature - May be deoxycytidine
misc_difference      25
                     note = misc_feature - May be 2'OH-thymidine
misc_difference      26
                     note = misc_feature - May be 2'-O-Methyl-2'-deoxyguanosine
misc_difference      27
                     note = misc_feature - May be 2'-O-Methyl-2'-deoxyadenosine
misc_difference      28
                     note = misc_feature - May be 2'-O-Methyl-2'-deoxyguanosine
misc_difference      29
                     note = misc_feature - May be 2'-O-Methyl-2'-deoxyuridine
misc_difference      30
                     note = misc_feature - May be 2'-O-Methyl-2'-deoxyuridine
misc_difference      31
                     note = misc_feature - May be 2'-O-Methyl-2'-deoxyuridine
misc_difference      32
                     note = misc_feature - May be 2'OH-adenosine
misc_difference      33
                     note = misc_feature - May be 2'-fluoro-2'-deoxycytidine
misc_difference      34
                     note = misc_feature - May be 2'-fluoro-2'-deoxycytidine
misc_difference      35
                     note = misc_feature - May be 2'-fluoro-2'-deoxyuridine
misc_difference      36
                     note = misc_feature - May be 2'-O-Methyl-2'-deoxyguanosine
misc_difference      37
                     note = misc_feature - May be 2'-fluoro-2'-deoxycytidine
misc_difference      38
                     note = misc_feature - May be 2'-O-Methyl-2'-deoxyguanosine
source               1..38
                     mol_type = other DNA
                     organism = synthetic construct
misc_feature         1..10
                     note = RNA
misc_feature         11
                     note = DNA
```

```
misc_feature          12..22
                      note = RNA
misc_feature          23
                      note = DNA
misc_feature          24
                      note = RNA
misc_feature          25
                      note = DNA
misc_feature          26..38
                      note = RNA
SEQUENCE: 64
cgccgcggtc tcaggcgctg agtctgagtt tacctgcg                          38

SEQ ID NO: 65         moltype = DNA  length = 38
FEATURE               Location/Qualifiers
misc_feature          1..38
                      note = Synthetic C5 specific aptamer
misc_difference       1
                      note = misc_feature - May be 2'-fluoro-2'-deoxycytidine
misc_difference       2
                      note = misc_feature - May be 2'-O-Methyl-2'-deoxyguanosine
misc_difference       3
                      note = misc_feature - May be 2'-fluoro-2'-deoxycytidine
misc_difference       4
                      note = misc_feature - May be 2'-fluoro-2'-deoxycytidine
misc_difference       5
                      note = misc_feature - May be 2'OH-guanosine
misc_difference       6
                      note = misc_feature - May be 2'-fluoro-2'-deoxycytidine
misc_difference       7
                      note = misc_feature - May be 2'-O-Methyl-2'-deoxyguanosine
misc_difference       8
                      note = misc_feature - May be 2'-O-Methyl-2'-deoxyguanosine
misc_difference       9
                      note = misc_feature - May be 2'-fluoro-2'-deoxyuridine
misc_difference       10
                      note = misc_feature - May be deoxycytidine
misc_difference       11
                      note = misc_feature - May be 2'OH-thymidine
misc_difference       12
                      note = misc_feature - May be deoxycytidine
misc_difference       13
                      note = misc_feature - May be 2'-O-Methyl-2'-deoxyadenosine
misc_difference       14
                      note = misc_feature - May be 2'-O-Methyl-2'-deoxyguanosine
misc_difference       15
                      note = misc_feature - May be 2'-O-Methyl-2'-deoxyguanosine
misc_difference       16
                      note = misc_feature - May be deoxycytidine
misc_difference       17
                      note = misc_feature - May be 2'OH-guanosine
misc_difference       18
                      note = misc_feature - May be 2'-fluoro-2'-deoxycytidine
misc_difference       19
                      note = misc_feature - May be 2'-fluoro-2'-deoxyuridine
misc_difference       20
                      note = misc_feature - May be 2'-O-Methyl-2'-deoxyguanosine
misc_difference       21
                      note = misc_feature - May be 2'-O-Methyl-2'-deoxyadenosine
misc_difference       22
                      note = misc_feature - May be 2'-O-Methyl-2'-deoxyguanosine
misc_difference       23
                      note = misc_feature - May be 2'OH-thymidine
misc_difference       24
                      note = misc_feature - May be deoxycytidine
misc_difference       25
                      note = misc_feature - May be 2'OH-thymidine
misc_difference       26
                      note = misc_feature - May be 2'-O-Methyl-2'-deoxyguanosine
misc_difference       27
                      note = misc_feature - May be 2'-O-Methyl-2'-deoxyadenosine
misc_difference       28
                      note = misc_feature - May be 2'-O-Methyl-2'-deoxyguanosine
misc_difference       29
                      note = misc_feature - May be 2'-fluoro-2'-deoxyuridine
misc_difference       30
                      note = misc_feature - May be 2'-fluoro-2'-deoxyuridine
misc_difference       31
                      note = misc_feature - May be 2'-fluoro-2'-deoxyuridine
```

```
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-O-Methyl-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 65
cgccgcggtc tcaggcgctg agtctgagtt tacctgcg                          38

SEQ ID NO: 66          moltype = DNA  length = 38
FEATURE                Location/Qualifiers
misc_feature           1..38
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be deoxyguanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be deoxycytidine
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
```

```
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'OH-thymidine
misc_difference         24
                        note = misc_feature - May be deoxycytidine
misc_difference         25
                        note = misc_feature - May be 2'OH-thymidine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
source                  1..38
                        mol_type = other DNA
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 66
cgccgcggtc tcaggcgctg agtctgagtt tacctgcg                         38

SEQ ID NO: 67           moltype = DNA  length = 38
FEATURE                 Location/Qualifiers
misc_feature            1..38
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
```

```
misc_difference        11
                       note = misc_feature - May be 2'OH-thymidine
misc_difference        12
                       note = misc_feature - May be deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be deoxycytidine
misc_difference        17
                       note = misc_feature - May be deoxyguanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'OH-cytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 67
cgccgcggtc tcaggcgctg agtctgagtt tacctgcg                          38

SEQ ID NO: 68          moltype = DNA  length = 38
FEATURE                Location/Qualifiers
misc_feature           1..38
```

-continued

| | |
|---|---|
| | note = Synthetic C5 specific aptamer |
| misc_difference | 1 |
| | note = misc_feature - May be 2'-fluoro-2'-deoxycytidine |
| misc_difference | 2 |
| | note = misc_feature - May be 2'-O-Methyl-2'-deoxyguanosine |
| misc_difference | 3 |
| | note = misc_feature - May be 2'-fluoro-2'-deoxycytidine |
| misc_difference | 4 |
| | note = misc_feature - May be 2'-fluoro-2'-deoxycytidine |
| misc_difference | 5 |
| | note = misc_feature - May be 2'OH-guanosine |
| misc_difference | 6 |
| | note = misc_feature - May be 2'-fluoro-2'-deoxycytidine |
| misc_difference | 7 |
| | note = misc_feature - May be 2'-O-Methyl-2'-deoxyguanosine |
| misc_difference | 8 |
| | note = misc_feature - May be 2'-O-Methyl-2'-deoxyguanosine |
| misc_difference | 9 |
| | note = misc_feature - May be 2'-fluoro-2'-deoxyuridine |
| misc_difference | 10 |
| | note = misc_feature - May be deoxycytidine |
| misc_difference | 11 |
| | note = misc_feature - May be 2'OH-thymidine |
| misc_difference | 12 |
| | note = misc_feature - May be deoxycytidine |
| misc_difference | 13 |
| | note = misc_feature - May be 2'-O-Methyl-2'-deoxyadenosine |
| misc_difference | 14 |
| | note = misc_feature - May be 2'-O-Methyl-2'-deoxyguanosine |
| misc_difference | 15 |
| | note = misc_feature - May be 2'-O-Methyl-2'-deoxyguanosine |
| misc_difference | 16 |
| | note = misc_feature - May be deoxycytidine |
| misc_difference | 17 |
| | note = misc_feature - May be 2'OH-guanosine |
| misc_difference | 18 |
| | note = misc_feature - May be 2'-fluoro-2'-deoxycytidine |
| misc_difference | 19 |
| | note = misc_feature - May be 2'-fluoro-2'-deoxyuridine |
| misc_difference | 20 |
| | note = misc_feature - May be 2'-O-Methyl-2'-deoxyguanosine |
| misc_difference | 21 |
| | note = misc_feature - May be 2'-O-Methyl-2'-deoxyadenosine |
| misc_difference | 22 |
| | note = misc_feature - May be 2'-O-Methyl-2'-deoxyguanosine |
| misc_difference | 23 |
| | note = misc_feature - May be 2'OH-thymidine |
| misc_difference | 24 |
| | note = misc_feature - May be deoxycytidine |
| misc_difference | 25 |
| | note = misc_feature - May be 2'OH-thymidine |
| misc_difference | 26 |
| | note = misc_feature - May be 2'-O-Methyl-2'-deoxyguanosine |
| misc_difference | 27 |
| | note = misc_feature - May be 2'-O-Methyl-2'-deoxyadenosine |
| misc_difference | 28 |
| | note = misc_feature - May be 2'-O-Methyl-2'-deoxyguanosine |
| misc_difference | 29 |
| | note = misc_feature - May be 2'-fluoro-2'-deoxyuridine |
| misc_difference | 30 |
| | note = misc_feature - May be 2'-fluoro-2'-deoxyuridine |
| misc_difference | 31 |
| | note = misc_feature - May be 2'-fluoro-2'-deoxyuridine |
| misc_difference | 32 |
| | note = misc_feature - May be deoxyadenosine |
| misc_difference | 33 |
| | note = misc_feature - May be 2'-fluoro-2'-deoxycytidine |
| misc_difference | 34 |
| | note = misc_feature - May be 2'-fluoro-2'-deoxycytidine |
| misc_difference | 35 |
| | note = misc_feature - May be 2'-fluoro-2'-deoxyuridine |
| misc_difference | 36 |
| | note = misc_feature - May be 2'-O-Methyl-2'-deoxyguanosine |
| misc_difference | 37 |
| | note = misc_feature - May be 2'-fluoro-2'-deoxycytidine |
| misc_difference | 38 |
| | note = misc_feature - May be 2'-O-Methyl-2'-deoxyguanosine |
| source | 1..38 |
| | mol_type = other DNA |

```
                        organism = synthetic construct
misc_feature            1..10
                        note = RNA
misc_feature            11
                        note = DNA
misc_feature            12..22
                        note = RNA
misc_feature            23
                        note = DNA
misc_feature            24
                        note = RNA
misc_feature            25
                        note = DNA
misc_feature            26..38
                        note = RNA
SEQUENCE: 68
cgccgcggtc tcaggcgctg agtctgagtt tacctgcg                          38

SEQ ID NO: 69           moltype = DNA  length = 40
FEATURE                 Location/Qualifiers
misc_feature            1..40
                        note = Synthetic C5 specific aptamer
misc_difference         1
                        note = misc_feature - May be 2'-O-Methyl-2'-deoxyguanosine
misc_difference         2
                        note = misc_feature - May be 2'-fluoro-2'-deoxycytidine
misc_difference         3
                        note = misc_feature - May be 2'-O-Methyl-2'-deoxyguanosine
misc_difference         4
                        note = misc_feature - May be 2'-fluoro-2'-deoxyuridine
misc_difference         5
                        note = misc_feature - May be 2'-fluoro-2'-deoxycytidine
misc_difference         6
                        note = misc_feature - May be 2'OH-guanosine
misc_difference         7
                        note = misc_feature - May be 2'-fluoro-2'-deoxycytidine
misc_difference         8
                        note = misc_feature - May be 2'-O-Methyl-2'-deoxyguanosine
misc_difference         9
                        note = misc_feature - May be 2'-O-Methyl-2'-deoxyguanosine
misc_difference         10
                        note = misc_feature - May be 2'-fluoro-2'-deoxyuridine
misc_difference         11
                        note = misc_feature - May be deoxycytidine
misc_difference         12
                        note = misc_feature - May be 2'OH-thymidine
misc_difference         13
                        note = misc_feature - May be deoxycytidine
misc_difference         14
                        note = misc_feature - May be 2'-O-Methyl-2'-deoxyadenosine
misc_difference         15
                        note = misc_feature - May be 2'-O-Methyl-2'-deoxyguanosine
misc_difference         16
                        note = misc_feature - May be 2'-O-Methyl-2'-deoxyguanosine
misc_difference         17
                        note = misc_feature - May be deoxycytidine
misc_difference         18
                        note = misc_feature - May be 2'OH-guanosine
misc_difference         19
                        note = misc_feature - May be 2'-fluoro-2'-deoxycytidine
misc_difference         20
                        note = misc_feature - May be 2'-fluoro-2'-deoxyuridine
misc_difference         21
                        note = misc_feature - May be 2'-O-Methyl-2'-deoxyguanosine
misc_difference         22
                        note = misc_feature - May be 2'-O-Methyl-2'-deoxyadenosine
misc_difference         23
                        note = misc_feature - May be 2'-O-Methyl-2'-deoxyguanosine
misc_difference         24
                        note = misc_feature - May be 2'OH-thymidine
misc_difference         25
                        note = misc_feature - May be deoxycytidine
misc_difference         26
                        note = misc_feature - May be 2'OH-thymidine
misc_difference         27
                        note = misc_feature - May be 2'-O-Methyl-2'-deoxyguanosine
misc_difference         28
                        note = misc_feature - May be 2'-O-Methyl-2'-deoxyadenosine
misc_difference         29
```

```
                        note = misc_feature - May be 2'-O-Methyl-2'-deoxyguanosine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'-fluoro-2'-deoxyuridine
misc_difference         33
                        note = misc_feature - May be 2'OH-adenosine
misc_difference         34
                        note = misc_feature - May be 2'-fluoro-2'-deoxycytidine
misc_difference         35
                        note = misc_feature - May be 2'-fluoro-2'-deoxycytidine
misc_difference         36
                        note = misc_feature - May be 2'-fluoro-2'-deoxyuridine
misc_difference         37
                        note = misc_feature - May be 2'-O-Methyl-2'-deoxyadenosine
misc_difference         38
                        note = misc_feature - May be 2'-fluoro-2'-deoxycytidine
misc_difference         39
                        note = misc_feature - May be 2'-O-Methyl-2'-deoxyguanosine
misc_difference         40
                        note = misc_feature - May be 2'-O-Methyl-2'-deoxycytidine
source                  1..40
                        mol_type = other DNA
                        organism = synthetic construct
misc_feature            1..11
                        note = RNA
misc_feature            12
                        note = DNA
misc_feature            13..23
                        note = RNA
misc_feature            24
                        note = DNA
misc_feature            25
                        note = RNA
misc_feature            26
                        note = DNA
misc_feature            27..40
                        note = RNA
SEQUENCE: 69
gcgtcgcggt ctcaggcgct gagtctgagt ttacctacgc                         40

SEQ ID NO: 70           moltype = DNA  length = 38
FEATURE                 Location/Qualifiers
misc_feature            1..38
                        note = Synthetic C5 specific aptamer
misc_difference         1
                        note = misc_feature - May be 2'-O-Methyl-2'-deoxyguanosine
misc_difference         2
                        note = misc_feature - May be 2'-O-Methyl-2'-deoxyguanosine
misc_difference         3
                        note = misc_feature - May be 2'-O-Methyl-2'-deoxyguanosine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be deoxycytidine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be deoxycytidine
```

```
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'OH-thymidine
misc_difference        24
                       note = misc_feature - May be deoxycytidine
misc_difference        25
                       note = misc_feature - May be 2'OH-thymidine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxycytidine
misc_difference        37
                       note = misc_feature - May be 2'-O-Methyl-2'-deoxycytidine
misc_difference        38
                       note = misc_feature - May be 2'-O-Methyl-2'-deoxycytidine
source                 1..38
                       mol_type = other DNA
                       organism = synthetic construct
misc_feature           1..10
                       note = RNA
misc_feature           11
                       note = DNA
misc_feature           12..22
                       note = RNA
misc_feature           23
                       note = DNA
misc_feature           24
                       note = RNA
misc_feature           25
                       note = DNA
misc_feature           26..38
                       note = RNA
SEQUENCE: 70
gggcgcggtc tcaggcgctg agtctgagtt tacctccc                          38

SEQ ID NO: 71          moltype = DNA  length = 39
FEATURE                Location/Qualifiers
misc_feature           1..39
                       note = Synthetic C5 specific aptamer
misc_difference        1
                       note = misc_feature - May be 2'-O-Methyl-2'-deoxyguanosine
misc_difference        2
                       note = misc_feature - May be 2'-fluoro-2'-deoxycytidine
misc_difference        3
                       note = misc_feature - May be 2'-O-Methyl-2'-deoxyguanosine
misc_difference        4
                       note = misc_feature - May be 2'-fluoro-2'-deoxycytidine
misc_difference        5
                       note = misc_feature - May be 2'-fluoro-2'-deoxycytidine
misc_difference        6
```

-continued

```
                      note = misc_feature - May be 2'OH-guanosine
misc_difference       7
                      note = misc_feature - May be 2'-fluoro-2'-deoxycytidine
misc_difference       8
                      note = misc_feature - May be 2'-O-Methyl-2'-deoxyguanosine
misc_difference       9
                      note = misc_feature - May be 2'-O-Methyl-2'-deoxyguanosine
misc_difference       10
                      note = misc_feature - May be 2'-fluoro-2'-deoxyuridine
misc_difference       11
                      note = misc_feature - May be deoxycytidine
misc_difference       12
                      note = misc_feature - May be 2'OH-thymidine
misc_difference       13
                      note = misc_feature - May be deoxycytidine
misc_difference       14
                      note = misc_feature - May be 2'-O-Methyl-2'-deoxyadenosine
misc_difference       15
                      note = misc_feature - May be 2'-O-Methyl-2'-deoxyguanosine
misc_difference       16
                      note = misc_feature - May be 2'-O-Methyl-2'-deoxyguanosine
misc_difference       17
                      note = misc_feature - May be deoxycytidine
misc_difference       18
                      note = misc_feature - May be 2'OH-guanosine
misc_difference       19
                      note = misc_feature - May be 2'-fluoro-2'-deoxycytidine
misc_difference       20
                      note = misc_feature - May be 2'-fluoro-2'-deoxyuridine
misc_difference       21
                      note = misc_feature - May be 2'-O-Methyl-2'-deoxyguanosine
misc_difference       22
                      note = misc_feature - May be 2'-O-Methyl-2'-deoxyadenosine
misc_difference       23
                      note = misc_feature - May be 2'-O-Methyl-2'-deoxyguanosine
misc_difference       24
                      note = misc_feature - May be 2'OH-thymidine
misc_difference       25
                      note = misc_feature - May be deoxycytidine
misc_difference       26
                      note = misc_feature - May be 2'OH-thymidine
misc_difference       27
                      note = misc_feature - May be 2'-O-Methyl-2'-deoxyguanosine
misc_difference       28
                      note = misc_feature - May be 2'-O-Methyl-2'-deoxyadenosine
misc_difference       29
                      note = misc_feature - May be 2'-O-Methyl-2'-deoxyguanosine
misc_difference       30
                      note = misc_feature - May be 2'-fluoro-2'-deoxyuridine
misc_difference       31
                      note = misc_feature - May be 2'-fluoro-2'-deoxyuridine
misc_difference       32
                      note = misc_feature - May be 2'-fluoro-2'-deoxyuridine
misc_difference       33
                      note = misc_feature - May be 2'OH-adenosine
misc_difference       34
                      note = misc_feature - May be 2'-fluoro-2'-deoxycytidine
misc_difference       35
                      note = misc_feature - May be 2'-fluoro-2'-deoxyuridine
misc_difference       36
                      note = misc_feature - May be 2'-O-Methyl-2'-deoxyguanosine
misc_difference       37
                      note = misc_feature - May be 2'-fluoro-2'-deoxycytidine
misc_difference       38
                      note = misc_feature - May be 2'-O-Methyl-2'-deoxyguanosine
misc_difference       39
                      note = misc_feature - May be 2'-O-Methyl-2'-deoxycytidine
source                1..39
                      mol_type = other DNA
                      organism = synthetic construct
misc_feature          1..11
                      note = RNA
misc_feature          12
                      note = DNA
misc_feature          13..23
                      note = RNA
misc_feature          24
                      note = DNA
misc_feature          25
```

```
                          note = RNA
misc_feature              26
                          note = DNA
misc_feature              27..39
                          note = RNA
SEQUENCE: 71
gcgccgcggt ctcaggcgct gagtctgagt ttactgcgc                        39

SEQ ID NO: 72             moltype = DNA  length = 43
FEATURE                   Location/Qualifiers
misc_feature              1..43
                          note = Synthetic C5 specific aptamer
misc_difference           1
                          note = misc_feature - May be 2'-O-Methyl-2'-deoxyguanosine
misc_difference           2
                          note = misc_feature - May be 2'-O-Methyl-2'-deoxyguanosine
misc_difference           3
                          note = misc_feature - May be 2'-O-Methyl-2'-deoxyadenosine
misc_difference           4
                          note = misc_feature - May be 2'-fluoro-2'-deoxycytidine
misc_difference           5
                          note = misc_feature - May be 2'-O-Methyl-2'-deoxyguanosine
misc_difference           6
                          note = misc_feature - May be 2'-fluoro-2'-deoxycytidine
misc_difference           7
                          note = misc_feature - May be 2'-fluoro-2'-deoxycytidine
misc_difference           8
                          note = misc_feature - May be 2'OH-guanosine
misc_difference           9
                          note = misc_feature - May be 2'-fluoro-2'-deoxycytidine
misc_difference           10
                          note = misc_feature - May be 2'-O-Methyl-2'-deoxyguanosine
misc_difference           11
                          note = misc_feature - May be 2'-O-Methyl-2'-deoxyguanosine
misc_difference           12
                          note = misc_feature - May be 2'-fluoro-2'-deoxyuridine
misc_difference           13
                          note = misc_feature - May be 2'-fluoro-2'-deoxycytidine
misc_difference           14
                          note = misc_feature - May be 2'-fluoro-2'-deoxyuridine
misc_difference           15
                          note = misc_feature - May be 2'-fluoro-2'-deoxycytidine
misc_difference           16
                          note = misc_feature - May be 2'-O-Methyl-2'-deoxyadenosine
misc_difference           17
                          note = misc_feature - May be 2'-O-Methyl-2'-deoxyguanosine
misc_difference           18
                          note = misc_feature - May be 2'-O-Methyl-2'-deoxyguanosine
misc_difference           19
                          note = misc_feature - May be 2'-fluoro-2'-deoxycytidine
misc_difference           20
                          note = misc_feature - May be 2'OH-guanosine
misc_difference           21
                          note = misc_feature - May be 2'-fluoro-2'-deoxycytidine
misc_difference           22
                          note = misc_feature - May be 2'-fluoro-2'-deoxyuridine
misc_difference           23
                          note = misc_feature - May be 2'-O-Methyl-2'-deoxyguanosine
misc_difference           24
                          note = misc_feature - May be 2'-O-Methyl-2'-deoxyadenosine
misc_difference           25
                          note = misc_feature - May be 2'-O-Methyl-2'-deoxyguanosine
misc_difference           26
                          note = misc_feature - May be 2'-fluoro-2'-deoxyuridine
misc_difference           27
                          note = misc_feature - May be 2'-fluoro-2'-deoxycytidine
misc_difference           28
                          note = misc_feature - May be 2'-fluoro-2'-deoxyuridine
misc_difference           29
                          note = misc_feature - May be 2'-O-Methyl-2'-deoxyguanosine
misc_difference           30
                          note = misc_feature - May be 2'-O-Methyl-2'-deoxyguanosine
misc_difference           31
                          note = misc_feature - May be 2'-fluoro-2'-deoxyuridine
misc_difference           32
                          note = misc_feature - May be 2'-fluoro-2'-deoxyuridine
misc_difference           33
                          note = misc_feature - May be 2'-fluoro-2'-deoxyuridine
misc_difference           34
```

```
                        note = misc_feature - May be 2'OH-adenosine
misc_difference         35
                        note = misc_feature - May be 2'-fluoro-2'-deoxycytidine
misc_difference         36
                        note = misc_feature - May be 2'-fluoro-2'-deoxyuridine
misc_difference         37
                        note = misc_feature - May be 2'-O-Methyl-2'-deoxyguanosine
misc_difference         38
                        note = misc_feature - May be 2'-fluoro-2'-deoxycytidine
misc_difference         39
                        note = misc_feature - May be 2'-O-Methyl-2'-deoxyguanosine
misc_difference         40
                        note = misc_feature - May be 2'-fluoro-2'-deoxyuridine
misc_difference         41
                        note = misc_feature - May be 2'-fluoro-2'-deoxycytidine
misc_difference         42
                        note = misc_feature - May be 2'-fluoro-2'-deoxyuridine
misc_difference         43
                        note = misc_feature - May be an inverted orientation T
                         (3'-3'-linked)
source                  1..43
                        mol_type = other DNA
                        organism = synthetic construct
misc_feature            1..42
                        note = RNA
misc_feature            43
                        note = DNA
SEQUENCE: 72
ggacgccgcg gtctcaggcg ctgagtctgg tttactgcgt ctt                    43

SEQ ID NO: 73           moltype = DNA  length = 42
FEATURE                 Location/Qualifiers
misc_feature            1..42
                        note = Synthetic C5 specific aptamer
misc_difference         1
                        note = misc_feature - May be 2'-O-Methyl-2'-deoxyguanosine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-O-Methyl-2'-deoxyguanosine
misc_difference         5
                        note = misc_feature - May be 2'-fluoro-2'-deoxycytidine
misc_difference         6
                        note = misc_feature - May be 2'-fluoro-2'-deoxycytidine
misc_difference         7
                        note = misc_feature - May be 2'OH-guanosine
misc_difference         8
                        note = misc_feature - May be 2'-fluoro-2'-deoxycytidine
misc_difference         9
                        note = misc_feature - May be 2'-O-Methyl-2'-deoxyguanosine
misc_difference         10
                        note = misc_feature - May be 2'-O-Methyl-2'-deoxyguanosine
misc_difference         11
                        note = misc_feature - May be 2'-fluoro-2'-deoxyuridine
misc_difference         12
                        note = misc_feature - May be deoxycytidine
misc_difference         13
                        note = misc_feature - May be 2'OH-thymidine
misc_difference         14
                        note = misc_feature - May be deoxycytidine
misc_difference         15
                        note = misc_feature - May be 2'-O-Methyl-2'-deoxyadenosine
misc_difference         16
                        note = misc_feature - May be 2'-O-Methyl-2'-deoxyguanosine
misc_difference         17
                        note = misc_feature - May be 2'-O-Methyl-2'-deoxyguanosine
misc_difference         18
                        note = misc_feature - May be deoxycytidine
misc_difference         19
                        note = misc_feature - May be 2'OH-guanosine
misc_difference         20
                        note = misc_feature - May be 2'-O-Methyl-2'-deoxycytidine
misc_difference         21
                        note = misc_feature - May be 2'-O-Methyl-2'-deoxyuridine
misc_difference         22
                        note = misc_feature - May be 2'-O-Methyl-2'-deoxyguanosine
misc_difference         23
```

-continued

```
                        note = misc_feature - May be 2'-O-Methyl-2'-deoxyadenosine
misc_difference         24
                        note = misc_feature - May be 2'-O-Methyl-2'-deoxyguanosine
misc_difference         25
                        note = misc_feature - May be 2'OH-thymidine
misc_difference         26
                        note = misc_feature - May be deoxycytidine
misc_difference         27
                        note = misc_feature - May be 2'OH-thymidine
misc_difference         28
                        note = misc_feature - May be 2'-O-Methyl-2'-deoxyguanosine
misc_difference         29
                        note = misc_feature - May be 2'-O-Methyl-2'-deoxyadenosine
misc_difference         30
                        note = misc_feature - May be 2'-O-Methyl-2'-deoxyguanosine
misc_difference         31
                        note = misc_feature - May be 2'OH-thymidine
misc_difference         32
                        note = misc_feature - May be 2'-fluoro-2'-deoxyuridine
misc_difference         33
                        note = misc_feature - May be 2'-fluoro-2'-deoxyuridine
misc_difference         34
                        note = misc_feature - May be 2'OH-adenosine
misc_difference         35
                        note = misc_feature - May be deoxycytidine
misc_difference         36
                        note = misc_feature - May be deoxycytidine
misc_difference         37
                        note = misc_feature - May be 2'OH-thymidine
misc_difference         38
                        note = misc_feature - May be 2'-O-Methyl-2'-deoxyguanosine
misc_difference         39
                        note = misc_feature - May be 2'-fluoro-2'-deoxycytidine
misc_difference         40
                        note = misc_feature - May be 2'-O-Methyl-2'-deoxyguanosine
misc_difference         41
                        note = misc_feature - May be 2'-O-Methyl-2'-deoxycytidine
misc_difference         42
                        note = misc_feature - May be 2'-O-Methyl-2'-deoxycytidine
source                  1..42
                        mol_type = other DNA
                        organism = synthetic construct
misc_feature            1..12
                        note = RNA
misc_feature            13
                        note = DNA
misc_feature            14..24
                        note = RNA
misc_feature            25
                        note = DNA
misc_feature            26
                        note = RNA
misc_feature            27
                        note = DNA
misc_feature            28..30
                        note = RNA
misc_feature            31
                        note = DNA
misc_feature            32..36
                        note = RNA
misc_feature            37
                        note = DNA
misc_feature            38..42
                        note = RNA
SEQUENCE: 73
ggcgccgcgg tctcaggcgc tgagtctgag tttacctgcg cc                    42

SEQ ID NO: 74           moltype = DNA  length = 40
FEATURE                 Location/Qualifiers
misc_feature            1..40
                        note = Synthetic C5 specific aptamer
misc_difference         1
                        note = misc_feature - May be 2'-O-Methyl-2'-deoxyguanosine
misc_difference         2
                        note = misc_feature - May be 2'-O-Methyl-2'-deoxyguanosine
misc_difference         3
                        note = misc_feature - May be 2'-O-Methyl-2'-deoxycytidine
misc_difference         4
                        note = misc_feature - May be 2'-O-Methyl-2'-deoxyguanosine
```

-continued

| | |
|---|---|
| misc_difference | 5<br>note = misc_feature - May be 2′-fluoro-2′-deoxycytidine |
| misc_difference | 6<br>note = misc_feature - May be 2′-fluoro-2′-deoxycytidine |
| misc_difference | 7<br>note = misc_feature - May be 2′OH-guanosine |
| misc_difference | 8<br>note = misc_feature - May be 2′-fluoro-2′-deoxycytidine |
| misc_difference | 9<br>note = misc_feature - May be 2′-O-Methyl-2′-deoxyguanosine |
| misc_difference | 10<br>note = misc_feature - May be 2′-O-Methyl-2′-deoxyguanosine |
| misc_difference | 11<br>note = misc_feature - May be 2′-fluoro-2′-deoxyuridine |
| misc_difference | 12<br>note = misc_feature - May be deoxycytidine |
| misc_difference | 13<br>note = misc_feature - May be 2′OH-thymidine |
| misc_difference | 14<br>note = misc_feature - May be deoxycytidine |
| misc_difference | 15<br>note = misc_feature - May be 2′-O-Methyl-2′-deoxyadenosine |
| misc_difference | 16<br>note = misc_feature - May be 2′-O-Methyl-2′-deoxyguanosine |
| misc_difference | 17<br>note = misc_feature - May be 2′-O-Methyl-2′-deoxyguanosine |
| misc_difference | 18<br>note = misc_feature - May be deoxycytidine |
| misc_difference | 19<br>note = misc_feature - May be 2′OH-guanosine |
| misc_difference | 20<br>note = misc_feature - May be 2′-O-Methyl-2′-deoxycytidine |
| misc_difference | 21<br>note = misc_feature - May be 2′-O-Methyl-2′-deoxyuridine |
| misc_difference | 22<br>note = misc_feature - May be 2′-O-Methyl-2′-deoxyguanosine |
| misc_difference | 23<br>note = misc_feature - May be 2′-O-Methyl-2′-deoxyadenosine |
| misc_difference | 24<br>note = misc_feature - May be 2′-O-Methyl-2′-deoxyguanosine |
| misc_difference | 25<br>note = misc_feature - May be 2′OH-thymidine |
| misc_difference | 26<br>note = misc_feature - May be deoxycytidine |
| misc_difference | 27<br>note = misc_feature - May be 2′OH-thymidine |
| misc_difference | 28<br>note = misc_feature - May be 2′-O-Methyl-2′-deoxyguanosine |
| misc_difference | 29<br>note = misc_feature - May be 2′-O-Methyl-2′-deoxyadenosine |
| misc_difference | 30<br>note = misc_feature - May be 2′-O-Methyl-2′-deoxythymidine |
| misc_difference | 31<br>note = misc_feature - May be 2′OH-thymidine |
| misc_difference | 32<br>note = misc_feature - May be 2′OH-adenosine |
| misc_difference | 33<br>note = misc_feature - May be deoxycytidine |
| misc_difference | 34<br>note = misc_feature - May be deoxycytidine |
| misc_difference | 35<br>note = misc_feature - May be 2′OH-thymidine |
| misc_difference | 36<br>note = misc_feature - May be 2′-O-Methyl-2′-deoxyguanosine |
| misc_difference | 37<br>note = misc_feature - May be deoxycytidine |
| misc_difference | 38<br>note = misc_feature - May be 2′-O-Methyl-2′-deoxyguanosine |
| misc_difference | 39<br>note = misc_feature - May be 2′-O-Methyl-2′-deoxycytidine |
| misc_difference | 40<br>note = misc_feature - May be 2′-O-Methyl-2′-deoxycytidine |
| source | 1..40<br>mol_type = other DNA<br>organism = synthetic construct |
| misc_feature | 1..12<br>note = RNA |
| misc_feature | 13<br>note = DNA |

```
misc_feature          14..24
                      note = RNA
misc_feature          25
                      note = DNA
misc_feature          26
                      note = RNA
misc_feature          27
                      note = DNA
misc_feature          28..29
                      note = RNA
misc_feature          30..31
                      note = DNA
misc_feature          32..34
                      note = RNA
misc_feature          35
                      note = DNA
misc_feature          36..40
                      note = RNA
SEQUENCE: 74
ggcgccgcgg tctcaggcgc tgagtctgat tacctgcgcc                        40

SEQ ID NO: 75         moltype = DNA  length = 42
FEATURE               Location/Qualifiers
misc_feature          1..42
                      note = Synthetic C5 specific aptamer
misc_difference       1
                      note = misc_feature - May be 2'-O-Methyl-2'-deoxyguanosine
misc_difference       2
                      note = misc_feature - May be 2'-O-Methyl-2'-deoxyguanosine
misc_difference       3
                      note = misc_feature - May be 2'-O-Methyl-2'-deoxycytidine
misc_difference       4
                      note = misc_feature - May be 2'-O-Methyl-2'-deoxyguanosine
misc_difference       5
                      note = misc_feature - May be deoxycytidine
misc_difference       6
                      note = misc_feature - May be deoxycytidine
misc_difference       7
                      note = misc_feature - May be 2'OH-guanosine
misc_difference       8
                      note = misc_feature - May be deoxycytidine
misc_difference       9
                      note = misc_feature - May be 2'-O-Methyl-2'-deoxyguanosine
misc_difference       10
                      note = misc_feature - May be 2'-O-Methyl-2'-deoxyguanosine
misc_difference       11
                      note = misc_feature - May be 2'OH-thymidine
misc_difference       12
                      note = misc_feature - May be deoxycytidine
misc_difference       13
                      note = misc_feature - May be 2'OH-thymidine
misc_difference       14
                      note = misc_feature - May be deoxycytidine
misc_difference       15
                      note = misc_feature - May be 2'-O-Methyl-2'-deoxyadenosine
misc_difference       16
                      note = misc_feature - May be 2'-O-Methyl-2'-deoxyguanosine
misc_difference       17
                      note = misc_feature - May be 2'-O-Methyl-2'-deoxyguanosine
misc_difference       18
                      note = misc_feature - May be deoxycytidine
misc_difference       19
                      note = misc_feature - May be 2'OH-guanosine
misc_difference       20
                      note = misc_feature - May be 2'-O-Methyl-2'-deoxycytidine
misc_difference       21
                      note = misc_feature - May be 2'-O-Methyl-2'-deoxyuridine
misc_difference       22
                      note = misc_feature - May be 2'-O-Methyl-2'-deoxyguanosine
misc_difference       23
                      note = misc_feature - May be 2'-O-Methyl-2'-deoxyadenosine
misc_difference       24
                      note = misc_feature - May be 2'-O-Methyl-2'-deoxyguanosine
misc_difference       25
                      note = misc_feature - May be 2'OH-thymidine
misc_difference       26
                      note = misc_feature - May be deoxycytidine
misc_difference       27
                      note = misc_feature - May be 2'OH-thymidine
```

```
misc_difference        28
                       note = misc_feature - May be 2'-O-Methyl-2'-deoxyguanosine
misc_difference        29
                       note = misc_feature - May be 2'-O-Methyl-2'-deoxyadenosine
misc_difference        30
                       note = misc_feature - May be 2'-O-Methyl-2'-deoxyguanosine
misc_difference        31
                       note = misc_feature - May be 2'OH-thymidine
misc_difference        32
                       note = misc_feature - May be 2'OH-thymidine
misc_difference        33
                       note = misc_feature - May be 2'OH-thymidine
misc_difference        34
                       note = misc_feature - May be 2'-O-Methyl-2'-deoxyadenosine
misc_difference        35
                       note = misc_feature - May be deoxycytidine
misc_difference        36
                       note = misc_feature - May be deoxycytidine
misc_difference        37
                       note = misc_feature - May be 2'OH-thymidine
misc_difference        38
                       note = misc_feature - May be 2'-O-Methyl-2'-deoxyguanosine
misc_difference        39
                       note = misc_feature - May be deoxycytidine
misc_difference        40
                       note = misc_feature - May be 2'-O-Methyl-2'-deoxyguanosine
misc_difference        41
                       note = misc_feature - May be 2'-O-Methyl-2'-deoxycytidine
misc_difference        42
                       note = misc_feature - May be 2'-O-Methyl-2'-deoxycytidine
source                 1..42
                       mol_type = other DNA
                       organism = synthetic construct
misc_feature           1..10
                       note = RNA
misc_feature           11
                       note = DNA
misc_feature           12
                       note = RNA
misc_feature           13
                       note = DNA
misc_feature           14..24
                       note = RNA
misc_feature           25
                       note = DNA
misc_feature           26
                       note = RNA
misc_feature           27
                       note = DNA
misc_feature           28..30
                       note = RNA
misc_feature           31..33
                       note = DNA
misc_feature           34..36
                       note = RNA
misc_feature           37
                       note = DNA
misc_feature           38..42
                       note = RNA
SEQUENCE: 75
ggcgccgcgg tctcaggcgc tgagtctgag tttacctgcg cc                      42

SEQ ID NO: 76          moltype = DNA  length = 42
FEATURE                Location/Qualifiers
misc_feature           1..42
                       note = Synthetic C5 specific aptamer
misc_difference        1
                       note = misc_feature - May be 2'-O-Methyl-2'-deoxyguanosine
misc_difference        2
                       note = misc_feature - May be 2'-O-Methyl-2'-deoxyguanosine
misc_difference        3
                       note = misc_feature - May be 2'-O-Methyl-2'-deoxycytidine
misc_difference        4
                       note = misc_feature - May be 2'-O-Methyl-2'-deoxyguanosine
misc_difference        5
                       note = misc_feature - May be deoxycytidine
misc_difference        6
                       note = misc_feature - May be deoxycytidine
misc_difference        7
```

-continued

```
                        note = misc_feature - May be 2'OH-guanosine
misc_difference         8
                        note = misc_feature - May be deoxycytidine
misc_difference         9
                        note = misc_feature - May be 2'-O-Methyl-2'-deoxyguanosine
misc_difference         10
                        note = misc_feature - May be 2'-O-Methyl-2'-deoxyguanosine
misc_difference         11
                        note = misc_feature - May be 2'OH-thymidine
misc_difference         12
                        note = misc_feature - May be deoxycytidine
misc_difference         13
                        note = misc_feature - May be 2'-O-Methyl-2'-deoxyuridine
misc_difference         14
                        note = misc_feature - May be 2'-O-Methyl-2'-deoxycytidine
misc_difference         15
                        note = misc_feature - May be 2'-O-Methyl-2'-deoxyadenosine
misc_difference         16
                        note = misc_feature - May be 2'-O-Methyl-2'-deoxyguanosine
misc_difference         17
                        note = misc_feature - May be 2'-O-Methyl-2'-deoxyguanosine
misc_difference         18
                        note = misc_feature - May be deoxycytidine
misc_difference         19
                        note = misc_feature - May be 2'OH-guanosine
misc_difference         20
                        note = misc_feature - May be 2'-O-Methyl-2'-deoxycytidine
misc_difference         21
                        note = misc_feature - May be 2'-O-Methyl-2'-deoxyuridine
misc_difference         22
                        note = misc_feature - May be 2'-O-Methyl-2'-deoxyguanosine
misc_difference         23
                        note = misc_feature - May be 2'-O-Methyl-2'-deoxyadenosine
misc_difference         24
                        note = misc_feature - May be 2'-O-Methyl-2'-deoxyguanosine
misc_difference         25
                        note = misc_feature - May be 2'-O-Methyl-2'-deoxyuridine
misc_difference         26
                        note = misc_feature - May be 2'-O-Methyl-2'-deoxycytidine
misc_difference         27
                        note = misc_feature - May be 2'-O-Methyl-2'-deoxyuridine
misc_difference         28
                        note = misc_feature - May be 2'-O-Methyl-2'-deoxyguanosine
misc_difference         29
                        note = misc_feature - May be 2'-O-Methyl-2'-deoxyadenosine
misc_difference         30
                        note = misc_feature - May be 2'-O-Methyl-2'-deoxyguanosine
misc_difference         31
                        note = misc_feature - May be 2'OH-thymidine
misc_difference         32
                        note = misc_feature - May be 2'OH-thymidine
misc_difference         33
                        note = misc_feature - May be 2'OH-thymidine
misc_difference         34
                        note = misc_feature - May be 2'-O-Methyl-2'-deoxyadenosine
misc_difference         35
                        note = misc_feature - May be deoxycytidine
misc_difference         36
                        note = misc_feature - May be deoxycytidine
misc_difference         37
                        note = misc_feature - May be 2'OH-thymidine
misc_difference         38
                        note = misc_feature - May be 2'-O-Methyl-2'-deoxyguanosine
misc_difference         39
                        note = misc_feature - May be deoxycytidine
misc_difference         40
                        note = misc_feature - May be 2'-O-Methyl-2'-deoxyguanosine
misc_difference         41
                        note = misc_feature - May be 2'-O-Methyl-2'-deoxycytidine
misc_difference         42
                        note = misc_feature - May be 2'-O-Methyl-2'-deoxycytidine
source                  1..42
                        mol_type = other DNA
                        organism = synthetic construct
misc_feature            1..10
                        note = RNA
misc_feature            11
                        note = DNA
misc_feature            12..30
```

```
                        note = RNA
misc_feature            31..33
                        note = DNA
misc_feature            34..36
                        note = RNA
misc_feature            37
                        note = DNA
misc_feature            38..42
                        note = RNA
SEQUENCE: 76
ggcgccgcgg tctcaggcgc tgagtctgag tttacctgcg cc                    42

SEQ ID NO: 77           moltype = RNA  length = 40
FEATURE                 Location/Qualifiers
misc_feature            1..40
                        note = Synthetic C5 specific aptamer
misc_difference         1
                        note = misc_feature - May have biotin conjugated to the 5'
                         end
misc_difference         1
                        note = misc_feature - May be 2'OH-adenosine
misc_difference         2
                        note = misc_feature - May be 2'OH-guanosine
misc_difference         3
                        note = misc_feature - May be 2'-fluoro-2'-deoxycytidine
misc_difference         4
                        note = misc_feature - May be 2'-O-Methyl-2'-deoxyguanosine
misc_difference         5
                        note = misc_feature - May be 2'-fluoro-2'-deoxycytidine
misc_difference         6
                        note = misc_feature - May be 2'-fluoro-2'-deoxycytidine
misc_difference         7
                        note = misc_feature - May be 2'OH-guanosine
misc_difference         8
                        note = misc_feature - May be 2'-fluoro-2'-deoxycytidine
misc_difference         9
                        note = misc_feature - May be 2'-O-Methyl-2'-deoxyguanosine
misc_difference         10
                        note = misc_feature - May be 2'-O-Methyl-2'-deoxyguanosine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-fluoro-2'-deoxyuridine
misc_difference         14
                        note = misc_feature - May be 2'-fluoro-2'-deoxycytidine
misc_difference         15
                        note = misc_feature - May be 2'-O-Methyl-2'-deoxyadenosine
misc_difference         16
                        note = misc_feature - May be 2'-O-Methyl-2'-deoxyguanosine
misc_difference         17
                        note = misc_feature - May be 2'-O-Methyl-2'-deoxyguanosine
misc_difference         18
                        note = misc_feature - May be 2'-fluoro-2'-deoxycytidine
misc_difference         19
                        note = misc_feature - May be 2'OH-guanosine
misc_difference         20
                        note = misc_feature - May be 2'-fluoro-2'-deoxycytidine
misc_difference         21
                        note = misc_feature - May be 2'-fluoro-2'-deoxyuridine
misc_difference         22
                        note = misc_feature - May be 2'-O-Methyl-2'-deoxyguanosine
misc_difference         23
                        note = misc_feature - May be 2'-O-Methyl-2'-deoxyadenosine
misc_difference         24
                        note = misc_feature - May be 2'-O-Methyl-2'-deoxyguanosine
misc_difference         25
                        note = misc_feature - May be 2'-fluoro-2'-deoxyuridine
misc_difference         26
                        note = misc_feature - May be 2'-fluoro-2'-deoxycytidine
misc_difference         27
                        note = misc_feature - May be 2'-fluoro-2'-deoxyuridine
misc_difference         28
                        note = misc_feature - May be 2'-O-Methyl-2'-deoxyguanosine
misc_difference         29
                        note = misc_feature - May be 2'-O-Methyl-2'-deoxyadenosine
misc_difference         30
                        note = misc_feature - May be 2'-O-Methyl-2'-deoxyguanosine
```

```
misc_difference        31
                       note = misc_feature - May be 2'-fluoro-2'-deoxyuridine
misc_difference        32
                       note = misc_feature - May be 2'-fluoro-2'-deoxyuridine
misc_difference        33
                       note = misc_feature - May be 2'-fluoro-2'-deoxyuridine
misc_difference        34
                       note = misc_feature - May be 2'OH-adenosine
misc_difference        35
                       note = misc_feature - May be 2'-fluoro-2'-deoxycytidine
misc_difference        36
                       note = misc_feature - May be 2'-fluoro-2'-deoxycytidine
misc_difference        37
                       note = misc_feature - May be 2'-fluoro-2'-deoxyuridine
misc_difference        38
                       note = misc_feature - May be 2'-O-Methyl-2'-deoxyguanosine
misc_difference        39
                       note = misc_feature - May be 2'-fluoro-2'-deoxycytidine
misc_difference        40
                       note = misc_feature - May be 2'-O-Methyl-2'-deoxyguanosine
source                 1..40
                       mol_type = other RNA
                       organism = synthetic construct
SEQUENCE: 77
agcgccgcgg tctcaggcgc tgagtctgag tttacctgcg                        40

SEQ ID NO: 78          moltype = DNA  length = 42
FEATURE                Location/Qualifiers
misc_feature           1..42
                       note = Synthetic C5 specific aptamer
misc_difference        1
                       note = misc_feature - May be 2'-O-Methyl-2'-deoxyguanosine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-O-Methyl-2'-deoxyguanosine
misc_difference        5
                       note = misc_feature - May be 2'-fluoro-2'-deoxycytidine
misc_difference        6
                       note = misc_feature - May be 2'-fluoro-2'-deoxycytidine
misc_difference        7
                       note = misc_feature - May be 2'OH-guanosine
misc_difference        8
                       note = misc_feature - May be 2'-fluoro-2'-deoxycytidine
misc_difference        9
                       note = misc_feature - May be 2'-O-Methyl-2'-deoxyguanosine
misc_difference        10
                       note = misc_feature - May be 2'-O-Methyl-2'-deoxyguanosine
misc_difference        11
                       note = misc_feature - May be 2'-fluoro-2'-deoxyuridine
misc_difference        12
                       note = misc_feature - May be deoxycytidine
misc_difference        13
                       note = misc_feature - May be 2'OH-thymidine
misc_difference        14
                       note = misc_feature - May be deoxycytidine
misc_difference        15
                       note = misc_feature - May be 2'-O-Methyl-2'-deoxyadenosine
misc_difference        16
                       note = misc_feature - May be 2'-O-Methyl-2'-deoxyguanosine
misc_difference        17
                       note = misc_feature - May be 2'-O-Methyl-2'-deoxyguanosine
misc_difference        18
                       note = misc_feature - May be deoxycytidine
misc_difference        19
                       note = misc_feature - May be 2'OH-guanosine
misc_difference        20
                       note = misc_feature - May be 2'-fluoro-2'-deoxycytidine
misc_difference        21
                       note = misc_feature - May be 2'-fluoro-2'-deoxyuridine
misc_difference        22
                       note = misc_feature - May be 2'-O-Methyl-2'-deoxyguanosine
misc_difference        23
                       note = misc_feature - May be 2'-O-Methyl-2'-deoxyadenosine
misc_difference        24
                       note = misc_feature - May be 2'-O-Methyl-2'-deoxyguanosine
misc_difference        25
```

```
                        note = misc_feature - May be 2'OH-thymidine
misc_difference         26
                        note = misc_feature - May be deoxycytidine
misc_difference         27
                        note = misc_feature - May be 2'OH-thymidine
misc_difference         28
                        note = misc_feature - May be 2'-O-Methyl-2'-deoxyguanosine
misc_difference         29
                        note = misc_feature - May be 2'-O-Methyl-2'-deoxyadenosine
misc_difference         30
                        note = misc_feature - May be 2'-O-Methyl-2'-deoxyguanosine
misc_difference         31
                        note = misc_feature - May be 2'-fluoro-2'-deoxyuridine
misc_difference         32
                        note = misc_feature - May be 2'-fluoro-2'-deoxyuridine
misc_difference         33
                        note = misc_feature - May be 2'-fluoro-2'-deoxyuridine
misc_difference         34
                        note = misc_feature - May be 2'OH-adenosine
misc_difference         35
                        note = misc_feature - May be 2'-fluoro-2'-deoxycytidine
misc_difference         36
                        note = misc_feature - May be 2'-fluoro-2'-deoxycytidine
misc_difference         37
                        note = misc_feature - May be 2'-fluoro-2'-deoxyuridine
misc_difference         38
                        note = misc_feature - May be 2'-O-Methyl-2'-deoxyguanosine
misc_difference         39
                        note = misc_feature - May be 2'-fluoro-2'-deoxycytidine
misc_difference         40
                        note = misc_feature - May be 2'-O-Methyl-2'-deoxyguanosine
misc_difference         41
                        note = misc_feature - May be 2'-O-Methyl-2'-deoxycytidine
misc_difference         42
                        note = misc_feature - May be 2'-O-Methyl-2'-deoxycytidine
source                  1..42
                        mol_type = other DNA
                        organism = synthetic construct
misc_feature            1..12
                        note = RNA
misc_feature            13
                        note = DNA
misc_feature            14..24
                        note = RNA
misc_feature            25
                        note = DNA
misc_feature            26
                        note = RNA
misc_feature            27
                        note = DNA
misc_feature            28..42
                        note = RNA
SEQUENCE: 78
ggcgccgcgg tctcaggcgc tgagtctgag tttacctgcg cc                      42

SEQ ID NO: 79           moltype = RNA  length = 42
FEATURE                 Location/Qualifiers
misc_feature            1..42
                        note = Synthetic C5 specific aptamer
misc_difference         1
                        note = misc_feature - May be 2'-O-Methyl-2'-deoxyguanosine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-O-Methyl-2'-deoxyguanosine
misc_difference         5
                        note = misc_feature - May be 2'-fluoro-2'-deoxycytidine
misc_difference         6
                        note = misc_feature - May be 2'-fluoro-2'-deoxycytidine
misc_difference         7
                        note = misc_feature - May be 2'OH-guanosine
misc_difference         8
                        note = misc_feature - May be 2'-fluoro-2'-deoxycytidine
misc_difference         9
                        note = misc_feature - May be 2'-O-Methyl-2'-deoxyguanosine
misc_difference         10
                        note = misc_feature - May be 2'-O-Methyl-2'-deoxyguanosine
```

```
misc_difference        11
                       note = misc_feature - May be 2'-fluoro-2'-deoxyuridine
misc_difference        12
                       note = misc_feature - May be 2'-O-Methyl-2'-deoxycytidine
misc_difference        13
                       note = misc_feature - May be 2'-O-Methyl-2'-deoxyuridine
misc_difference        14
                       note = misc_feature - May be 2'-O-Methyl-2'-deoxycytidine
misc_difference        15
                       note = misc_feature - May be 2'-O-Methyl-2'-deoxyadenosine
misc_difference        16
                       note = misc_feature - May be 2'-O-Methyl-2'-deoxyguanosine
misc_difference        17
                       note = misc_feature - May be 2'-O-Methyl-2'-deoxyguanosine
misc_difference        18
                       note = misc_feature - May be 2'-O-Methyl-2'-deoxycytidine
misc_difference        19
                       note = misc_feature - May be 2'OH-guanosine
misc_difference        20
                       note = misc_feature - May be 2'-fluoro-2'-deoxycytidine
misc_difference        21
                       note = misc_feature - May be 2'-fluoro-2'-deoxyuridine
misc_difference        22
                       note = misc_feature - May be 2'-O-Methyl-2'-deoxyguanosine
misc_difference        23
                       note = misc_feature - May be 2'-O-Methyl-2'-deoxyadenosine
misc_difference        24
                       note = misc_feature - May be 2'-O-Methyl-2'-deoxyguanosine
misc_difference        25
                       note = misc_feature - May be 2'-O-Methyl-2'-deoxyuridine
misc_difference        26
                       note = misc_feature - May be 2'-O-Methyl-2'-deoxycytidine
misc_difference        27
                       note = misc_feature - May be 2'-O-Methyl-2'-deoxyuridine
misc_difference        28
                       note = misc_feature - May be 2'-O-Methyl-2'-deoxyguanosine
misc_difference        29
                       note = misc_feature - May be 2'-O-Methyl-2'-deoxyadenosine
misc_difference        30
                       note = misc_feature - May be 2'-O-Methyl-2'-deoxyguanosine
misc_difference        31
                       note = misc_feature - May be 2'-fluoro-2'-deoxyuridine
misc_difference        32
                       note = misc_feature - May be 2'-fluoro-2'-deoxyuridine
misc_difference        33
                       note = misc_feature - May be 2'-fluoro-2'-deoxyuridine
misc_difference        34
                       note = misc_feature - May be 2'OH-adenosine
misc_difference        35
                       note = misc_feature - May be 2'-fluoro-2'-deoxycytidine
misc_difference        36
                       note = misc_feature - May be 2'-fluoro-2'-deoxycytidine
misc_difference        37
                       note = misc_feature - May be 2'-fluoro-2'-deoxyuridine
misc_difference        38
                       note = misc_feature - May be 2'-O-Methyl-2'-deoxyguanosine
misc_difference        39
                       note = misc_feature - May be 2'-fluoro-2'-deoxycytidine
misc_difference        40
                       note = misc_feature - May be 2'-O-Methyl-2'-deoxyguanosine
misc_difference        41
                       note = misc_feature - May be 2'-O-Methyl-2'-deoxycytidine
misc_difference        42
                       note = misc_feature - May be 2'-O-Methyl-2'-deoxycytidine
source                 1..42
                       mol_type = other RNA
                       organism = synthetic construct
SEQUENCE: 79
ggcgccgcgg tctcaggcgc tgagtctgag tttacctgcg cc                    42

SEQ ID NO: 80          moltype = DNA  length = 39
FEATURE                Location/Qualifiers
misc_feature           1..39
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
```

-continued

| | |
|---|---|
| | note = misc_feature - May be 2'-fluoro-2'-deoxycytidine |
| misc_difference | 4 |
| | note = misc_feature - May be 2'-fluoro-2'-deoxycytidine |
| misc_difference | 5 |
| | note = misc_feature - May be 2'OH-guanosine |
| misc_difference | 6 |
| | note = misc_feature - May be 2'-fluoro-2'-deoxycytidine |
| misc_difference | 7 |
| | note = misc_feature - May be 2'-O-Methyl-2'-deoxyguanosine |
| misc_difference | 8 |
| | note = misc_feature - May be 2'-O-Methyl-2'-deoxyguanosine |
| misc_difference | 9 |
| | note = misc_feature - May be 2'-fluoro-2'-deoxyuridine |
| misc_difference | 10 |
| | note = misc_feature - May be 2'-fluoro-2'-deoxycytidine |
| misc_difference | 11 |
| | note = misc_feature - May be 2'-fluoro-2'-deoxyuridine |
| misc_difference | 12 |
| | note = misc_feature - May be 2'-fluoro-2'-deoxycytidine |
| misc_difference | 13 |
| | note = misc_feature - May be 2'-O-Methyl-2'-deoxyadenosine |
| misc_difference | 14 |
| | note = misc_feature - May be 2'-O-Methyl-2'-deoxyguanosine |
| misc_difference | 15 |
| | note = misc_feature - May be 2'-O-Methyl-2'-deoxyguanosine |
| misc_difference | 16 |
| | note = misc_feature - May be 2'-fluoro-2'-deoxycytidine |
| misc_difference | 17 |
| | note = misc_feature - May be 2'OH-guanosine |
| misc_difference | 18 |
| | note = misc_feature - May be 2'-fluoro-2'-deoxycytidine |
| misc_difference | 19 |
| | note = misc_feature - May be 2'-fluoro-2'-deoxyuridine |
| misc_difference | 20 |
| | note = misc_feature - May be 2'-O-Methyl-2'-deoxyguanosine |
| misc_difference | 21 |
| | note = misc_feature - May be 2'-O-Methyl-2'-deoxyadenosine |
| misc_difference | 22 |
| | note = misc_feature - May be 2'-O-Methyl-2'-deoxyguanosine |
| misc_difference | 23 |
| | note = misc_feature - May be 2'-fluoro-2'-deoxyuridine |
| misc_difference | 24 |
| | note = misc_feature - May be 2'-fluoro-2'-deoxycytidine |
| misc_difference | 25 |
| | note = misc_feature - May be 2'-fluoro-2'-deoxyuridine |
| misc_difference | 26 |
| | note = misc_feature - May be 2'-O-Methyl-2'-deoxyguanosine |
| misc_difference | 27 |
| | note = misc_feature - May be 2'-O-Methyl-2'-deoxyadenosine |
| misc_difference | 28 |
| | note = misc_feature - May be 2'-O-Methyl-2'-deoxyguanosine |
| misc_difference | 29 |
| | note = misc_feature - May be 2'-fluoro-2'-deoxyuridine |
| misc_difference | 30 |
| | note = misc_feature - May be 2'-fluoro-2'-deoxyuridine |
| misc_difference | 31 |
| | note = misc_feature - May be 2'-fluoro-2'-deoxyuridine |
| misc_difference | 32 |
| | note = misc_feature - May be 2'-O-Methyl-2'-deoxyadenosine |
| misc_difference | 33 |
| | note = misc_feature - May be 2'-fluoro-2'-deoxycytidine |
| misc_difference | 34 |
| | note = misc_feature - May be 2'-fluoro-2'-deoxycytidine |
| misc_difference | 35 |
| | note = misc_feature - May be 2'-fluoro-2'-deoxyuridine |
| misc_difference | 36 |
| | note = misc_feature - May be 2'-O-Methyl-2'-deoxyguanosine |
| misc_difference | 37 |
| | note = misc_feature - May be 2'-fluoro-2'-deoxycytidine |
| misc_difference | 38 |
| | note = misc_feature - May be 2'-O-Methyl-2'-deoxyguanosine |
| misc_difference | 39 |
| | note = misc_feature - May be an inverted orientation T (3'-3'-linked) |
| source | 1..39 |
| | mol_type = other DNA |
| | organism = synthetic construct |
| misc_feature | 1..38 |
| | note = RNA |

```
misc_feature            39
                        note = DNA
SEQUENCE: 80
cgccgcggtc tcaggcgctg agtctgagtt tacctgcgt                          39

SEQ ID NO: 81           moltype = DNA  length = 39
FEATURE                 Location/Qualifiers
misc_feature            1..39
                        note = Synthetic C5 specific aptamer
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be 2'-fluoro-2'-deoxycytidine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be 2'-fluoro-2'-deoxycytidine
misc_difference         17
                        note = misc_feature - May be 2'OH-guanosine
misc_difference         18
                        note = misc_feature - May be 2'-O-Methyl-2'-deoxycytidine
misc_difference         19
                        note = misc_feature - May be 2'-O-Methyl-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'-fluoro-2'-deoxyuridine
misc_difference         24
                        note = misc_feature - May be 2'-fluoro-2'-deoxycytidine
misc_difference         25
                        note = misc_feature - May be 2'-fluoro-2'-deoxyuridine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
```

```
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
misc_difference        39
                       note = misc_feature - May be an inverted orientation T
                        (3'-3'-linked)
source                 1..39
                       mol_type = other DNA
                       organism = synthetic construct
misc_feature           1..38
                       note = RNA
misc_feature           39
                       note = DNA
SEQUENCE: 81
cgccgcggtc tcaggcgctg agtctgagtt tacctgcgt                         39

SEQ ID NO: 82          moltype = DNA  length = 39
FEATURE                Location/Qualifiers
misc_feature           1..39
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be 2'-fluoro-2'-deoxycytidine
misc_difference        11
                       note = misc_feature - May be 2'-fluoro-2'-deoxyuridine
misc_difference        12
                       note = misc_feature - May be 2'-fluoro-2'-deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be 2'-fluoro-2'-deoxycytidine
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'-fluoro-2'-deoxyuridine
misc_difference        24
                       note = misc_feature - May be 2'-fluoro-2'-deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
```

```
misc_difference        29
                       note = misc_feature - May be 2'OH-thymidine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
misc_difference        39
                       note = misc_feature - May be an inverted orientation T
                        (3'-3'-linked)
source                 1..39
                       mol_type = other DNA
                       organism = synthetic construct
misc_feature           1..28
                       note = RNA
misc_feature           29
                       note = DNA
misc_feature           30..38
                       note = RNA
misc_feature           39
                       note = DNA
SEQUENCE: 82
cgccgcggtc tcaggcgctg agtctgagtt tacctgcgt                         39

SEQ ID NO: 83          moltype = DNA  length = 39
FEATURE                Location/Qualifiers
misc_feature           1..39
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be 2'-fluoro-2'-deoxycytidine
misc_difference        11
                       note = misc_feature - May be 2'-fluoro-2'-deoxyuridine
misc_difference        12
                       note = misc_feature - May be 2'-fluoro-2'-deoxycytidine
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be 2'-fluoro-2'-deoxycytidine
misc_difference        17
                       note = misc_feature - May be 2'OH-guanosine
misc_difference        18
                       note = misc_feature - May be 2'-O-Methyl-2'-deoxycytidine
misc_difference        19
                       note = misc_feature - May be 2'-O-Methyl-2'-deoxyuridine
```

```
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'-fluoro-2'-deoxyuridine
misc_difference        24
                       note = misc_feature - May be 2'-fluoro-2'-deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'-O-Methyl-2'-deoxyadenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
misc_difference        39
                       note = misc_feature - May be an inverted orientation T
                        (3'-3'-linked)
source                 1..39
                       mol_type = other DNA
                       organism = synthetic construct
misc_feature           1..38
                       note = RNA
misc_feature           39
                       note = DNA
SEQUENCE: 83
cgccgcggtc tcaggcgctg agtctgagtt tacctgcgt                         39

SEQ ID NO: 84          moltype = DNA  length = 39
FEATURE                Location/Qualifiers
misc_feature           1..39
                       note = Synthetic C5 specific aptamer
misc_difference        1
                       note = misc_feature - May be 2'-fluoro-2'-deoxycytidine
misc_difference        2
                       note = misc_feature - May be 2'-O-Methyl-2'-deoxyguanosine
misc_difference        3
                       note = misc_feature - May be 2'-fluoro-2'-deoxycytidine
misc_difference        4
                       note = misc_feature - May be 2'-fluoro-2'-deoxycytidine
misc_difference        5
                       note = misc_feature - May be 2'OH-guanosine
misc_difference        6
                       note = misc_feature - May be 2'-fluoro-2'-deoxycytidine
misc_difference        7
                       note = misc_feature - May be 2'-O-Methyl-2'-deoxyguanosine
misc_difference        8
                       note = misc_feature - May be 2'-O-Methyl-2'-deoxyguanosine
misc_difference        9
                       note = misc_feature - May be 2'-fluoro-2'-deoxyuridine
misc_difference        10
                       note = misc_feature - May be 2'-fluoro-2'-deoxycytidine
misc_difference        11
                       note = misc_feature - May be 2'-fluoro-2'-deoxyuridine
misc_difference        12
                       note = misc_feature - May be 2'-fluoro-2'-deoxycytidine
```

```
misc_difference        13
                       note = misc_feature - May be 2'-O-Methyl-2'-deoxyadenosine
misc_difference        14
                       note = misc_feature - May be 2'-O-Methyl-2'-deoxyguanosine
misc_difference        15
                       note = misc_feature - May be 2'-O-Methyl-2'-deoxyguanosine
misc_difference        16
                       note = misc_feature - May be 2'-fluoro-2'-deoxycytidine
misc_difference        17
                       note = misc_feature - May be 2'OH-guanosine
misc_difference        18
                       note = misc_feature - May be 2'-O-Methyl-2'-deoxycytidine
misc_difference        19
                       note = misc_feature - May be 2'-O-Methyl-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'-fluoro-2'-deoxyuridine
misc_difference        24
                       note = misc_feature - May be 2'-fluoro-2'-deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'OH-thymidine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'-O-Methyl-2'-deoxyadenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
misc_difference        39
                       note = misc_feature - May be an inverted orientation T
                        (3'-3'-linked)
source                 1..39
                       mol_type = other DNA
                       organism = synthetic construct
misc_feature           1..28
                       note = RNA
misc_feature           29
                       note = DNA
misc_feature           30..38
                       note = RNA
misc_feature           39
                       note = DNA
SEQUENCE: 84
cgccgcggtc tcaggcgctg agtctgagtt tacctgcgt                         39

SEQ ID NO: 85          moltype = DNA  length = 39
FEATURE                Location/Qualifiers
misc_feature           1..39
                       note = Synthetic C5 specific aptamer
misc_difference        1
                       note = misc_feature - May have a 20 kDa polyethylene glycol
                        group attached via a hexylamine linker
misc_difference        1
                       note = misc_feature - May be 2'-fluoro-2'-deoxycytidine
misc_difference        2
```

-continued

| | |
|---|---|
| | note = misc_feature - May be 2'-O-Methyl-2'-deoxyguanosine |
| misc_difference | 3 |
| | note = misc_feature - May be 2'-fluoro-2'-deoxycytidine |
| misc_difference | 4 |
| | note = misc_feature - May be 2'-fluoro-2'-deoxycytidine |
| misc_difference | 5 |
| | note = misc_feature - May be 2'OH-guanosine |
| misc_difference | 6 |
| | note = misc_feature - May be 2'-fluoro-2'-deoxycytidine |
| misc_difference | 7 |
| | note = misc_feature - May be 2'-O-Methyl-2'-deoxyguanosine |
| misc_difference | 8 |
| | note = misc_feature - May be 2'-O-Methyl-2'-deoxyguanosine |
| misc_difference | 9 |
| | note = misc_feature - May be 2'-fluoro-2'-deoxyuridine |
| misc_difference | 10 |
| | note = misc_feature - May be 2'-fluoro-2'-deoxycytidine |
| misc_difference | 11 |
| | note = misc_feature - May be 2'-fluoro-2'-deoxyuridine |
| misc_difference | 12 |
| | note = misc_feature - May be 2'-fluoro-2'-deoxycytidine |
| misc_difference | 13 |
| | note = misc_feature - May be 2'-O-Methyl-2'-deoxyadenosine |
| misc_difference | 14 |
| | note = misc_feature - May be 2'-O-Methyl-2'-deoxyguanosine |
| misc_difference | 15 |
| | note = misc_feature - May be 2'-O-Methyl-2'-deoxyguanosine |
| misc_difference | 16 |
| | note = misc_feature - May be 2'-fluoro-2'-deoxycytidine |
| misc_difference | 17 |
| | note = misc_feature - May be 2'OH-guanosine |
| misc_difference | 18 |
| | note = misc_feature - May be 2'-fluoro-2'-deoxycytidine |
| misc_difference | 19 |
| | note = misc_feature - May be 2'-fluoro-2'-deoxyuridine |
| misc_difference | 20 |
| | note = misc_feature - May be 2'-O-Methyl-2'-deoxyguanosine |
| misc_difference | 21 |
| | note = misc_feature - May be 2'-O-Methyl-2'-deoxyadenosine |
| misc_difference | 22 |
| | note = misc_feature - May be 2'-O-Methyl-2'-deoxyguanosine |
| misc_difference | 23 |
| | note = misc_feature - May be 2'-fluoro-2'-deoxyuridine |
| misc_difference | 24 |
| | note = misc_feature - May be 2'-fluoro-2'-deoxycytidine |
| misc_difference | 25 |
| | note = misc_feature - May be 2'-fluoro-2'-deoxyuridine |
| misc_difference | 26 |
| | note = misc_feature - May be 2'-O-Methyl-2'-deoxyguanosine |
| misc_difference | 27 |
| | note = misc_feature - May be 2'-O-Methyl-2'-deoxyadenosine |
| misc_difference | 28 |
| | note = misc_feature - May be 2'-O-Methyl-2'-deoxyguanosine |
| misc_difference | 29 |
| | note = misc_feature - May be 2'-fluoro-2'-deoxyuridine |
| misc_difference | 30 |
| | note = misc_feature - May be 2'-fluoro-2'-deoxyuridine |
| misc_difference | 31 |
| | note = misc_feature - May be 2'-fluoro-2'-deoxyuridine |
| misc_difference | 32 |
| | note = misc_feature - May be 2'OH-adenosine |
| misc_difference | 33 |
| | note = misc_feature - May be 2'-fluoro-2'-deoxycytidine |
| misc_difference | 34 |
| | note = misc_feature - May be 2'-fluoro-2'-deoxycytidine |
| misc_difference | 35 |
| | note = misc_feature - May be 2'-fluoro-2'-deoxyuridine |
| misc_difference | 36 |
| | note = misc_feature - May be 2'-O-Methyl-2'-deoxyguanosine |
| misc_difference | 37 |
| | note = misc_feature - May be 2'-fluoro-2'-deoxycytidine |
| misc_difference | 38 |
| | note = misc_feature - May be 2'-O-Methyl-2'-deoxyguanosine |
| misc_difference | 39 |
| | note = misc_feature - May be an inverted orientation T (3'-3'-linked) |
| source | 1..39 |
| | mol_type = other DNA |
| | organism = synthetic construct |

```
misc_feature            1..38
                        note = RNA
misc_feature            39
                        note = DNA
SEQUENCE: 85
cgccgcggtc tcaggcgctg agtctgagtt tacctgcgt                          39

SEQ ID NO: 86           moltype = DNA  length = 39
FEATURE                 Location/Qualifiers
misc_feature            1..39
                        note = Synthetic C5 specific aptamer
misc_difference         1
                        note = misc_feature - May have a 30 kDa polyethylene glycol
                         group attached via a hexylamine linker
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be 2'-fluoro-2'-deoxycytidine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be 2'-fluoro-2'-deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'-fluoro-2'-deoxyuridine
misc_difference         24
                        note = misc_feature - May be 2'-fluoro-2'-deoxycytidine
misc_difference         25
                        note = misc_feature - May be 2'-fluoro-2'-deoxyuridine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
```

-continued

```
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
misc_difference         39
                        note = misc_feature - May be an inverted orientation T
                         (3'-3'-linked)
source                  1..39
                        mol_type = other DNA
                        organism = synthetic construct
misc_feature            1..38
                        note = RNA
misc_feature            39
                        note = DNA
SEQUENCE: 86
cgccgcggtc tcaggcgctg agtctgagtt tacctgcgt                          39

SEQ ID NO: 87           moltype = DNA  length = 39
FEATURE                 Location/Qualifiers
misc_feature            1..39
                        note = Synthetic C5 specific aptamer
misc_difference         1
                        note = misc_feature - May have a hexylamine terminal group
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be 2'-fluoro-2'-deoxycytidine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be 2'-fluoro-2'-deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'-fluoro-2'-deoxyuridine
misc_difference         24
                        note = misc_feature - May be 2'-fluoro-2'-deoxycytidine
misc_difference         25
```

```
                        note = misc_feature - May be 2'-fluoro-2'-deoxyuridine
misc_difference         26
                        note = misc_feature - May be 2'-O-Methyl-2'-deoxyguanosine
misc_difference         27
                        note = misc_feature - May be 2'-O-Methyl-2'-deoxyadenosine
misc_difference         28
                        note = misc_feature - May be 2'-O-Methyl-2'-deoxyguanosine
misc_difference         29
                        note = misc_feature - May be 2'-fluoro-2'-deoxyuridine
misc_difference         30
                        note = misc_feature - May be 2'-fluoro-2'-deoxyuridine
misc_difference         31
                        note = misc_feature - May be 2'-fluoro-2'-deoxyuridine
misc_difference         32
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
misc_difference         39
                        note = misc_feature - May be an inverted orientation T
                         (3'-3'-linked)
source                  1..39
                        mol_type = other DNA
                        organism = synthetic construct
misc_feature            1..38
                        note = RNA
misc_feature            39
                        note = DNA
SEQUENCE: 87
cgccgcggtc tcaggcgctg agtctgagtt tacctgcgt                          39

SEQ ID NO: 88           moltype = DNA  length = 39
FEATURE                 Location/Qualifiers
misc_feature            1..39
                        note = Synthetic C5 specific aptamer
misc_difference         1
                        note = misc_feature - May have a 10 kDa polyethylene glycol
                         group attached via a hexylamine linker
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be 2'-fluoro-2'-deoxycytidine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be 2'-fluoro-2'-deoxycytidine
```

```
misc_difference        17
                       note = misc_feature - May be 2'OH-guanosine
misc_difference        18
                       note = misc_feature - May be 2'-fluoro-2'-deoxycytidine
misc_difference        19
                       note = misc_feature - May be 2'-fluoro-2'-deoxyuridine
misc_difference        20
                       note = misc_feature - May be 2'-O-Methyl-2'-deoxyguanosine
misc_difference        21
                       note = misc_feature - May be 2'-O-Methyl-2'-deoxyadenosine
misc_difference        22
                       note = misc_feature - May be 2'-O-Methyl-2'-deoxyguanosine
misc_difference        23
                       note = misc_feature - May be 2'-fluoro-2'-deoxyuridine
misc_difference        24
                       note = misc_feature - May be 2'-fluoro-2'-deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
misc_difference        39
                       note = misc_feature - May be an inverted orientation T
                        (3'-3'-linked)
source                 1..39
                       mol_type = other DNA
                       organism = synthetic construct
misc_feature           1..38
                       note = RNA
misc_feature           39
                       note = DNA
SEQUENCE: 88
cgccgcggtc tcaggcgctg agtctgagtt tacctgcgt                         39

SEQ ID NO: 89          moltype = RNA  length = 75
FEATURE                Location/Qualifiers
misc_feature           1..75
                       note = Synthetic C5 specific aptamer
source                 1..75
                       mol_type = other RNA
                       organism = synthetic construct
SEQUENCE: 89
gggagaggag agaacgttct accttggttt ggcacaggca tacatacgca ggggtcgatc  60
gatcgatcat cgatg                                                   75

SEQ ID NO: 90          moltype = RNA  length = 32
FEATURE                Location/Qualifiers
misc_feature           1..32
                       note = Synthetic C5 specific aptamer
source                 1..32
                       mol_type = other RNA
                       organism = synthetic construct
SEQUENCE: 90
ccttggtttg gcacaggcat acatacgcag gg                                32

SEQ ID NO: 91          moltype = RNA  length = 47
```

-continued

```
FEATURE              Location/Qualifiers
misc_feature         1..47
                     note = Synthetic C5 specific aptamer
source               1..47
                     mol_type = other RNA
                     organism = synthetic construct
SEQUENCE: 91
cgttctacct tggtttggca caggcataca tacgcagggg tcgatcg               47

SEQ ID NO: 92        moltype = DNA  length = 39
FEATURE              Location/Qualifiers
misc_feature         1..39
                     note = Synthetic C5 specific aptamer
misc_difference      1
                     note = misc_feature - May have a 40 kDa polyethylene glycol
                      group attached via a hexylamine linker
misc_difference      1
                     note = misc_feature - May be 2'-fluoro-2'-deoxycytidine
misc_difference      2
                     note = misc_feature - May be 2'-O-Methyl-2'-deoxyguanosine
misc_difference      3
                     note = misc_feature - May be 2'-fluoro-2'-deoxycytidine
misc_difference      4
                     note = misc_feature - May be 2'-fluoro-2'-deoxycytidine
misc_difference      5
                     note = misc_feature - May be 2'OH-guanosine
misc_difference      6
                     note = misc_feature - May be 2'-fluoro-2'-deoxycytidine
misc_difference      7
                     note = misc_feature - May be 2'-O-Methyl-2'-deoxyguanosine
misc_difference      8
                     note = misc_feature - May be 2'-O-Methyl-2'-deoxyguanosine
misc_difference      9
                     note = misc_feature - May be 2'-fluoro-2'-deoxyuridine
misc_difference      10
                     note = misc_feature - May be 2'-fluoro-2'-deoxycytidine
misc_difference      11
                     note = misc_feature - May be 2'-fluoro-2'-deoxyuridine
misc_difference      12
                     note = misc_feature - May be 2'-fluoro-2'-deoxycytidine
misc_difference      13
                     note = misc_feature - May be 2'-O-Methyl-2'-deoxyadenosine
misc_difference      14
                     note = misc_feature - May be 2'-O-Methyl-2'-deoxyguanosine
misc_difference      15
                     note = misc_feature - May be 2'-O-Methyl-2'-deoxyguanosine
misc_difference      16
                     note = misc_feature - May be 2'-fluoro-2'-deoxycytidine
misc_difference      17
                     note = misc_feature - May be 2'OH-guanosine
misc_difference      18
                     note = misc_feature - May be 2'-fluoro-2'-deoxycytidine
misc_difference      19
                     note = misc_feature - May be 2'-fluoro-2'-deoxyuridine
misc_difference      20
                     note = misc_feature - May be 2'-O-Methyl-2'-deoxyguanosine
misc_difference      21
                     note = misc_feature - May be 2'-O-Methyl-2'-deoxyadenosine
misc_difference      22
                     note = misc_feature - May be 2'-O-Methyl-2'-deoxyguanosine
misc_difference      23
                     note = misc_feature - May be 2'-fluoro-2'-deoxyuridine
misc_difference      24
                     note = misc_feature - May be 2'-fluoro-2'-deoxycytidine
misc_difference      25
                     note = misc_feature - May be 2'-fluoro-2'-deoxyuridine
misc_difference      26
                     note = misc_feature - May be 2'-O-Methyl-2'-deoxyguanosine
misc_difference      27
                     note = misc_feature - May be 2'-O-Methyl-2'-deoxyadenosine
misc_difference      28
                     note = misc_feature - May be 2'-O-Methyl-2'-deoxyguanosine
misc_difference      29
                     note = misc_feature - May be 2'-fluoro-2'-deoxyuridine
misc_difference      30
                     note = misc_feature - May be 2'-fluoro-2'-deoxyuridine
misc_difference      31
                     note = misc_feature - May be 2'-fluoro-2'-deoxyuridine
misc_difference      32
```

```
                        note = misc_feature - May be 2'OH-adenosine
misc_difference         33
                        note = misc_feature - May be 2'-fluoro-2'-deoxycytidine
misc_difference         34
                        note = misc_feature - May be 2'-fluoro-2'-deoxycytidine
misc_difference         35
                        note = misc_feature - May be 2'-fluoro-2'-deoxyuridine
misc_difference         36
                        note = misc_feature - May be 2'-O-Methyl-2'-deoxyguanosine
misc_difference         37
                        note = misc_feature - May be 2'-fluoro-2'-deoxycytidine
misc_difference         38
                        note = misc_feature - May be 2'-O-Methyl-2'-deoxyguanosine
misc_difference         39
                        note = misc_feature - May be an inverted orientation T
                         (3'-3'-linked)
source                  1..39
                        mol_type = other DNA
                        organism = synthetic construct
misc_feature            1..38
                        note = RNA
misc_feature            39
                        note = DNA
SEQUENCE: 92
cgccgcggtc tcaggcgctg agtctgagtt tacctgcgt                          39

SEQ ID NO: 93           moltype = RNA  length = 38
FEATURE                 Location/Qualifiers
misc_feature            1..38
                        note = Synthetic C5 specific aptamer
misc_difference         1
                        note = misc_feature - May have a 20 kDa polyethylene glycol
                         group attached via a hexylamine linker
misc_difference         1
                        note = misc_feature - May be 2'-fluoro-2'-deoxycytidine
misc_difference         2
                        note = misc_feature - May be 2'-O-Methyl-2'-deoxyguanosine
misc_difference         3
                        note = misc_feature - May be 2'-fluoro-2'-deoxycytidine
misc_difference         4
                        note = misc_feature - May be 2'-fluoro-2'-deoxycytidine
misc_difference         5
                        note = misc_feature - May be 2'OH-guanosine
misc_difference         6
                        note = misc_feature - May be 2'-fluoro-2'-deoxycytidine
misc_difference         7
                        note = misc_feature - May be 2'-O-Methyl-2'-deoxyguanosine
misc_difference         8
                        note = misc_feature - May be 2'-O-Methyl-2'-deoxyguanosine
misc_difference         9
                        note = misc_feature - May be 2'-fluoro-2'-deoxyuridine
misc_difference         10
                        note = misc_feature - May be 2'-fluoro-2'-deoxycytidine
misc_difference         11
                        note = misc_feature - May be 2'-fluoro-2'-deoxyuridine
misc_difference         12
                        note = misc_feature - May be 2'-fluoro-2'-deoxycytidine
misc_difference         13
                        note = misc_feature - May be 2'-O-Methyl-2'-deoxyadenosine
misc_difference         14
                        note = misc_feature - May be 2'-O-Methyl-2'-deoxyguanosine
misc_difference         15
                        note = misc_feature - May be 2'-O-Methyl-2'-deoxyguanosine
misc_difference         16
                        note = misc_feature - May be 2'-fluoro-2'-deoxycytidine
misc_difference         17
                        note = misc_feature - May be 2'OH-guanosine
misc_difference         18
                        note = misc_feature - May be 2'-fluoro-2'-deoxycytidine
misc_difference         19
                        note = misc_feature - May be 2'-fluoro-2'-deoxyuridine
misc_difference         20
                        note = misc_feature - May be 2'-O-Methyl-2'-deoxyguanosine
misc_difference         21
                        note = misc_feature - May be 2'-O-Methyl-2'-deoxyadenosine
misc_difference         22
                        note = misc_feature - May be 2'-O-Methyl-2'-deoxyguanosine
misc_difference         23
                        note = misc_feature - May be 2'-fluoro-2'-deoxyuridine
```

```
misc_difference        24
                       note = misc_feature - May be 2'-fluoro-2'-deoxycytidine
misc_difference        25
                       note = misc_feature - May be 2'-fluoro-2'-deoxyuridine
misc_difference        26
                       note = misc_feature - May be 2'-O-Methyl-2'-deoxyguanosine
misc_difference        27
                       note = misc_feature - May be 2'-O-Methyl-2'-deoxyadenosine
misc_difference        28
                       note = misc_feature - May be 2'-O-Methyl-2'-deoxyguanosine
misc_difference        29
                       note = misc_feature - May be 2'-fluoro-2'-deoxyuridine
misc_difference        30
                       note = misc_feature - May be 2'-fluoro-2'-deoxyuridine
misc_difference        31
                       note = misc_feature - May be 2'-fluoro-2'-deoxyuridine
misc_difference        32
                       note = misc_feature - May be 2'OH-adenosine
misc_difference        33
                       note = misc_feature - May be 2'-fluoro-2'-deoxycytidine
misc_difference        34
                       note = misc_feature - May be 2'-fluoro-2'-deoxycytidine
misc_difference        35
                       note = misc_feature - May be 2'-fluoro-2'-deoxyuridine
misc_difference        36
                       note = misc_feature - May be 2'-O-Methyl-2'-deoxyguanosine
misc_difference        37
                       note = misc_feature - May be 2'-fluoro-2'-deoxycytidine
misc_difference        38
                       note = misc_feature - May be 2'-O-Methyl-2'-deoxyguanosine
misc_difference        38
                       note = misc_feature - May have a 20 kDa polyethylene glycol
                        group attached via a hexylamine linker
source                 1..38
                       mol_type = other RNA
                       organism = synthetic construct
SEQUENCE: 93
cgccgcggtc tcaggcgctg agtctgagtt tacctgcg                          38

SEQ ID NO: 94          moltype = RNA  length = 80
FEATURE                Location/Qualifiers
misc_feature           1..80
                       note = Synthetic C5 specific aptamer
source                 1..80
                       mol_type = other RNA
                       organism = synthetic construct
SEQUENCE: 94
gggagaggag agaacgttct accttggttt ggcccaggca tatatacgca gggattgatc  60
cgttacgact agcatcgatg                                              80

SEQ ID NO: 95          moltype = RNA  length = 79
FEATURE                Location/Qualifiers
misc_feature           1..79
                       note = Synthetic C5 specific aptamer
source                 1..79
                       mol_type = other RNA
                       organism = synthetic construct
SEQUENCE: 95
gggagaggag agaacgttct accttaggtt cgcactgtca tacatacaca cgggcaatcg  60
gttacgacta gcatcgatg                                               79

SEQ ID NO: 96          moltype = RNA  length = 75
FEATURE                Location/Qualifiers
misc_feature           1..75
                       note = Synthetic C5 specific aptamer
misc_difference        34
                       note = misc_feature - n is a, c, g, or u
misc_difference        43
                       note = misc_feature - n is a, c, g, or u
source                 1..75
                       mol_type = other RNA
                       organism = synthetic construct
SEQUENCE: 96
gggagaggag agaacgttct accttggttt ggcncaggca tanatacgca cgggtcgatc  60
ggttacgact agcat                                                   75

SEQ ID NO: 97          moltype = AA  length = 126
FEATURE                Location/Qualifiers
REGION                 1..126
```

-continued

```
                        note = ankyrin binding domain
source                  1..126
                        mol_type = protein
                        organism = unidentified
SEQUENCE: 97
GSDLGKKLLE AARAGQDDEV RILMANGADV NTADSTGWTP LHLAVPWGHL EIVEVLLKYG  60
ADVNAKDFQG WTPLHLAAAI GHQEIVEVLL KNGADVNAQD KFGKTAFDIS IDNGNEDLAE  120
ILQKAA                                                            126

SEQ ID NO: 98           moltype = AA  length = 552
FEATURE                 Location/Qualifiers
REGION                  1..552
                        note = recombinant human soluble VEGF receptor fusion
                         protein
source                  1..552
                        mol_type = protein
                        organism = synthetic construct
SEQUENCE: 98
MVSYWDTGVL LCALLSCLLL TGSSSGGRPF VEMYSEIPEI IHMTEGRELV IPCRVTSPNI  60
TVTLKKFPLD TLIPDGKRII WDSRKGFIIS NATYKEIGLL TCEATVNGHL YKTNYLTHRQ  120
TNTIIDVVLS PSHGIELSVG EKLVLNCTAR TELNVGIDFN WEYPSSKHQH KKLVNRDLKT  180
QSGSEMKKFL STLTIDGVTR SDQGLYTCAA SSGLMTKKNS TFVRVHEKPF VAFGSGMESL  240
VEATVGERVR LPAKYLGYPP PEIKWYKNGI PLESNHTIKA GHVLTIMEVS ERDTGNYTVI  300
LTNPISKEKQ SHVVSLVVYV PPGPGDKTHT CPLCPAPELL GGPSVFLFPP KPKDTLMISR  360
TPEVTCVVVD VSHEDPEVKF NWYVDGVEVH NAKTKPREEQ YNSTYRVVSV LTVLHQDWLN  420
GKEYKCKVSN KALPAPIEKT ISKAKGQPRE PQVYTLPPSR DELTKNQVSL TCLVKGFYPS  480
DIAVEWESNG QPENNYKATP PVLDSDGSFF LYSKLTVDKS RWQQGNVFSC SVMHEALHNH  540
YTQKSLSLSP GK                                                     552
```

METHODS FOR TREATING OR PREVENTING OPHTHALMOLOGICAL CONDITIONS

CROSS REFERENCE TO RELATED APPLICATIONS

This application is a continuation of U.S. application Ser. No. 17/958,710, filed Oct. 3, 2022, which is a continuation of U.S. application Ser. No. 17/676,811, filed February 2022, now U.S. Pat. No. 11,491,176 issued on Nov. 8, 2022, which is a continuation of U.S. application Ser. No. 17/346,556, filed Jun. 14, 2021, now U.S. Pat. No. 11,273,171 issued on Mar. 15, 2022, which is a continuation of U.S. application Ser. No. 16/434,018, filed Jun. 19, 2019, which is a continuation of U.S. application Ser. No. 14/329,702, filed Jul. 11, 20114, which claims the benefit of U.S. provisional application Nos. 61/845,938, filed Jul. 12, 2013, 61/845,935, filed Jul. 12, 2013, 61/845,936, filed Jul. 12, 2013, 61/866,502, filed Aug. 15, 2013, 61/866,503, filed Aug. 15, 2013, 61/866,507, filed Aug. 15, 2013, 61/911,854, filed Dec. 4, 2013, 61/911,860, filed Dec. 4, 2013, 61/911,894, filed Dec. 4, 2013, 61/926,812, filed Jan. 13, 2014, 61/926,825, filed Jan. 13, 2014, 61/926,848, filed Jan. 13, 2014, 61/931,116, filed Jan. 24, 2014, 61/931,125, filed Jan. 24, 2014, and 61/931,135, filed Jan. 24, 2014, each of which is incorporated by reference herein in its entirety.

SEQUENCE LISTING

The Sequence Listing XML associated with this application is provided in text format in lieu of a paper copy, and is hereby incorporated by reference into the specification. The name of the text file containing the Sequence Listing is A112-4_US_6_SL.xml. The text file is about 1.4 MB, was created on Aug. 7, 2023, and is being submitted electronically via EFS-Web.

FIELD OF THE INVENTION

This invention relates to methods and compositions useful for the treatment or prevention of an ophthalmological disease or disorder, comprising administration of an effective amount of Antagonist A or another pharmaceutically acceptable salt thereof.

BACKGROUND OF THE INVENTION

Various disorders of the eye are characterized, caused by, or result in choroidal, retinal or iris neovascularization or retinal edema. One of these disorders is macular degeneration. Age-related macular degeneration (AMD) is a disease that affects approximately one in ten Americans over the age of 65. One type of AMD, "wet-AMD," accounts only for approximately 10% of age-related macular degeneration cases but results in approximately 90% of cases of legal blindness from macular degeneration in the elderly. Another disorder of the eye is diabetic retinopathy. Diabetic retinopathy can affect up to 80% of all patients having diabetes for 10 years or more and is the third leading cause of adult blindness, accounting for almost 7% of blindness in the USA. Other disorders include hypertensive retinopathy, central serous chorioretinopathy, cystoid macular edema, Coats disease and ocular or adnexal neoplasms such as choroidal hemangioma, retinal pigment epithelial carcinoma, retinal vein occlusions and intraocular lymphoma.

Therefore, although advances in the understanding of the molecular events accompanying neovascularization have been made, there exists a need to utilize this understanding to develop improved methods for treating or preventing neovascular diseases disorders, including ocular neovascular diseases and disorders such as the neovascularization that occurs with AMD, diabetic retinopathy, and retinal vein occlusions.

SUMMARY OF THE INVENTION

The present invention relates to methods and compositions useful for the treatment or prevention of an ophthalmological disease or disorder.

The present invention provides a method for treating or preventing wet age-related macular degeneration (wet AMD), comprising administering to a subject in need thereof (a) Antagonist A or another pharmaceutically acceptable salt thereof and (b) an VEGF antagonist, wherein (a) and (b) are administered in an amount that is effective for treating or preventing wet AMD, and wherein the administering occurs once every month, ±about seven days, for a first administration period of at least 3 consecutive months, followed by administering (a) and (b) for a second administration period at a frequency of at least every other month±about seven days beginning at two months±about seven days after the day of the last month of the first administration period on which (a) and (b) are administered.

Also provided herein is a method for treating or preventing sub-retinal fibrosis, comprising administering to a subject in need thereof (a) Antagonist A or another pharmaceutically acceptable salt thereof in an amount that is effective for treating or preventing sub-retinal fibrosis.

A method for treating or preventing von Hippel-Lindau (VHL) disease, comprising administering to a subject in need thereof Antagonist A or another pharmaceutically acceptable salt thereof in an amount that is effective for treating or preventing VHL disease is also provided herein.

BRIEF DESCRIPTION OF THE DRAWINGS

Reference is made to the following detailed description, which sets forth illustrative embodiments and the accompanying drawings of which:

FIG. 5A shows the mean change in visual acuity for patients in each of the indicated baseline lesion quartiles, and FIG. 5B shows the mean change in visual acuity for patients with the indicated baseline vision.

FIG. 7A shows the percentage of patients who demonstrated a visual acuity of 20/40 or better; FIG. 7B shows the percentage of patients who demonstrated a visual acuity of 20/25 or better; and FIG. 7C shows the percentage of patients who demonstrated a visual acuity of 20/200 or worse.

FIG. 8A shows the results in all patients, and FIG. 8B shows the results in patients with a visual outcome >3-lines.

DETAILED DESCRIPTION OF THE INVENTION

Figure 1A:
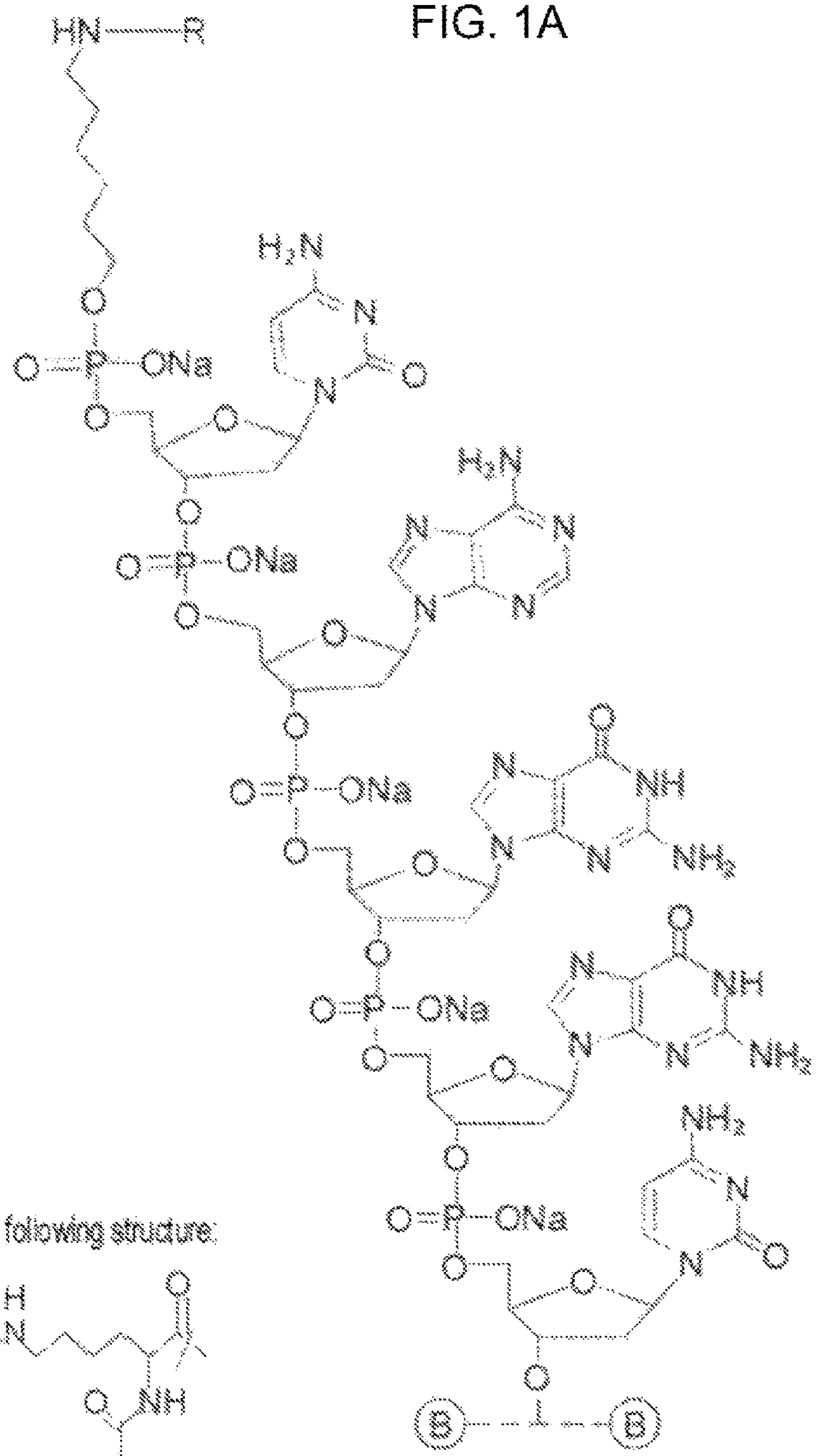
FIGS. 1A-F show the chemical structure of Antagonist A, wherein the 5' end of its aptamer (SEQ ID NO: 1) is modified with $Me(OCH_2CH_2)_nOC(O)NH(CH_2)_4CH(NHC(O)O(CH_2CH_2O)_nMe)C(O)NH(CH_2)_6$—, where n is about 450. The designations Ⓑ-Ⓕ indicate a continuation from a previous panel.
Figure 1A:
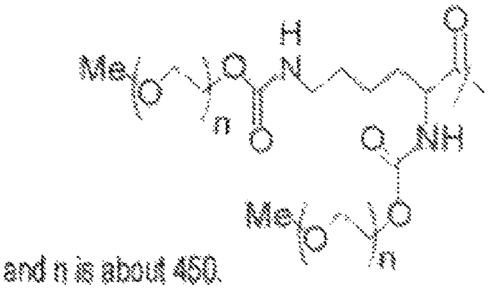
Figure 1B:
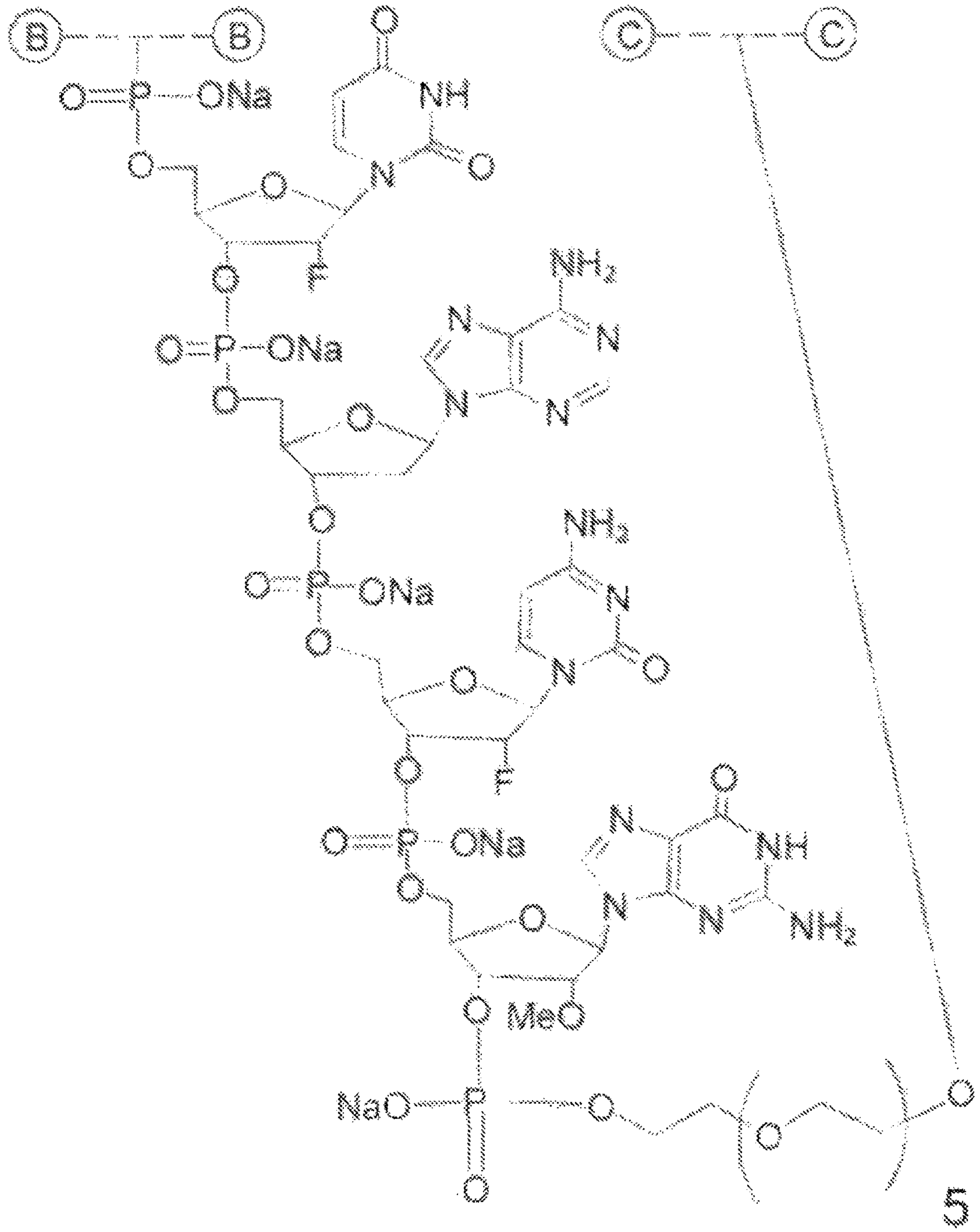
Figure 1C:
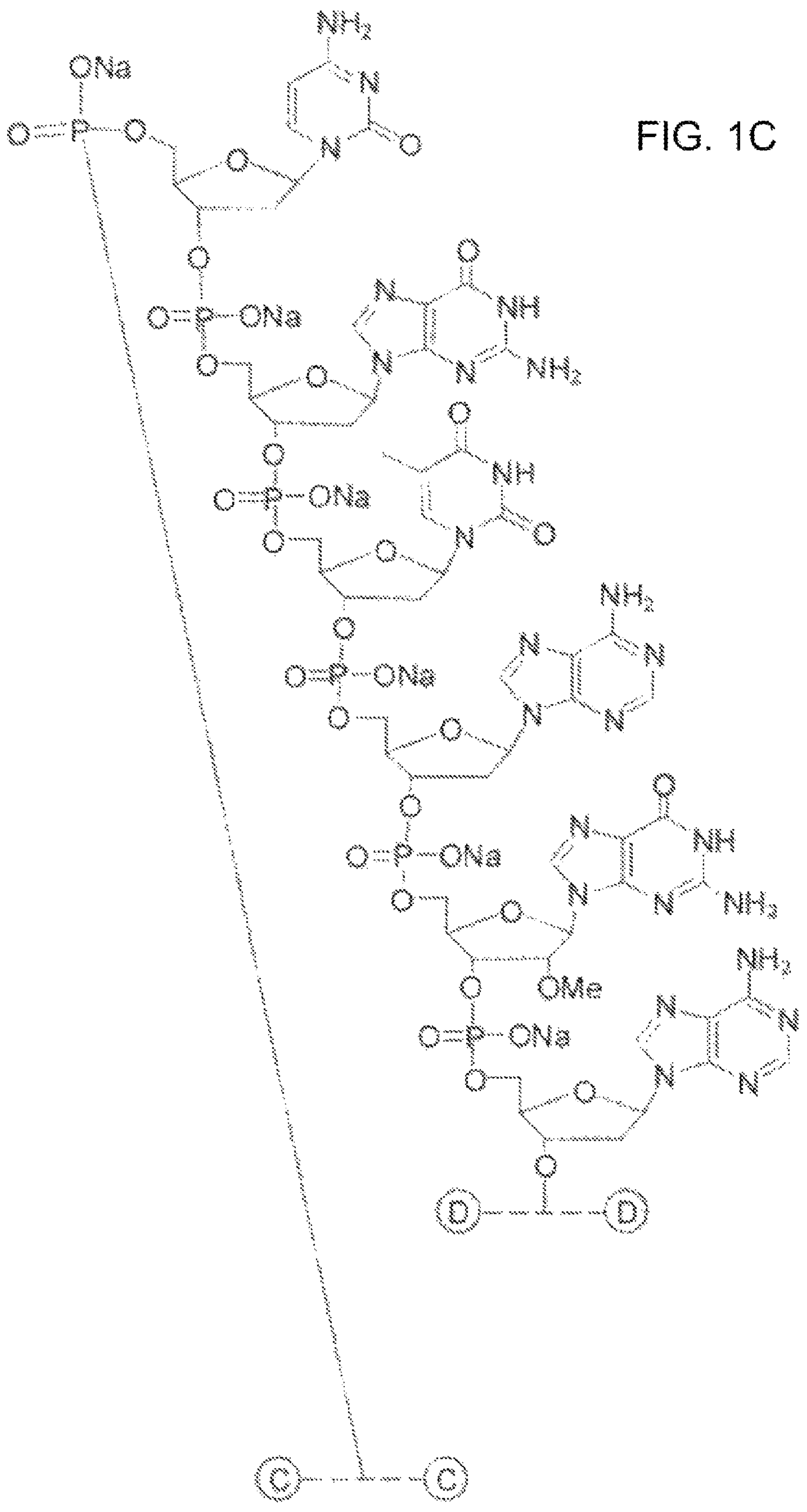
Figure 1D:
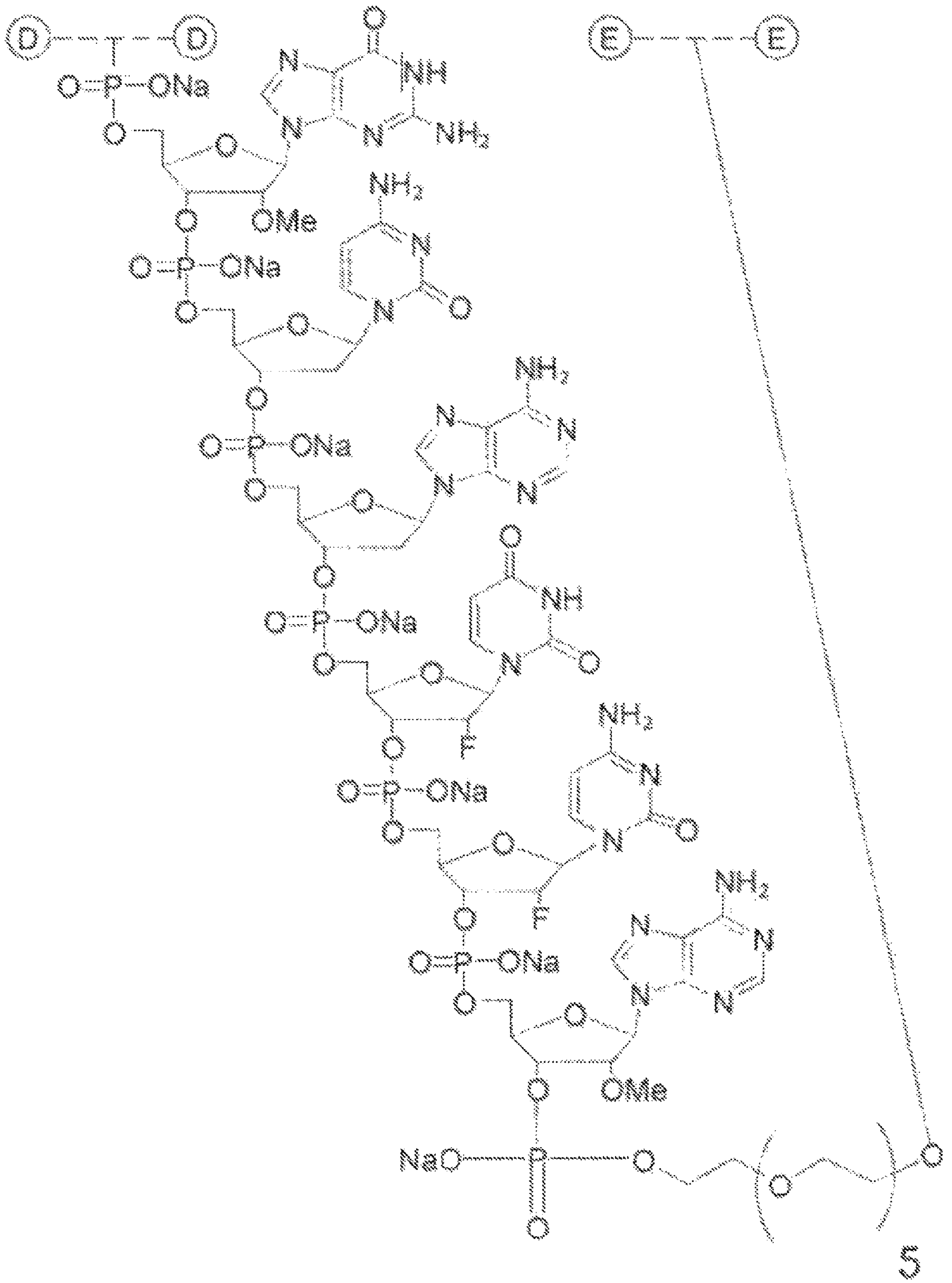
Figure 1E:
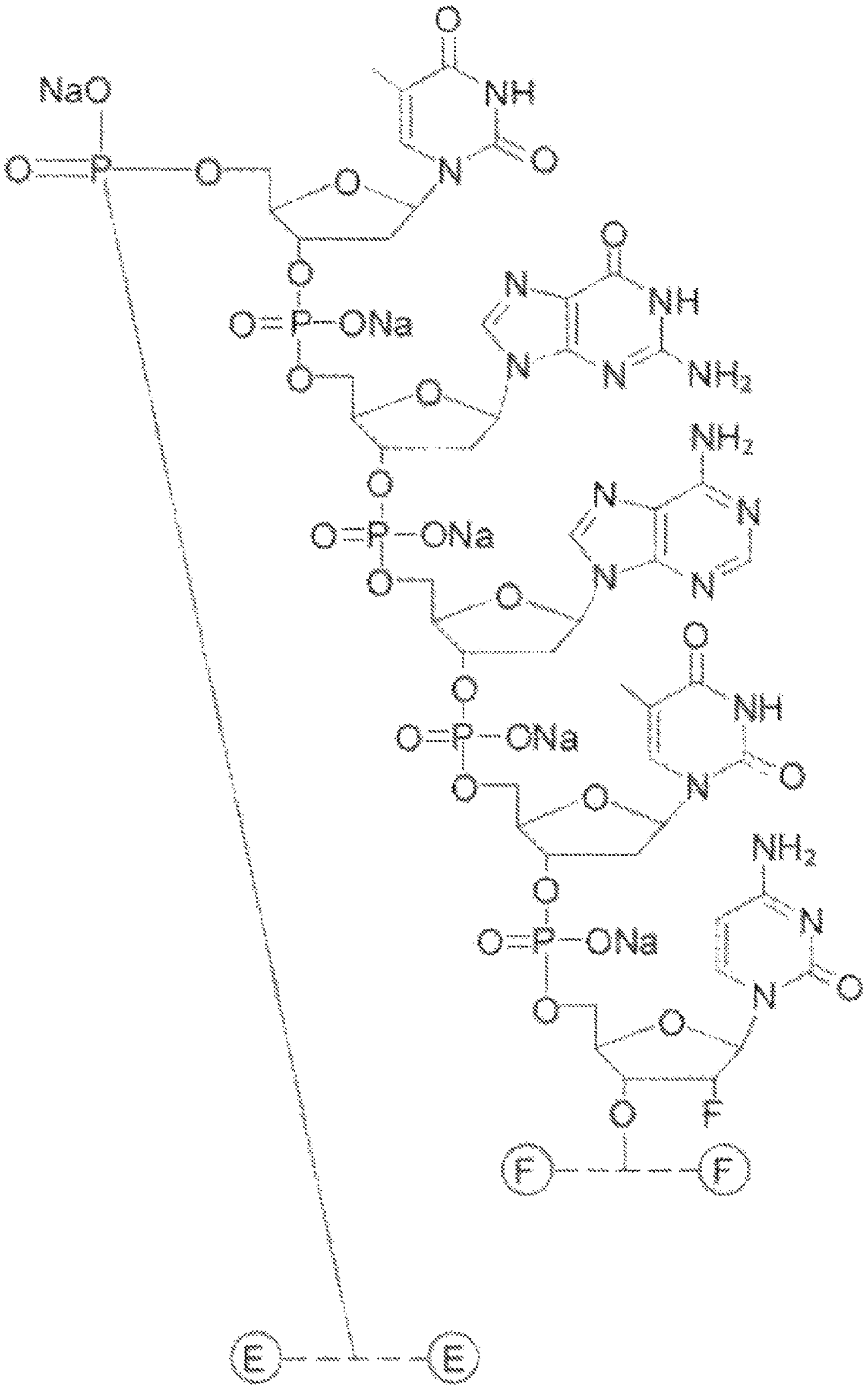
Figure 1F:
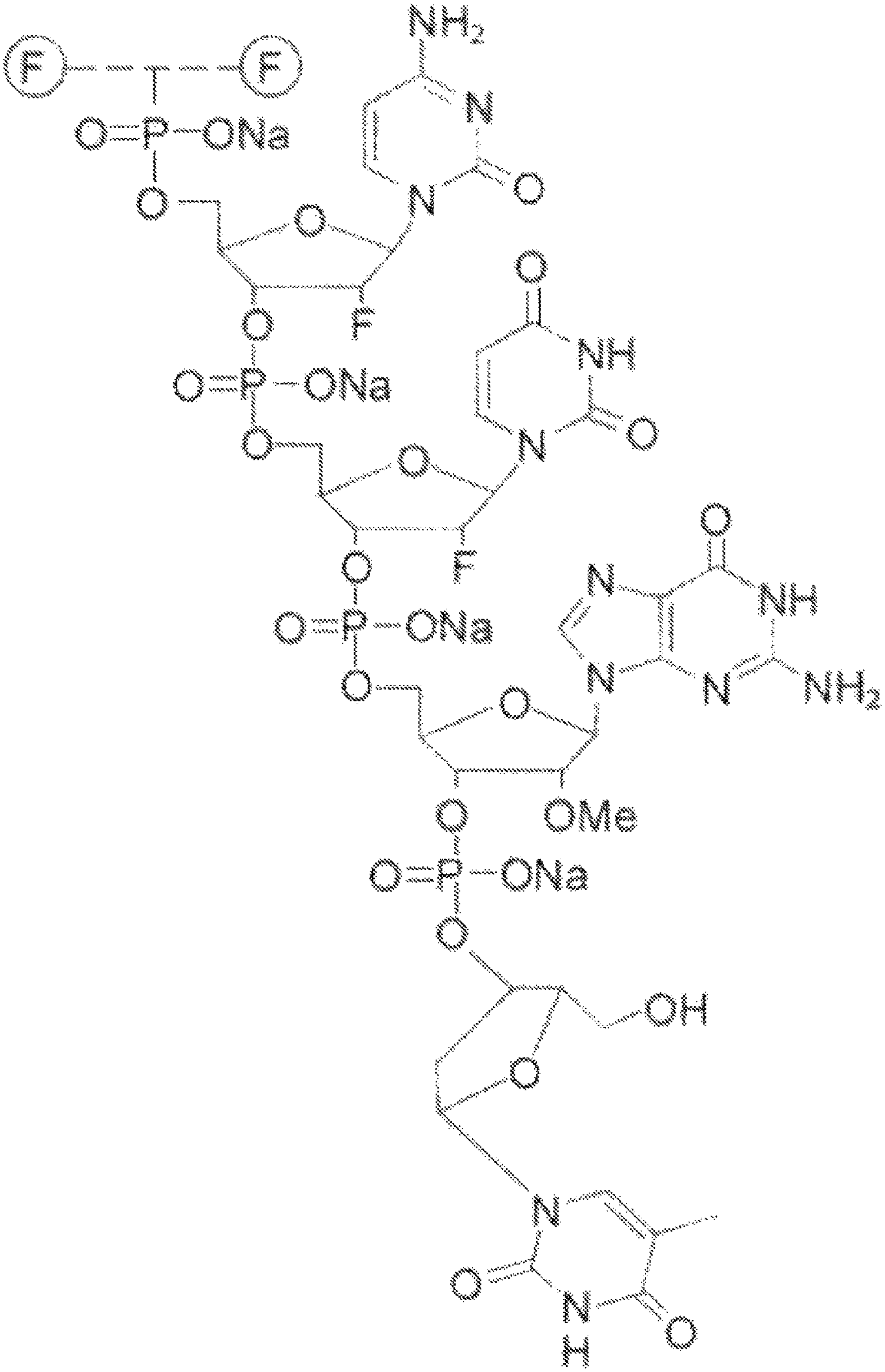

In certain aspects, the present invention provides new and improved methods and compositions for treating and preventing ophthalmological diseases and disorders, including, e.g., new uses, combination therapies, treatment and dosing regimens, and coformulations.

In one aspect, the invention provides methods for treating or preventing an ophthalmological disease or disorder, comprising administering to a subject in need thereof an effective amount of Antagonist A or another pharmaceutically acceptable salt thereof. In particular embodiments, the subject is administered Antagonist A or another pharmaceutically acceptable salt thereof and not administered an anti-C5 agent. In some embodiments, the subject is administered Antagonist A or another pharmaceutically acceptable salt thereof and not administered a VEGF antagonist.

In particular embodiments, the Antagonist A or another pharmaceutically acceptable salt thereof is administered in combination with a VEGF antagonist. In one embodiment, Antagonist A or another pharmaceutically acceptable salt thereof is administered in combination with ranibizumab, bevacizumab, aflibercept, pegaptanib sodium, or ESBA1008.

In particular embodiments, the Antagonist A or another pharmaceutically acceptable salt thereof is administered in combination with a VEGF antagonist and an anti-C5 agent. In one embodiment, Antagonist A or another pharmaceutically acceptable salt thereof is administered in combination with a VEGF antagonist (e.g., ranibizumab, bevacizumab, aflibercept, pegaptanib sodium, or ESBA1008), and ARC1905.

The invention also provides treatment regimens, including treatment and dosing regimens, related to the coadministration of Antagonist A or another pharmaceutically acceptable salt thereof and a VEGF antagonist, optionally also in combination with an anti-C5 agent.

In further embodiments, another agent (e.g., an agent that is not Antagonist A, VEGF antagonist or an anti-C5 agent) that is useful for treating or preventing an ophthalmological disease or disorder is administered. In some embodiments, the methods comprise administering one or more (e.g., two) VEGF antagonists and/or one or more (e.g., two) anti-C5 agents to the subject in need thereof.

In another aspect, the invention provides methods for treating or preventing an ophthalmological disease or disorder, comprising administering to a subject in need thereof an effective amount of an anti-C5 agent (e.g., ARC1905). In particular embodiments, the subject is not administered Antagonist A or another pharmaceutically acceptable salt thereof. In some embodiments, the subject is not administered a VEGF antagonist.

In addition, the invention provides coformulations that comprise Antagonist A or another pharmaceutically acceptable salt thereof and a VEGF antagonist. In certain embodiments, the coformulations further comprise an anti-C5 agent. In certain embodiments, the coformulations are pharmaceutically compositions comprising an effective amount of Antagonist A or another pharmaceutically acceptable salt thereof and VEGF antagonist, and a pharmaceutically acceptable carrier or vehicle. In certain embodiments, the coformulations are pharmaceutically compositions comprising an effective amount of Antagonist A or another pharmaceutically acceptable salt thereof, VEGF antagonist, and anti-C5 agent, and a pharmaceutically acceptable carrier or vehicle.

In one embodiment, the present invention provides methods for treating or preventing an ophthalmological disease or disorder, comprising administering to a subject in need thereof Antagonist A or another pharmaceutically acceptable salt thereof and optionally a VEGF antagonist, wherein the methods further comprise performing a surgery to treat the ophthalmological disease or disorder and/or administration of an anti-C5 agent.

Definitions and Abbreviations

As used herein, the following terms and phrases shall have the meanings set forth below. Unless defined otherwise, all technical and scientific terms used herein have the same meaning as commonly understood to one of skill in the art to which this invention belongs.

The term "about" when used in connection with a referenced numeric indication means the referenced numeric indication plus or minus up to 10% of that referenced numeric indication. For example, "about 100" means from 90 to 110 and "about six" means from 5.4 to 6.6.

The term "antagonist" refers to an agent that inhibits, either partially or fully, the activity or production of a target molecule. In particular, the term "antagonist," as applied selectively herein, means an agent capable of decreasing levels of gene expression, mRNA levels, protein levels or protein activity of the target molecule. Illustrative forms of antagonists include, for example, proteins, polypeptides, peptides (such as cyclic peptides), antibodies or antibody fragments, peptide mimetics, nucleic acid molecules, antisense molecules, ribozymes, aptamers, RNAi molecules, and small organic molecules. Illustrative non-limiting mechanisms of antagonist inhibition include repression of ligand synthesis and/or stability (e.g., using, antisense, ribozymes or RNAi compositions targeting the ligand gene/nucleic acid), blocking of binding of the ligand to its cognate receptor (e.g., using anti-ligand aptamers, antibodies or a soluble, decoy cognate receptor), repression of receptor synthesis and/or stability (e.g., using, antisense, ribozymes or RNAi compositions targeting the ligand receptor gene/nucleic acid), blocking of the binding of the receptor to its cognate receptor (e.g., using receptor antibodies) and blocking of the activation of the receptor by its cognate ligand (e.g., using receptor tyrosine kinase inhibitors). In addition, the antagonist may directly or indirectly inhibit the target molecule.

The term "antibody fragment" includes a portion of an antibody that is an antigen binding fragment or single chains thereof. An antibody fragment can be a synthetically or genetically engineered polypeptide. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those in the art, and the fragments can be screened for utility in the same manner as whole antibodies.

The term "aptamer" refers to a peptide or nucleic acid that has an inhibitory effect on a target. Inhibition of the target by the aptamer can occur by binding of the target, by catalytically altering the target, by reacting with the target in a way which modifies the target or the functional activity of the target, by ionically or covalently attaching to the target as in a suicide inhibitor or by facilitating the reaction between the target and another molecule. Aptamers can be peptides, ribonucleotides, deoxyribonucleotides, other nucleic acids or a mixture of the different types of nucleic acids. Aptamers can comprise one or more modified amino acid, bases, sugars, polyethylene glycol spacers or phosphate backbone units as described in further detail herein.

A nucleotide sequence is "complementary" to another nucleotide sequence if each of the bases of the two sequences matches, i.e., are capable of forming Watson Crick base pairs. The complement of a nucleic acid strand can be the complement of a coding strand or the complement of a non-coding strand.

The phrase "conserved residue" refers to an amino acid of a group of amino acids having particular common properties. A functional way to define common properties among individual amino acids is to analyze the normalized frequencies of amino acid changes among corresponding proteins of homologous organisms. According to such analyses, groups of amino acids may be characterized where amino acids within a group exchange preferentially with each other, and therefore resemble each other most in their impact on the overall protein structure (Schulz, G. E. and R. H. Schirmer, *Principles of Protein Structure*, Springer-Verlag). Examples of amino acid groups defined in this manner include:

(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic nonpolar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

Members of each of the above groups are conserved residues.

The term "label" includes, but is not limited to, a radioactive isotope, a fluorophore, a chemiluminescent moiety, an enzyme, an enzyme substrate, an enzyme cofactor, an enzyme inhibitor, a dye, a metal ion, a ligand (e.g., biotin or a hapten) and the like. Examples of fluorophore labels include fluorescein, rhodamine, dansyl, umbelliferone, Texas red, luminol, NADPH, alpha-beta-galactosidase and horseradish peroxidase.

The term "nucleic acid" refers to a polynucleotide such as deoxyribonucleic acid (DNA) or ribonucleic acid (RNA). The term also includes analogs of RNA or DNA made from nucleotide analogs, and, as applicable to the embodiment being described, single (sense or antisense) and double-stranded polynucleotides, ESTs, chromosomes, cDNAs, mRNAs, and rRNAs.

The terms "RNA interference," "RNAi," "miRNA," and "siRNA" refer to any method by which expression of a gene or gene product is decreased by introducing into a target cell one or more double-stranded RNAs, which are homologous to a gene of interest (particularly to the messenger RNA of the gene of interest, e.g., PDGF or VEGF).

The term "neovascularization" refers to new blood vessel formation in abnormal tissue or in abnormal positions.

The term "angiogenesis" refers to formation of new blood vessels in normal or in abnormal tissue or positions.

The term "ophthalmological disease" includes diseases of the eye and the ocular adnexa.

The term "ocular neovascular disorder" refers to an ocular disorder characterized by neovascularization. In one embodiment, the ocular neovascular disorder is a disorder other than cancer. Examples of ocular neovascular disorders include diabetic retinopathy and age-related macular degeneration.

The term "mammal" includes a human, monkey, cow, hog, sheep, horse, dog, cat, rabbit, rat and mouse. In certain embodiments, a subject is a mammal.

The term "PDGF" refers to a platelet-derived growth factor that regulates cell growth or division. As used herein, the term "PDGF" includes the various subtypes of PDGF including PDGF-B (see SEQ ID NOS: 2 (nucleic acid) and 3 (polypeptide)), PDGF-A (see SEQ ID NOS: 4 (nucleic acid) and 5 (polypeptide), PDGF-C (see SEQ ID NOS: 6 (nucleic acid) and 7 (polypeptide)), PDGF-D, variants 1 (see SEQ ID NOS: 8 (nucleic acid) and 9 (polypeptide)) and 2 (see SEQ ID NOS: 10 (nucleic acid) and 11 (polypeptide)), and dimerized forms thereof, including PDGF-AA, PDGF-AB, PDGF-BB, PDGF-CC, and PDGF-DD. Platelet derived growth factors includes homo- or heterodimers of A-chain (PDGF-A) and B-chain (PDGF-B) that exert their action via binding to and dimerization of two related receptor tyrosine kinase platelet-derived growth factor cell surface receptors (i.e., PDGFRs), PDGFR-α (see SEQ ID NOS: 12 (nucleic acid) and 13 (polypeptide)) and PDGFR-β (see SEQ ID NOS: 14 (nucleic acid) and 15 (polypeptide)). In addition, PDGF-C and PDGF-D, two additional protease-activated ligands for the PDGFR complexes, have been identified (Li et al., (2000) *Nat. Cell. Biol.* 2: 302-9; Bergsten et al., (2001) *Nat. Cell. Biol.* 3: 512-6; and Uutele et al., (2001) *Circulation* 103: 2242-47). Due to the different ligand binding specificities of the PDGFRs, it is known that PDGFR-α/α binds PDGF-AA, PDGF-BB, PDGF-AB, and PDGF-CC; PDGFR-β/β binds PDGF-BB and PDGF-DD; whereas PDGFR-α/β binds PDGF-AB, PDGF-BB, PDGF-CC, and PDGF-DD (Betsholtz et al., (2001) *BioEssays* 23: 494-507). As used herein, the term "PDGF" also refers to those members of the class of growth factors that induce DNA synthesis and mitogenesis through the binding and activation of a PDGFR on a responsive cell type. PDGFs can effect, for example: directed cell migration (chemotaxis) and cell activation; phospholipase activation; increased phosphatidylinositol turnover and prostaglandin metabolism; stimulation of both collagen and collagenase synthesis by responsive cells; alteration of cellular metabolic activities, including matrix synthesis, cytokine production, and lipoprotein uptake; induction, indirectly, of a proliferative response in cells lacking PDGF receptors; and potent vasoconstrictor activity. The term "PDGF" can be used to refer to a "PDGF" polypeptide, a "PDGF" encoding gene or nucleic acid, or a dimerized form thereof.

The term "PDGF-A" refers to an A chain polypeptide of PDGF or its corresponding encoding gene or nucleic acid.

The term "PDGF-B" refers to a B chain polypeptide of PDGF or its corresponding encoding gene or nucleic acid.

The term "PDGF-C" refers to a C chain polypeptide of PDGF or its corresponding encoding gene or nucleic acid.

The term "PDGF-D" refers to a D chain polypeptide of PDGF or its corresponding encoding gene or nucleic acid, including variants 1 and 2 of the D chain polypeptide of PDGF.

The term "PDGF-AA" refers to a dimer having two PDGF-A chain polypeptides.

The term "PDGF-AB" refers to a dimer having one PDGF-A chain polypeptide and one PDGF-B chain polypeptide.

The term "PDGF-BB" refers to a dimer having two PDGF-B chain polypeptides.

The term "PDGF-CC" refers to a dimer having two PDGF-C chain polypeptides.

The term "PDGF-DD" refers to a dimer having two PDGF-D chain polypeptides.

The term "VEGF" refers to a vascular endothelial growth factor that induces angiogenesis or an angiogenic process. As used herein, the term "VEGF" includes the various subtypes of VEGF (also known as vascular permeability factor (VPF) and VEGF-A) (see SEQ ID NOS: 16 (nucleic acid) and 17 (polypeptide)) that arise by, e.g., alternative splicing of the VEGF-A/VPF gene including $VEGF_{121}$, $VEGF_{165}$ and $VEGF_{189}$. Further, as used herein, the term "VEGF" includes VEGF-related angiogenic factors such as PIGF (placenta growth factor), VEGF-B, VEGF-C, VEGF-D and VEGF-E, which act through a cognate VEFG receptor (i.e., VEGFR) to induce angiogenesis or an angiogenic process. The term "VEGF" includes any member of the class of growth factors that binds to a VEGF receptor such as VEGFR-1 (Flt-1) (see SEQ ID NOS: 18 (nucleic acid) and 19 (polypeptide)), VEGFR-2 (KDR/Flk-1) (see SEQ ID NOS: 20 (nucleic acid) and 21 (polypeptide)), or VEGFR-3 (FLT-4). The term "VEGF" can be used to refer to a "VEGF" polypeptide or a "VEGF" encoding gene or nucleic acid.

The term "PDGF antagonist" refers to an agent that reduces, or inhibits, either partially or fully, the activity or production of a PDGF. In certain embodiments, the PDGF antagonist inhibits one or more of PDGF-A, PDGF-B, PDGF-C and PDGF-D. In certain embodiments, the PDGF antagonist inhibits one or more of PDGF-A, PDGF-B, and PDGF-C. In some embodiments, the PDGF antagonist inhibits a dimerized form of PDGF, such as PDGF-AA, PDGF-AB, PDGF-BB, PDGF-CC, and PDGF-DD. In certain embodiments, the PDGF antagonist inhibits PDGF-BB. In other embodiments, the PDGF antagonist inhibits PDGF-AB. A PDGF antagonist can directly or indirectly reduce or inhibit the activity or production of a specific PDGF such as PDGF-B. Furthermore, "PDGF antagonists" consistent with the above definition of "antagonist," include agents that act on a PDGF ligand or its cognate receptor so as to reduce or inhibit a PDGF-associated receptor signal. Examples of "PDGF antagonists" include antisense molecules, ribozymes or RNAi that target a PDGF nucleic acid; anti-PDGF aptamers, anti-PDGF antibodies to PDGF itself or its receptor, or soluble PDGF receptor decoys that prevent binding of a PDGF to its cognate receptor; antisense molecules, ribozymes or RNAi that target a cognate PDGF receptor (PDGFR) nucleic acid; anti-PDGFR aptamers or anti-PDGFR antibodies that bind to a cognate PDGFR receptor; and PDGFR tyrosine kinase inhibitors.

The term "VEGF antagonist" refers to an agent that reduces, or inhibits, either partially or fully, the activity or production of a VEGF. In certain embodiments, the VEGF antagonist inhibits one or more of VEGF-A, VEGF-B, VEGF-C and VEGF-D. A VEGF antagonist can directly or indirectly reduce or inhibit the activity or production of a specific VEGF such as $VEGF_{165}$. Furthermore, "VEGF antagonists" consistent with the above definition of "antagonist," include agents that act on either a VEGF ligand or its cognate receptor so as to reduce or inhibit a VEGF-associated receptor signal. Examples of "VEGF antagonists" include antisense molecules, ribozymes or RNAi that target a VEGF nucleic acid; anti-VEGF aptamers, anti-VEGF antibodies to VEGF itself or its receptor, or soluble VEGF receptor decoys that prevent binding of a VEGF to its cognate receptor; antisense molecules, ribozymes, or RNAi that target a cognate VEGF receptor (VEGFR) nucleic acid;

anti-VEGFR aptamers or anti-VEGFR antibodies that bind to a cognate VEGFR receptor; and VEGFR tyrosine kinase inhibitors. In certain embodiments, the VEGF antagonist is a peptide, e.g., a peptide comprising three or more amino acid residues. In certain embodiments, the VEGF antagonist is a bicyclic peptide.

The term "effective amount" when used in connection with an active agent, refers to an amount of the active agent, e.g., a PDGF antagonist, a VEGF antagonist or an anti-C5 agent, alone or in combination with another active agent, that is useful to treat or prevent an ophthalmological disease or disorder. The "effective amount" can vary depending upon the mode of administration, specific locus of the ophthalmological disease or disorder, the age, body weight, and general health of the subject. The effective amount of two or more active agents is the combined amount of the active agents that is useful for treating or preventing an ophthalmological disease or disorder, even if the amount of one of the agents, in the absence of one or more of the other agents, is ineffective to treat or prevent the ophthalmological disease or disorder.

A "variant" of polypeptide X refers to a polypeptide having the amino acid sequence of polypeptide X in which is altered in one or more amino acid residues. The variant can have "conservative" changes, wherein a substituted amino acid has similar structural or chemical properties (e.g., replacement of leucine with isoleucine). More rarely, a variant can have "nonconservative" changes (e.g., replacement of glycine with tryptophan). Analogous minor variations may also include amino acid deletions or insertions, or both. Guidance in determining which amino acid residues may be substituted, inserted, or deleted without eliminating biological or immunological activity can be determined using computer programs well known in the art, for example, LASERGENE software (DNASTAR).

The term "variant," when used in the context of a polynucleotide sequence, can encompass a polynucleotide sequence related to that of gene or the coding sequence thereof. This definition also includes, for example, "allelic," "splice," "species," or "polymorphic" variants. A splice variant can have significant identity to a reference molecule, but will generally have a greater or lesser number of polynucleotides due to alternative splicing of exons during mRNA processing. The corresponding polypeptide can possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species.

The term "anti-C5 agent" refers to an agent that reduces, or inhibits, either partially or fully, the activity or production of a C5 complement protein or a variant thereof. An anti-C5 agent can directly or indirectly reduce or inhibit the activity or production of a C5 complement protein or variant thereof. An anti-C5 agent can reduce or inhibit the conversion of C5 complement protein into its component polypeptides C5a and C5b. Anti-C5 agents can also reduce or inhibit the activity or production of C5a and/or C5b. Examples of "anti-C5 agents" include antisense molecules, ribozymes or RNAi that target a C5 nucleic acid; anti-C5 aptamers including anti-C5a and anti-C5b aptamers, anti-C5 antibodies directed against C5, C5a, C5b, or C5b-9, or soluble C5 receptor decoys that prevent binding of a C5 complement protein or variant or fragment thereof (e.g., C5a or C5b) to a binding partner or receptor.

Agents Useful for Treatment or Prevention of an Opthalmological Disease or Disorder Antagonist A Antagonist A is a PEGylated, anti-PDGF aptamer having the sequence CAGGCUACGC GTAGAGCAUC ATGATCCUGT (SEQ ID NO: 1) (see Example 3 of US Patent Application Publication No. 20050096257, incorporated herein by reference in its entirety) having 2'-fluoro-2'-deoxyuridine at positions 6, 19 and 28; 2'-fluoro-2'-deoxycytidine at positions 8, 20, 26, and 27; 2'-O-Methyl-2'-deoxyguanosine at positions 9, 14, 16, and 29; 2'-O-Methyl-2'-deoxyadenosine at position 21; an inverted orientation T (i.e., 3'-3'-linked) at position 30; and two hexaethylene-glycol phosphoramidite linkages that join together the $9^{th}$ and $10^{th}$ nucleotides and $21^{st}$ and $22^{nd}$ nucleotides via phosphodiester linkages between the linker and the respective nucleotides.

The chemical name of Antagonist A is [(monomethoxy 20K polyethylene glycol carbamoyl-N2-) (monomethoxy 20K polyethylene glycol carbamoyl-N6-)]-lysine-amido-6-hexandilyl-(1-5)-2'-deoxycytidylyl-(3'-5')-2'-deoxyadenylyl-(3'-5')-2'-deoxyguanylyl-(3'-5')-2'-deoxyguanylyl-(3'-5)-2'-deoxycytidylyl-(3'-5)-2'-deoxy-2'-fluorouridylyl-(3'-5')-2'-deoxyadenylyl-(3'-5')-2'-deoxy-2'-fluorocytidylyl-(3'-5')-2'-deoxy-2'-methoxyguanylyl-(3'-1)-$PO_3$-hexa(ethyloxy)-(18-5)-2'-deoxycytidylyl-(3'-5')-2'-deoxyguanylyl-(3'-5')-thymidylyl-(3'-5)-2'-deoxyadenylyl-(3'-5')-2'-deoxy-2'-methoxyguanylyl-(3'-5)-2'-deoxyadenylyl-(3'-5)-2'-deoxy-2'-methoxyguanylyl-(3'-5)-2'-deoxycytidylyl-(3'-5)-2'-deoxyadenylyl-(3'-5)-2'-deoxy-2'-fluorouridylyl-(3'-5)-2'-deoxy-2'-fluorocytidylyl-(3'-5)-2'-deoxy-2'-methoxyadenylyl-(3'-1)-$PO_3$-hexa(ethyloxy)-(18-5)-thymidylyl-(3'-5)-2'-deoxyguanylyl-(3'-5)-2'-deoxyadenylyl-(3'-5)-thymidylyl-(3'-5)-2'-deoxy-2'-fluorocytidylyl-(3'-5)-2'-deoxy-2'-fluorocytidylyl-(3'-5)-2'-deoxy-2'-fluorouridylyl-(3'-5)-2'-deoxy-2'-methoxyguanylyl-(3'-3)-thymidine.

The structure of Antagonist A is shown in FIG. 1.

The sequence of Antagonist A is:

5'-[mPEG2 40 kD]-[HN—$(CH_2)_6O$] $CAGGCU_fAC_fG_m$ $[PO_3(CH_2CH_2O)_6]$ $CGTAG_mAG_mCAU_fC_fA_m$ $[PO_3(CH_2CH_2O)_6]TGATC_fC_fU_fG_m$-[3T]-3', whose aptamer sequence is set forth in (SEQ ID NO: 1), where [3T] refers to an inverted thymidine nucleotide that is attached to the 3' end of the oligonucleotide at the 3' position on the ribose sugar, and [mPEG2 40 kD] represents two 20 kD polyethylene glycol (PEG) polymer chains, in one embodiment two about 20 kD PEG polymer chains, that are covalently attached to the two amino groups of a lysine residue via carbamate linkages. This moiety is in turn linked with the oligonucleotide via the amino linker described below.

[HN—$(CH_2)_6O$] represents a bifunctional α-hydroxy-ω-amino linker that is covalently attached to the PEG polymer via an amide bond. The linker is attached to the oligonucleotide at the 5'-end of Antagonist A by a phosphodiester linkage.

$[PO_3(CH_2CH_2O)_6]$ represents the hexaethylene glycol (HEX) moieties that join segments of the oligonucleotide via phosphodiester linkages. Antagonist A has two HEX linkages that join together the $9^{th}$ and $10^{th}$ nucleotides and $21^{st}$ and $22^{nd}$ nucleotides via phosphodiester linkages between the linker and the respective nucleotides.

C, A, G, and T represent the single letter code for the 2'-deoxy derivatives of cytosine, adenosine, guanosine, and thymidine nucleic acids, respectively. Antagonist A has four 2'-deoxyribocytosine, six 2'-deoxyriboadenosine, four 2'-deoxyriboguanosine, and four 2'-deoxyribothymidine.

$G_m$ and $A_m$ represent 2'-methoxy substituted forms of guanosine and adenosine, respectively. Antagonist A has four 2'-methoxyguanosines and one 2'-methoxyadenosine. $C_f$ and $U_f$ represent the 2'-fluoro substituted forms of cytosine and uridine, respectively. Antagonist A has four 2'-fluorocytosines and three 2'-fluorouridines.

The phosphodiester linkages in the oligonucleotide, with the exception of the 3'-terminus, connect the 5'- and 3'-oxygens of the ribose ring with standard nucleoside phosphodiester linkages. The phosphodiester linkage between the 3'-terminal thymidine and the penultimate $G_m$ links their respective 3'-oxygens, which is referred to as the 3',3'-cap.

Antagonist A has a molecular weight from 40,000 to 60,000 Daltons, in one embodiment from about 40,000 to about 60,000 Daltons, and can be colorless to slightly yellow in solution. Antagonist A can be present in a solution of monobasic sodium phosphate monohydrate and dibasic sodium phosphate heptahydrate as buffering agents and sodium chloride as a tonicity adjuster. Antagonist A is a hydrophilic polymer. The Antagonist A is soluble in water and in phosphate-buffered saline (PBS), as assessed by visual inspection, to at least 50 mg (based on oligonucleotide weight)/mL solution.

Antagonist A can be synthesized using an iterative chemical synthesis procedure to produce the oligonucleotide portion, which is then covalently bonded to a pegylation reagent, as further described in Example 4 of US Patent Publication NO. 2012/0100136.

Antagonist A is a persodium salt. Other pharmaceutically acceptable salts, however, of Antagonist are useful in the compositions and methods disclosed herein.

VEGF Antagonists

In some embodiments, the VEGF antagonist is ranibizumab (commercially available under the trademark Lucentis® (Genentech, San Francisco, CA); see FIG. 1 of U.S. Pat. No. 7,060,269 for the heavy chain and light chain variable region sequences), bevacizumab (commercially available under the trademark Avastin® (Genentech, San Francisco, CA); see FIG. 1 of U.S. Pat. No. 6,054,297 for the heavy chain and light chain variable region sequences), aflibercept (commercially available under the trademark Eylea® (Regeneron, Tarrytown, NY), KH902 VEGF receptor-Fc fusion protein (see Zhang et al. (2008) Mol Vis. 14:37-49), 2C3 antibody (see U.S. Pat. No. 6,342,221, Column 8, lines 48-67, Column 9, lines 1-21), ORA102 (available from Ora Bio, Ltd.), pegaptanib (e.g., pegaptanib sodium; commercially available under the trademark Macugen® (Valeant Pharmaceuticals, Bridgewater, NJ; see FIG. 1 of U.S. Pat. No. 6,051,698)), bevasiranib (see Dejneka et al. (2008) Mol Vis. 14:997-1005), SIRNA-027 (Shen et al. (2006) Gene Ther. 13:225-34), decursin (see U.S. Pat. No. 6,525,089 (Column 3, lines 5-16)), decursinol (see Ahn et al. (1997) Planta Med. 63:360-1), picropodophyllin (see Economou (2008) Investigative Ophthalmology & Visual Science. 49:2620-6), guggulsterone (see Kim et al. (2008) Oncol. Rep. 20:1321-7), PLG101 (see Ahmadi and Lim (2008) Expert Opin Pharmacother. 9:3045-52), PLG201 (see Ahmadi and Lim (2008)), eicosanoid LXA4 (see Baker et al (2009) J Immun. 182:3819-26), PTK787 (commercially available under the trademark Vitalanib™; see Barakat and Kaiser (2009) Expert Opin Investig Drugs 18:637-46), pazopanib (see Takahashi et al. (2009) Arch Ophthalmol. 127:494-9), axitinib (see Hu-Lowe et al. (2008) Clin Cancer Res. 14:7272-83), CDDO-Me (see Sogno et al. (2009) Recent Results Cancer Res. 181:209-12), CDDO-Imm (see Sogno et al. (2009)), shikonin (see Hisa et al. (1998) Anticancer Res. 18:783-90), beta-hydroxyisovalerylshikonin (see Hisa et al. (1998)), ganglioside GM3 (Chung et al. (2009) Glycobio. 19:229-39), DC101 antibody (see U.S. Pat. No. 6,448,077, Column 2, lines 61-65), Mab25 antibody (see U.S. Pat. No. 6,448,077, Column 2, lines 61-65), Mab73 antibody (see U.S. Pat. No. 6,448,077, Column 2, lines 61-65), 4A5 antibody (see U.S. Pat. No. 6,383,484, Column 12, lines 50-54), 4E10 antibody (see U.S. Pat. No. 6,383,484, Column 10, lines 66-67, Column 11, lines 1-2), 5F12 antibody (see U.S. Pat. No. 6,383,484, Column 10, lines 62-65), VA01 antibody (see U.S. Pat. No. 5,730,977, Column 6, lines 26-30), BL2 antibody (U.S. Pat. No. 5,730,977, Column 6, lines 30-32), VEGF-related protein (see U.S. Pat. No. 6,451,764, FIG. 1), sFLT01 (see Pechan et al. (2009) Gene Ther. 16:10-6), sFLT02 (see Pechan et al. (2009)), Peptide B3 (see Lacal et al. (2008) Eur J Cancer 44:1914-21), TG100801 (see Palanki et al. (2008) J Med Chem. 51:1546-59), sorafenib (commercially available under the trademark Nexavar™; see Kernt et al. (2008) Acta Ophthalmol. 86:456-8), G6-31 antibody (see Crawford et al. (2009) Cancer Cell 15:21-34), ESBA1008 (see U.S. Pat. No. 8,349,322), tivozanib (see U.S. Pat. No. 6,821,987, incorporated by reference in its entirety; Campas et al. (2009) Drugs Fut 2009, 34(10): 793), or a pharmaceutically acceptable salt thereof.

In another embodiment, the VEGF antagonist is an antibody or an antibody fragment which binds to an epitope VEGF-A (SEQ ID NO: 22) or VEGF-B (SEQ ID NO: 23), or any portion of the epitopes. In one embodiment, the VEGF antagonist is an antibody or antibody fragment that binds to one or more of an epitope of VEGF (e.g., SEQ ID NOS: 22 and 23). In another embodiment, the VEGF antagonist is an antibody or an antibody fragment which binds to an epitope of VEGF, such as an epitope of VEGF-A, VEGF-B, VEGF-C, VEGF-D, or VEGF-E. In some embodiments, the VEGF antagonist binds to an epitope of VEGF such that binding of VEGF and VEGFR are inhibited. In one embodiment, the epitope encompasses a component of the three dimensional structure of VEGF that is displayed, such that the epitope is exposed on the surface of the folded VEGF molecule. In one embodiment, the epitope is a linear amino acid sequence from VEGF.

In some embodiments, an inhibitory antibody directed against VEGF is known in the art, e.g., those described in U.S. Pat. Nos. 6,524,583, 6,451,764 (VRP antibodies), U.S. Pat. Nos. 6,448,077, 6,416,758, 6,403,088 (to VEGF-C), U.S. Pat. No. 6,383,484 (to VEGF-D), U.S. Pat. No. 6,342,221 (anti-VEGF antibodies), U.S. Pat. No. 6,342,219 6,331,301 (VEGF-B antibodies), and U.S. Pat. No. 5,730,977, and PCT publications WO96/30046, WO 97/44453, and WO 98/45331, the contents of which are incorporated by reference in their entirety.

Other non-antibody VEGF antagonists include antibody mimetics (e.g., Affibody® molecules, affilins, affitins, anticalins, avimers, Kunitz domain peptides, and monobodies) with VEGF antagonist activity. This includes recombinant binding proteins comprising an ankyrin repeat domain that binds VEGF-A and prevents it from binding to VEGFR-2. One example is MP0112, also known as AGN 150998 (DARPin®). The ankyrin binding domain may have an amino acid sequence of SEQ ID NO: 97.

Recombinant binding proteins comprising an ankyrin repeat domain that binds VEGF-A and prevents it from binding to VEGFR-2 are described in more detail in WO2010/060748 and WO2011/135067.

Further specific antibody mimetics with VEGF antagonist activity are the 40 kD pegylated anticalin PRS-050 and the monobody angiocept (CT-322).

The aforementioned non-antibody VEGF antagonist may be modified to further improve their pharmacokinetic properties or bioavailability. For example, a non-antibody VEGF antagonist may be chemically modified (e.g., pegylated) to extend its in vivo half-life. Alternatively or in addition, it may be modified by glycosylation or the addition of further glycosylation sites not present in the protein sequence of the natural protein from which the VEGF antagonist was derived.

Other non-antibody VEGF antagonist immunoadhesin currently in pre-clinical development is a recombinant human soluble VEGF receptor fusion protein similar to VEGF-trap containing extracellular ligand-binding domains 3 and 4 from VEGFR2/KDR, and domain 2 from VEGFR1/Flt-1; these domains are fused to a human IgG Fc protein fragment (Li et al., 2011 *Molecular Vision* 17:797-803). This antagonist binds to isoforms VEGF-A. VEGF-B and VEGF-C. The molecule is prepared using two different production processes resulting in different glycosylation patterns on the final proteins. The two glycoforms are referred to as KH902 (conbercept) and KH906. The fusion protein can have the amino acid sequence of SEQ ID NO: 98 and, like VEGF-trap, can be present as a dimer. This fusion protein and related molecules are further characterized in EP1767546.

Anti-C5 Agents

In certain embodiments, the anti-C5 agent modulates a function of a C5 complement protein or a variant thereof. In some embodiments, the anti-C5 agent inhibits a function of C5 complement protein or a variant thereof. In one embodiment, the function inhibited by the anti-C5 agent is C5 complement protein cleavage.

A C5 complement protein variant as used herein encompasses a variant that performs substantially the same function as a C5 complement protein function. A C5 complement protein variant in some embodiments comprises substantially the same structure and in some embodiments comprises at least 80% sequence identity, in some embodiments at least 90% sequence identity, and in some embodiments at least 95% sequence identity to the amino acid sequence of the C5 complement protein comprising the amino acid sequence SEQ ID NO: 24.

In some embodiments, the anti-C5 agent is selected from a nucleic acid molecule, an aptamer, an antisense molecule, an RNAi molecule, a protein, a peptide, a cyclic peptide, an antibody or antibody fragment, a sugar, a polymer, or a small molecule. In certain embodiments, the anti-C5 agent is an anti-C5 agent described in PCT Patent Application Publication No. WO 2007/103549.

In particular embodiments, the anti-C5 agent is an anti-C5 aptamer. Aptamers are nucleic acid molecules having specific binding affinity to molecules through interactions other than classic Watson-Crick base pairing. Aptamers, like peptides generated by phage display or monoclonal antibodies ("mAbs"), are capable of specifically binding to selected targets and modulating the target's activity, e.g., through binding aptamers may block their target's ability to function. The aptamers may be unpegylated or pegylated. In particular embodiments, the aptamers may contain one or more 2' sugar modifications, such as 2'-O-alkyl (e.g., 2'-O-methyl or 2'-O-methoxyethyl) or 2'-fluoro modifications.

Illustrative C5 specific aptamers include the aptamers disclosed in PCT Publication No. WO 2007/103549, which is incorporated by reference in its entirety. Illustrative C5 specific aptamers include the aptamers ARC185 (SEQ ID NO: 25), ARC186 (SEQ ID NO: 26), ARC188 (SEQ ID NO: 27), ARC189 (SEQ ID NO: 28), ARC243 (SEQ ID NO: 29), ARC244 (SEQ ID NO: 30), ARC250 (SEQ ID NO: 31), ARC296 (SEQ ID NO: 32), ARC297 (SEQ ID NO: 33), ARC330 (SEQ ID NO: 34), ARC331 (SEQ ID NO: 35), ARC332 (SEQ ID NO: 36), ARC333 (SEQ ID NO: 37), ARC334 (SEQ ID NO: 38), ARC411 (SEQ ID NO: 39), ARC412 (SEQ ID NO: 40), ARC413 (SEQ ID NO: 41), ARC414 (SEQ ID NO: 42), ARC415 (SEQ ID NO: 43), ARC416 (SEQ ID NO: 44), ARC417 (SEQ ID NO: 45), ARC418 (SEQ ID NO: 46), ARC419 (SEQ ID NO: 47), ARC420 (SEQ ID NO: 48), ARC421 (SEQ ID NO: 49), ARC422 (SEQ ID NO: 50), ARC423 (SEQ ID NO: 51), ARC424 (SEQ ID NO: 52), ARC425 (SEQ ID NO: 53), ARC426 (SEQ ID NO: 54), ARC427 (SEQ ID NO: 55), ARC428 (SEQ ID NO: 56), ARC429 (SEQ ID NO: 57), ARC430 (SEQ ID NO: 58), ARC431 (SEQ ID NO: 59), ARC432 (SEQ ID NO: 60), ARC433 (SEQ ID NO: 61), ARC434 (SEQ ID NO: 62), ARC435 (SEQ ID NO: 63), ARC436 (SEQ ID NO: 64), ARC437 (SEQ ID NO: 65), ARC438 (SEQ ID NO: 66), ARC439 (SEQ ID NO: 67), ARC440 (SEQ ID NO: 68), ARC457 (SEQ ID NO: 69), ARC458 (SEQ ID NO: 70), ARC459 (SEQ ID NO: 71), ARC473 (SEQ ID NO: 72), ARC522 (SEQ ID NO: 73), ARC523 (SEQ ID NO: 74), ARC524 (SEQ ID NO: 75), ARC525 (SEQ ID NO: 76), ARC532 (SEQ ID NO: 77), ARC543 (SEQ ID NO: 78), ARC544 (SEQ ID NO: 79), ARC550 (SEQ ID NO: 80), ARC551 (SEQ ID NO: 81), ARC552 (SEQ ID NO: 82), ARC553 (SEQ ID NO: 83), ARC554 (SEQ ID NO: 84), ARC657 (SEQ ID NO: 85), ARC658 (SEQ ID NO: 86), ARC672 (SEQ ID NO: 87), ARC706 (SEQ ID NO: 88), ARC913 (SEQ ID NO: 89), ARC874 (SEQ ID NO: 90), ARC954 (SEQ ID NO: 91), ARC1537 (SEQ ID NO: 92), ARC1730 (SEQ ID NO: 93), or a pharmaceutically acceptable salt thereof.

In some embodiments, the anti-C5 agent is an aptamer with SEQ ID NO: 94, 95, or 96.

In a particular embodiment, the anti-C5 agent is a C5 specific aptamer comprising the nucleotide sequence of SEQ ID NO: 26 conjugated to a polyethylene glycol moiety via a linker. In some embodiments, the polyethylene glycol moiety has a molecular weight greater than about 10 kDa, particularly a molecular weight of about 20 kDa, more particularly about 30 kDa and more particularly about 40 kDa. In some embodiments, the polyethylene glycol moiety is conjugated via a linker to the 5' end of the aptamer. In some embodiments, the PEG conjugated to the 5' end of is a PEG of about 40 kDa molecular weight. In particular embodiments the about 40 kDa PEG is a branched PEG. In some embodiments the branched about 40 kDa PEG is 1,3-bis(mPEG-[about 20 kDa])-propyl-2-(4'-butamide). In other embodiments the branched about 40 kDa PEG is 2,3-bis(mPEG-[about 20 kDa])-propyl-1-carbamoyl.

In a particular embodiment, the C5 specific aptamer is a compound, ARC187, having the structure set forth below:

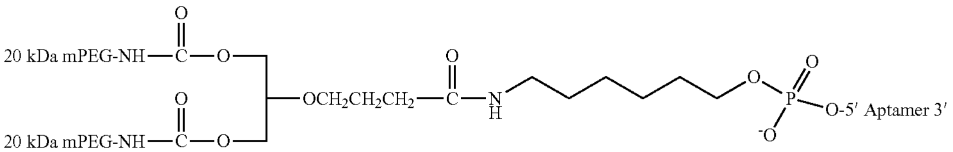

or a pharmaceutically acceptable salt thereof, where Aptamer= fCmGfCfCGfCmGmGfUfCfUfC-mAmGmGfCGfCfUmGmAmGfUfCfUmGmAmGfUfUfUAfCfCfUmGfCmG-3T (SEQ ID NO: 26)

wherein fC and fU=2'-fluoro nucleotides, and mG and mA=2'-OMe nucleotides and all other nucleotides are 2'-OH and where 3T indicates an inverted deoxy thymidine. In some embodiments, each 20 kDa mPEG of the above structure has a molecular weight of about 20 kDa.

In another particular embodiment, the C5 specific aptamer is a compound, ARC1905, having the structure set forth below:

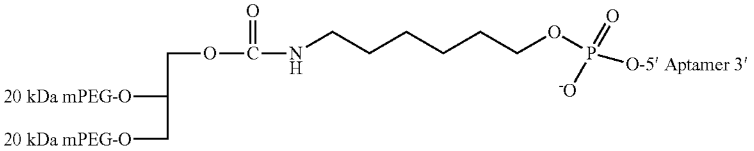

or a pharmaceutically acceptable salt thereof, where Aptamer=fCmGfCfCGfCmGmGfUfCfUfCmAmGmGfCGfCfUmGmAmGfUfCfUmGmAmGfUfUfUAfCfCfUmGfCmG-3T (SEQ ID NO: 26)

wherein fC and fU=2'-fluoro nucleotides, and mG and mA=2'-OMe nucleotides and all other nucleotides are 2'-OH and where 3T indicates and inverted deoxy thymidine. In some embodiments, each 20 kDa mPEG of the above structure has a molecular weight of about 20 kDa.

In other embodiments, the anti-C5 agent is an antisense oligonucleotide or ribozyme targeted to C5 that effects C5 inhibition by inhibiting protein translation from the messenger RNA or by targeting degradation of the corresponding C5 mRNA.

In still other embodiments, the anti-C5 agent is an anti-C5 RNA interference (RNAi) construct. Certain double stranded oligonucleotides useful to effect RNAi against C5 complement protein are less than 30 base pairs in length and may comprise about 25, 24, 23, 22, 21, 20, 19, 18 or 17 base pairs of ribonucleic acid and comprise a sequence with substantial sequence identity to the mRNA sequence of complement C5 protein, particularly human complement C5 protein. Optionally, the dsRNA oligonucleotides may include 3' overhang ends. Non-limiting illustrative 2-nucleotide 3' overhangs are composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., (2001) Nature, 411: 494-8).

Other Agents for Treatment or Prevention of an Ophthalmological Disease or Disorder In another embodiment, another agent useful for treating or preventing an ophthalmological disease or disorder is volociximab or a pharmaceutically acceptable salt thereof (Ramakrishnan et al. (2008) J Exp Ther Oncol. 5:273-86, which is hereby incorporated by reference in its entirety).

In some embodiments, a plurality of aptamers can be associated with a single Non-Immunogenic, High Molecular Weight Compound, such as Polyalkylene Glycol or PEG, or a Lipophilic Compound, such as a glycerolipid. The aptamers can all be to one target or to different targets. In embodiments where a compound comprises more than one PDGF aptamer, there can be an increase in avidity due to multiple binding interactions with a target, such as PDGF or VEGF. In yet further embodiments, a plurality of Polyalkylene Glycol, PEG, glycerol lipid molecules can be attached to each other. In these embodiments, one or more aptamers can be associated with each Polyalkylene Glycol, PEG, or glycerol lipid. This can result in an increase in avidity of each aptamer to its target. In addition, in embodiments where there are aptamers to PDGF or aptamers to PDGF and different Targets associated with Polyalkylene Glycol, PEG, or glycerol lipid, a drug can also be associated with, e.g., covalently bonded to, Polyalkylene Glycol, PEG, or glycerol lipid. Thus the compound would provide targeted delivery of the drug, with Polyalkylene Glycol, PEG, or glycerol lipid serving as a Linker, optionally, with one or more additional linkers.

Aptamers can be 5'-capped and/or 3'-capped with a 5'-5' inverted nucleoside cap structure at the 5' end and/or a 3'-3' inverted nucleoside cap structure at the 3' end. In several embodiments, Antagonist A, Antagonist B, Antagonist C, Antagonist D, pegaptanib, bevasiranib and Sirna-027 are 5' or 3' end-capped.

Methods for Treating or Preventing an Ophthalmological Disease or Disorder

The invention provides methods and compositions useful for treating or preventing ophthalmological diseases and disorders, including but not limited to any of the ophthalmological diseases and disorders described herein.

In some embodiments, the methods for treating or preventing an ophthalmological disease or disorder disclosed herein improve retinal attachment success, improve visual acuity, or stabilize vision. In some embodiments, the methods disclosed herein prevent or retard the rate of further vision loss in a subject.

In some embodiments, administration of Antagonist A or another pharmaceutically acceptable salt thereof in combination with a VEGF antagonist or pharmaceutically acceptable salt thereof and/or an anti-C5 agent improves retinal attachment success, improves visual acuity, or stabilizes vision to a degree that is greater than administration of Antagonist A or another pharmaceutically acceptable salt thereof alone, the VEGF antagonist or pharmaceutically acceptable salt thereof alone, or the anti-C5 agent alone. In some embodiments, the administration of Antagonist A or another pharmaceutically acceptable salt thereof and the VEGF antagonist or pharmaceutically acceptable salt thereof, and optionally, an anti-C5 agent, has a synergistic effect in treating or preventing an ophthalmological disease or disorder. For example, the administration of both Antagonist A or another pharmaceutically acceptable salt thereof and a VEGF antagonist or pharmaceutically acceptable salt thereof can improve retinal attachment success, improve visual acuity, or stabilize vision to a degree that is greater than an additive effect of administering both Antagonist A or another pharmaceutically acceptable salt thereof and the VEGF antagonist or pharmaceutically acceptable salt thereof. In some embodiments, administration of Antagonist A, alone or in combination with a VEGF antagonist and/or an anti-C5 agent, according to the methods described herein, e.g., treatment or dosing regimens, improves retinal attachment success, improves visual acuity, or stabilizes vision to a degree that is greater than administration of Antagonist A, alone or in combination with a VEGF antagonist and/or an anti-C5 agent, according to previously described methods.

In particular embodiments, any of the methods and compositions of the present invention are used to treat or prevent an ophthalmological disease or disorder in particular subjects. For example, in certain embodiments, subjects treated according to a method described herein are defined or identified based on their previous treatments for the disease or disorder, specific manifestations of their disease or disorder being treated, and/or other characteristics. In one embodiment, the subject has a defined phenotype or medical history.

Accordingly, any of the methods described herein may further comprise identifying the subject to be treated, such as by determining whether the subject was previously administered a VEGF antagonist for treating or preventing the disease or disorder or whether the subject had previously failed monotherapy with a VEGF antagonist, e.g., by inquiring of the subject or his health care provider, or by reviewing the subject's medical records.

In one embodiment, the subject was previously treated with a VEGF antagonist or anti-VEGF monotherapy for any ocular disease or disorder for which a VEGF antagonist is used, or for any of the ocular diseases or disorders described herein (e.g., wet-type AMD).

In particular embodiments, the methods and compositions described herein are useful for treating or preventing an ophthalmological disease or disorder in a subject who is anti-VEGF resistant, was previously administered or treated with anti-VEGF monotherapy, does not respond or had not responded favorably or adequately to anti-VEGF monotherapy, and/or failed monotherapy with a VEGF antagonist. In some embodiments, a subject who failed monotherapy is anti-VEGF resistant, has complement-mediated inflammation, and/or did not respond adequately to anti-VEGF monotherapy. In one embodiment, the subject who failed monotherapy with a VEGF antagonist is a subject who experienced a poor visual or anatomic outcome after treatment or administration with a VEGF antagonist. In one embodiment, the subject did not exhibit improved vision or exhibited reduced vision following anti-VEGF monotherapy.

In certain embodiments, the subject does not respond or had not responded favorably or adequately to anti-VEGF monotherapy, as determined by the subject's vision loss or by the subject's lack of significant vision gain following anti-VEGF monotherapy. In one embodiment, the subject's lack of significant vision gain following anti-VEGF monotherapy is determined by the subject's loss of ability to read one or more, in some embodiments three or more, and in some embodiments fifteen or more, letters of a standardized chart of vision testing, e.g., the Early Treatment for Diabetic Retinopathy Study Chart ("ETDRS chart"). In some embodiments, the vision testing is as described in Early Treatment Diabetic Retinopathy Study Research Group (ETDRS), Manual of Operations, Baltimore: ETDRS Coordinating Center, University of Maryland. Available from: National Technical Information Service, 5285 Port Royal Road, Springfield, VA 22161; Accession No. PB85 223006/AS; Ferris et al., Am J Ophthalmol 94:91-96, 1982; or Example 4, as described herein. In some embodiments, the vision testing uses one or more charts available via the Web from the site www.nci.nih.gov, using the relative reference/photo/keyword.asp?conditions=Eye+Charts&match=all, e.g., ETDRS visual acuity Chart 1, 2 and/or R.

In another embodiment, the subject's vision loss following anti-VEGF monotherapy is determined by the subject's loss of ability to read one or more, in some embodiments three or more, letters or lines of a standardized chart of vision testing, e.g., the ETDRS chart, from baseline. In one embodiment, the subject's lack of significant vision gain following anti-VEGF monotherapy is determined by the subject's inability to read an additional one or more, in some embodiment three or more, and in some embodiments fifteen or more, letters of a standardized chart of vision testing, e.g., the ETDRS chart, from baseline. In another embodiment, the subject's lack of significant vision gain following anti-VEGF monotherapy is determined by the subject's inability to read an additional one or more, in some embodiments three or more, lines of a standardized chart of visual testing, e.g., the ETDRS chart, from baseline. In some embodiments, a subject's vision loss or lack of significant vision gain is determined by the subject's visual loss or anatomic signs of poor treatment response, for example, persistent leakage, increased hemorrhage, persistent or increased retinal pigment epithelium (RPE) detachment, signs of neovascular activity, or growth of neovascularization or increased deposition of abnormal matrix or fibrosis. In particular embodiments, a subject's vision loss or lack of significant vision gain is determined at 12 weeks or at 24 weeks following the initiation of treatment.

In certain embodiments, the subject is anti-VEGF-resistant to a VEGF antagonist, e.g., anti-VEGF monotherapy. In one embodiment, a subject is anti-VEGF resistant if the subject was previously administered with a VEGF antagonist, e.g., anti-VEGF monotherapy, that did not result in the treatment or prevention of the ophthalmological disease or disorder; resulted in only a temporary treatment or prevention of the ophthalmological disease or disorder and rendered the subject in further need of treatment or prevention of the ophthalmological disease or disorder; or that resulted in the subject's visual decline and rendered the subject in further need of treatment or prevention of the ophthalmological disease or disorder.

In another embodiment, a subject is anti-VEGF resistant if the subject was previously treated or administered with an anti-VEGF treatment, e.g., anti-VEGF monotherapy, and failed to achieve any visual gain or experienced visual decline. In some embodiments, the subject did not respond adequately to anti-VEGF treatment. In one embodiment, the subject was administered the anti-VEGF treatment for one year or longer. In some such embodiments, the subject is in need of treatment for wet AMD.

Accordingly, the present invention provides methods for treating, preventing, or stabilizing wet AMD in a subject, such as a subject who has failed monotherapy with a VEGF antagonist (e.g., is anti-VEGF resistant, has complement-mediated inflammation, and/or did not respond adequately to anti-VEGF monotherapy). In particular embodiments, the methods comprise determining whether the subject was previously administered or treated with anti-VEGF monotherapy. In certain embodiments, anti-VEGF monotherapy means administration of only one or more VEGF antagonists. In certain embodiments, anti-VEGF monotherapy includes the optional administration of other drugs that are not agents specifically adapted for treating an ophthalmological disease or disorder, e.g, wet AMD.

In certain embodiments, the methods and compositions described herein are useful for treating or preventing an ophthalmological disease or disorder in a subject that is treatment-naïve. In some embodiments, the subject is treatment-naïve if the subject was not previously treated for the ophthalmological disease or disorder. In some embodiments, the subject is treatment-naïve if the subject was not previously administered or treated with a VEGF antagonist or anti-VEGF monotherapy ("anti-VEGF-treatment-naïve"). In particular embodiments, the methods further comprise determining whether the subject was previously treated for the ophthalmological disease or disorder or administered a VEGF antagonist or anti-VEGF monotherapy, e.g., by inquiring of the subject or his or her health care provider, or by reviewing the subject's medical records. In certain embodiments, anti-VEGF monotherapy means administration of only one or more VEGF antagonists. In certain embodiments, anti-VEGF monotherapy includes the optional administration of other drugs that are not agents specifically adapted for treating an ophthalmological disease or disorder, e.g, wet AMD. In some embodiments, the subject is treatment-naïve if the subject was not previously treated for AMD (e.g., wet AMD). In some embodiments, the subject is treatment-naïve if the subject was not previously treated, or has underwent no previous treatment for AMD (e.g., wet AMD) in either eye. In yet other embodiments, the subject is treatment-naïve if the subject was not previously treated, or has underwent no previous treatment, for AMD (e.g., wet AMD; e.g., in either eye) except for one or more oral supplements of vitamins and minerals. In some embodiments, the subject is treatment-naïve if the subject was not previously administered a therapeutic agent used for the treatment of AMD (e.g., wet AMD).

In certain embodiments, the subject has complement-mediated inflammation. In certain embodiments, the subject is anti-VEGF resistant and has complement-mediated inflammation. In certain embodiments, the complement-mediated inflammation is present in an eye of the subject. In certain embodiments, the complement-mediated inflammation results from previous administration with anti-VEGF monotherapy. In other embodiments, the subject has or has been diagnosed with complement-mediated inflammation. In still other embodiments, the subject did not respond adequately to anti-VEGF monotherapy and has or has been diagnosed with complement-mediated inflammation. In certain embodiments, complement-mediated inflammation is diagnosed in the subject using a genetic screening method. Such genetic screening methods are known to those of skill in the art and include, but are not limited to, screening for mutations in complement genes, such as complement factor H (CFH), CFI, CFHR5, and MCP, BF, and C2 genes.

In certain embodiments, the methods and compositions described herein are useful for treating or preventing an ophthalmological disease or disorder in a subject who is newly diagnosed with the ophthalmological disease or disorder. In some embodiments, the subject is newly diagnosed if the subject was not previously diagnosed for the ophthalmological disease or disorder. In some embodiments, the subject is newly diagnosed with age-related macular degeneration. In some embodiments, the subject is newly diagnosed with dry age-related macular degeneration. In some embodiments, the subject is newly diagnosed with wet-type AMD. In particular embodiments, the methods further comprise determining whether the subject was previously diagnosed for the ophthalmological disease or disorder, e.g., by inquiring of the subject or his or her health care provider, or by reviewing the subject's medical records.

In some embodiments of the invention, the methods and compositions described herein are useful for treating or preventing an ophthalmological disease or disorder that is a neovascular disorder. In other embodiments of the invention, the ophthalmological disease or disorder results in retinal edema. Illustrative ophthalmological diseases or disorders that can be treated or prevented are described herein.

Treatment or Prevention of Age-Related Macular Degeneration

In one embodiment, the ophthalmological disease or disorder treated or prevented by any of the methods or compositions described herein is age-related macular degeneration. Vision changes that can be associated with macular degeneration include distortions and/or blind spots (scotoma) detected using an Amsler grid, changes in dark adaptation (diagnostic of rod cell health), changes in color interpretation (diagnostic of cone cell health), or a decrease in visual acuity. Examples of age-related macular degeneration are nonneovascular (also known as "dry") and neovascular (also known as "wet" or "exudative") macular degeneration.

In one embodiment, the dry age-related macular degeneration is associated with the formation of drusen. In one embodiment, treating or preventing dry macular degeneration encompasses treating or preventing an abnormality of the retinal pigment epithelium and/or underlying vasculature, known as choriocapilaries. Examples of abnormalities of the retinal pigment epithelium include geographic atrophy, non-geographic atrophy, focal hypopigmentation, and focal hyperpigmentation. In another embodiment, treating or preventing wet age-related macular degeneration encompasses treating or preventing choroidal neovascularization or pigment epithelial detachment.

In one embodiment, the invention provides methods for treating or preventing wet age-related macular degeneration. Another aspect of the present invention is methods for treating, preventing, or inhibiting a choroidal neovascular complex in a subject, e.g., inhibiting the formation or growth of a choroidal neovascular complex.

In another aspect of the invention, the invention provides methods for treating or preventing choroidal neovascularization in a subject. In some embodiments, the choroidal neovascularization is subfoveal choroidal neovascularization. In some embodiments, the subfoveal choroidal neovascularization is due to age-related macular degeneration. In one embodiment, the subfoveal choroidal neovascularization is secondary to exudative type AMD. In other embodiments, the subfoveal choroidal neovascularization is present in subjects who have exudative type AMD, and in other embodiments, subfoveal choroidal neovascularization is present in subjects who do not have exudative type AMD.

In some embodiments, the subfoveal choroidal neovascularization is secondary to inflammatory, traumatic, myopic, idiopathic or neoplastic afflictions of the macula.

In some embodiments, wet age-related macular degeneration is classified according to the appearance of its choroidal neovascularization (CNV), into classic, occult or mixed (classic and occult) CNV types, as determined by an angiography, known as fluorescence angiography. Classic, occult or mixed (classic and occult) CNV classification can be based on the time, intensity and level of definition of dye appearance, and leakage from the CNV, as assessed by the fluorescein angiography. In some embodiments, the subject has classic CNV (e.g., pure classic) or mixed CNV (predominantly or minimally classic CNV). In some embodiments, the subject has occult CNV (e.g., pure occult CNV).

The administration of Antagonist A or another pharmaceutically acceptable salt thereof and the VEGF antagonist and/or anti-C5 agent can have a synergistic effect in treating or preventing classic CNV or occult CNV. For example, administration of both Antagonist A or another pharmaceutically acceptable salt thereof and the VEGF antagonist can improve visual acuity or stabilize vision to a degree that is greater than an additive effect of both Antagonist A or another pharmaceutically acceptable salt thereof and the VEGF antagonist. In another example, administration of both Antagonist A or another pharmaceutically acceptable salt thereof and the VEGF antagonist can reduce CNV or inhibit the growth of CNV to a greater degree than administration of Antagonist A or another pharmaceutically acceptable salt thereof or the VEGF antagonist. In some embodiments, administration of both Antagonist A or another pharmaceutically acceptable salt thereof and the VEGF antagonist can reduce CNV in a shorter timeframe or with a lower dosage amount or frequency, as compared to the timeframe or dosage amount with administration of Antagonist A or another pharmaceutically acceptable salt thereof or the VEGF antagonist. In some embodiments, administration of both Antagonist A or another pharmaceutically acceptable salt thereof and the VEGF antagonist can reduce CNV or inhibit the growth of CNV to a greater degree than an additive effect of both Antagonist A or another pharmaceutically acceptable salt thereof and the VEGF antagonist. In some embodiments, administration of both Antagonist A or another pharmaceutically acceptable salt thereof and the VEGF antagonist can reduce CNV in a shorter timeframe or with a lower dosage amount or frequency, as compared to an additive timeframe, dosage amount or frequency with administration of both Antagonist A or another pharmaceutically acceptable salt thereof and the VEGF antagonist.

In one embodiment, the present invention provides methods for treating, preventing, or stabilizing non-exudative type ("dry type") AMD. In one embodiment, Antagonist A or another pharmaceutically acceptable salt thereof, an anti-C5 agent, the combination of Antagonist A or another pharmaceutically acceptable salt thereof and an anti-C5 agent, or the combination of an anti-C5 agent and a VEGF antagonist is administered in an amount effective to maintain about the same level of drusen or reduce the level of drusen (e.g., amount, size, number, area and/or morphology) (e.g., size, number, area and/or morphology) as compared to the subject's drusen level prior to administration of Antagonist A or another pharmaceutically acceptable salt thereof, the anti-C5 agent, the combination of Antagonist A or another pharmaceutically acceptable salt thereof and the anti-C5 agent, or the combination of an anti-C5 agent and a VEGF antagonist, respectively. In a particular embodiment, the level of drusen is reduced by at least or about 5%, at least or about 10%, at least or about 20%, at least or about 30%, at least or about 40%, or at least or about 50%.

In some embodiments, Antagonist A or another pharmaceutically acceptable salt thereof, an anti-C5 agent, the combination of Antagonist A or another pharmaceutically acceptable salt thereof and the anti-C5 agent, or the combination of the anti-C5 agent and a VEGF antagonist is administered in an amount effective to inhibit, slow, or prevent the progression of non-exudative type AMD to geographic atrophy (GA). GA is an advanced form of non-exudative type AMD. In other embodiments, the Antagonist A or another pharmaceutically acceptable salt thereof and/or the anti-C5 agent or a pharmaceutically acceptable salt thereof is administered in an amount effective to reduce the growth or area of a GA lesion over time as compared to that in a subject not receiving Antagonist A or another pharmaceutically acceptable salt thereof and/or the anti-C5 agent. In other embodiments, the anti-C5 agent or a pharmaceutically acceptable salt thereof and a VEGF antagonist is administered in an amount effective to reduce the growth or area of a GA lesion over time as compared to that in a subject not receiving the anti-C5 agent and/or the VEGF antagonist. In a particular embodiment, the change in area or growth of the geographic atrophy lesion over time is reduced by at least or about 5%, at least or about 10%, at least or about 20%, at least or about 30%, at least or about 40%, or at least or about 50%. Methods of identifying and assessing the size of geographic lesions are known to those of skill in the art and include autofluorescence imaging and optical coherence tomography.

In particular embodiments, a subject in whom non-exudative AMD converts to exudative AMD, e.g., when new blood vessels invade the overlying retina, is treated. The present invention further provides methods for treating, preventing, or stabilizing drusen retinopathy secondary to complement-mediated immune disorders, including drusen retinopathy secondary to membranoproliferative glomerulonephritis type II disease. In some embodiments, Antagonist A or another pharmaceutically acceptable salt thereof and/or an anti-C5 agent and/or a VEGF antagonist is administered in an amount effective to reduce retinal drusen in subjects having or having been diagnosed with membranoproliferative glomerulonephritis type II disease or exudative-type AMD as compared to the level of retinal drusen prior to administration of Antagonist A or another pharmaceutically acceptable salt thereof and/or an anti-C5 agent and/or a VEGF antagonist. In certain embodiments, the level of drusen is reduced by at least or about 5%, at least or about 10%, at least or about 20%, at least or about 30%, at least or about 40%, or at least or about 50%.

In one embodiment, the ophthalmological disease or disorder is polypoidal choroidal vasculopathy (PCV), a variant of wet AMD.

Treatment or Prevention of a Condition Associated with Choroidal Neovascularization In one embodiment, the ophthalmological disease or disorder is a condition associated with choroidal neovascularization. Examples of conditions associated with choroidal neovascularization include a degenerative, inflammatory, traumatic or idiopathic condition. Treating or preventing a degenerative disorder associated with choroidal neovascularization also encompasses treating or preventing a heredodegerative disorder. Examples of heredodegenerative disorders include vitelliform macular dystrophy, fundus flavimaculatus and optic nerve head drusen. Examples of degenerative conditions associated with choroidal neovascularization include myopic degeneration or angioid streaks. In some embodiments, treating or preventing an inflammatory disorder associated with choroidal neovascularization encompasses treating or preventing ocular histoplasmosis syndrome, multifocal choroiditis, serpininous choroiditis, toxoplasmosis, toxocariasis, rubella, Vogt-Koyanagi-Harada syndrome, Behcet syndrome or sympathetic ophthalmia. In some embodiments, treating or preventing a traumatic disorder associated with choroidal neovascularization encompasses treating or preventing choroidal rupture or a traumatic condition caused by intense photocoagulation.

Treatment or Prevention of Proliferative Retinopathy

One particular aspect of the invention provides methods and compositions for treating or preventing proliferative vitreoretinopathy (PVR). In some embodiments, the PVR is a moderate form. In other embodiments, the PVR is a severe form. In some embodiments, the PVR is a recurrent form. In one embodiment, the subject with PVR also has or had retinal detachment, or the subject has PVR associated with retinal detachment, or PVR related scarring (e.g., scarring resulting from PVR, e.g., retinal scarring). In some embodiments, the PVR is characterized based on the configuration of the retina and the location of the scar tissue, such as in shown in Table 2 (See Lean J, et al. *Classification of proliferative vitreoretinopathy used in the silicone study. The Silicone study group. Ophthalmology* 1989; 96:765-771). Any of these categories or types of PVR can be treated or prevented according to the present invention.

TABLE 2

Classification of PVR

| Type no. | Type of contraction | Location of PVR | Summary of Clinical Signs |
|---|---|---|---|
| 1 | Focal | Posterior | Starfold |
| 2 | Diffuse | Posterior | Confluent irregular retinal folds in posterior retina; remainder of retina drawn posteriorly; optic disc may not be visible |
| 3 | Sub-retinal | Posterior | “Napkin ring” around disc or “clothesline” elevation of retina |
| 4 | Circumferential | Anterior | Irregular retinal folds in the anterior retina; series of radial folds more posteriorly; peripheral retina within vitreous base stretched inward |
| 5 | Perpendicular | Anterior | Smooth circumferential fold of retina at insertion of posterior hyaloid |
| 6 | Anterior | Anterior | Circumferential fold of retina at insertion of posterior hyaloid pulled forward; trough of peripheral retina anteriorly; ciliary processes stretched with possible hypotony; iris retracted |

The present methods for treating PVR can further comprise administering another agent useful for treating PVR, such as a corticosteriod; antineoplastic drug, such as 5-fluorouracil; colchicine; retinoid; heparin; epidermal growth factor receptor (EGFR) inhibitor, such as gefitinib or erlotinib.

Another aspect of the invention is methods for treating or preventing a proliferative retinopathy, such as one related to PVR (e.g., treating or preventing an ocular manifestation of a proliferative retinopathy), such as proliferative diabetic retinopathy, sickle cell retinopathy, post traumatic retinopathy, hyperviscosity syndromes, Aortic arch syndromes, ocular ischemic syndromes, carotid-cavernous fistula, multiple sclerosis, retinal vasculitis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, sickling hemoglobinopathies, AC and C-ß thalassemia, small vessel hyalinosis, incontinentia pigmenti, Eales' disease, branch retinal artery or vein occlusion, frosted branch angiitis, idiopathic retinal vasculitis, aneurysms, neuroretinitis, retinal embolization, retinopathy of prematurity, Uveitis, pars planitis, acute retinal necrosis, birdshot retinochoroidopathy, long-standing retinal detachment, choroidal melanoma, radiation retinopathy, familial exudative vitreoretinopathy, inherited retinal venous beading, retinoschisis, retinitis pigmentosa, or autosomal dominant vitreoretinochoroidopathy.

Another aspect of the invention is methods for treating or preventing a disease or condition that is a cause that results in proliferative retinopathy or PVR. In one embodiment, post-retinal detachment (e.g., that causes or results in PVR) is treated or prevented. In another embodiment, proliferative diabetic retinopathy (e.g., that causes or results in PVR) or sickle-cell retinopathy (e.g., that causes or results in PVR), as well as scarring caused by one or more of these disorders is treated or prevented.

Treatment or Prevention of Glaucoma

In one embodiment, the opthalmological disease or disorder is glaucoma. In one embodiment the glaucoma is open angle glaucoma, primary open angle glaucoma, secondary open angle glaucoma, closed angle glaucoma, glaucoma that is associated with diabetes, glaucoma that is associated with diabetic retinopathy, angle closure glaucoma, narrow angle glaucoma or acute glaucoma.

Treatment or Prevention of a Neoplasm

In one embodiment, the ophthalmological disease or disorder is a neoplasm. Examples of neoplasms include an eyelid tumor, a conjunctival tumor, a choroidal tumor, an iris tumor, an optic nerve tumor, a retinal tumor, an infiltrative intraocular tumor or an orbital tumor. Examples of an eyelid tumor include basal cell carcinoma, squamous carcinoma, sebaceous carcinoma, malignant melanoma, capillary hemangioma, hydrocystoma, nevus or seborrheic keratosis. Examples of a conjunctival tumor include conjunctival Kaposi's sarcoma, squamous carcinoma, intraepithelial neoplasia of the conjunctiva, epibular dermoid, lymphoma of the conjunctiva, melanoma, pingueculum, or pterygium. Examples of a choroidal tumor include choroidal nevus, choroidal hemangioma, metastatic choroidal tumor, choroidal osteoma, choroidal melanoma, ciliary body melanoma or nevus of Ota. Examples of an iris tumor include anterior uveal metastasis, iris cyst, iris melanocytoma, iris melanoma, or pearl cyst of the iris. Examples of an optic nerve tumor include optic nerve melanocytoma, optic nerve sheath meningioma, choroidal melanoma affecting the optic nerve, or circumpapillary metastasis with optic neuropathy. Examples of a retinal tumor include retinal pigment epithelial (RPE) hypertrophy, RPE adenoma, RPE carcinoma, retinoblastoma, or hamartoma of the RPE. In some embodiments, the present invention provides methods for inhibiting retinal pigment epithelium (RPE) or glial cells, such as inhibiting the migration of RPE or glial cells. Examples of an infiltrative intraocular tumor include chronic lymphocytic leukemia, infiltrative choroidopathy, or intraocular lymphoma. Examples of an orbital tumor include adenoid cystic carcinoma of the lacrimal gland, cavernous hemangioma of the orbit, lymphangioma of the orbit, orbital mucocele, orbital pseudotumor, orbital rhabdomyosarcoma, periocular hemangioma of childhood, or sclerosing orbital psuedotumor.

Another aspect of the invention is methods for treating or preventing von Hippel-Lindau (VHL) disease (e.g., treating or preventing visual loss associated VHL disease). In some embodiments, VHL disease is characterized by tumors. The tumors may be malignant or benign. In another embodiment, a benign or malignant tumor in the eye (e.g., ocular tumor) or a cyst (e.g., an ocular cyst), associated with VHL is treated or prevented. In some embodiments, the tumors are hemangioblastomas. In some embodiments, the tumors are von Hippel angioma or retinal capillary hemangiomas (e.g., juxtapapillary hemangioma).

In some embodiments, the subject with VHL disease has a deficiency of the protein "pVHL."

In some embodiments, the VHL disease is severe (e.g., a subject with severe VHL disease has a lesion that cannot be effectively treated with a non-pharmacologic modality (e.g., laser or cryotherapy), for example, as the lesion resides over or adjacent to a significant neural structure (e.g., optic nerve, macula, papillomacular bundle) that can be damaged with laser or cryotherapy).

In some embodiments, the methods for treating or preventing VHL disease comprise treating an ocular or non-ocular manifestation (e.g., benign or malignant neoplasm or cyst of the kidney, adrenal gland, pancreas, brain, spinal cord, inner ear, epididymis, or broad ligament) of VHL.

In some embodiments, the subjected being treated has a family history of VHL disease or one or more of retinal capillary hemangioma (RCH), spinal or cerebellar hemangioblastoma, pheochromocytoma, multiple pancreatic cysts, epididymal or broad ligament cystadenoma, multiple renal cysts, and renal cell carcinoma. In some embodiments, the subject has one or more RCH, spinal and cerebellar hemangioblastoma, pheochromocytoma, multiple pancreatic cysts, epididymal or broad ligament cystadenomas, multiple renal cysts, or renal cell carcinoma before the age of 60 years. In some embodiments, the subject has two or more hemangioblastomas of the retina or brain or a single hemangioblastoma in association with a visceral manifestation, such as kidney or pancreatic cysts; renal cell carcinoma; adrenal or extra-adrenal pheochromocytomas; endolymphatic sac tumors; papillary cystadenomas of the epididymis or broad ligament; or neuroendocrine tumors of the pancreas. In some embodiments, the subject has a disease-causing germline mutation in the VHL gene.

In some embodiments, the subject has RCH that exhibit activity, such as associated intra- or sub-retinal exudation or lipid deposition (which may reflect ongoing vascular incompetence and is not reflective of residual changes following previous treatment or secondary to coexistent retinal traction); increased size of the tumor compared to a previous time point as assessed by fundus photography or fluorescein angiography (FA); associated intra-, sub-, or pre-retinal hemorrhage not secondary to previous treatment, as assessed by fundus photography or FA; appearance of new feeder vessels or greater dilation or tortuosity of existing feeder vessels compared to a previous time point; and/or vitreous cell or haze indicative of vitreous exudation, in the absence of other ocular features potentially responsible for such findings. In some embodiments, the subject has RCH that is not readily treatable using cryotherapy or thermal laser because of its size, posterior location, poor previous response to conventional therapy, or other factors.

In some embodiments, methods or compositions of the invention are used to treat or prevent a complication of VHL, visual dysfunction (e.g., from VHL), or a fibrous complication of VHL (e.g., fibrous meningioma). In certain embodiments, the methods or compositions of the present invention are used to treat a manifestation of VHL as vascular proliferation that comprises fine, superficial, juxtapapillary vessels that are often associated with fibrovascular proliferation and epiretinal membrane formation.

Treatment or Prevention of Scarring or Fibrosis

Another aspect the invention provides methods for treating, inhibiting or preventing scarring or fibrosis (e.g., scarring or fibrosis is under the macular region of the retina). In some embodiments, the scarring is a fibrovascular scar (e.g., in the retina). In some embodiments, the fibrosis is hepatic, pulmonary or renal fibrosis. In some embodiments, the fibrosis is ocular fibrosis. In some embodiments, the fibrosis is sub-retinal fibrosis (e.g., associated with neovascular AMD). In some embodiments, the sub-retinal fibrosis is not associated with neovascular AMD. In some embodiments, the fibrosis is subfoveal fibrosis. In some embodiments, the subfoveal fibrosis is with retinal atrophy. In some embodiments, subfoveal fibrosis or sub-retinal fibrosis develops after administration of a VEGF antagonist, e.g., anti-VEGF monotherapy.

In some embodiments, the scarring results from glaucoma surgery, or follows glaucoma surgery, such as trabeculectomy, filtering surgery (such as partial thickness filtering surgery), glaucoma filtering procedures, minimally invasive glaucoma surgery, glaucoma valve implant surgery, glaucoma seton surgery, glaucoma tube shunt placement, glaucoma stent placement, or combined cataract and glaucoma surgery. In some embodiments, the methods of the present invention are useful to treat or prevent scarring relating to or resulting from glaucoma surgery (e.g., that can result in scar related proliferation). In some embodiments, the scarring is sub-retinal scarring. In some embodiments, the scarring is sub-retinal scarring that occurs following choroidal neovascular regression.

In particular embodiments, methods for treating, inhibiting or preventing sub-retinal fibrosis (e.g., reducing the formation of sub-retinal fibrosis) comprise administering to a subject in need thereof an effective amount of Antagonist A or another pharmaceutically acceptable salt thereof and a VEGF antagonist. In some embodiments, the subject has or is diagnosed with AMD (e.g., wet AMD). In some embodiments, the subject has or is diagnosed with advanced wet AMD.

Treatment or Prevention of Other Ophthalmological Diseases and Disorders

In certain embodiments, the ophthalmological disease or disorder is a cataract (e.g., age-related cataract), diabetic macula edema, macular telangiectasia (e.g., type 1 or 2 macular telangiectasia), atrophic macular degeneration, chorioretinopathy (e.g., central serous chorioretinopathy), retinal inflammatory vasculopathy, pathological retinal angiogenesis, age-related maculopathy, retinoblastoma, Pseudoxanthoma elasticum, a vitreoretinal disease, choroidal sub-retinal neovascularization, central serous chorioretinopathy, ischemic retinopathy, hypertensive retinopathy or diabetic retinopathy (e.g., nonproliferative or proliferative diabetic retinopathy, such as macular edema or macular ischemia), retinopathy of prematurity (e.g., associated with abnormal growth of blood vessels in the vascular bed supporting the developing retina), venous occlusive disease (e.g., a retinal vein occlusion, branch retinal vein occlusion or central retinal vein occlusion), arterial occlusive disease (e.g., branch retinal artery occlusion (BRAO), central retinal artery occlusion or ocular ischemic syndrome), central serous chorioretinopathy (CSC), cystoid macular edema (CME) (e.g., affecting the central retina or macula, or after cataract surgery), retinal telangiectasia (e.g., characterized by dilation and tortuosity of retinal vessels and formation of multiple aneurysms, idiopathic JXT, Leber's miliary aneurysms, or Coats' disease), arterial macroaneurysm, retinal angiomatosis, radiation-induced retinopathy (RIRP), or rubeosis iridis (e.g., associated with the formation of neovascular glaucoma, diabetic retinopathy, central retinal vein occlusion, ocular ischemic syndrome, or chronic retinal detachment).

In other embodiments, the ophthalmological disease or disorder is sickle cell disease (SCD), anemia, or sickle cell retinopathy (e.g., non-neovascular or non-proliferative ocular manifestations). In some embodiments, vaso-occlusive phenomena or hemolysis associated with SCD is treated or prevented. In some embodiments, ocular manifestations of SCD include vascular occlusions in the conjunctiva, iris, retina, or choroid. Non-neovascular or non-proliferative ocular manifestations can include conjunctival vascular occlusions which transform smooth vessels into comma-shaped fragments, iris atrophy, retinal "salmon patch" hemorrhages, retinal pigmentary changes and other abnormalities of the retinal vasculature, macula, choroid, and optic disc. In some embodiments, neovascularization or the proliferative ocular manifestation involves the growth of abnormal vascular fronds which can lead to vitreous hemorrhage, retinal detachment, epiretinal membranes, resulting in vision loss. In some embodiments, the methods further comprise performing another treatment, such as diathermy, cryotherapy, laser photocoagulation or surgery (e.g., vitrectomy).

In one embodiment, the ophthalmological disease or disorder is a condition associated with peripheral retinal neovascularization. Examples of conditions associated with peripheral retinal neovascularization include ischemic vascular disease, inflammatory disease with possible ischemia, incontinentia pigmenti, retinitis pigmentosa, retinoschisis or chronic retinal detachment.

Examples of ischemic vascular disease include proliferative diabetic retinopathy, branch retinal vein occlusion, branch retinal arteriolar occlusion, carotid cavernous fistula, sickling hemoglobinopathy, non-sickling hemoglobinopathy, IRVAN syndrome (retinal vasculitic disorder characterized by idiopathic retinal vasculitis, an aneurysm, and neuroretinitis), retinal embolization, retinopathy of prematurity, familial exudative vitreoretinopathy, hyperviscosity syndrome, aortic arch syndrome or Eales disease. Examples of sickling hemoglobinopathy include SS hemoglobinopathy and SC hemoglobinopathy. Examples of non-sickling hemoglobinopathy include AC hemoglobinopathy and AS hemoglobinopathy. Examples of hyperviscosity syndrome include leukemia, Waldenstrom macroglobulinemia, multiple myeloma, polycythemia or myeloproliferative disorder.

In some embodiments, treating or preventing an inflammatory disease with possible ischemia encompasses treating or preventing retinal vasculitis associated with systemic disease, retinal vasculitis associated with an infectious agent, uveitis or birdshot retinopathy. Examples of systemic diseases include systemic lupus erythematosis, Behcet's disease, inflammatory bowel disease, sarcoidosis, multiple sclerosis, Wegener's granulomatosis and polyarteritis nodosa. Examples of infectious agents include a bacterial agent that is the causative agent for syphilis, tuberculosis, Lyme disease or cat-scratch disease, a virus such as herpesvirus, or a parasite such as *Toxocara canis* or *Toxoplasma gondii*. Examples of uveitis include pars planitis or Fuchs uveitis syndrome.

Compositions for Therapeutic or Prophylactic Administration

Antagonist A or another pharmaceutically acceptable salt thereof, VEGF antagonists, or anti-C5 agents can be administered as a component of a composition that further comprises a pharmaceutically acceptable carrier or vehicle, e.g., a pharmaceutical composition. In certain embodiments, each therapeutic agent is administered to the subject in a separate composition. However, in other embodiments, two or more therapeutic agents may be administered to the subject in the same composition. In one embodiment, a composition of the invention comprises an effective amount of Antagonist A or another pharmaceutically acceptable salt thereof, a VEGF antagonist, and/or an anti-C5 agent and a pharmaceutically acceptable carrier or vehicle. In another embodiment, a composition comprising Antagonist A or another pharmaceutically acceptable salt thereof and another composition comprising a VEGF antagonist are administered. In some embodiments, another composition comprising an anti-C5 agent is administered. In some embodiments, a composition comprising Antagonist A or another pharmaceutically acceptable salt thereof and a VEGF antagonist is administered. In some embodiments, another composition comprising an anti-C5 agent is also administered.

Administration of each antagonist may be by any suitable means that results in an amount of Antagonist A or another pharmaceutically acceptable salt thereof, VEGF antagonist, and/or anti-C5 agent that is effective for the treatment or prevention of an ophthalmological disease or disorder. Each antagonist, for example, can be admixed with a suitable carrier substance, and is generally present in an amount of 1-95% by weight of the total weight of the composition. The composition may be provided in a dosage form that is suitable for ophthalmic, oral, parenteral (e.g., intravenous, intramuscular, subcutaneous), rectal, transdermal, nasal, or inhalant administration. In one embodiment, the composition is in a form that is suitable for injection directly in the eye. The composition may be in form of, e.g., tablets, capsules, pills, powders, granulates, suspensions, emulsions, solutions, gels including hydrogels, pastes, ointments, creams, plasters, delivery devices, suppositories, enemas, injectables, implants, sprays, drops or aerosols. The compositions comprising one or more antagonists can be formulated according to conventional pharmaceutical practice (see, e.g., Remington: *The Science and Practice of Pharmacy*, (20th ed.) ed. A. R. Gennaro, 2000, Lippincott Williams & Wilkins, Philadelphia, Pa. and *Encyclopedia of Pharmaceutical Technology*, eds., J. Swarbrick and J. C. Boylan, 1988-2002, Marcel Dekker, New York).

The compositions are, in one useful aspect, administered parenterally (e.g., by intramuscular, intraperitoneal, intravenous, intraocular, intravitreal, retro-bulbar, subconjunctival, subtenon or subcutaneous injection or implant) or systemically. Formulations for parenteral or systemic administration include sterile aqueous or non-aqueous solutions, suspensions, or emulsions. A variety of aqueous carriers can be used, e.g., water, buffered water, saline, and the like. Examples of other suitable vehicles include polypropylene glycol, polyethylene glycol, vegetable oils, gelatin, hydrogels, hydrogenated napthalenes, and injectable organic esters, such as ethyl oleate. Such formulations may also contain auxiliary substances, such as preserving, wetting, buffering, emulsifying, and/or dispersing agents. Biocompatible, biodegradable lactide polymer, lactide/glycolide copolymer, or polyoxyethylene-polyoxypropylene copolymers may be used to control the release of the active ingredients.

Alternatively, the compositions can be administered by oral ingestion. Compositions intended for oral use can be prepared in solid or liquid forms, according to any method known to the art for the manufacture of pharmaceutical compositions.

Solid dosage forms for oral administration include capsules, tablets, pills, powders, and granules. Generally, these pharmaceutical preparations contain active ingredients admixed with non-toxic pharmaceutically acceptable excipients. These include, for example, inert diluents, such as calcium carbonate, sodium carbonate, lactose, sucrose, glucose, mannitol, cellulose, starch, calcium phosphate, sodium phosphate, kaolin and the like. Binding agents, buffering agents, and/or lubricating agents (e.g., magnesium stearate) may also be used. Tablets and pills can additionally be prepared with enteric coatings. The compositions may optionally contain sweetening, flavoring, coloring, perfuming, and preserving agents in order to provide a more palatable preparation.

Compositions useful for ophthalmic use include tablets comprising one or more antagonists in admixture with a pharmaceutically acceptable excipient. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The antagonists of the present invention may be admixed in a tablet or other vehicle, or may be partitioned. In one example, one antagonist is contained on the inside of the tablet, and the other antagonist is on the outside, such that a substantial portion of the other antagonist is released prior to the release of the contained antagonist. If desired, antagonists in a tablet form may be administered using a drug delivery device (see below).

For example, compositions of the present invention may be administered intraocularly by intravitreal injection into the eye as well as by subconjunctival and subtenon injections. Other routes of administration include transcleral, retrobulbar, intraperitoneal, intramuscular, and intravenous. Alternatively, compositions can be administered using a drug delivery device or an intraocular implant (see below).

In one embodiment, Antagonist A or another pharmaceutically acceptable salt thereof or VEGF antagonist (e.g., ranibizumab, bevacizumab, aflibercept, pegaptanib sodium, or ESBA1008) is administered intravitreally with a 30-gauge or 27-gauge needle. In some embodiments, a 0.5 inch needle is used. In one embodiment, Antagonist A or another pharmaceutically acceptable salt thereof is administered intravitreally with a 30-gauge 0.5 inch needle and a VEGF antagonist (e.g., ranibizumab, bevacizumab, aflibercept, pegaptanib sodium, or ESBA1008) is administered intravitreally with a 27-gauge needle. In some embodiments, 50 μL (1.5 mg in 0.05 mL) of Antagonist A or another pharmaceutically acceptable salt thereof is administered intravitreally with a 30-gauge 0.5 inch needle and 50 μL of a VEGF antagonist (e.g., 0.5 mg of ranibizumab, 1.25 mg of bevacizumab, or 2.0 mg of aflibercept) is administered intravitreally with a 27-gauge needle.

Liquid dosage forms for oral administration can include pharmaceutically acceptable emulsions, solutions, suspensions, syrups, and soft gelatin capsules. These forms can contain inert diluents commonly used in the art, such as water or an oil medium, and can also include adjuvants, such as wetting agents, emulsifying agents, and suspending agents.

In some instances, the compositions can also be administered topically, for example, by patch or by direct application to a region, such as the epidermis or the eye, susceptible to or affected by a neovascular disorder, or by iontophoresis.

In one embodiment, the compositions can comprise one or more pharmaceutically acceptable excipients. In one embodiment, excipients for compositions that comprise an antagonist include, but are not limited to, buffering agents, nonionic surfactants, preservatives, tonicity agents, sugars, amino acids, and pH-adjusting agents. Suitable buffering agents include, but are not limited to, monobasic sodium phosphate, dibasic sodium phosphate, and sodium acetate. Suitable nonionic surfactants include, but are not limited to, polyoxyethylene sorbitan fatty acid esters such as polysorbate 20 and polysorbate 80. Suitable preservatives include, but are not limited to, benzyl alcohol. Suitable tonicity agents include, but are not limited to sodium chloride, mannitol, and sorbitol. Suitable sugars include, but are not limited to, α,α-trehalose. Suitable amino acids include, but are not limited to glycine and histidine. Suitable pH-adjusting agents include, but are not limited to, hydrochloric acid, acetic acid, and sodium hydroxide. In one embodiment, the pH-adjusting agent or agents are present in an amount effective to provide a pH of about 3 to about 8, about 4 to about 7, about 5 to about 6, about 6 to about 7, or about 7 to about 7.5. In one embodiment, the compositions do not comprise a preservative. In another embodiment, the composition does not comprise an antimicrobial agent. In another embodiment, the composition does not comprise a bacteriostat. Suitable excipients for a VEGF antagonist also include those described in U.S. Pat. No. 7,365,166, the contents of which are herein incorporated by reference in their entirety.

In one embodiment, the composition is in the form of an aqueous solution that is suitable for injection. In one embodiment, a composition is in the form of an aqueous solution that is suitable for injection. In one embodiment, a composition comprises Antagonist A or another pharmaceutically acceptable salt thereof, a buffering agent, a pH-adjusting agent, and water for injection. In another embodiment, a composition comprises Antagonist A or another pharmaceutically acceptable salt thereof, monobasic sodium phosphate, dibasic sodium phosphate, sodium chloride, hydrochloride acid, and sodium hydroxide.

In one embodiment, the composition comprises a VEGF antagonist, a buffering agent, a sugar, a nonionic surfactant, and water for injection. In another embodiment, the composition comprises a VEGF antagonist, monobasic sodium phosphate, dibasic sodium phosphate, α,α-trehalose dehydrate, and polysorbate 20. In one embodiment, the composition comprises a VEGF antagonist, a buffering agent, a pH-adjusting agent, a tonicity agent, and water that is suitable for injection. In another embodiment, the composition comprises a VEGF antagonist, monobasic sodium phosphate, dibasic sodium phosphate, sodium chloride, hydrochloric acid, and sodium hydroxide. In one embodiment, the VEGF antagonist is a pegylated anti-VEGF aptamer, e.g., pegaptanib sodium In another embodiment, the VEGF antagonist is ranibizumab, bevacizumab, aflibercept or ESBA1008. This invention provides the pharmaceutically acceptable salts of the antagonists. An antagonist of the present invention can possess a sufficiently basic functional group, which can react with any of a number of inorganic and organic acids, to form a pharmaceutically acceptable salt. A pharmaceutically-acceptable acid addition salt is formed from a pharmaceutically-acceptable acid, as is well known in the art. Such salts include the pharmaceutically acceptable salts listed in Journal of Pharmaceutical Science, 66, 2-19 (1977) and The Handbook of Pharmaceutical Salts; Properties, Selection, and Use. P. H. Stahl and C. G. Wermuth (ED.s), Verlag, Zurich (Switzerland) 2002, which are hereby incorporated by reference in their entirety.

Examples of a pharmaceutically acceptable salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts. The term "pharmaceutically acceptable salt" includes a hydrate of a compound of the invention and also refers to a salt of an antagonist of the present invention having an acidic functional group, such as a carboxylic acid functional group or a hydrogen phosphate functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. In one embodiment, the pharmaceutically acceptable salt is a sodium salt. In another embodiment, the pharmaceutically acceptable salt is a persodium salt.

The present invention further provides comprising Antagonist A or another pharmaceutically acceptable salt thereof. In one embodiment, the present compositions comprise about 30.0 mg of Antagonist A or another pharmaceutically acceptable salt thereof, about 0.3 mg of monobasic sodium phosphate monohydrate, about 2.1 mg of dibasic sodium phosphate heptahydrate and about 9.0 mg of sodium chloride per about 1 mL. In some embodiments, hydrochloric acid and/or sodium hydroxide are present as needed to adjust the pH of the composition. In some embodiments, the pH is about pH 5.5 to about pH 7.5 or about pH 6.0.

In some embodiments, the compositions comprise about 3% (w/v) of Antagonist A or another pharmaceutically acceptable salt thereof, about 0.03% (w/v) of monobasic sodium phosphate monohydrate, about 0.2% (w/v) of dibasic sodium phosphate heptahydrate, about 0.9% (w/v) of sodium chloride and about 95.9% (w/v) of water. In some embodiments, hydrochloric acid and/or sodium hydroxide are present as needed to adjust the pH of the composition. In some embodiments, the pH is about pH 5.5 to about pH 7.5 or about pH 6.0.

In certain embodiments, the concentration of Antagonist A or another pharmaceutically acceptable salt thereof, a VEGF antagonist (e.g., ranibizumab, bevacizumab, aflibercept, ESBA1008 or pegaptanib sodium), and/or an anti-C5 agent (e.g., ARC1905 or a pharmaceutically acceptable salt thereof) in a composition is about 0.002 mg/mL to about 50 mg/mL. In some embodiments, the concentration of Antagonist A or another pharmaceutically acceptable salt thereof, a VEGF antagonist (e.g., ranibizumab, bevacizumab, aflibercept, ESBA1008 or pegaptanib sodium), and/or an anti-C5 agent (e.g., ARC1905 or a pharmaceutically acceptable salt thereof) in a composition is less than or about 100 mg/mL, less than about 50 mg/mL, less than about 40 mg/mL, less than about 30 mg/mL, less than about 25 mg/mL, less than about 20 mg/mL, less than about 15 mg/mL, less than about 10 mg/mL, or less than about 5 mg/mL. In certain embodiments, the concentration of Antagonist A or another pharmaceutically acceptable salt thereof, a VEGF antagonist (e.g., ranibizumab, bevacizumab, aflibercept, ESBA1008 or pegaptanib sodium), and/or an anti-C5 agent (e.g., ARC1905 or a pharmaceutically acceptable salt thereof) in a composition is about 0.3 mg/mL to about 100 mg/mL, about 0.3 mg/mL to about 50 mg/mL, about 0.3 mg/mL to about 40 mg/mL, about 0.3 mg/mL to about 30 mg/mL, about 0.3 to about 25 mg/mL, about 0.3 mg/mL to about 20 mg/mL, about 0.3 mg/mL to about 15 mg/mL, about 0.3 mg/mL to about 10 mg/mL, about 1 mg/mL to about 100 mg/mL, about 1 mg/mL to about 50 mg/mL, about 1 mg/mL to about 40 mg/mL, about 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 5 mg/mL, about 5 mg/mL to about 100 mg/mL, or about 5 mg/mL to about 50 mg/mL.

In certain embodiments, methods of the invention comprise administering Antagonist A and optionally one or both of a VEGF antagonist and an anti-C5 agent as a component of a pharmaceutical composition. In one embodiment, the present invention provides compositions comprising an effective amount of: (a) Antagonist A or another pharmaceutically acceptable salt thereof; and (b) a VEGF antagonist or a pharmaceutically acceptable salt thereof. In certain embodiments, the compositions further comprise an effective amount of an anti-C5 agent or a pharmaceutically acceptable salt thereof. In some embodiments, the compositions stabilize one or more of the Antagonist A or another pharmaceutically acceptable salt thereof, the VEGF antagonist, and the anti-C5 agent. In certain embodiments, the Antagonist A or another pharmaceutically acceptable salt thereof, the VEGF antagonist and/or the anti-C5 agent does not adversely affect the activity of the other active agent(s) present in the composition. In particular embodiments, at least about 90% of one or more of the active agents in the composition, e.g., Antagonist A or another pharmaceutically acceptable salt thereof, VEGF antagonist, or anti-C5 agent, is chemically stable when the composition is stored at a temperature of from about 2.0° C. to about 8.0° C. for at least about twelve weeks.

In particular embodiments, Antagonist A or another pharmaceutically acceptable salt thereof, the VEGF antagonist or the anti-C5 agent is chemically stable when it shows no sign of decomposition or modification resulting in formation of a new chemical entity. In particular embodiments, Antagonist A or another pharmaceutically acceptable salt thereof, the VEGF antagonist or the anti-C5 agent is chemically stable when at least about 50%, at least about 60%, at least about 70%, at least about 80%, at least about 90%, a least about 95%, or at least about 99% of Antagonist A or another pharmaceutically acceptable salt thereof, the VEGF antagonist or the anti-C5 agent shows no sign of decomposition or modification resulting in formation of a new chemical entity, e.g., when stored at a temperature of from about 2.0° C. to about 8.0° C. for at least about twelve weeks.

In certain embodiments, the Antagonist A or another pharmaceutically acceptable salt thereof does not adversely affect the activity of the VEGF antagonist (e.g., ranibizumab, bevacizumab, aflibercept, pegaptanib sodium, or ESBA1008) or the ARC1905 or a pharmaceutically acceptable salt thereof. In certain embodiments, the VEGF antagonist (e.g., ranibizumab, bevacizumab, aflibercept, pegaptanib sodium, or ESBA1008) does not adversely affect the activity of the Antagonist A or another pharmaceutically acceptable salt thereof, or ARC1905 or a pharmaceutically acceptable salt thereof. In certain embodiments, ARC1905 or a pharmaceutically acceptable salt thereof does not adversely affect the activity of the Antagonist A or another pharmaceutically acceptable salt thereof, or the VEGF antagonist (e.g., ranibizumab, bevacizumab, aflibercept, pegaptanib sodium, or ESBA1008).

In particular embodiments, the compositions comprise Antagonist A or another pharmaceutically acceptable salt thereof; and ranibizumab, bevacizumab, aflibercept, pegaptanib sodium or ESBA1008, or a pharmaceutically acceptable salt thereof, and the compositions are physically or chemically stable with respect to both active agents at a particular pH or suitable for parenteral administration. In particular embodiments, the compositions comprise Antagonist A or another pharmaceutically acceptable salt thereof; ranibizumab, bevacizumab, aflibercept, pegaptanib sodium or ESBA1008 or a pharmaceutically acceptable salt thereof; and ARC1905 or a pharmaceutically acceptable salt thereof, and the compositions are physically or chemically stable with respect to all active agents at a particular pH or suitable for parenteral administration. In particular embodiments, a composition is physically stable if at least about 50%, at least about 60%, at least about 70%, at least about 80%, at least about 90%, at least about 95%, or at least about 99% of all active agents, i.e., the Antagonist A or another pharmaceutically acceptable salt thereof, the VEGF antagonist, and the anti-C5 agent (when present) present in the composition show no sign of aggregation, precipitation or denaturation upon visual examination of color or clarity, or as measured by UV light scattering or by size exclusion chromatography (SEC) or differential scanning calorimetry (DSC).

In particular embodiments, the compositions of the invention are considered physically stable if after storage the average number of particles detected does not exceed about 50 particles/mL, where the particles have a diameter >about 10 μm and does not exceed 5 particles/mL, where the particles have a diameter >25 μm, as measured by the Light Obscuration Particle Count Test described in (788) *Particulate Matter in Injections*, Revised Bulletin, Official Oct. 1, 2011, The United States Pharmacopeial Convention.

In particular embodiments, the compositions are considered physically stable if after storage the average number of particles detected does not exceed 50 particles/mL, where the particles have a diameter >10 μm; does not exceed 5 particles/mL, where the particles have a diameter >25 μm; and does not exceed 2 particles/mL, where the particles have a diameter >50 μm, as measured by the microscopic method particle count test described in (788) *Particulate Matter in Injections*, Revised Bulletin, Official Oct. 1, 2011, The United States Pharmacopeial Convention.

In particular embodiments, the compositions comprise Antagonist A or another pharmaceutically acceptable salt thereof, a VEGF antagonist (e.g., ranibizumab, bevacizumab, aflibercept, ESBA1008 or pegaptanib sodium) and, optionally, an anti-C5 agent (e.g., ARC1905 or a pharmaceutically acceptable salt thereof) and are chemically stable for at least eight weeks or at least twelve weeks at 25° C. or for at least twelve weeks or at least sixteen weeks or at least 24 weeks at 4° C. In particular embodiments, at least 80% of each of Antagonist A or another pharmaceutically acceptable salt thereof, VEGF antagonist, and anti-C5 agent (if present) show no sign of decomposition or modification resulting in formation of a new chemical entity under at least one of these conditions.

In particular embodiments, compositions comprise the following: (1) Antagonist A or another pharmaceutically acceptable salt thereof; (2) a VEGF antagonist; optionally, (3) an anti-C5 agent; (4) a buffer; optionally, (5) a tonicity modifier; and, optionally, (6) a surfactant. In specific embodiments of such compositions, the buffer is an acetate, phosphate, Tris or histidine buffer, or a mixture thereof; the tonicity modifier is sodium chloride, mannitol, sorbitol, or trehalose, or a mixture thereof; and the surfactant is polysorbate 20. In various embodiments, Antagonist A or another pharmaceutically acceptable salt thereof is present in compositions of the invention at a concentration of about 0.1 mg/mL to about 200 mg/mL; and the VEGF antagonist is present at a concentration of about 0.1 mg/mL to about 200 mg/mL. When present, the anti-C5 agent is present at a concentration of about 0.1 mg/mL to about 200 mg/mL. The buffer is present at a concentration of about 1 mM to about 200 mM; the tonicity modifier is present at a concentration of about 10 mM to about 200 mM (sodium chloride), about 1% to about 10% (w/v) (sorbitol), or about 1% to about 20% (w/v) (trehalose); and the surfactant, when present, is present at a concentration of about 0.005% to about 0.05% or a concentration of about 0.001% to about 0.05%.

In particular embodiments, the ratio of the concentration (mass of Antagonist A or another pharmaceutically acceptable salt thereof less that of its —R group/volume of composition) of Antagonist A or another pharmaceutically acceptable salt thereof to the concentration (mass/volume of composition) of the VEGF antagonist (e.g., ranibizumab, bevacizumab, aflibercept, pegaptanib sodium, or ESBA1008), ARC1905, or a pharmaceutically acceptable salt thereof, present in the composition is less than, or less than or equal to, 25.0, less than, or less than or equal to, 10.0, less than, or less than or equal to, 9.0, less than, or less than or equal to, 8.0, less than, or less than or equal to, 7.0, less than, or less than or equal to, 6.0, less than, or less than or equal to, 5.0, less than, or less than or equal to, 4.0, less than, or less than or equal to, 3.0, less than, or less than or equal to, 2.0 or less than, or less than or equal to, 1.0. Antagonist A's —R group is depicted in FIG. 1. In particular embodiments, the ratio of the concentration (mass of Antagonist A or another pharmaceutically acceptable salt thereof less that of its —R group/volume of composition) of Antagonist A or another pharmaceutically acceptable salt thereof to the concentration (mass/volume of composition) of the VEGF antagonist (e.g., ranibizumab, bevacizumab, aflibercept, pegaptanib sodium, or ESBA1008), ARC1905, or a pharmaceutically acceptable salt thereof, present in the composition is in the range of about 1 to about 10, about 2 to about 5, about 3 about 4, or about 5. In certain embodiments, the compositions comprise Antagonist A or another pharmaceutically acceptable salt thereof, a VEGF antagonist (e.g., ranibizumab, bevacizumab, aflibercept, pegaptanib sodium, or ESBA1008), and ARC1905 or a pharmaceutically acceptable salt thereof.

In one particular embodiment, the compositions comprise Antagonist A or another pharmaceutically acceptable salt thereof, a VEGF antagonist (e.g., ranibizumab, bevacizumab, aflibercept, ESBA1008, or pegaptanib sodium), and, optionally, an anti-C5 agent (e.g., ARC1905 or a pharmaceutically acceptable salt thereof), wherein the ratio of the concentration of PDGF antagonist to the concentration of VEGF antagonist (and/or anti-C5 agent) is less than 2; and the compositions further comprise sodium chloride at a concentration of about 10 mM to about 200 mM, histidine at a concentration of about 1 mM to about 100 mM, and polysorbate (e.g., polysorbate 20) at a concentration of about 0.005% to about 0.05%, where the pH of the composition is about 5.5 to about 7.0.

In certain embodiments, the compositions comprise one or more of a tonicity modifier, a surfactant, and a buffer suitable to achieve or maintain the particular pH or be suitable for parenteral administration. Appropriate buffers include those described herein as well as others known in the art, such as, e.g., Good's buffers, e.g., IVIES.

In certain embodiments, the compositions comprise Antagonist A or another pharmaceutically acceptable salt thereof, a VEGF antagonist (e.g., ranibizumab, bevacizumab, aflibercept, ESBA1008 or pegaptanib sodium), and a tonicity modifier that is sorbitol or sodium chloride, or mixtures thereof. In certain embodiments, the compositions further comprise an anti-C5 agent (e.g., ARC1905 or a pharmaceutically acceptable salt thereof). In particular embodiments, the tonicity modifier is sorbitol, and the pH of the composition is about 5.0 to about 8.0, about 5.0 to about 7.0, about 6.0 or about 7.0. In particular embodiments, the tonicity modifier is sodium chloride, and the pH of the composition is about 5.0 to about 8.0, about 5.0 to about 7.0, about 5.5 to about 7.5, about 6.0 to about 8.0, about 8.0, about 7.0, or about 6.0. In certain embodiments, the tonicity modifier is sorbitol at about 1% to about 10% (w/v), or about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v). In particular embodiments, the tonicity modifier is sodium chloride at a concentration of about 10 mM to about 200 mM, about 50 mM to 200 mM, about 75 mM to about 200 mM, about 50 mM to about 150 mM, about 100 mM, about 110 mM, about 120 mM, about 130 mM about 140 mM or about 150 mM. In one embodiment, the tonicity modifier is sodium chloride at a concentration of about 130 mM. In other embodiments, the tonicity modifier is sodium chloride at a concentration of about 75 mM or about 120 mM. With respect to tonicity modifier concentration, "mM" refers to millimoles of the tonicity modifier per liter of composition.

In certain embodiments, the compositions comprise Antagonist A or another pharmaceutically acceptable salt thereof, a VEGF antagonist (e.g., ranibizumab, bevacizumab, aflibercept, ESBA1008 or pegaptanib sodium), and a buffer capable of achieving or maintaining the pH of the composition within a desired range. In certain embodiments, the compositions further comprise an anti-C5 agent (e.g., ARC1905 or a pharmaceutically acceptable salt thereof). In certain embodiments, the compositions comprise histidine (e.g., L-histidine or a pharmaceutically acceptable salt thereof) or phosphate as a buffer, e.g., sodium phosphate, potassium phosphate, or both. In certain embodiments, the buffer is present at a concentration of about 1 mM to about 200 mM, about 1 mM to about 150 mM, about 1 mM to about 20 mM, about 1 mM to about 10 mM, about 2 mM to about 100 mM, about 2 mM to about 20 mM, about 5 mM to about 20 mM, or about 10 mM. In particular embodiments, the pH of the buffered composition is about 5.0 to about 8.0, about 5.0 to about 7.0, about 5.5 to about 7.5, about 5.5 to about 7.0, or about 6.0. In one embodiment, the buffered composition has a pH of about 5.5 to about 7.0. In certain embodiments, the buffer comprises histidine at a concentration of about 1 mM to about 200 mM, about 1 mM to about 150 mM, about 2 mM to about 100 mM, about 5 mM to about 20 mM, or about 10 mM, and the buffered composition has a pH of about 5.5 to about 7.0, or about 6.0. In one particular embodiment, the buffer comprises histidine at a concentration of about 10 mM and the pH of the histidine-buffered composition is about 6.0. With respect to buffer concentration, "mM" refers to millimoles of buffer (e.g., histidine) per liter of composition.

In certain embodiments, the compositions comprise Antagonist A or another pharmaceutically acceptable salt thereof, a VEGF antagonist (e.g., ranibizumab, bevacizumab, aflibercept, ESBA1008 or pegaptanib sodium), and a buffer that comprises phosphate, alone or in combination with histidine. In certain embodiments, the compositions further comprise an anti-C5 agent (e.g., ARC1905 or a pharmaceutically acceptable salt thereof). The phosphate buffer may be, e.g., a sodium phosphate or potassium phosphate buffer. In certain embodiments, the buffer comprises phosphate at a concentration of about 1 mM to about 200 mM, about 1 mM to about 50 mM, about 2 mM to about 200 mM, about 2 mM to about 50 mM, about 5 mM to about 200 mM, about 5 mM to about 100 mM, about 5 mM to about 50 mM, about 10 mM to about 150 mM, about 10 mM to about 100 mM, about 5 mM, about 10 mM, about 25 mM, or about 50 mM. In particular embodiments, the pH of the buffered composition is about 5.0 to about 8.0, about 6.0 to about 8.0, about 5.5 to about 7.5, about 5.5 to about 7.0, about 6.0, about 7.0, or about 8.0. In one embodiment, the buffer comprises phosphate, and the buffered composition has a pH of about 6.0 to about 8.0. In certain embodiments, the buffer comprises phosphate at a concentration of about 5 mM to about 200 mM, about 5 mM to about 150 mM, about 5 mM to about 100 mM, about 5 mM, about 8 mM, about 10 mM, about 25 mM, or about 50 mM, and the buffered composition has a pH of about 5.5 to about 7.5, about 5.5 to about 7.0, or about 6.0. In one particular embodiment, the buffer comprises phosphate at a concentration of about 10 mM, and the buffered composition has a pH of about 6.2.

In certain embodiments, the compositions comprise Antagonist A or another pharmaceutically acceptable salt thereof), a VEGF antagonist (e.g., ranibizumab, bevacizumab, aflibercept, ESBA1008 or pegaptanib sodium), and a surfactant. In certain embodiments, the compositions further comprise an anti-C5 agent (e.g., ARC1905 or a pharmaceutically acceptable salt thereof). In particular embodiments, the surfactant is polysorbate 20 at a concentration of about 0.001% (w/v) to about 0.05% (w/v), about 0.002% (w/v) to about 0.05% (w/v), about 0.005% (w/v) to about 0.05% (w/v), about 0.01% (w/v) to about 0.05% (w/v), or about 0.02% (w/v).

In one embodiment, the compositions comprise Antagonist A or another pharmaceutically acceptable salt thereof, a VEGF antagonist (e.g., ranibizumab, bevacizumab, aflibercept, ESBA1008 or pegaptanib sodium), histidine, and NaCl. In certain embodiments, the compositions further comprise an anti-C5 agent (e.g., ARC1905 or a pharmaceutically acceptable salt thereof). The composition may further comprise polysorbate.

In certain embodiments, the compositions comprise an effective amount of: (a) about 0.3 mg/mL to about 30 mg/mL of Antagonist A or another pharmaceutically acceptable salt thereof; (b) about 0.5 mg/mL to about 20 mg/mL of a VEGF antagonist (e.g., ranibizumab, bevacizumab, aflibercept, ESBA1008 or pegaptanib sodium); and one or both of: (c) a buffer capable of achieving or maintaining the pH of the compositions at about pH 5.0 to about pH 8.0; and (d) a tonicity modifier. In certain embodiments, the compositions further comprise (e) about 0.3 mg/mL to about 30 mg/mL of an anti-C5 agent (e.g., ARC1905 or a pharmaceutically acceptable salt thereof). In certain embodiments, the buffer is about 1 mM to about 20 mM L-histidine or about 1 mM to about 20 mM sodium phosphate, and the tonicity modifier is about 10 mM to about 200 mM NaCl, about 1% to about 20% (w/v) sorbitol, or about 1% to about 20% (w/v) trehalose. In particular embodiments, the compositions further comprise: (f) about 0.001% (w/v) to about 0.05% (w/v) surfactant.

In certain embodiments, the compositions comprise: (a) about 0.3 mg/mL to about 30 mg/mL of Antagonist A or another pharmaceutically acceptable salt thereof; and (b) about 0.5 mg/mL to about 20 mg/mL of a VEGF antagonist (e.g., ranibizumab, bevacizumab, aflibercept, ESBA1008 or pegaptanib sodium). In certain embodiments, the compositions further comprise (c) about 0.3 mg/mL to about 30 mg/mL of an anti-C5 agent (e.g., ARC1905 or a pharmaceutically acceptable salt thereof). In certain embodiments, any of these the compositions further comprise one or both of: (d) about 1 mM to about 20 mM L-histidine; and (e) about 10 mM to about 200 mM NaCl. In further embodiments, the compositions further comprise: (f) about 0.001% (w/v) to about 0.05% (w/v) surfactant, which is optionally polysorbate. In a particular embodiment, the compositions comprise: (a) about 0.3 mg/mL to about 30 mg/mL of Antagonist A or another pharmaceutically acceptable salt thereof; (b) about 0.5 mg/mL to about 20 mg/mL of a VEGF antagonist (e.g., ranibizumab, bevacizumab, aflibercept, ESBA1008 or pegaptanib sodium); (c) about 1 mM to about 20 mM L-histidine; and (d) about 10 mM to about 200 mM NaCl, wherein the pH of the compositions is about pH 5.0 to about pH 7.0. In certain embodiments, the compositions further comprise (e) about 0.3 mg/mL to about 30 mg/mL of an anti-C5 agent (e.g., ARC1905 or a pharmaceutically acceptable salt thereof). In certain embodiments, the compositions further comprise: (f) about 0.01% (w/v) polysorbate 20.

In certain embodiments, compositions comprise: (a) about 1.0 mg/mL to about 100 mg/mL, or about 5.0 mg/mL to about 50 mg/mL of Antagonist A or another pharmaceutically acceptable salt thereof); and (b) about 1.0 mg/mL to about 50 mg/mL of a VEGF antagonist (e.g., ranibizumab, bevacizumab, aflibercept, ESBA1008 or pegaptanib sodium). In certain embodiments, the compositions further comprise (c) about 1.0 mg/mL to about 100 mg/mL of an anti-C5 agent (e.g., ARC1905 or a pharmaceutically acceptable salt thereof). In other embodiments, any of the compositions further comprise one or both of (d) about 1 mM to about 20 mM L-histidine; and (e) about 10 mM to about 200 mM NaCl. In further embodiments, any of the compositions further comprise: (f) about 0.001% (w/v) to about 0.05% (w/v) surfactant, which is optionally polysorbate.

In certain embodiments, compositions comprise: (a) about 0.3 mg/mL to about 30 mg/mL of Antagonist A or another pharmaceutically acceptable salt thereof); (b) about 0.5 mg/mL to about 20 mg/mL of a VEGF antagonist (e.g., ranibizumab, bevacizumab, aflibercept, ESBA1008 or pegaptanib sodium); and one or both of (c) a buffer capable of achieving or maintaining the pH of the composition to about pH 5.0 to about pH 8.0; and (d) a tonicity modifier. In certain embodiments, the compositions further comprise about 0.3 mg/mL to about 30 mg/mL of an anti-C5 agent (e.g., ARC1905 or a pharmaceutically acceptable salt thereof). In particular embodiments, the buffer, where present, is about 1 mM to about 20 mM L-histidine or about 1 mM to about 20 mM sodium phosphate; and the tonicity modifier, where present, is about 10 mM to about 200 mM NaCl, about 1% to about 20% (w/v) sorbitol, or about 1% to about 20% (w/v) trehalose. In certain embodiments, the buffer is about 1 mM to about 20 mM L-histidine; and the tonicity modifier is about 10 mM to about 200 mM NaCl, wherein the pH of the compositions is about pH 5.0 to about pH 7.0.

Any of the compositions can also comprise a surfactant, e.g., about 0.001% (w/v) to about 0.05% (w/v) surfactant.

In certain embodiments the compositions comprise: (a) about 3 mg/mL to about 90 mg/mL Antagonist A or another pharmaceutically acceptable salt thereof; (b) about 1.0 mg/mL to about 30 mg/mL of a VEGF antagonist (e.g., ranibizumab, bevacizumab, aflibercept, ESBA1008 or pegaptanib sodium); and one or both of (c) a buffer capable of achieving or maintaining the pH of the compositions to about pH 5.0 to about pH 8.0; and (d) a tonicity modifier. In certain embodiments, any of the compositions further comprises (e) about 3 mg/mL to about 90 mg/mL of an anti-C5 agent (e.g., ARC1905 or a pharmaceutically acceptable salt thereof). In particular embodiments, the buffer, where present, comprises about 1 mM to about 100 mM sodium phosphate or about 1.0 mM to about 10 mM histidine·HCl; and the tonicity modifier, where present, is about 0.5% (w/v) to about 10% (w/v) trehalose.

In certain embodiments, a composition of the invention comprises: (a) about 0.3 mg/mL to about 30 mg/mL Antagonist A or another pharmaceutically acceptable salt thereof; (b) about 0.5 mg/mL to about 20 mg/mL ranibizumab or a pharmaceutically acceptable salt thereof; and one or both of: (c) a buffer capable of achieving or maintaining the pH of the composition at about pH 5.0 to about pH 8.0; and (d) a tonicity modifier. In certain embodiments, the buffer is about 1 mM to about 20 mM L-histidine or about 1 mM to about 20 mM sodium phosphate, and the tonicity modifier is about 10 mM to about 200 mM NaCl, about 1% to about 20% (w/v) sorbitol, or about 1% to about 20% (w/v) trehalose. In particular embodiments, the composition of the invention further comprises: (e) about 0.001% (w/v) to about 0.05% (w/v) surfactant. In particular embodiments, the composition further comprises: (f) an anti-C5 agent, another PDGF antagonist, or another VEGF antagonist. In particular embodiments, the anti-C5 agent is ARC 186, ARC 187, or ARC1905, and the other VEGF antagonist is bevacizumab or aflibercept.

In certain embodiments, a composition of the invention comprises: (a) about 0.3 mg/mL to about 30 mg/mL Antagonist A or another pharmaceutically acceptable salt thereof; and (b) about 0.5 mg/mL to about 25 mg/mL bevacizumab or a pharmaceutically acceptable salt thereof; and one or both of: (c) a buffer capable of achieving or maintaining the pH of the composition at about pH 5.0 to about pH 8.0; and (d) a tonicity modifier. In certain embodiments, the buffer is about 5 mM to about 200 mM sodium phosphate or about 5 mM to about 200 mM Tris·HCl, and the tonicity modifier is about 10 mM to about 200 mM NaCl, about 1% to about 20% (w/v) sorbitol, or about 1% to about 20% (w/v) trehalose. In particular embodiments, the composition of the invention further comprises: (e) about 0.001% (w/v) to about 0.05% (w/v) surfactant. In particular embodiments, the composition further comprises: (f) an anti-C5 agent, another PDGF antagonist, and/or another VEGF antagonist. In particular embodiments, the anti-C5 agent is ARC186, ARC187, or ARC1905, and the other VEGF antagonist is ranibizumab or aflibercept.

In certain embodiments, a composition of the invention comprises: (a) about 0.3 mg/mL to about 30 mg/mL Antagonist A or another pharmaceutically acceptable salt thereof; (b) about 5 mg/mL to about 40 mg/mL aflibercept or a pharmaceutically acceptable salt thereof; and one or more of: (c) a buffer capable of achieving or maintaining the pH of the composition at about pH 5.0 to about pH 8.0; (d) a tonicity modifier; and (e) 0 to about 10% (w/v) sucrose. In certain embodiments, the buffer is about 5 mM to about 50 mM phosphate, and the tonicity modifier is about 10 mM to about 200 mM NaCl. In particular embodiments, the composition of the invention further comprises: (f) about 0.001% (w/v) to about 0.05% (w/v) surfactant. In particular embodiments, the composition further comprises: (g) an anti-C5 agent, another PDGF antagonist, and/or another VEGF antagonist. In particular embodiments, the anti-C5 agent is ARC186, ARC187, or ARC1905, and the other VEGF antagonist is ranibizumab or bevacizumab.

In certain embodiments, a composition of the invention comprises: (a) about 3 mg/mL to about 90 mg/mL Antagonist A or another pharmaceutically acceptable salt thereof; (b) about 1.0 mg/mL to about 30 mg/mL ranibizumab or a pharmaceutically acceptable salt thereof; and one or both of: (c) a buffer capable of achieving or maintaining the pH of the composition at about pH 5.0 to about pH 8.0; and (d) a tonicity modifier. In certain embodiments, the buffer comprises about 1 mM to about 100 mM sodium phosphate or about 1.0 mM to about 10 mM histidine·HCl, and the tonicity modifier is about 0.5% (w/v) to about 10% (w/v) trehalose. In particular embodiments, the composition further comprises: (e) an anti-C5 agent, another PDGF antagonist, and/or another VEGF antagonist. In particular embodiments, the anti-C5 agent is ARC186, ARC187, or ARC1905, and the other VEGF antagonist is bevacizumab or aflibercept.

Illustrative compositions include F1-F31, as described in Tables 3 and 4. Illustrative compositions are also described in PCT Application Publication No. WO2013/181495. Any of these compositions may further comprise an anti-C5 agent, such as ARC1905 or a pharmaceutically acceptable salt thereof.

TABLE 3

Composition Matrix for Illustrative Antagonist A:Ranibizumab Compositions

| Comp. | Buffer | pH | Tonicity Modifier | [Ant. A] (mg/mL) | [ran.] (mg/mL) | Polysorbate 20 (% w/v) |
|---|---|---|---|---|---|---|
| F1 | 10 mM Sodium Phosphate | 7.3 | 150 mM NaCl | 3 | 0 | 0% |
| F2 | 10 mM Sodium Acetate | 5.0 | 5% (w/v) Sorbitol | 3 | 5 | 0.01% |
| F3 | 10 mM Sodium Acetate | 5.0 | 130 mM NaCl | 3 | 5 | 0.01% |
| F4 | 10 mM Histidine•HCl | 5.5 | 10% (w/v) Trehalose | 0 | 5 | 0.01% |
| F5 | 10 mM Histidine•HCl | 6.0 | 5% (w/v) Sorbitol | 3 | 5 | 0.01% |
| F6 | 10 mM Histidine•HCl | 6.0 | 130 mM NaCl | 3 | 5 | 0.01% |
| F7 | 10 mM Sodium Phosphate | 7.0 | 5% (w/v) Sorbitol | 3 | 5 | 0.01% |
| F8 | 10 mM Sodium Phosphate | 7.0 | 130 mM NaCl | 3 | 5 | 0.01% |
| F9 | 10 mM Tris•HCl | 8.0 | 5% (w/v) Sorbitol | 3 | 5 | 0.01% |
| F10 | 10 mM Tris•HCl | 8.0 | 130 mM NaCl | 3 | 5 | 0.01% |
| F11 | 5 mM Sodium Phosphate + 5 mM Histidine | 6.5 | 75 mM NaCl + 5% (w/v) Trehalose | 3 | 5 | 0.005% |
| F27 | 10 mM Sodium Phosphate | 7.3 | 150 mM NaCl | 30 | 0 | 0% |
| F28 | 10 mM Histidine•HCl | 5.5 | 10% (w/v) Trehalose | 0 | 10 | 0.01% |
| F29 | 10 mM Histidine•HCl | 5.5 | 10% (w/v) Trehalose | 0 | 40 | 0.01% |
| F30 | 5 mM Sodium Phosphate + 5 mM Histidine•HCl | | 75 mM NaCl + 5% (w/v) Trehalose | 15 | 5 | 0.005% |
| F31 | 8 mM Sodium Phosphate + 2 mM Histidine•HCl | | 120 mM NaCl + 2% (w/v) Trehalose | 24 | 8 | 0.002% |

"Ant. A" is Antagonist A;
"ran." is ranibizumab

TABLE 4

Composition Matrix for Illustrative Antagonist A:Bevacizumab Compositions

| Comp. | Buffer | pH | Tonicity Modifier | Antagonist A Concentration (mg/mL, oligo wt.) | Bevacizumab Concentration (mg/mL) | Surfactant |
|---|---|---|---|---|---|---|
| F12 | 10 mM Phosphate | 7.3 | 150 mM Sodium Chloride | 30 | 0.0 | 0% |
| F13 | 50 mM Acetate | 4 | 5% (w/v) Sorbitol | 3 | 12.5 | 0.02% Polysorbate 20 |
| F14 | 50 mM Acetate | 4 | 130 mM Sodium Chloride | 3 | 12.5 | 0.02% Polysorbate 20 |

TABLE 4-continued

Composition Matrix for Illustrative Antagonist A:Bevacizumab Compositions

| Comp. | Buffer | pH | Tonicity Modifier | Antagonist A Concentration (mg/mL, oligo wt.) | Bevacizumab Concentration (mg/mL) | Surfactant |
|---|---|---|---|---|---|---|
| F15 | 50 mM Acetate | 5 | 5% (w/v) Sorbitol | 3 | 12.5 | 0.02% Polysorbate 20 |
| F16 | 50 mM Acetate | 5 | 130 mM Sodium Chloride | 3 | 12.5 | 0.02% Polysorbate 20 |
| F17 | 50 mM Phosphate | 6 | 5% (w/v) Sorbitol | 3 | 12.5 | 0.02% Polysorbate 20 |
| F18 | 50 mM Phosphate | 6.2 | 6% (w/v) Trehalose | 0 | 12.5 | 0.02% Polysorbate 20 |
| F19 | 50 mM Phosphate | 6 | 130 mM Sodium Chloride | 3 | 12.5 | 0.02% Polysorbate 20 |
| F20 | 50 mM Phosphate | 7 | 5% (w/v) Sorbitol | 3 | 12.5 | 0.02% Polysorbate 20 |
| F21 | 50 mM Phosphate | 7 | 130 mM Sodium Chloride | 3 | 12.5 | 0.02% Polysorbate 20 |
| F22 | 50 mM Tris | 8 | 5% (w/v) Sorbitol | 3 | 12.5 | 0.02% Polysorbate 20 |
| F23 | 50 mM Tris | 8 | 130 mM Sodium Chloride | 3 | 12.5 | 0.02% Polysorbate 20 |
| F24 | 30 mM Phosphate | 6.3 | 75 mM sodium Chloride + 3% (w/v) Trehalose | 15 | 12.5 | 0.02% Polysorbate 20 |
| F25 | 10 mM Phosphate | 7.3 | 150 mM Sodium Chloride | 3 | 0.0 | 0% |
| F26 | 30 mM Phosphate | 6.3 | 75 mM sodium Chloride + 3% (w/v) Trehalose | 3 | 12.5 | 0.02% Polysorbate 20 |

Administration and Dosage

The methods or compositions according to the invention can be administered alone or in conjunction with another therapy and can be provided at home, a doctor's office, a clinic, a hospital's outpatient department, or a hospital. Treatment can begin at a hospital so that the doctor can observe the therapy's effects closely and make any adjustments that are needed. The duration of the administration can depend on the type of ophthalmological disease or disorder being treated or prevented, the age and condition of the subject, the stage and type of the subject's disease or disorder, and how the subject responds to the treatment. Additionally, a subject having a greater risk of developing an ophthalmological disease or disorder (e.g., a diabetic patient) can receive treatment to inhibit or delay the onset of symptoms. In one embodiment, the present methods or compositions allow for the administration of a relatively lower dose of each antagonist.

The dosage and frequency of administration of each antagonist can be controlled independently. For example, one antagonist can be administered three times per day, while the other antagonist can be administered once per day. Administration can be performed in on-and-off cycles that include rest periods so that the subject's body has a chance to recover from a side effect, if any. The antagonists can also be present in the same composition.

In other embodiments, Antagonist A or another pharmaceutically acceptable salt thereof and optionally, a VEGF antagonist and/or anti-C5 agent are administered prior to, during, and/or after another treatment. In one embodiment, Antagonist A or another pharmaceutically acceptable salt thereof and the VEGF antagonist and/or anti-C5 agent are administered concurrently, such as in a co-formulation, prior to, during, and/or after the other treatment. In other embodiments, Antagonist A or another pharmaceutically acceptable salt thereof and the VEGF antagonist are administered sequentially, prior to, during, and/or after the other treatment. In some embodiments, Antagonist A or another pharmaceutically acceptable salt thereof is administered prior to the administration of the VEGF antagonist. In other embodiments, Antagonist A or another pharmaceutically acceptable salt thereof is administered subsequent to the administration of the VEGF antagonist. In some embodiments, the other treatment is performing surgery. Examples of other treatment include pneumatic retinopexy, laser retinopexy, scleral buckling, and pars plana vitrectomy (PPV), laser photocoagulation, or cryotherapy.

Administration of a composition disclosed herein with performing another treatment can improve retinal attachment success, improve visual acuity, reduce choroidal neovascularization or stabilize vision to a degree that is greater than performing the other treatment alone. For example, in some embodiments, the administration of both Antagonist A or another pharmaceutically acceptable salt thereof with performing another treatment can improve retinal attachment success, improve visual acuity, or stabilize vision to a degree that is greater than an additive effect of both Antagonist A or another pharmaceutically acceptable salt thereof with performing the other treatment. In some embodiments, the synergistic effect is in reducing the size or growth of a tumor (e.g., in treating or preventing VHL disease, retinal capillary hemangioma, or von Hippel angioma). In some embodiments, the synergistic effect is reducing or inhibiting scarring or fibrosis (e.g., ocular scarring of fibrosis, such as subretinal fibrosis).

Administration of both Antagonist A or another pharmaceutically acceptable salt thereof and the VEGF antagonist can improve retinal attachment success, improve visual acuity, or stabilize vision to a degree that is greater than administration of Antagonist A or another pharmaceutically acceptable salt thereof or the VEGF antagonist. In some embodiments, the administration of Antagonist A or another pharmaceutically acceptable salt thereof and the VEGF antagonist can have a synergistic effect in treating or preventing an ophthalmological disease or disorder. For example, the administration of both Antagonist A or another pharmaceutically acceptable salt thereof and the VEGF antagonist can improve retinal attachment success, improve visual acuity, or stabilize vision to a degree that is greater than an additive effect of administering both Antagonist A or another pharmaceutically acceptable salt thereof and the VEGF antagonist. In some embodiments, the synergistic effect is in reducing the size or growth of a tumor (e.g., in treating or preventing VHL disease, retinal capillary hemangioma, or von Hippel angioma). In some embodiments, the synergistic effect is reducing or inhibiting scarring or fibrosis (e.g., ocular scarring of fibrosis, such as subretinal fibrosis).

In some embodiments, the methods comprise administering Antagonist A or another pharmaceutically acceptable salt thereof, VEGF antagonist and anti-C5 agent, in which two or more of Antagonist A or another pharmaceutically acceptable salt thereof, the VEGF antagonist and the anti-C5 agent are present in the same composition. In certain embodiments, the PDGF antagonist and the VEGF antagonist are present in the same composition; in certain embodiments, Antagonist A or another pharmaceutically acceptable salt thereof and the anti-C5 agent are present in the same composition; and in certain embodiments, the VEGF antagonist and the anti-C5 agent are present in the same composition. In some embodiments, all three of Antagonist A or another pharmaceutically acceptable salt thereof, the VEGF antagonist and the anti-C5 agent are present in the same composition.

In some embodiments, Antagonist A or another pharmaceutically acceptable salt thereof, the VEGF antagonist and the anti-C5 agent are administered sequentially. In one embodiment, Antagonist A or another pharmaceutically acceptable salt thereof is administered prior to the VEGF antagonist or the anti-C5 agent. In one embodiment, the VEGF antagonist is administered prior to Antagonist A or another pharmaceutically acceptable salt thereof or the anti-C5 agent. In one embodiment, the anti-C5 agent is administered prior to the VEGF antagonist or Antagonist A or another pharmaceutically acceptable salt thereof. In one embodiment, Antagonist A or another pharmaceutically acceptable salt thereof is administered prior to the VEGF antagonist and anti-C5 agent. In one embodiment, the VEGF antagonist is administered prior to Antagonist A or another pharmaceutically acceptable salt thereof and the —C5 agent. In one embodiment, the anti-C5 agent is administered prior to the VEGF antagonist and PDGF antagonist.

In certain embodiments, the subject is administered two or more active agents (e.g., Antagonist A or another pharmaceutically acceptable salt thereof and a VEGF antagonist) in a staggered dosing regimen, wherein one or more of the two or more active agents is administered before another one or more of the two or more active agents is administered to the subject.

In certain embodiments, the one or more active agent(s) is administered at least one day before the other one or more active agent(s). Accordingly, in some embodiments the present methods comprise administering on one or more days Antagonist A or another pharmaceutically acceptable salt thereof, one or more VEGF antagonists or one or more anti-C5 agents.

In one embodiment, the order of administration is: Antagonist A or another pharmaceutically acceptable salt thereof, followed by VEGF antagonist, followed by anti-C5 agent. In another embodiment, the order of administration is: Antagonist A or another pharmaceutically acceptable salt thereof, followed by anti-C5 agent, followed by VEGF antagonist. In another embodiment, the order of administration is: VEGF antagonist, followed by anti-C5 agent, followed by Antagonist A or another pharmaceutically acceptable salt thereof. In another embodiment, the order of administration is: VEGF antagonist, followed by Antagonist A or another pharmaceutically acceptable salt thereof, followed by anti-C5 agent. In yet another embodiment the order of administration is: anti-C5 agent, followed by Antagonist A or another pharmaceutically acceptable salt thereof, followed by VEGF antagonist. In another embodiment the order of administration is: anti-C5 agent, followed by VEGF antagonist, followed by PDGF antagonist.

In some embodiments, the Antagonist A or another pharmaceutically acceptable salt thereof and the VEGF antagonist are administered concurrently, and the anti-C5 agent is administered prior to or subsequent to administration of the PDGF antagonist and VEGF antagonist. In some embodiments, Antagonist A or another pharmaceutically acceptable salt thereof and the anti-C5 agent are administered concurrently, and the VEGF antagonist is administered prior to or subsequent to administration of Antagonist A or another pharmaceutically acceptable salt thereof and the VEGF antagonist. In some embodiments, the VEGF antagonist and anti-C5 agent are administered concurrently, and Antagonist A or another pharmaceutically acceptable salt thereof is administered prior to or subsequent to administration of the anti-C5 agent and VEGF antagonist.

In other embodiments, the order of administration is: Antagonist A or another pharmaceutically acceptable salt thereof, followed by VEGF antagonist and anti-C5 agent, wherein the VEGF antagonist and anti-C5 agent are present in the same composition. In another embodiment, the order of administration is: VEGF antagonist, followed by anti-C5 agent and Antagonist A or another pharmaceutically acceptable salt thereof, wherein the anti-C5 agent and PDGF antagonist are present in the same composition. In yet another embodiment the order of administration is: anti-C5 agent, followed by Antagonist A or another pharmaceutically acceptable salt thereof and VEGF antagonist, wherein the PDGF antagonist and VEGF antagonist are present in the same composition.

In still other embodiments, the order of administration is: Antagonist A or another pharmaceutically acceptable salt thereof and VEGF antagonist, wherein Antagonist A or another pharmaceutically acceptable salt thereof and the VEGF antagonist are present in the same composition, followed by anti-C5 agent. In another embodiment, the order of administration is: Antagonist A or another pharmaceutically acceptable salt thereof and anti-C5 agent, wherein Antagonist A or another pharmaceutically acceptable salt thereof and the anti-C5 agent are present in the same composition, followed by VEGF antagonist. In another embodiment, the order of administration is: VEGF antagonist and anti-C5 agent, wherein the VEGF antagonist and anti-C5 agent are present in the same composition, followed by Antagonist A or another pharmaceutically acceptable salt thereof.

For example, Antagonist A or another pharmaceutically acceptable salt thereof can be administered prior to or subsequent to administration of a VEGF antagonist and/or an anti-C5 agent; a VEGF antagonist can be administered prior to or subsequent to administration of Antagonist A or another pharmaceutically acceptable salt thereof and/or anti-C5 agent; or an anti-C5 agent can be administered prior to or subsequent to administration of Antagonist A or another pharmaceutically acceptable salt thereof and/or a VEGF antagonist.

In some embodiments, the present methods comprise administering a first agent prior to administering a second agent. In some embodiments, the present methods comprise administering a first agent prior to administering a second agent and administering the second agent prior to administering a third agent.

In some embodiments, the present methods comprise concurrently administering a first agent and a second agent. In some embodiments, the present methods comprise concurrently administering a first agent and a second agent prior to administering a third agent.

In some embodiments, the present methods comprise administering a first agent prior to concurrently administering a second agent and third agent.

In some embodiments, the present methods comprise concurrently administering a first agent, a second agent and a third agent.

Illustrative groups of first agent, second agent and third agent are set forth below in Tables 5 and 6.

TABLE 5

| Group | First Agent | Second Agent | Third Agent |
|---|---|---|---|
| A | Antagonist A or another pharmaceutically acceptable salt thereof | VEGF antagonist | Anti-C5 Agent |
| B | Antagonist A or another pharmaceutically acceptable salt thereof | Anti-C5 Agent | VEGF antagonist |
| C | VEGF antagonist | Antagonist A or another pharmaceutically acceptable salt thereof | Anti-C5 Agent |
| D | VEGF antagonist | Anti-C5 Agent | Antagonist A or another pharmaceutically acceptable salt thereof |
| E | Anti-C5 Agent | Antagonist A or another pharmaceutically acceptable salt thereof | VEGF antagonist |
| F | Anti-C5 Agent | VEGF antagonist | Antagonist A or another pharmaceutically acceptable salt thereof |

TABLE 6

| Group | First Agent | Second Agent | Third Agent |
|---|---|---|---|
| A | Antagonist A | ranibizumab | ARC1905 |
| B | Antagonist A | bevacizumab | ARC1905 |
| C | Antagonist A | aflibercept | ARC1905 |
| D | Antagonist A | pegaptanib sodium | ARC1905 |
| E | Antagonist A | ESBA1008 | ARC1905 |
| F | Antagonist A | ARC1905 | ranibizumab |
| G | Antagonist A | ARC1905 | bevacizumab |
| H | Antagonist A | ARC1905 | aflibercept |
| I | Antagonist A | ARC1905 | pegaptanib sodium |
| J | Antagonist A | ARC1905 | ESBA1008 |
| K | ranibizumab | Antagonist A | ARC1905 |
| L | bevacizumab | Antagonist A | ARC1905 |
| M | aflibercept | Antagonist A | ARC1905 |
| N | pegaptanib sodium | Antagonist A | ARC1905 |
| O | ESBA1008 | Antagonist A | ARC1905 |
| P | ranibizumab | ARC1905 | Antagonist A |
| Q | bevacizumab | ARC1905 | Antagonist A |
| R | aflibercept | ARC1905 | Antagonist A |
| S | pegaptanib sodium | ARC1905 | Antagonist A |
| T | ESBA1008 | ARC1905 | Antagonist A |
| U | ARC1905 | Antagonist A | ranibizumab |
| V | ARC1905 | Antagonist A | bevacizumab |
| W | ARC1905 | Antagonist A | aflibercept |
| X | ARC1905 | Antagonist A | pegaptanib sodium |

TABLE 6-continued

| Group | First Agent | Second Agent | Third Agent |
|---|---|---|---|
| Y | ARC1905 | Antagonist A | ESBA1008 |
| Z | ARC1905 | ranibizumab | Antagonist A |
| AA | ARC1905 | bevacizumab | Antagonist A |
| AB | ARC1905 | aflibercept | Antagonist A |
| AC | ARC1905 | pegaptanib sodium | Antagonist A |
| AD | ARC1905 | ESBA1008 | Antagonist A |

In some embodiments, the present methods comprise administering Antagonist A or another pharmaceutically acceptable salt thereof and two or more VEGF antagonists. In some embodiments, the present methods comprise administering Antagonist A or another pharmaceutically acceptable salt thereof and two or more anti-C5 agents. In some embodiments, the present methods comprise administering a VEGF antagonist and two or more anti-C5 agents.

In some embodiments, the present methods comprise administering Antagonist A or another pharmaceutically acceptable salt thereof prior to administering two or more VEGF antagonists. In some embodiments, the present methods comprise administering Antagonist A or another pharmaceutically acceptable salt thereof prior to administering a first VEGF antagonist and administering the first VEGF antagonist prior to administering a second VEGF antagonist.

In some embodiments, the present methods comprise concurrently administering Antagonist A or another pharmaceutically acceptable salt thereof and a VEGF antagonist. In some embodiments, the present methods comprise concurrently administering Antagonist A or another pharmaceutically acceptable salt thereof and a first VEGF antagonist prior to administering a second VEGF antagonist.

In some embodiments, the present methods comprise administering Antagonist A or another pharmaceutically acceptable salt thereof prior to concurrently administering a first VEGF antagonist and a second VEGF antagonist.

In some embodiments, the present methods comprise concurrently administering Antagonist A or another pharmaceutically acceptable salt thereof, a first VEGF antagonist and a second VEGF antagonist.

In some embodiments, the present methods comprise administering a VEGF antagonist prior to administering two PDGF antagonists (e.g., Antagonist A or another pharmaceutically acceptable salt thereof and another PDGF antagonist). In some embodiments, the present methods comprise administering a VEGF antagonist prior to administering a first PDGF antagonist and administering the first PDGF antagonist prior to administering a second PDGF antagonist.

In some embodiments, the present methods comprise concurrently administering a VEGF antagonist and Antagonist A or another pharmaceutically acceptable salt thereof. In some embodiments, the present methods comprise concurrently administering a VEGF antagonist and a first PDGF antagonist prior to administering a second PDGF antagonist.

In some embodiments, the present methods comprise administering a VEGF antagonist prior to concurrently administering a first PDGF antagonist and a second PDGF antagonist.

In some embodiments, the present methods comprise concurrently administering a VEGF antagonist, a first PDGF antagonist and a second PDGF antagonist.

In some embodiments, the present methods comprise administering Antagonist A or another pharmaceutically acceptable salt thereof prior to administering two or more anti-C5 agents. In some embodiments, the present methods comprise administering Antagonist A or another pharmaceutically acceptable salt thereof prior to administering a first anti-C5 agent and administering the first anti-C5 agent prior to administering a second anti-C5 agent.

In some embodiments, the present methods comprise concurrently administering Antagonist A or another pharmaceutically acceptable salt thereof and an anti-C5 agent. In some embodiments, the present methods comprise concurrently administering Antagonist A or another pharmaceutically acceptable salt thereof and a first anti-C5 agent prior to administering a second anti-C5 agent.

In some embodiments, the present methods comprise administering Antagonist A or another pharmaceutically acceptable salt thereof prior to concurrently administering a first anti-C5 agent and a second anti-C5 agent.

In some embodiments, the present methods comprise concurrently administering Antagonist A or another pharmaceutically acceptable salt thereof, a first anti-C5 agent and a second anti-C5 agent.

In some embodiments, the present methods comprise administering an anti-C5 agent prior to administering two or more PDGF antagonists. In some embodiments, the present methods comprise administering an anti-C5 agent prior to administering a first PDGF antagonist and administering the first PDGF antagonist prior to administering a second PDGF antagonist.

In some embodiments, the present methods comprise concurrently administering an anti-C5 agent and Antagonist A or another pharmaceutically acceptable salt thereof. In some embodiments, the present methods comprise concurrently administering an anti-C5 agent and a first PDGF antagonist prior to administering a second PDGF antagonist.

In some embodiments, the present methods comprise administering an anti-C5 agent prior to concurrently administering a first PDGF antagonist and a second PDGF antagonist.

In some embodiments, the present methods comprise concurrently administering an anti-C5 agent, a first PDGF antagonist and a second PDGF antagonist.

In some embodiments, the present methods comprise administering a VEGF antagonist prior to administering two or more anti-C5 agents. In some embodiments, the present methods comprise administering a VEGF antagonist prior to administering a first anti-C5 agent and administering the first anti-C5 agent prior to administering a second anti-C5 agent.

In some embodiments, the present methods comprise concurrently administering a VEGF antagonist and an anti-C5 agent. In some embodiments, the present methods comprise concurrently administering a VEGF antagonist and a first anti-C5 agent prior to administering a second anti-C5 agent.

In some embodiments, the present methods comprise administering a VEGF antagonist prior to concurrently administering a first anti-C5 agent and a second anti-C5 agent.

In some embodiments, the present methods comprise concurrently administering a VEGF antagonist, a first anti-C5 agent and a second anti-C5 agent.

In some embodiments, the present methods comprise administering an anti-C5 agent prior to administering two or more VEGF antagonists. In some embodiments, the present methods comprise administering an anti-C5 agent prior to administering a first VEGF antagonist and administering the first VEGF antagonist prior to administering a second VEGF antagonist.

In some embodiments, the present methods comprise concurrently administering an anti-C5 agent and a VEGF antagonist. In some embodiments, the present methods comprise concurrently administering an anti-C5 agent and a first VEGF antagonist prior to administering a second VEGF antagonist.

In some embodiments, the present methods comprise administering an anti-C5 agent prior to concurrently administering a first VEGF antagonist and a second VEGF antagonist.

In some embodiments, the present methods comprise concurrently administering an anti-C5 agent, a first VEGF antagonist and a second VEGF antagonist.

In some embodiments, the first agent and second agent are PDGF antagonists, which can be the same or different. In some embodiment, the first agent and second agent are VEGF antagonists, which can be the same or different. In some embodiments, the first agent and second agent are anti-C5 agents, which can be the same or different.

In some embodiments, the first agent and third agent are PDGF antagonists, which can be the same or different. In some embodiment, the first agent and third agent are VEGF antagonists, which can be the same or different. In some embodiments, the first agent and third agent are anti-C5 agents, which can be the same or different.

In some embodiments, the second agent and third agent are PDGF antagonists, which can be the same or different. In some embodiment, the second agent and third agent are VEGF antagonists, which can be the same or different. In some embodiments, the second agent and third agent are anti-C5 agents, which can be the same or different.

Illustrative groups of first agent, second agent and third agent are set forth below in Tables 7, 8, 9 and 10.

TABLE 7

| Group | First Agent | Second Agent | Third Agent |
|---|---|---|---|
| A | PDGF Antagonist | VEGF antagonist | VEGF antagonist |
| B | VEGF antagonist | PDGF Antagonist | VEGF antagonist |
| C | VEGF antagonist | VEGF antagonist | PDGF Antagonist |
| D | PDGF Antagonist | Anti-C5 Agent | Anti-C5 Agent |
| E | Anti-C5 Agent | PDGF Antagonist | Anti-C5 Agent |
| F | Anti-C5 Agent | Anti-C5 Agent | PDGF Antagonist |
| G | PDGF Antagonist | PDGF Antagonist | VEGF antagonist |
| H | PDGF Antagonist | VEGF antagonist | PDGF Antagonist |
| I | VEGF antagonist | PDGF Antagonist | PDGF Antagonist |
| J | PDGF Antagonist | PDGF Antagonist | Anti-C5 Agent |
| K | PDGF Antagonist | Anti-C5 Agent | PDGF Antagonist |
| L | Anti-C5 Agent | PDGF Antagonist | PDGF Antagonist |

TABLE 8

| Group | First Agent | Second Agent | Third Agent |
|---|---|---|---|
| A | PDGF Antagonist | First VEGF antagonist | Second VEGF antagonist |
| B | First VEGF antagonist | PDGF Antagonist | Second VEGF antagonist |
| C | First VEGF antagonist | Second VEGF antagonist | PDGF Antagonist |
| D | PDGF Antagonist | First Anti-C5 Agent | Second Anti-C5 Agent |
| E | First Anti-C5 Agent | PDGF Antagonist | Second Anti-C5 Agent |
| F | First Anti-C5 Agent | Second Anti-C5 Agent | PDGF Antagonist |
| G | First PDGF Antagonist | Second PDGF Antagonist | VEGF antagonist |
| H | First PDGF Antagonist | VEGF antagonist | Second PDGF Antagonist |
| I | VEGF antagonist | First PDGF Antagonist | Second PDGF Antagonist |
| J | First PDGF Antagonist | Second PDGF Antagonist | Anti-C5 Agent |
| K | First PDGF Antagonist | Anti-C5 Agent | Second PDGF Antagonist |
| L | Anti-C5 Agent | First PDGF Antagonist | Second PDGF Antagonist |

TABLE 9

| Group | First Agent | Second Agent | Third Agent |
|---|---|---|---|
| A | Antagonist A | ranibizumab | Antagonist A |
| B | Antagonist A | ranibizumab | ranibizumab |
| C | Antagonist A | bevacizumab | Antagonist A |
| D | Antagonist A | bevacizumab | bevacizumab |
| E | Antagonist A | aflibercept | Antagonist A |
| F | Antagonist A | aflibercept | aflibercept |
| G | Antagonist A | pegaptanib sodium | Antagonist A |
| H | Antagonist A | pegaptanib sodium | pegaptanib sodium |
| I | Antagonist A | ESBA1008 | Antagonist A |
| J | Antagonist A | ESBA1008 | ESBA1008 |
| K | Antagonist A | ARC1905 | Antagonist A |
| L | Antagonist A | ARC1905 | ARC1905 |
| M | ranibizumab | Antagonist A | ranibizumab |
| N | ranibizumab | Antagonist A | Antagonist A |
| O | bevacizumab | Antagonist A | bevacizumab |
| P | bevacizumab | Antagonist A | Antagonist A |
| Q | aflibercept | Antagonist A | aflibercept |
| R | aflibercept | Antagonist A | Antagonist A |
| S | pegaptanib sodium | Antagonist A | pegaptanib sodium |
| T | pegaptanib sodium | Antagonist A | Antagonist A |
| U | ESBA1008 | Antagonist A | ESBA1008 |
| V | ESBA1008 | Antagonist A | Antagonist A |
| W | ARC1905 | Antagonist A | ARC1905 |
| X | ARC1905 | Antagonist A | Antagonist A |
| Y | ranibizumab | ranibizumab | Antagonist A |
| Z | bevacizumab | bevacizumab | Antagonist A |
| AA | aflibercept | aflibercept | Antagonist A |
| AB | pegaptanib sodium | pegaptanib sodium | Antagonist A |
| AC | ESBA1008 | ESBA1008 | Antagonist A |
| AD | ARC1905 | ARC1905 | Antagonist A |
| AE | ranibizumab | ranibizumab | bevacizumab |
| AF | ranibizumab | bevacizumab | ranibizumab |
| AG | ranibizumab | ranibizumab | aflibercept |
| AH | ranibizumab | aflibercept | ranibizumab |
| AI | ranibizumab | ranibizumab | pegaptanib sodium |
| AJ | ranibizumab | pegaptanib sodium | ranibizumab |
| AK | ranibizumab | ranibizumab | ESBA1008 |
| AL | ranibizumab | ESBA1008 | ranibizumab |
| AM | ranibizumab | ranibizumab | ARC1905 |
| AN | ranibizumab | ARC1905 | ranibizumab |
| AO | bevacizumab | bevacizumab | ranibizumab |
| AP | bevacizumab | ranibizumab | bevacizumab |
| AQ | bevacizumab | bevacizumab | aflibercept |
| AR | bevacizumab | aflibercept | bevacizumab |
| AS | bevacizumab | bevacizumab | pegaptanib sodium |
| AT | bevacizumab | pegaptanib sodium | bevacizumab |
| AU | bevacizumab | bevacizumab | ESBA1008 |
| AV | bevacizumab | ESBA1008 | bevacizumab |
| AW | bevacizumab | bevacizumab | ARC1905 |
| AX | bevacizumab | ARC1905 | bevacizumab |
| AY | aflibercept | aflibercept | ranibizumab |
| AZ | aflibercept | ranibizumab | aflibercept |
| BA | aflibercept | aflibercept | bevacizumab |
| BB | aflibercept | bevacizumab | aflibercept |
| BC | aflibercept | aflibercept | pegaptanib sodium |
| BD | aflibercept | pegaptanib sodium | aflibercept |
| BE | aflibercept | aflibercept | ESBA1008 |
| BF | aflibercept | ESBA1008 | aflibercept |

TABLE 9-continued

| Group | First Agent | Second Agent | Third Agent |
|---|---|---|---|
| BG | aflibercept | aflibercept | ARC1905 |
| BH | aflibercept | ARC1905 | aflibercept |
| BI | pegaptanib sodium | pegaptanib sodium | ranibizumab |
| BJ | pegaptanib sodium | ranibizumab | pegaptanib sodium |
| BK | pegaptanib sodium | pegaptanib sodium | bevacizumab |
| BL | pegaptanib sodium | bevacizumab | pegaptanib sodium |
| BM | pegaptanib sodium | pegaptanib sodium | aflibercept |
| BN | pegaptanib sodium | aflibercept | pegaptanib sodium |
| BO | pegaptanib sodium | pegaptanib sodium | ESBA1008 |
| BP | pegaptanib sodium | ESBA1008 | pegaptanib sodium |
| BQ | pegaptanib sodium | pegaptanib sodium | ARC1905 |
| BR | pegaptanib sodium | ARC1905 | pegaptanib sodium |
| BS | ESBA1008 | ESBA1008 | ranibizumab |
| BT | ESBA1008 | ranibizumab | ESBA1008 |
| BU | ESBA1008 | ESBA1008 | bevacizumab |
| BV | ESBA1008 | bevacizumab | ESBA1008 |
| BW | ESBA1008 | ESBA1008 | aflibercept |
| BX | ESBA1008 | aflibercept | ESBA1008 |
| BY | ESBA1008 | ESBA1008 | pegaptanib sodium |
| BZ | ESBA1008 | pegaptanib sodium | ESBA1008 |
| CA | ESBA1008 | ESBA1008 | ARC1905 |
| CB | ESBA1008 | ARC1905 | ESBA1008 |
| CC | ARC1905 | ARC1905 | ranibizumab |
| CD | ARC1905 | ranibizumab | ARC1905 |
| CE | ARC1905 | ARC1905 | bevacizumab |
| CF | ARC1905 | bevacizumab | ARC1905 |
| CO | ARC1905 | ARC1905 | aflibercept |
| CH | ARC1905 | aflibercept | ARC1905 |
| CI | ARC1905 | ARC1905 | pegaptanib sodium |
| CJ | ARC1905 | pegaptanib sodium | ARC1905 |
| CK | ARC1905 | ARC1905 | ESBA1008 |
| CL | ARC1905 | ESBA1008 | ESBA1008 |

TABLE 10

| Group | First Agent | Second Agent | Third Agent |
|---|---|---|---|
| A | Antagonist A | ranibizumab | bevacizumab |
| B | Antagonist A | ranibizumab | aflibercept |
| C | Antagonist A | ranibizumab | pegaptanib sodium |
| D | Antagonist A | bevacizumab | aflibercept |
| E | Antagonist A | bevacizumab | pegaptanib sodium |
| F | Antagonist A | aflibercept | pegaptanib sodium |
| G | ranibizumab | bevacizumab | Antagonist A |
| H | ranibizumab | aflibercept | Antagonist A |
| I | ranibizumab | pegaptanib sodium | Antagonist A |
| J | bevacizumab | aflibercept | Antagonist A |
| K | bevacizumab | pegaptanib sodium | Antagonist A |
| L | aflibercept | pegaptanib sodium | Antagonist A |
| M | ranibizumab | Antagonist A | bevacizumab |
| N | ranibizumab | Antagonist A | aflibercept |
| O | ranibizumab | Antagonist A | pegaptanib sodium |
| P | bevacizumab | Antagonist A | aflibercept |
| Q | bevacizumab | Antagonist A | pegaptanib sodium |
| R | aflibercept | Antagonist A | pegaptanib sodium |
| S | bevacizumab | ranibizumab | Antagonist A |

TABLE 10-continued

| Group | First Agent | Second Agent | Third Agent |
|---|---|---|---|
| T | aflibercept | ranibizumab | Antagonist A |
| U | pegaptanib sodium | ranibizumab | Antagonist A |
| V | aflibercept | bevacizumab | Antagonist A |
| W | pegaptanib sodium | bevacizumab | Antagonist A |
| X | pegaptanib sodium | aflibercept | Antagonist A |
| Y | bevacizumab | Antagonist A | ranibizumab |
| Z | aflibercept | Antagonist A | ranibizumab |
| AA | pegaptanib sodium | Antagonist A | ranibizumab |
| AB | aflibercept | Antagonist A | bevacizumab |
| AC | pegaptanib sodium | Antagonist A | bevacizumab |
| AD | pegaptanib sodium | Antagonist A | aflibercept |
| AE | Antagonist A | ARC187 | ARC1905 |
| AF | Antagonist A | ARC1905 | ARC187 |
| AG | ARC187 | ARC1905 | Antagonist A |
| AH | ARC1905 | ARC187 | Antagonist A |
| AI | ARC187 | Antagonist A | ARC1905 |
| AJ | ARC1905 | Antagonist A | ARC187 |

In one embodiment, two or more agents are administered concurrently. In one embodiment, the two or more agents administered concurrently are present in the same composition. In another embodiment, the two or more agents administered concurrently are each present in a separate composition.

In certain embodiments, the time period from administration of a first agent to administration of a second agent is at least 1 min, at least 5 min, at least 10 min, at least 15 min, at least 30 min, or at least one hour. In certain embodiments, the time period from administration of a first agent to administration of a second agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from administration of a first agent to administration of a second agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, a second agent is administered within 90 days, 30 days, 10 days, 5 days, 2 days, 1 day, 24 hours, 1 hour, 30 minutes, 10 minutes, 5 minutes or one minute after administration of a second agent.

In certain embodiments, the time period from administration of a second agent to administration of a third agent is at least 1 min, at least 5 min, at least 10 min, at least 15 min, at least 30 min, or at least one hour. In certain embodiments, the time period between administration of a second agent and administration of a third agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period between administration of a second agent and administration of a third agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, a third agent is administered within 90 days, 30 days, 10 days, 5 days, 2 days, 1 day, 24 hours, 1 hour, 30 minutes, 10 minutes, 5 minutes or one minute after administration of a second agent.

In certain embodiments, the time period between concurrent administration of a first agent and a second agent and administration of a third agent is at least 1 min, at least 5 min, at least 10 min, at least 15 min, at least 30 min, or at least one hour. In certain embodiments, the time period between concurrent administration of a first agent and a second agent and administration of a third agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from concurrent administration of a first agent and a second agent to administration of a third agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, administration of a third agent is within 90 days, 30 days, 10 days, 5 days, 2 days, 1 day, 24 hours, 1 hour, 30 minutes, 10 minutes, 5 minutes or one minute of concurrent administration of a first agent and a second agent.

In certain embodiments, the time period from administration of a first agent to concurrent administration a second agent and a third agent is at least 1 min, at least 5 min, at least 10 min, at least 15 min, at least 30 min, or at least one hour. In certain embodiments, the time period from administration of a first agent to concurrent administration of a second agent and a third agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from administration of a first agent to concurrent administration of a second agent and a third agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, concurrent administration of a second agent and a third agent is within 90 days, 30 days, 10 days, 5 days, 2 days, 1 day, 24 hours, 1 hour, 30 minutes, 10 minutes, 5 minutes or one minute of administration of a first agent.

The administration of two or more, such as three or more, active agents (e.g., Antagonist A or another pharmaceutically acceptable salt thereof, a VEGF antagonist and an anti-C5 agent) can have a synergistic effect in treating or preventing a disease or disorder, e.g., an ophthalmological disease or disorder. For example, administration of Antagonist A or another pharmaceutically acceptable salt thereof, VEGF antagonist and anti-C5 agent (or any two of these active agents) can improve retinal attachment success, improve visual acuity, reduce choroidal neovascularization or stabilize vision to a degree that is greater than an additive effect of the active agents.

In certain embodiments, the invention provides methods for treating or preventing an ophthalmological disease or disorder, comprising administering to a subject in need thereof one or more, in some embodiments two or more or three or more, active agents via an apparatus. In other embodiments, the methods further comprise performing surgery on the subject. In other embodiments, the methods further comprise administering another active agent, such as an antineoplastic drug, including but not limited to any of those described herein. In particular embodiments, the methods further comprise administering another active agent and performing surgery on the subject.

In some embodiments, administration of Antagonist A or another pharmaceutically acceptable salt thereof, and optionally a VEGF antagonist and/or an anti-C5 agent to a subject results in improved vision, such as increased visual acuity. In some embodiments, the subject experienced moderate vision loss, defined as losing 15 letters or more from baseline on ETDRS visual acuity testing, measured at week 24, prior to treatment with Antagonist A or another pharmaceutically acceptable salt thereof.

In some embodiments, visual acuity testing is as described in Early Treatment Diabetic Retinopathy Study Research Group (ETDRS), Manual of Operations, Baltimore: ETDRS Coordinating Center, University of Maryland. Available from: National Technical Information Service, 5285 Port Royal Road, Springfield, VA 22161; Accession No. PB85 223006/AS; Ferris et al., Am J Ophthalmol 94:91-96, 1982; or Example 4, as described herein. In some embodiments, the visual acuity testing uses one or more charts available via the Web from the site www.nci.nih.gov, using the relative reference/photo/keyword.asp?conditions=Eye+Charts&match=all, e.g., ETDRS visual acuity Chart 1, 2 and/or R.

In other embodiments, administration of Antagonist A or another pharmaceutically acceptable salt thereof and a VEGF antagonist results in fewer ocular adverse events, a decrease in size of RCH (e.g., measured by fundus photography and FA), a decrease in exudation (measured by fundus photography, OCT, and FA), or a decrease in epiretinal proliferation or retinal traction (assessed by fundus photography), compared to those experienced by a subject who was not administered with Antagonist A or another pharmaceutically acceptable salt thereof. In some embodiments, the subject does not require, and the methods do not comprise, ablative treatment of RCH or ocular surgery.

In some embodiments, administration of Antagonist A or another pharmaceutically acceptable salt thereof, and optionally a VEGF antagonist and/or an anti-C5 agent, to a subject results in improved vision independent of baseline lesion size or baseline vision, compared to vision of a subject who was not administered with Antagonist A or another pharmaceutically acceptable salt thereof, or compared to a subject administered anti-VEGF monotherapy. In some embodiments, administration of Antagonist A or another pharmaceutically acceptable salt thereof, and optionally a VEGF antagonist and/or an anti-C5 agent, to a subject results in the subject having a visual acuity of 20/40 or better, or 20/25 or better vision. In some embodiments, administration of Antagonist A or another pharmaceutically acceptable salt thereof, and optionally a VEGF antagonist and/or an anti-C5 agent to a subject results in an increased reduction in CNV size in the subject, compared to CNV size in a patient who was not administered with Antagonist A or another pharmaceutically acceptable salt thereof, or compared to a subject administered anti-VEGF monotherapy. In some embodiments, administration of Antagonist A or another pharmaceutically acceptable salt thereof, and optionally a VEGF antagonist and/or an anti-C5 agent, to a subject results in a reduction in CNV size (e.g., reduction in disc area (DA) size). In some embodiments, administration of Antagonist A or another pharmaceutically acceptable salt thereof, and optionally a VEGF antagonist and/or an anti-C5 agent to a subject result in an increased reduction in DA in the subject, compared to DA in a patient who was not administered with Antagonist A or another pharmaceutically acceptable salt thereof, or compared to a subject administered anti-VEGF monotherapy. In some embodiments, the increased reduction in CNV size is in subjects with small baseline CNV, e.g., less than or equal to 1.62 DA (disc area). In some embodiments, the increased reduction in CNV size (e.g., in disc area) is in subjects with large baseline CNV, e.g., greater than 1.62 DA. In some embodiments, administration of Antagonist A or another pharmaceutically acceptable salt thereof, and optionally a VEGF antagonist and/or an anti-C5 agent, to a subject results in neovascular regression. In some embodiments, administration of Antagonist A or another pharmaceutically acceptable salt thereof, and optionally a VEGF antagonist and/or an anti-C5 agent, to a subject results in reduced neovascular growth, compared to that occurring in a subject who was not administered with Antagonist A or another pharmaceutically acceptable salt thereof, or compared to a subject administered anti-VEGF monotherapy. In some embodiments, the reduced neovascular growth is anti-fibrosis. In some embodiments, administration of Antagonist A or another pharmaceutically acceptable salt thereof, and optionally a VEGF antagonist and/or an anti-C5 agent, to a subject results in a decrease in or absence of hyper-reflective material, e.g., sub-retinal hyper-reflective material, such as a decrease in the size of sub-retinal hyper-reflective material (SHRM) as evidenced by spectral domain optical coherence tomography (SD-OCT). In some embodiments, administration of Antagonist A or another pharmaceutically acceptable salt thereof, and optionally a VEGF antagonist and/or an anti-C5 agent, to a subject results in an increase in resolution of hyper-reflective material, e.g., sub-retinal hyper-reflective material, such as compared to a subject who was not administered with Antagonist A or another pharmaceutically acceptable salt thereof, or compared to a subject administered a VEGF antagonist, anti-VEGF monotherapy, and/or an anti-C5 agent.

In some embodiments, a subject with improved vision has a greater than 3-line, 4-line or 5-line gain in visual acuity. In one embodiment, a subject's visual acuity is determined using a protocol such as the Early Treatment for Diabetic Retinopathy Study ("ETDRS") or the Age-Related Eye Disease Study ("AREDS") protocol. In some embodiments, visual acuity is measured using a modified ETDRS and/or AREDS protocol, such as the measurement of visual acuity described in Ferris et al., Am J Ophthalmol 94:91-96, 1982. In some embodiments, visual acuity is measured as described in Early Treatment Diabetic Retinopathy Study Research Group (ETDRS), Manual of Operations, Baltimore: ETDRS Coordinating Center, University of Maryland. Available from: National Technical Information Service, 5285 Port Royal Road, Springfield, VA 22161; Accession No. PB85 223006/AS. In other embodiments, visual acuity testing is measured as described in Example 4 below. In some embodiments, the visual acuity testing uses one or more charts available via the Web from the site www.nci.nih.gov, using the relative reference/photo/keyword.asp?conditions=Eye+Charts&match=all, e.g., ETDRS visual acuity Chart 1, 2 and/or R.

In one embodiment, a subject's visual acuity is determined by one or more of the following procedures: (1) measurement of best-corrected visual acuity (BCVA) with required manifest refraction; (2) measurement of corrected visual acuity with conditional manifest refraction; or (3) measurement of corrected visual acuity without manifest refraction.

In one embodiment, each of the PDGF and VEGF antagonists is administered in an amount effective to treat or prevent an ophthalmological disease or disorder. The amount of antagonist that is admixed with the carrier materials to produce a single dosage can vary depending upon the subject being treated and the particular mode of administration.

The dosage of each antagonist can depend on several factors including the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used. Furthermore, the exact individual dosages can be adjusted somewhat depending on a variety of factors, including the specific combination of antagonists being administered, the time of administration, the route of administration, the nature of the formulation, the rate of excretion, the particular ophthalmological disease or disorder being treated, the severity of the disorder, and the anatomical location of the neovascular disorder. Some variations in the dosage can be expected.

Generally, when orally administered to a subject, the dosage of an antagonist of the present invention is normally 0.001 mg/kg/day to 100 mg/kg/day, 0.01 mg/kg/day to 50 mg/kg/day, or 0.1 mg/kg/day to 10 mg/kg/day. Generally, when orally administered to a human, the dosage of an antagonist of the present invention is normally 0.001 mg to 300 mg per day, 1 mg to 200 mg per day, or 5 mg to 50 mg per day. Dosages up to 200 mg per day may be necessary. For administration of an antagonist of the present invention by parenteral injection, the dosage is normally 0.1 mg to 250 mg per day, 1 mg to 20 mg per day, or 3 mg to 5 mg per day. Injections may be given up to four times daily. In some embodiments, the dosage of a PDGF or VEGF antagonist for use in the present invention is normally 0.1 mg to 1500 mg per day, or 0.5 mg to 10 mg per day, or 0.5 mg to 5 mg per day. A dosage of up to 3000 mg per day can be administered.

In some embodiments, for administration by parenteral injection of a three active agents (e.g., Antagonist A or another pharmaceutically acceptable salt thereof, VEGF antagonist and an anti-C5 agent or other combination disclosed herein), the dosage of each of the PDGF antagonist, VEGF antagonist and anti-C5 agent, is typically 0.1 mg to 250 mg per day, 1 mg to 20 mg per day, or 3 mg to 5 mg per day. Injections may be given up to four times daily. Generally, when parenterally administered, the dosage of Antagonist A or another pharmaceutically acceptable salt thereof, VEGF antagonist, or anti-C5 agent is typically 0.1 mg to 1500 mg per day, or 0.5 mg to 10 mg per day, or 0.5 mg to 5 mg per day. A dosage of at least up to 3000 mg per day can be administered.

In some embodiments, in which Antagonist A or another pharmaceutically acceptable salt thereof, VEGF antagonist and/or anti-C5 agent are ophthalmologically administered to a human, for example intravitreally, the dosage of each of Antagonist A or another pharmaceutically acceptable salt thereof, VEGF antagonist and anti-C5 agent is typically 0.003 mg to 5.0 mg per eye per administration, or 0.03 mg to 3.0 mg per eye per administration, or 0.1 mg to 1.0 mg per eye per administration. In one embodiment, the dosage of each of Antagonist A or another pharmaceutically acceptable salt thereof, VEGF antagonist and anti-C5 agent is about 0.03 mg, about 0.3 mg, about 0.5 mg, about 1.0 mg, about 1.25 mg, about 1.5 mg, about 2.0 mg or about 3.0 mg per eye. In one embodiment, the dosage Antagonist A or another pharmaceutically acceptable salt thereof is about 0.03 mg, about 0.3 mg, about 0.5 mg, about 1.0 mg, about 1.25 mg, about 1.5 mg, about 2.0 mg, about 3.0 mg, or about 4.0 mg per eye. In another embodiment, the dosage of a VEGF antagonist (e.g., ranibizumab, bevacizumab, aflibercept, ESBA1008 or pegaptanib sodium) is about 0.03 mg, about 0.3 mg, about 0.5 mg, about 1.0 mg, about 1.25 mg, about 1.5 mg, about 1.65 mg, about 2.0 mg, about 3.0 mg, or about 4.0 mg per eye. In another embodiment, the dosage of the anti-C5 agent (e.g., ARC1905 or a pharmaceutically acceptable salt thereof) is about 0.03 mg, about 0.3 mg, about 0.5 mg, about 1.0 mg, about 1.25 mg, about 1.5 mg, about 1.65 mg, about 2.0 mg, about 3.0 mg, or about 4.0 per eye.

In certain embodiments where a subject is administered both Antagonist A or another pharmaceutically acceptable salt thereof and a VEGF antagonist, and optionally an anti-C5 agent, the dosage of Antagonist A or another pharmaceutically acceptable salt thereof) is about 1.5 mg, and the dosage of the VEGF antagonist (e.g., ranibizumab) is about 0.5 mg. In certain embodiments where a subject is administered both Antagonist A or another pharmaceutically acceptable salt thereof and a VEGF antagonist, the dosage of Antagonist A or another pharmaceutically acceptable salt thereof is about 3.0 mg, and the dosage of the VEGF antagonist (e.g., ranibizumab) is about 0.5 mg. In certain embodiments, a subject is administered both Antagonist A or another pharmaceutically acceptable salt thereof and a VEGF antagonist, wherein the dosage of Antagonist A or another pharmaceutically acceptable salt thereof) is about 1.5 mg, and the dosage of the VEGF antagonist (e.g., bevacizumab) is about 1.25 mg. In certain embodiments, a subject is administered both Antagonist A or another pharmaceutically acceptable salt thereof and a VEGF antagonist, wherein the dosage of Antagonist A or another pharmaceutically acceptable salt thereof is about 3.0 mg, and the dosage of the VEGF antagonist (e.g., bevacizumab) is about 1.25 mg. In certain embodiments, a subject is administered both Antagonist A or another pharmaceutically acceptable salt thereof and a VEGF antagonist, wherein the dosage of Antagonist A or another pharmaceutically acceptable salt thereof is about 1.5 mg, and the dosage of the VEGF antagonist (e.g., aflibercept) is about 2.0 mg. In certain embodiments, a subject is administered both Antagonist A or another pharmaceutically acceptable salt thereof and a VEGF antagonist, wherein the dosage of Antagonist A or another pharmaceutically acceptable salt thereof is about 3.0 mg, and the dosage of the VEGF antagonist (e.g., aflibercept) is about 2.0 mg. In certain embodiments, a subject is administered both Antagonist A or another pharmaceutically acceptable salt thereof and a VEGF antagonist, wherein the dosage of Antagonist A or another pharmaceutically acceptable salt thereof is about 1.5 mg, and the dosage of the VEGF antagonist, e.g., pegaptanib sodium, is about 1.65 mg. In certain embodiments, a subject is administered both Antagonist A or another pharmaceutically acceptable salt thereof and a VEGF antagonist, wherein the dosage of Antagonist A or another pharmaceutically acceptable salt thereof is about 3.0 mg, and the dosage of the VEGF antagonist, e.g., pegaptanib sodium, is about 1.65 mg.

The dosage can range from about 0.01 mL to about 0.2 mL administered per eye, or about 0.03 mL to about 0.15 mL administered per eye, or about 0.05 mL to about 0.10 mL administered per eye.

Antagonist A or a pharmaceutically acceptable salt thereof can be delivered intravitreally at up to about 30 mg/ml with injection volumes up to 100 μL.

Illustrative Antagonist A/VEGF antagonist combination pairs and their dosages are set forth in Table 11:

TABLE 11

| Combination No. | PDGF Antagonist | VEGF Antagonist |
|---|---|---|
| 1 | Antagonist A (about 1.5 mg) | ranibizumab (about 0.5 mg) |
| 2 | Antagonist A (about 3.0 mg) | ranibizumab (about 0.5 mg) |
| 3 | Antagonist A (about 1.5 mg) | bevacizumab (about 1.25 mg) |
| 4 | Antagonist A (about 3.0 mg) | bevacizumab (about 1.25 mg) |
| 5 | Antagonist A (about 1.5 mg) | aflibercept (about 2.0 mg) |
| 6 | Antagonist A (about 3.0 mg) | aflibercept (about 2.0 mg) |
| 7 | Antagonist A (about 3.0 mg) | pegaptanib sodium (about 1.65 mg) |
| 8 | Antagonist A (about 3.0 mg) | pegaptanib sodium (about 1.65 mg) |

In particular embodiments wherein the subject is administered an anti-C5 agent in combination with Antagonist A or another pharmaceutically acceptable salt thereof and the VEGF antagonist, the anti-C5 agent may be administered at a dosage of about 0.03 mg, about 0.3 mg, about 0.5 mg, about 1.0 mg, about 1.25 mg, about 1.5 mg, about 2.0 mg or about 3.0 mg per eye.

In certain embodiments, ocular dosages of compositions comprising anti-C5 aptamers, such as ARC1905 and ARC187, or a pharmaceutically acceptable salt thereof, can range from about 0.01 mg to about 5 mg/eye or from about 0.1 mg to about 3 mg/eye. For instance, ocular dosages of compositions comprising ARC1905, ARC187, or a pharmaceutically acceptable salt thereof may be about 0.01 mg, about 0.03 mg, about 0.05 mg, about 0.1 mg, about 0.3 mg, about 0.5 mg, about 1 mg, about 1.5 mg, about 2 mg, about 2.5 mg, about 3 mg, about 3.5 mg, about 4 mg, about 4.5 mg, or about 5 mg. Such dosages may be administered ocularly, for example by intravitreal injection, weekly, biweekly, monthly, or quarterly, optionally by a sustained release device or formulation. In some embodiments, the anti-C5 aptamers (e.g., ARC1905, ARC187, or a pharmaceutically acceptable salt thereof) can be administered in multiple injections (e.g., intravitreal injections) over a period of months separated by varying time intervals. In certain such embodiments, initial injections received early in the treatment regimen are separated by a shorter interval than injections received later in the treatment regimen. For instance, one dosage regimen, particularly useful in methods for treating, preventing, or stabilizing AMD (e.g., non-exudative type AMD or geographic atrophy), comprises administering initial injections at the start of treatment (e.g., first two, three, four, or five injections) of anti-C5 aptamer (e.g., ARC1905, ARC187, or a pharmaceutically acceptable salt thereof) on a monthly basis and administering subsequent injections at longer intervals (e.g., every three, four, five, or six months). By way of example, the first three injections of anti-C5 aptamer are administered to a subject every month, whereas the fourth and fifth injections are administered three or four months after the previous injection. Intervals between injections of anti-C5 aptamer may be adjusted based on the subject's response to treatment as measured, for example, by change in geographic atrophy lesion size or improvement or stabilization of visual acuity.

In some embodiments, an anti-C5 aptamer is administered to a subject with a VEGF antagonist, wherein the dosage of the anti-C5 aptamer is about 0.03 mg, and the dosage of the VEGF antagonist, e.g., ranibizumab, is about 0.5 mg. In certain embodiments, a subject is administered both an anti-C5 aptamer and a VEGF antagonist, wherein the dosage of the anti-C5 aptamer is about 1.0 mg, and the dosage of the VEGF antagonist, e.g., ranibizumab, is about 0.5 mg. In certain embodiments, a subject is administered both an anti-C5 aptamer and a VEGF antagonist, wherein the dosage of the anti-C5 aptamer is about 2.0 mg, and the dosage of the VEGF antagonist, e.g., ranibizumab, is about 0.5 mg.

In some embodiments, an anti-C5 aptamer is administered to a subject with a VEGF antagonist, wherein the dosage of the anti-C5 aptamer is about 0.03 mg, and the dosage of the VEGF antagonist, e.g., bevacizumab, is about 1.25 mg. In certain embodiments, a subject is administered both an anti-C5 aptamer and a VEGF antagonist, wherein the dosage of the anti-C5 aptamer is about 1.0 mg, and the dosage of the VEGF antagonist, e.g., bevacizumab, is about 1.25 mg. In certain embodiments, a subject is administered both an anti-C5 aptamer and a VEGF antagonist, wherein the dosage of the anti-C5 aptamer is about 2.0 mg, and the dosage of the VEGF antagonist, e.g., bevacizumab, is about 1.25 mg.

In some embodiments, an anti-C5 aptamer is administered to a subject with a VEGF antagonist, wherein the dosage of the anti-C5 aptamer is about 0.03 mg, and the dosage of the VEGF antagonist, e.g., aflibercept, is about 2.0 mg. In certain embodiments, a subject is administered both an anti-C5 aptamer and a VEGF antagonist, wherein the dosage of the anti-C5 aptamer is about 1.0 mg, and the dosage of the VEGF antagonist, e.g., aflibercept, is about 2.0 mg. In certain embodiments, a subject is administered both an anti-C5 aptamer and a VEGF antagonist, wherein the dosage of the anti-C5 aptamer is about 2.0 mg, and the dosage of the VEGF antagonist, e.g., aflibercept, is about 2.0 mg.

Administration of each antagonist can, independently, be one to four times daily or one to four times per month or one to six times per year or once every two, three, four or five years. Administration can be for the duration of one day or one month, two months, three months, six months, one year, two years, three years, and may even be for the life of the patient. In one embodiment, the administration is performed once a month for three months. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

In addition to treating pre-existing ophthalmological diseases and disorders, the compositions can be administered prophylactically in order to prevent or slow the onset of these disease and disorders. The term "prevent" encompasses inhibiting or delaying the onset or progression of a disease or disorder. In prophylactic applications, the composition can be administered to a patient susceptible to or otherwise at risk of a particular ophthalmological disease or disorder.

In one embodiment, Antagonist A or another pharmaceutically acceptable salt thereof and the VEGF antagonist are administered to a subject in need of treatment therewith, typically in the form of an injectable pharmaceutical composition. Antagonist A or another pharmaceutically acceptable salt thereof and VEGF antagonist can be administered either in separate compositions or in a pharmaceutical composition comprising both the PDGF antagonist and VEGF antagonist. The administration can be by injection, for example by intraocular injection, or by using a drug delivery device. Parenteral, systemic, or transdermal administration is also within the scope of the invention. The administration of Antagonist A or another pharmaceutically acceptable salt thereof and the VEGF antagonist can be sequential in time or concurrent. When administered sequentially, the administration of each can be by the same or different route. In one embodiment, Antagonist A or another pharmaceutically acceptable salt thereof is administered within 90 days, 30 days, 10 days, 5 days, 24 hours, 1 hour, 30 minutes, 10 minutes, 5 minutes or one minute of administration of a VEGF antagonist. Where Antagonist A or another pharmaceutically acceptable salt thereof is administered prior to the VEGF antagonist, the VEGF antagonist is administered within a time and in an amount such that the total amount of Antagonist A or another pharmaceutically acceptable salt thereof and VEGF antagonist is effective to treat or prevent an ophthalmological disease or disorder. Where the VEGF antagonist is administered prior to Antagonist A or another pharmaceutically acceptable salt thereof, Antagonist A or another pharmaceutically acceptable salt thereof is administered within a time and in an amount such that the total amount of Antagonist A or another pharmaceutically acceptable salt thereof and VEGF antagonist is effective to treat or prevent an ophthalmological disease or disorder.

In one embodiment, Antagonist A or another pharmaceutically acceptable salt thereof or VEGF antagonist (e.g., ranibizumab, bevacizumab, pegaptanib sodium, ESBA1008 or aflibercept) is administered intravitreally with a 30-gauge or 27-gauge needle. In some embodiments, a 0.5 inch needle is used. In one embodiment, Antagonist A or another pharmaceutically acceptable salt thereof is administered intravitreally with a 30-gauge 0.5 inch needle and a VEGF antagonist (e.g., ranibizumab, bevacizumab, pegaptanib sodium, ESBA1008 or aflibercept) is administered intravitreally with a 27-gauge needle. In some embodiments, 50 μL (1.5 mg in 0.05 mL) of Antagonist A or another pharmaceutically acceptable salt thereof is administered intravitreally with a 30-gauge 0.5 inch needle and 50 μL (0.5 mg in 0.05 mL) of a VEGF antagonist (e.g., ranibizumab, bevacizumab, pegaptanib sodium or aflibercept) is administered intravitreally with a 27-gauge needle.

In certain embodiments where Antagonist A or another pharmaceutically acceptable salt thereof such as Antagonist A or another pharmaceutically acceptable salt thereof is used in combination with a VEGF antagonist, such as ranibizumab, bevacizumab, ESBA1008, pegaptanib sodium or aflibercept, one of these two agents is first administered to the subject, and then the other agent is administered to the subject. In particular embodiments, the two agents are both administered to the same eye of the subject. In particular embodiments, the two agents are both administered to both eyes of the subject. The two agents may be administered to an eye in either order, i.e., Antagonist A or another pharmaceutically acceptable salt thereof may be administered first, and then the VEGF antagonist administered, or the VEGF antagonist may be administered first, and then Antagonist A or another pharmaceutically acceptable salt thereof administered. The agent administered second may be administered immediately following administration of the agent administered first, or the agent administered second may be administered after a time period following administration of the agent administered first.

In certain embodiments, the time period from administration of the first agent to administration of the second agent is at least 1 min, at least 5 min, at least 10 min, at least 15 min, at least 30 min, or at least one hour. In certain embodiments, the time period from administration of the first agent to administration of the second agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from administration of the first agent to administration of the second agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min.

In certain embodiments, the present invention provides methods for treating or preventing any of the ophthalmological diseases described herein, comprising providing to a subject in need thereof Antagonist A or another pharmaceutically acceptable salt thereof at a first time point, and providing to the subject a VEGF antagonist, e.g., aflibercept, bevacizumab, ranibizumab, ESBA1008, or pegaptanib sodium, at a second time point, wherein the amount of time between the first time point and the second time point is about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days.

In certain embodiments, Antagonist A or another pharmaceutically acceptable salt thereof and the VEGF antagonist are administered intravitreally. In certain embodiments, about 1.5 mg or 3.0 mg of Antagonist A or another pharmaceutically acceptable salt thereof to an eye, and about 0.5 mg, about 1.25 mg, about 1.65 mg, or about 2.0 mg of the VEGF antagonist is administered to an eye. In some embodiments, the VEGF antagonist is administered intravitreally about 30 minutes after Antagonist A or another pharmaceutically acceptable salt thereof is administered intravitreally. In some embodiments, Antagonist A or another pharmaceutically acceptable salt thereof is administered intravitreally about 30 minutes after the VEGF antagonist is administered intravitreally.

In one embodiment, a VEGF antagonist is administered to at least one eye of the subject, about 1 hour is allowed to elapse following administration of the VEGF antagonist, and then Antagonist A or another pharmaceutically acceptable salt thereof is administered to the same eye. In one embodiment, Antagonist A or another pharmaceutically acceptable salt thereof is administered to at least one eye of the subject, about 1 hour is allowed to lapse following administration of the PDGF antagonist, and then a VEGF antagonist is administered to the same eye.

In certain embodiments, the PDGF antagonist and the VEGF antagonist are administered to each eye in a total combined volume of less than or about 50 μL, less than or about 60 μL, less than or about 70 μL, less than or about 80 μL, less than or about 90 μL, less than or about 100 μL, less than or about 120 μL, less than or about 150 μL, or less than or about 200 μL.

In certain embodiments, Antagonist A or another pharmaceutically acceptable salt thereof, VEGF antagonist and anti-C5 agent are administered intraocularly, e.g., intravitreally. In particular embodiments, Antagonist A or another pharmaceutically acceptable salt thereof, VEGF antagonist and anti-C5 agent are administered to the mammal via a single injection, e.g., a single intraocular or intravitreal injection. In particular embodiments, Antagonist A or another pharmaceutically acceptable salt thereof, VEGF antagonist and anti-C5 agent are administered sequentially. In certain embodiments, two or more of Antagonist A or another pharmaceutically acceptable salt thereof, a VEGF antagonist and an anti-C5 agent are administered at the same time, e.g., in the same composition. In particular embodiments, one of Antagonist A or another pharmaceutically acceptable salt thereof, a VEGF antagonist and an anti-C5 agent is administered, and within about 30 seconds, one or two of others are subsequently administered. In particular embodiments, all three of Antagonist A or another pharmaceutically acceptable salt thereof, a VEGF antagonist and an anti-C5 agent are administered within about 30 seconds or one minute of each other. In other embodiments, one of Antagonist A or another pharmaceutically acceptable salt thereof, a VEGF antagonist and an anti-C5 agent is administered, and one or both of the others are administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In other embodiments, one or two of Antagonist A or another pharmaceutically acceptable salt thereof, VEGF antagonist and anti-C5 agent are administered, and the other is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In certain embodiments, one of the PDGF antagonist, VEGF antagonist and anti-C5 agent is administered; and another is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later; and the remaining one is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In certain embodiments wherein two of Antagonist A or another pharmaceutically acceptable salt thereof, VEGF antagonist and anti-C5 agent are present in the same composition, the composition is administered and the PDGF antagonist, VEGF antagonist or anti-C5 agent that is not present in the composition is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In other embodiments wherein two of Antagonist A or another pharmaceutically acceptable salt thereof, VEGF antagonist and anti-C5 agent are present in the same composition, Antagonist A or another pharmaceutically acceptable salt thereof, VEGF antagonist or anti-C5 agent that is not present in the composition is administered, and the composition is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later.

In certain embodiments, Antagonist A or another pharmaceutically acceptable salt thereof, e.g., Antagonist A or another pharmaceutically acceptable salt thereof, is administered about every 24 hours for two or more, three or more, four or more, five or more, six or more, or seven or more days, and a VEGF antagonist, e.g., aflibercept, bevacizumab, ESBA1008, pegaptanib sodium or ranibizumab, is administered about 48 hours following the first administration of Antagonist A or another pharmaceutically acceptable salt thereof. In certain embodiments, Antagonist A or another pharmaceutically acceptable salt thereof is administered on each of four successive days, i.e., day 1, day 2, day 3 and day 4, and the VEGF antagonist (e.g., bevacizumab, ranibizumab, ESBA1008, pegaptanib sodium or aflibercept) is administered on the third day, i.e., day 3. In particular embodiments, a composition comprising Antagonist A or another pharmaceutically acceptable salt thereof, e.g., Antagonist A or another pharmaceutically acceptable salt thereof, is administered to a subject, and a composition comprising a VEGF antagonist is administered to the subject about forty-eight hours later.

In one embodiment, about 50 mg/kg of Antagonist A or another pharmaceutically acceptable salt thereof (e.g., Antagonist A or another pharmaceutically acceptable salt thereof) is administered, e.g., intraperitoneally, on day 1, day 2, day 3 and day 4, and about 1 mg/kg of a VEGF antagonist (e.g., bevacizumab, ranibizumab, ESBA1008, pegaptanib sodium, or aflibercept) is administered on day 3. In one embodiment, about 50 mg/kg of Antagonist A or another pharmaceutically acceptable salt thereof (e.g., Antagonist A or another pharmaceutically acceptable salt thereof) is administered on day 1, day 2, day 3 and day 4, and about 5 mg/kg of a VEGF antagonist (e.g., bevacizumab, ranibizumab, ESBA1008, pegaptanib sodium, or aflibercept) is administered on day 3.

In one embodiment, about 50 mg/kg of Antagonist A or another pharmaceutically acceptable salt thereof is administered on day 1, day 2, day 3 and day 4, and about 1 mg/kg of aflibercept is administered on day 3. In one embodiment, about 50 mg/kg of Antagonist A or another pharmaceutically acceptable salt thereof is administered on day 1, day 2, day 3 and day 4, and about 5 mg/kg of aflibercept is administered on day 3.

In one embodiment, about 0.03 mg, about 0.3 mg, about 0.5 mg, about 1.0 mg, about 1.5 mg or about 3.0 mg of Antagonist A or another pharmaceutically acceptable salt thereof (e.g., Antagonist A or another pharmaceutically acceptable salt thereof) is administered intravitreally on day 1, day 2, day 3 and day 4, and about 0.5 mg, about 1.0 mg, about 1.5 mg, about 1.65 mg, about 3.0 mg, or about 4.0 mg of a VEGF antagonist (e.g., bevacizumab, ranibizumab, ESBA1008, pegaptanib sodium, or aflibercept) is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 0.5 mg of ranibizumab is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 1.25 mg of bevacizumab is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 2.0 mg of aflibercept is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 1.65 mg of pegaptanib sodium is administered intravitreally on day 3.

In some embodiments, Antagonist A or another pharmaceutically acceptable salt thereof and VEGF antagonist are administered every four weeks or every 30 days, for six treatments. In some embodiments, the VEGF antagonist is ranibizumab. In some embodiments, 0.3 mg of Antagonist A or another pharmaceutically acceptable salt thereof and 0.5 mg of ranibizumab are administered every four weeks or every 30 days, for six treatments. In some embodiments, 1.5 mg of Antagonist A or another pharmaceutically acceptable salt thereof and 0.5 mg of ranibizumab are administered every four weeks or every 30 days, for six treatments.

In some embodiments, 0.3 mg of Antagonist A or another pharmaceutically acceptable salt thereof and 1.25 mg of bevacizumab, 2.0 mg of aflibercept, or 1.65 mg of pegaptanib sodium are administered every four weeks or every 30 days, for six treatments. In some embodiments, 1.5 mg of Antagonist A or another pharmaceutically acceptable salt thereof and 1.25 mg of bevacizumab, 2.0 mg of aflibercept, or 1.65 mg of pegaptanib sodium are administered every four weeks or every 30 days, for six treatments.

In some embodiments, the methods comprise administering Antagonist A or another pharmaceutically acceptable salt thereof, bevacizumab and aflibercept. In some embodiments, the methods comprise administering Antagonist A or another pharmaceutically acceptable salt thereof, bevacizumab and aflibercept every four weeks or every 30 days, for six treatments. In some embodiments, the methods comprise administering 1.5 mg of Antagonist A or another pharmaceutically acceptable salt thereof, 1.25 mg of bevacizumab, and 2 mg of aflibercept. In some embodiments, the methods comprise administering 1.5 mg of Antagonist A or another pharmaceutically acceptable salt thereof, 1.25 mg of bevacizumab, and 2 mg of aflibercept every four weeks or every 30 days, for six treatments.

In some embodiments, the methods comprise administering to a subject in need thereof (a) Antagonist A or another pharmaceutically acceptable salt thereof and (b) an VEGF antagonist, wherein (a) and (b) are administered in an amount that is effective for treating or preventing an ocular condition (e.g., wet AMD), and wherein the administering occurs once every month, ±about seven days, for 12 consecutive months.

In some embodiments, the methods comprise administering to a subject in need thereof (a) Antagonist A or another pharmaceutically acceptable salt thereof and (b) an VEGF antagonist, wherein: (a) and (b) are administered in an amount that is effective for treating or preventing an ocular condition (e.g., wet AMD); and the administering occurs once every month, ±about seven days, for a first 12 consecutive months, and immediately thereafter once every two months, ±about seven days, for a second 12 consecutive months, commencing on the second month of the second 12 consecutive months.

In some embodiments, the methods comprise administering to a subject in need thereof (a) Antagonist A or another pharmaceutically acceptable salt thereof and (b) an VEGF antagonist, wherein: (a) and (b) are administered in an amount that is effective for treating or preventing an ocular condition (e.g., wet AMD); and the administering occurs once every month, ±about seven days, for 24 consecutive months is also provided herein.

In some embodiments, the methods comprise administering to a subject in need thereof (a) Antagonist A or another pharmaceutically acceptable salt thereof and (b) an VEGF antagonist, wherein: (a) and (b) are administered in an amount that is effective for treating or preventing an ocular condition (e.g., wet AMD); and the administering occurs once every month, ±about seven days, for three consecutive months, and immediately thereafter once every two months, ±about seven days, for 12 consecutive months, commencing on the second month of the 12 consecutive months.

In some embodiments, the methods comprise continuous treatment, continuous and discontinuous treatments, and/or retreatments, e.g., for the treatment or preventing of wet-type AMD or subfoveal neovascular AMD. In some embodiments, continuous treatment comprises administering to Antagonist A or another pharmaceutically acceptable salt thereof and an anti-VEGF agent monthly (±7 days) for at least 1, 2, 3, 4, 5, 6, 7, 8, 9, 10, 11, or 12 consecutive months. In some embodiments, Antagonist A or a pharmaceutically acceptable salt thereof is administered within about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours of administration of the VEGF antagonist. In some embodiments, the VEGF antagonist is administered prior to administration of Antagonist A or a pharmaceutically acceptable salt thereof. In other embodiments, Antagonist A or a pharmaceutically acceptable salt thereof is administered prior to administration of the VEGF antagonist. In some embodiments, Antagonist A or a pharmaceutically acceptable salt thereof and a VEGF antagonist are administered as a co-formulation. In some embodiments, the amount of Antagonist A or a pharmaceutically acceptable salt thereof administered is about 1.5 mg/eye and the amount of VEGF antagonist administered is about 0.5 mg/eye (e.g., ranibizumab), about 1.25 mg/eye (e.g., bevacizumab), about 1.65 mg/eye (e.g., pegaptanib sodium), or about 2.0 mg/eye (e.g., aflibercept).

In some embodiments, the methods further comprise measuring the subject's visual acuity. In some embodiments, the subject's visual acuity is measured once every month, ±about seven days. In some embodiments, visual acuity is stable when it is stable for three consecutive months. In some embodiments, visual acuity is stable when at each of the last two of the three consecutive months, visual acuity is within 5 ETDRS letters (better or worse) of the subject's visual acuity at the first of the three consecutive months (i.e., the month immediately preceding the first of the two consecutive following months).

In some embodiments, a subject is administered in accordance with the present methods until the subject's visual acuity is stable. In some embodiments, a subject is administered in accordance with the present methods until the subject's visual acuity is stable for three consecutive months. In some embodiments, a subject is administered in accordance with the present methods until the subject's visual acuity at each of the last two of the three consecutive months is ≤a five-ETDRS-letter difference from the subject's visual acuity of the first of the three consecutive months. In some embodiments, a subject is administered in accordance with the present methods until the subject experiences no new or significant intraretinal or sub-retinal hemorrhage, or no increase of ≥50 μm in foveal intraretinal fluid. In some embodiments, a subject is administered in accordance with the present methods until the subject's visual acuity measured at each of the last two of the three consecutive months is ≤a five-ETDRS-letter difference from the subject's visual acuity of the first of the three consecutive months, and the subject experiences no new or significant intraretinal or sub-retinal hemorrhage, and no increase of ≥50 μm in foveal intraretinal fluid.

In some embodiments, discontinuous treatment is administered after continuous treatment, in which discontinuous treatment is based on a physician's discretion, and the subject has stabilized vision as determined by ≤a five-ETDRS-letter difference in the subject's visual acuity after continuous and discontinuous treatment.

In some embodiments, subjects with a loss of visual acuity of >5 ETDRS letters from the previous monthly assessment, new and significant intraretinal or sub-retinal hemorrhage, and/or an increase of ≥50 μm in foveal intraretinal fluid are retreated.

In some embodiments, the continuous method comprises administering Antagonist A or another pharmaceutically acceptable salt thereof and a VEGF antagonist in an amount that is effective for treating or preventing wet AMD, wherein the administering occurs once every month, ±about seven days, for 12 consecutive months. In some embodiments, the methods further comprise measuring the subject's visual acuity at one month, ±about seven days, immediately following the 12 consecutive months, wherein the subject's visual acuity measured on the twelfth of the 12 consecutive months and the one month immediately following the 12 consecutive months is ≤a five-ETDRS-letter difference in the subject's visual acuity measured on the eleventh of the 12 consecutive months.

In some embodiments, the methods further comprise measuring the subject's visual acuity once every month, ±about seven days, on each of an additional 11 consecutive months. In some embodiments, the subject's visual acuity measured on any two consecutive months of the additional 11 consecutive months is ≤a five-ETDRS-letter difference in the subject's visual acuity measured on a month immediately preceding the two consecutive months.

In some embodiments, the subject's visual acuity measured on the twelfth of the 12 consecutive months and the one month immediately following the 12 consecutive months is not ≤a five-ETDRS-letter difference in the subject's visual acuity measured on the eleventh of the 12 consecutive months and the subject is retreated. In some embodiments, retreatment comprises administering to the patient on the one month immediately following the 12 consecutive months Antagonist A or another pharmaceutically acceptable salt thereof and a VEGF antagonist in an amount that is effective for treating or preventing wet AMD, measuring the patient's visual acuity on a month, ±about seven days, immediately following the one month immediately following the 12 consecutive months, and administering to the subject on each immediately following month Antagonist A or another pharmaceutically acceptable salt thereof and a VEGF antagonist in an amount that is effective for treating or preventing wet AMD, until the subject's visual acuity on any two consecutive following months is ≤a five-ETDRS-letter difference in the subject's visual acuity measured on a month immediately preceding the first of the two consecutive following months. In some embodiments, the total number of months does not exceed 24.

In some embodiments, wherein the subject's visual acuity measured on the one month immediately following the 12 consecutive months is not ≤a five-ETDRS-letter difference in the subject's visual acuity measured on the twelfth of the 12 consecutive months and is not solely attributable to newly diagnosed foveal atrophy or worsening ocular media opacity, the method further comprises administering to the subject on the one month immediately following the 12 consecutive months Antagonist A or another pharmaceutically acceptable salt thereof and a VEGF antagonist in an amount that is effective for treating or preventing wet AMD; and administering to the subject on each immediately following month (a) and (b) in an amount that is effective for treating or preventing wet AMD, until the subject's visual acuity measured on any two consecutive following months is ≤a five-ETDRS-letter difference in the subject's visual acuity measured on a month immediately preceding the first of the two consecutive following months. In some embodiments, the total number of months does not exceed 24.

In some embodiments, wherein the subject presents intraretinal or sub-retinal hemorrhage or a ≥50 μm increase in foveal intraretinal fluid at one month, ±about seven days, immediately following the 12 consecutive months, the method further comprises administering to the subject on the one month immediately following the 12 consecutive months Antagonist A or another pharmaceutically acceptable salt thereof an a VEGF antagonist in an amount that is effective for treating or preventing wet AMD; and administering to the subject on each immediately following month (a) and (b) in an amount that is effective for treating or preventing wet AMD, until the subject's visual acuity measured on any two consecutive following months is ≤a five-ETDRS-letter difference in the subject's visual acuity measured on a month immediately preceding the first of the two consecutive following months. In some embodiments, the total number of months does not exceed 24.

Also provided herein is a method comprising administering Antagonist A or another pharmaceutically acceptable salt thereof and a VEGF antagonist intravitreally once every month, ±about seven days, for a first 12 consecutive months, and immediately thereafter once every two months, ±about seven days, for a second 12 consecutive months, commencing on the second month of the second 12 consecutive months. In some embodiments, Antagonist A or a pharmaceutically acceptable salt thereof is administered within about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours of administration of the VEGF antagonist. In some embodiments, the VEGF antagonist is administered prior to administration of Antagonist A or a pharmaceutically acceptable salt thereof. In other embodiments, Antagonist A or a pharmaceutically acceptable salt thereof is administered prior to administration of the VEGF antagonist. In some embodiments, Antagonist A or a pharmaceutically acceptable salt thereof and a VEGF antagonist are administered as a co-formulation. In some embodiments, the amount of Antagonist A or a pharmaceutically acceptable salt thereof administered is about 1.5 mg/eye and the amount of VEGF antagonist administered is about 0.5 mg/eye (e.g., ranibizumab), about 1.25 mg/eye (e.g., bevacizumab), about 1.65 mg/eye (e.g., pegaptanib sodium), or about 2.0 mg/eye (e.g., aflibercept).

In some embodiments, the method further comprises measuring the subject's visual acuity once every month, ±about seven days, during the first 12 consecutive months and second 12 consecutive months. In some embodiments, the subject's visual acuity measured on any one of the first, third, fifth, seven, ninth and eleventh months of the second consecutive 12 months decreased at least five ETDRS letters relative to the patient's visual acuity measured on the month immediately preceding the first, third, fifth, seven, ninth or eleventh month of the second consecutive 12 months.

In some embodiments, the methods further comprises administering to the subject an amount of Antagonist A or a pharmaceutically acceptable salt thereof and a VEGF antagonist effective for treating or preventing wet AMD on the month in which the subject's visual acuity measured the decrease of at least five ETDRS letters relative to the patient's visual acuity measured on the immediately preceding month.

In some embodiments, the method further comprises administering Antagonist A or a pharmaceutically acceptable salt thereof and a VEGF antagonist on any one of the first, third, fifth, seven, ninth and eleventh months of the second consecutive 12 months.

In some embodiments, the decrease in visual acuity is attributed to solely newly diagnosed foveal atrophy or opacified ocular media.

In some embodiments, the subject presents intraretinal or sub-retinal hemorrhage or a ≥50 μm increase in foveal intraretinal fluid on any one of the first, third, fifth, seven, ninth and eleventh months of the second consecutive 12 months.

In some embodiments, the method further comprises administering Antagonist A or a pharmaceutically acceptable salt thereof and a VEGF antagonist on month in which the subject presents intraretinal or sub-retinal hemorrhage or a ≥50 μm increase in foveal intraretinal fluid.

Also provided herein is a method comprising administering Antagonist A or another pharmaceutically acceptable salt thereof and a VEGF antagonist intravitreally once every month, ±about seven days, for 24 consecutive months. In other embodiments, Antagonist A or another pharmaceutically acceptable salt thereof and a VEGF antagonist are administered intravitreally once a month for three months and then every other month for the next 21 months. In some embodiments, Antagonist A or a pharmaceutically acceptable salt thereof is administered within about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours of administration of the VEGF antagonist. In some embodiments, the VEGF antagonist is administered prior to administration of Antagonist A or a pharmaceutically acceptable salt thereof. In other embodiments, Antagonist A or a pharmaceutically acceptable salt thereof is administered prior to administration of the VEGF antagonist. In some embodiments, Antagonist A or a pharmaceutically acceptable salt thereof and a VEGF antagonist are administered as a co-formulation. In some embodiments, the amount of Antagonist A or a pharmaceutically acceptable salt thereof administered is about 1.5 mg/eye and the amount of VEGF antagonist administered is about 0.5 mg/eye (e.g., ranibizumab), about 1.25 mg/eye (e.g., bevacizumab), about 1.65 mg/eye (e.g., pegaptanib sodium), or about 2.0 mg/eye (e.g., aflibercept).

In some embodiments, the methods comprise administering to a subject in need thereof (a) Antagonist A or another pharmaceutically acceptable salt thereof and (b) an VEGF antagonist, wherein (a) and (b) are administered in an amount that is effective for treating or preventing an ophthalmological disease or disorder (e.g., wet AMD), and wherein the administering occurs once every month, ±about seven days, for a first administration period of at least 3 consecutive months, followed by administering (a) and (b) for a second administration period at a frequency of at least every other month±about seven days beginning at two months±about seven days after the day of the last month of the first administration period on which (a) and (b) are administered. In some embodiments, the first administration period is for at least 6 consecutive months. In some embodiments, the VEGF antagonist is ranibizumab or bevacizumab, wherein (a) and (b) are administered at a frequency of once every month±about seven days during the second administration period and wherein the second administration period is at least about nine months.

In some embodiments, the methods further comprise measuring the subject's visual acuity on a day that is prior to and within about one month of administration of (a) and (b). In some embodiments, the methods further comprise administering to the subject (a) and (b) in an amount that is effective for treating or preventing an ophthalmological disease or disorder (e.g., wet AMD), until the subject's visual acuity on any two consecutive following months is ≤a five-ETDRS-letter difference in the subject's visual acuity measured on a month immediately preceding the first of the two consecutive following months.

In some embodiments, the method further comprise administering to the subject (a) and (b) every other month in an amount that is effective for treating or preventing an ophthalmological disease or disorder (e.g., wet AMD), until the subject's visual acuity on any two consecutive visual acuity assessments is not ≤a five-ETDRS-letter difference in the subject's visual acuity measured on a visual acuity assessment immediately preceding the first of the two consecutive visual acuity assessments.

In other embodiments, the methods further comprise administering to the subject (a) and (b) every month in an amount that is effective for treating or preventing an ophthalmological disease or disorder (e.g., wet AMD), until the subject's visual acuity on any two consecutive following months is ≤a five-ETDRS-letter difference in the subject's visual acuity measured on a month immediately preceding the first of the two consecutive following months.

In some embodiments, the methods comprise administering to a subject in need thereof (a) Antagonist A or another pharmaceutically acceptable salt thereof and (b) aflibercept, wherein (a) and (b) are administered in an amount that is effective for treating or preventing an ophthalmological disease or disorder (e.g., wet AMD), and wherein the administering occurs once every month, ±about seven days, for a first administration period of at least 3 consecutive months, followed by administering (a) and (b) for a second administration period at a frequency of at least every other month±about seven days beginning at two months ±about seven days after the day of the last month of the first administration period on which (a) and (b) are administered.

In some embodiments, the subject has intraretinal or sub-retinal hemorrhage or a ≥50 μm increase in foveal intraretinal fluid at one month, ±about seven days, immediately following the second administration period. In some embodiments, the methods further comprise administering to the subject on each month±about seven days, beginning on the month that immediately follows the second administration period (a) and (b) in an amount that is effective for treating or preventing wet AMD, until the subject's visual acuity measured on any two consecutive months that follow the 12 consecutive months is ≤a five-ETDRS-letter difference in the subject's visual acuity measured on a month immediately preceding the first of the two consecutive months.

In some embodiments, the total number of months of treatment does not exceed 24.

Pharmaceutical compositions according to the invention may be formulated to release Antagonist A or another pharmaceutically acceptable salt thereof, a VEGF antagonist, or an anti-C5 agent, substantially immediately upon administration or at any predetermined time period after administration, using controlled release formulations. For example, a pharmaceutical composition can be provided in sustained-release form. The use of immediate or sustained release compositions depends on the nature of the condition being treated. If the condition consists of an acute disorder, treatment with an immediate release form can be utilized over a prolonged release composition. For certain preventative or long-term treatments, a sustained released composition can also be appropriate.

Administration of one or both of the antagonists of, or an anti-C5 agent, in controlled release formulations can be useful where the antagonist, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of degradation or metabolism of the therapeutic antagonist. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes. Methods for preparing such sustained or controlled release formulations are well known in the art.

Antagonist A or another pharmaceutically acceptable salt thereof, the VEGF antagonist, or the anti-C5 agent can also be delivered using a drug-delivery device such as an implant. Such implants can be biodegradable and/or biocompatible, or can be non-biodegradable. The implants can be permeable to Antagonist A or another pharmaceutically acceptable salt thereof, the VEGF antagonist, or the anti-C5 agent. Ophthalmic drug delivery devices can be inserted into a chamber of the eye, such as the anterior or posterior chamber or can be implanted in or on the sclera, choroidal space, or an avascularized region exterior to the vitreous. In one embodiment, the implant can be positioned over an avascular region, such as on the sclera, so as to allow for transcleral diffusion of Antagonist A or another pharmaceutically acceptable salt thereof, the VEGF antagonist, or the anti-C5 agent to the desired site of treatment, e.g., the intraocular space and macula of the eye. Furthermore, the site of transcleral diffusion can be proximal to a site of neovascularization such as a site proximal to the macula. Suitable drug delivery devices are described, for example, in U.S. Publication Nos. 2008/0286334; 2008/0145406; 2007/0184089; 2006/0233860; 2005/0244500; 2005/0244471; and 2005/0244462, and U.S. Pat. Nos. 6,808,719 and 5,322,691, the contents of each of which is herein incorporated by reference in its entirety.

In one embodiment, the implant comprises Antagonist A or another pharmaceutically acceptable salt thereof and/or VEGF antagonist dispersed in a biodegradable polymer matrix. The matrix can comprise PLGA (polylactic acid-polyglycolic acid copolymer), an ester-end capped polymer, an acid end-capped polymer, or a mixture thereof. In another embodiment, the implant comprises Antagonist A or another pharmaceutically acceptable salt thereof and/or a VEGF antagonist, a surfactant, and lipophilic compound. The lipophilic compound can be present in an amount of about 80-99% by weight of the implant. Suitable lipophilic compounds include, but are not limited to, glyceryl palmitostearate, diethylene glycol monostearate, propylene glycol monostearate, glyceryl monostearate, glyceryl monolinoleate, glyceryl monooleate, glyceryl monopalmitate, glyceryl monolaurate, glyceryl dilaurate, glyceryl monomyristate, glyceryl dimyristate, glyceryl monopalmitate, glyceryl dipalmitate, glyceryl monostearate, glyceryl distearate, glyceryl monooleate, glyceryl dioleate, glyceryl monolinoleate, glyceryl dilinoleate, glyceryl monoarachidate, glyceryl diarachidate, glyceryl monobehenate, glyceryl dibehenate, and mixtures thereof. In another embodiment, the implant comprises Antagonist A or another pharmaceutically acceptable salt thereof and/or a VEGF antagonist housed within a hollow sleeve. The PDGF antagonist or VEGF antagonist, or both, are delivered to the eye by inserting the sleeve into the eye, releasing the implant from the sleeve into the eye, and then removing the sleeve from the eye. An example of this delivery device is described in U.S. Publication No. 2005/0244462, which is hereby incorporated by reference in its entirety.

In one embodiment, the implant is a flexible ocular insert device adapted for the controlled sustained release of Antagonist A or another pharmaceutically acceptable salt thereof and/or a VEGF antagonist into the eye. In one embodiment, the device includes an elongated body of a polymeric material in the form of a rod or tube containing Antagonist A or another pharmaceutically acceptable salt thereof, VEGF antagonist or both, and with at least two anchoring protrusions extending radially outwardly from the body. The device may have a length of at least 8 mm and the diameter of its body portion including the protrusions does not exceed 1.9 mm. The sustained release mechanism can, for example, be by diffusion or by osmosis or bioerosion. The insert device can be inserted into the upper or lower formix of the eye so as to be independent of movement of the eye by virtue of the formix anatomy. The protrusions can be of various shapes such as, for example, ribs, screw threads, dimples or bumps, truncated cone-shaped segments or winding braid segments. In a further embodiment, the polymeric material for the body is selected as one which swells in a liquid environment. Thus a device of smaller initial size can be employed. The insert device can be of a size and configuration such that, upon insertion into the upper or lower formix, the device remains out of the field of vision so as to be well retained in place and imperceptible by a recipient over a prolonged period of use. The device can be retained in the upper or lower formix for 7 to 14 days or longer. An example of this device is described in U.S. Pat. No. 5,322,691, which is hereby incorporated by reference in its entirety.

Kits

The invention relates to kits comprising one or more pharmaceutical compositions and instructions for use. At least two antagonists can be formulated together or in separate compositions and in individual dosage amounts. The antagonists are also useful when formulated as pharmaceutically acceptable salts. In one embodiment, the kits comprise a composition comprising Antagonist A or another pharmaceutically acceptable salt thereof and a pharmaceutically acceptable carrier or vehicle and another composition comprising a VEGF antagonist and a pharmaceutically acceptable carrier or vehicle. In another embodiment, the kits comprise a composition comprising a VEGF antagonist, Antagonist A or another pharmaceutically acceptable salt thereof and a pharmaceutically acceptable carrier or vehicle. Each of the kits' compositions can be contained in a container. In some embodiments, the kits comprise an anti-C5 agent.

The kits can comprise (1) an amount of Antagonist A or another pharmaceutically acceptable salt thereof and a pharmaceutically acceptable carrier, vehicle, or diluent in a first unit dosage form; (2) an amount of a VEGF antagonist and a pharmaceutically acceptable carrier, vehicle, or diluent in a second unit dosage form; and (3) a container. The container can be used to separate components and include, for example, a divided bottle or a divided foil packet. The separate antagonist compositions may also, if desired, be contained within a single, undivided container. In some embodiments, the kits comprise an anti-C5 agent.

The kits can also comprise directions for the administration of the antagonists. The kits are particularly advantageous when the separate components are administered in different dosage forms, are administered at different dosage levels, or when titration of the individual antagonists is desired.

EXAMPLES

Example 1: Antagonist A and Ranibizumab Combination Therapy for Treating Subfoveal Neovascular Lesions Secondary to Neovascular Age-Related Macular Degeneration (NVAMD)

In this study, 449 subjects with subfoveal neovascular lesions secondary to NVAMD received six monthly intravitreous injections of Antagonist A given in combination with ranibizumab (administered as Lucentis®, commercially available from Genentech, South San Francisco, CA). Antagonist A was injected as the formulation shown in Table 12. The primary efficacy endpoint in the study was the mean change in visual acuity from baseline at the week 24 visit. As pre-specified in the analysis plan, the Hochberg procedure (Hochberg, Y. (1988). A sharper Bonferroni procedure for multiple tests of significance. *Biometrika.* 75, 800-802) was employed to account for multiple dose comparisons.

The subjects were randomized in a 1:1:1 ratio to the groups shown in Table 13.

TABLE 12

Antagonist A Formulation

| Name of Ingredient | Reference to Standards | Function | 30 mg/mL Solution Composition | 30 mg/mL Percent (w/v) |
|---|---|---|---|---|
| Antagonist A | In-house standard | Drug substance | 30.0 mg | 3% |
| Monobasic Sodium Phosphate Monohydrate | USP/Ph. Eur | pH buffering agent | 0.3 mg | 0.03% |
| Dibasic Sodium Phosphate Heptahydrate | USP/Ph. Eur | pH buffering agent | 2.1 mg | 0.2% |
| Sodium Chloride | USP/Ph. Eur | Tonicity adjuster | 9.0 mg | 0.9% |
| Hydrochloric Acid | NF/Ph. Eur | pH adjuster | As needed | |
| Sodium Hydroxide | NF/Ph. Eur | pH adjuster | As needed | |
| Water for Injection | USP/Ph. Eur | Diluent | q.s. | 95.9% |
| Nitrogen | NF/Ph. Eur | Inert gas overlay | — | — |
| Total Volume | | | 1 ml | |
| Volume in Final Drug Product Presentation | | | 230 microliters | |

TABLE 13

Antagonist A and Ranibizumab Combination Therapy for Subfoveal Neovascular Lesions Secondary to NVAMD Treatment Groups

| Group No. | Group Name | Treatment Regimen |
|---|---|---|
| 1 | Combination Therapy (0.3 mg) | Subjects were administered 0.3 mg/eye of Antagonist A and 0.5 mg/eye of Lucentis ® |
| 2 | Combination Therapy (1.5 mg) | Subjects were administered 1.5 mg/eye of Antagonist A and 0.5 mg/eye of Lucentis ® |
| 3 | Ranibizumab Monotherapy | Subjects were administered Antagonist A Sham and 0.5 mg/eye of Lucentis ® |

Figure 2:
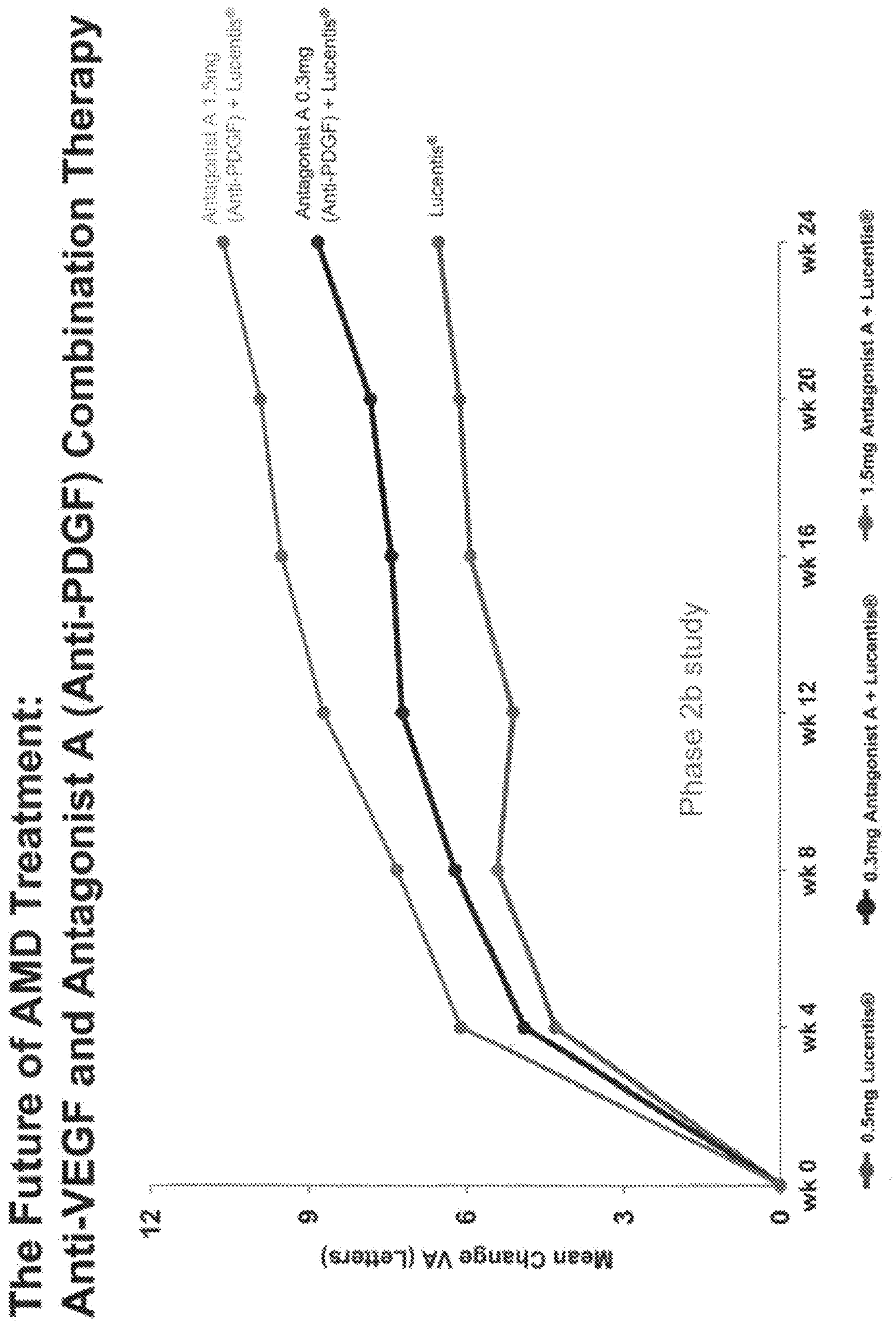
FIG. 2 shows a graph depicting the mean change in visual acuity in wet AMD patients in a phase 2b clinical trial, who were treated with 0.5 mg of Lucentis® alone or with 0.5 mg of Lucentis® and either 1.5 mg of Antagonist A or 0.3 mg of Antagonist A.
Figure 3:
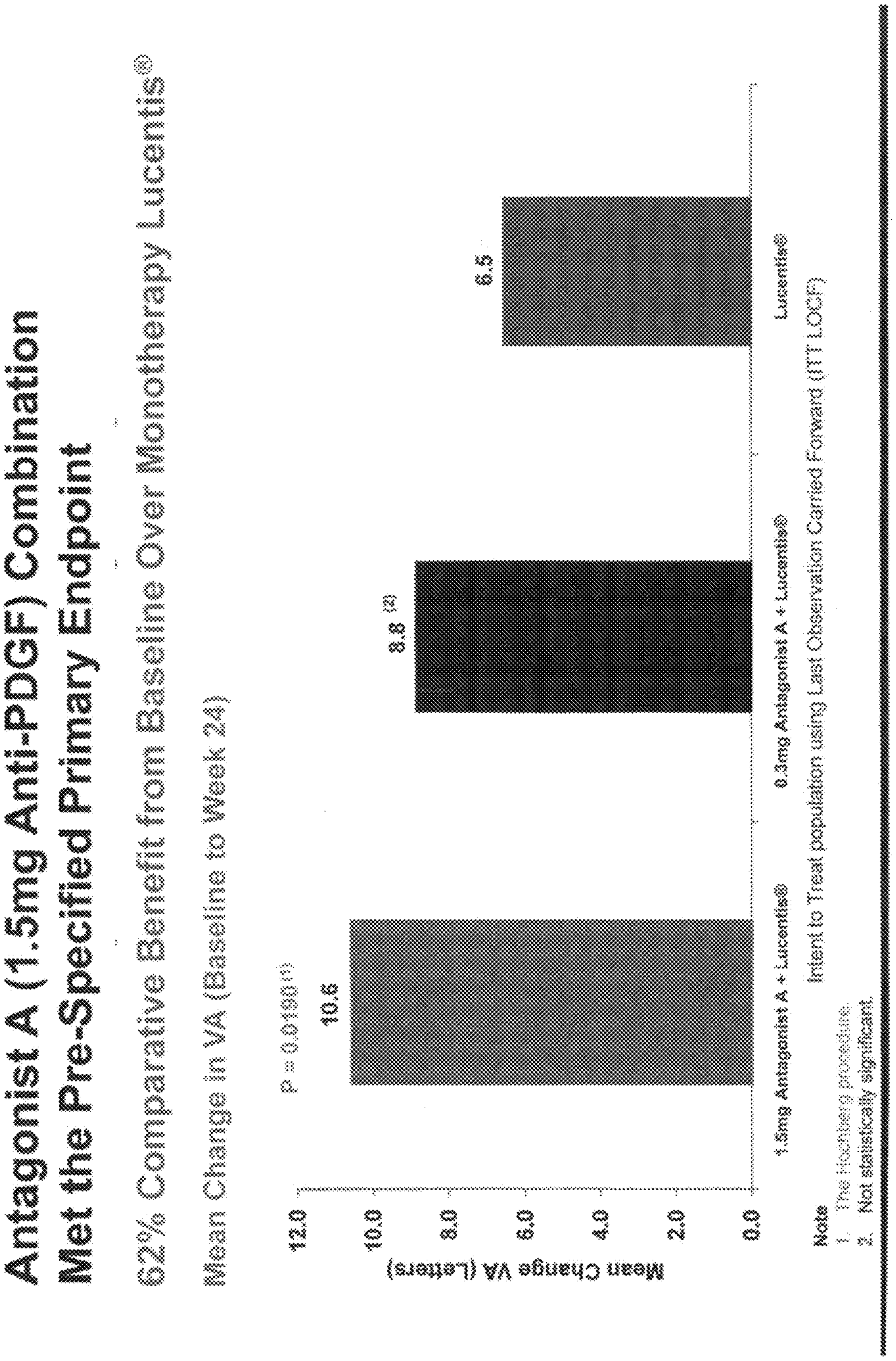
FIG. 3 shows a bar graph showing comparative visual-acuity benefit in wet AMD patients with treatment with 0.5 mg of Lucentis® and either 1.5 mg or 0.3 mg of Antagonist A as compared to treatment with Lucentis® monotherapy (0.5 mg).

Combination therapy proved superior in terms of mean visual gain when compared to eyes that were treated with anti-VEGF monotherapy. Subjects treated with Lucentis® and either 1.5 mg/eye or 0.3 mg/eye Antagonist A showed an increase in visual acuity compared with those treated with Lucentis® alone (FIG. 2). The combination of 1.5 mg/eye of Antagonist A and 0.5 mg of Lucentis® met the pre-specified, alpha protected primary endpoint of superiority in mean change of visual acuity gain compared to ranibizumab monotherapy from baseline to 24 weeks (10.6 ETDRS letters at week 24, compared to 6.5 letters, p=0.019, representing a 62% additional benefit). (FIG. 3) Subjects treated with Lucentis® and either 1.5 mg or 0.3 mg Antagonist A showed a 62% comparative benefit from baseline compared to treatment with Lucentis® alone.

Figure 4:
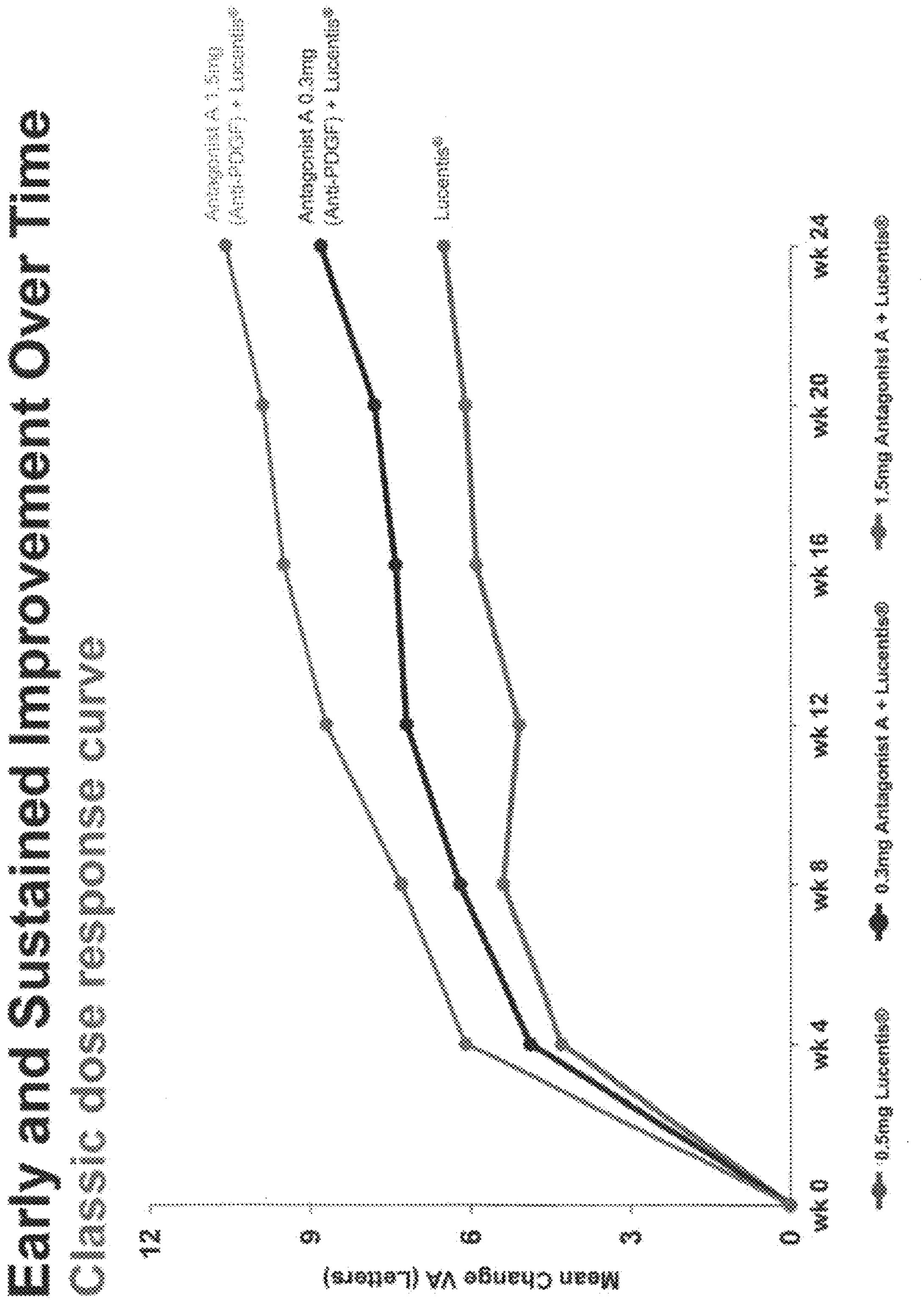
FIG. 4 shows a graph depicting the early and sustained visual-acuity improvement over time in wet AMD patients treated with Lucentis® monotherapy (0.5 mg) or with 0.5 mg of Lucentis® and either 1.5 mg of Antagonist or 0.3 mg of Antagonist A.

In addition, the mean change in vision over time demonstrated the benefit of combination therapy at each measured time point over 24 weeks. (FIG. 4) That benefit was sustained during the study and demonstrated increasing differentiation of the curves at study closure.

Figure 5A:
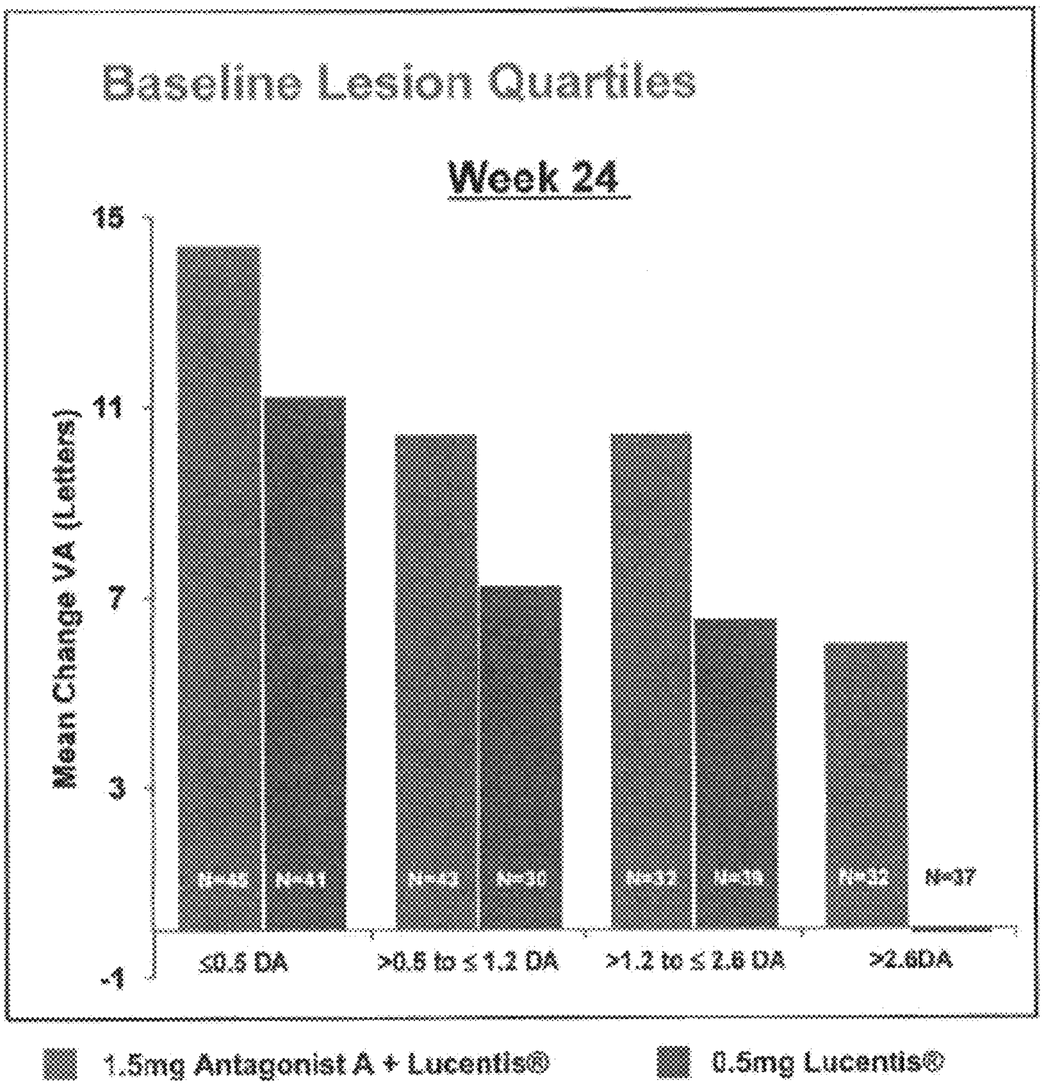
FIGS. 5A and 5B provide bar graphs showing that the increased efficacy of treatment with 0.5 mg of Lucentis® and either 1.5 mg or 0.3 mg of Antagonist A as compared to treatment with Lucentis® monotherapy (0.5 mg) in patients with wet AMD is independent of baseline lesion size or baseline vision.
Figure 5B:
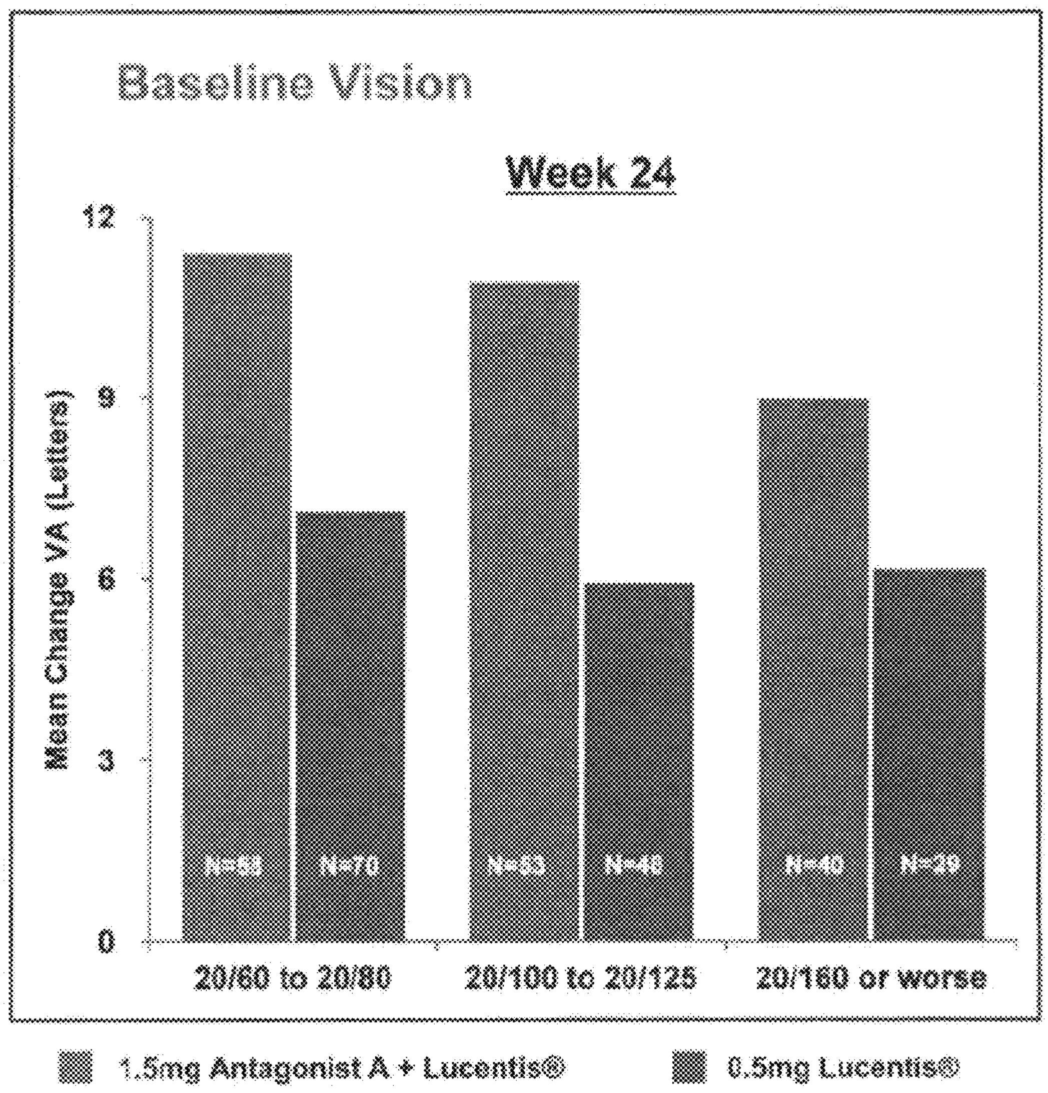

Treatment with 0.5 mg of Lucentis® and either 1.5 mg or 0.3 mg Antagonist A in wet AMD patients also had increased efficacy as compared to patients treated with Lucentis® alone, independent of baseline lesion size or vision. (FIGS. 5A and 5B)

Figure 6A:
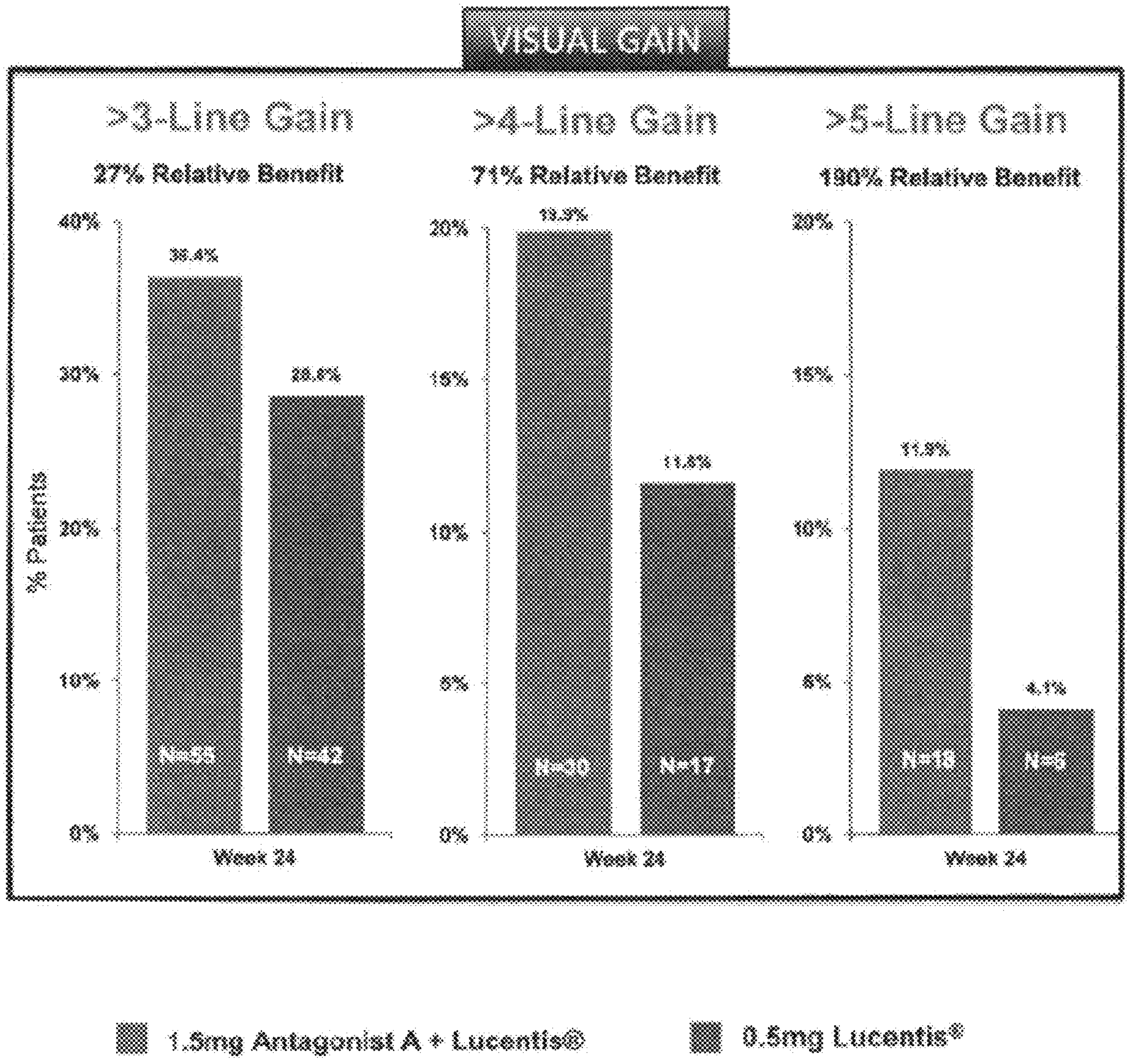
FIGS. 6A and 6B provide bar graphs showing that the cohort of patients treated with a combination of 0.5 mg of Lucentis® and 1.5 mg of Antagonist A included a greater proportion of patients with significant visual gain (FIG. 6A) and fewer patients with visual loss (FIG. 6B) as compared to the cohort of patients with treated Lucentis® monotherapy (0.5 mg).

A greater percentage of subjects in the Combination Therapy (1.5 mg) group achieved enhanced visual outcomes compared to those in the Ranibizumab Monotherapy group with respect to multiple treatment endpoints at week 24, as shown in FIG. 6A, and Table 14.

TABLE 14

Percentage of Subjects in the Combination Therapy (1.5 mg) Group and Ranibizumab Monotherapy Group with Visual Acuity Improvement

| Treatment Endpoint | Percentage of Patients | |
|---|---|---|
| | Combination Therapy (1.5 mg) | Ranibizumab Monotherapy |
| >3-lines of visual acuity improvement | 36.4% | 28.6% |
| >4-lines of visual acuity improvement | 19.9% | 11.6% |
| >5-lines of visual acuity improvement | 11.9% | 4.1% |
| ≥20/40 vision after treatment | 37.0% | 31.9% |
| ≥20/25 vision after treatment | 12.3% | 5.6% |

Figure 6B:
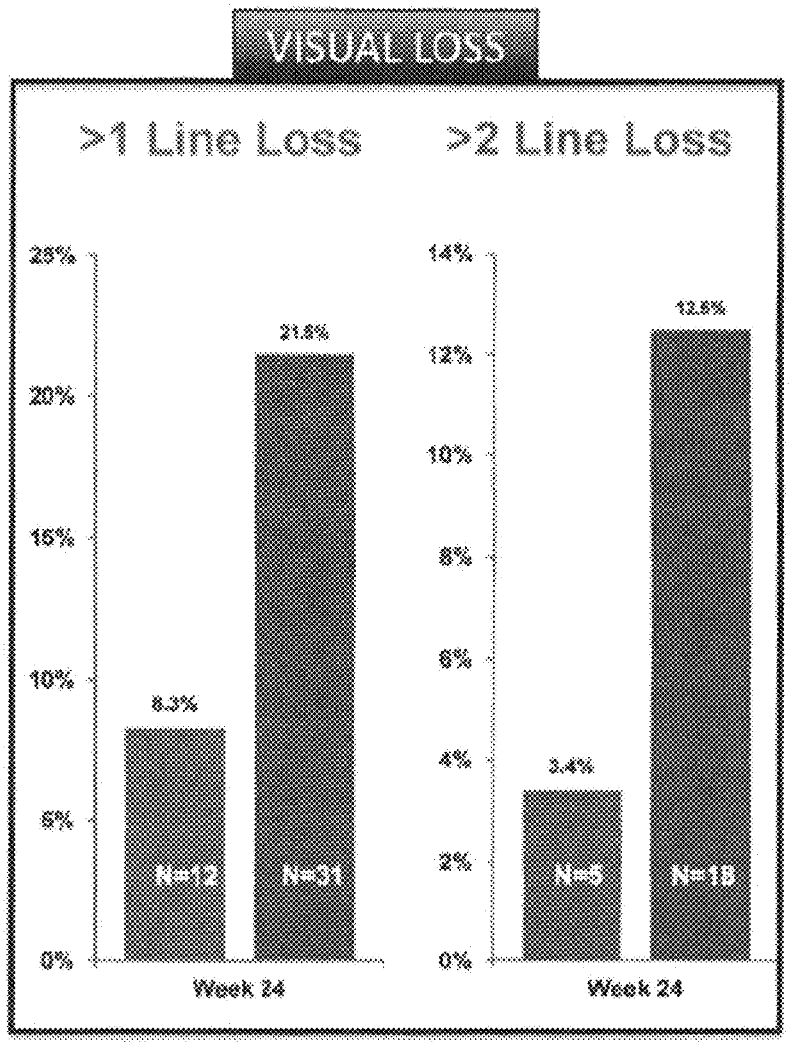

Moreover, fewer subjects in the Combination Therapy (1.5 mg) group demonstrated a loss of visual acuity as compared to the number of subjects in the Ranibizumab Monotherapy group at week 24, as shown in FIG. 6B and Table 15.

TABLE 15

Percentage of Subjects in the Combination Therapy (1.5 mg) Group and Ranibizumab Monotherapy Group with Visual Acuity Loss

| Treatment Endpoint | Percentage of Patients | |
|---|---|---|
| | Combination Therapy (1.5 mg) | Ranibizumab Monotherapy |
| ≥1-lines of visual acuity loss | 8.3% | 21.5% |
| ≥2-lines of visual acuity loss | 3.4% | 12.5% |
| ≤20/125 vision after treatment | 19.2% | 27.8% |
| ≤20/200 vision after treatment | 10.3% | 13.9% |

Figure 7A:
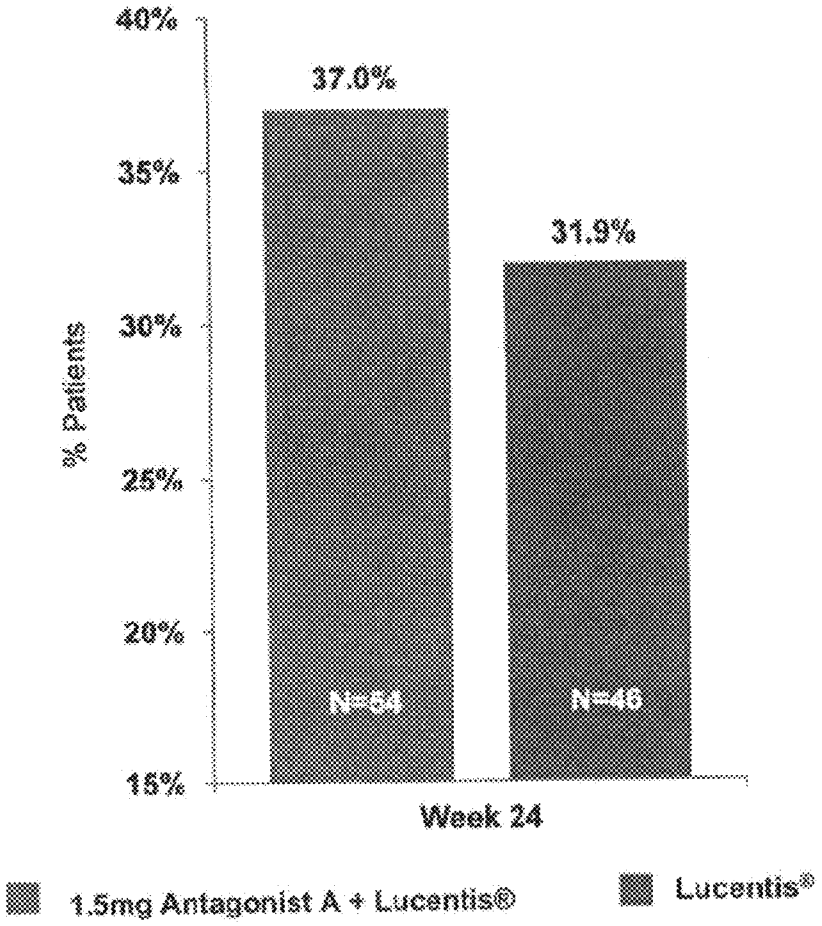
FIGS. 7A-C provide bar graphs showing that patients treated with 0.5 mg of Lucentis® and 1.5 mg of Antagonist A exhibited a greater mean improvement in final visual acuity as compared to patients treated with Lucentis® monotherapy (0.5 mg).
Figure 7B:
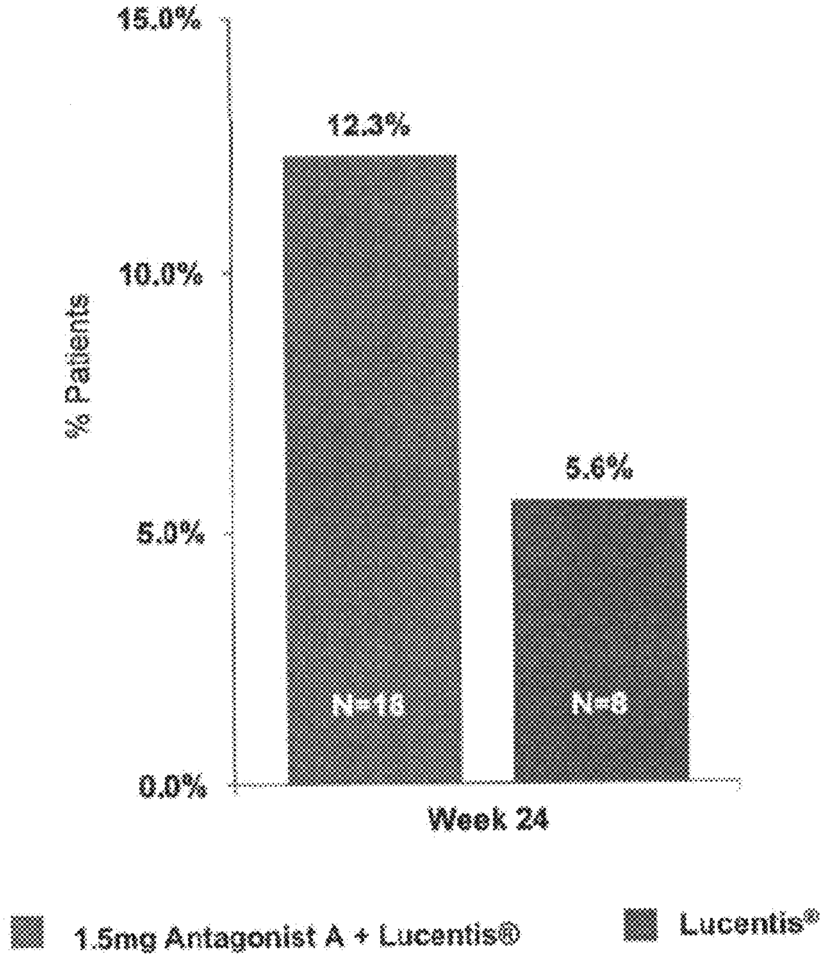
Figure 7C:
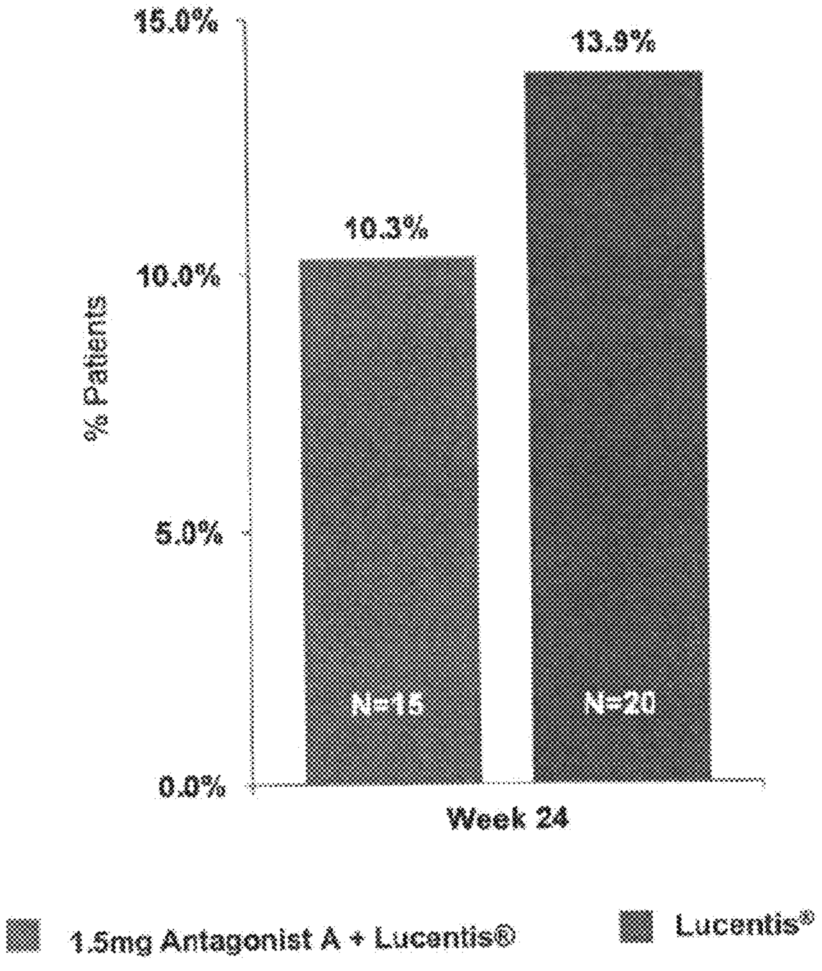
Figure 8A:
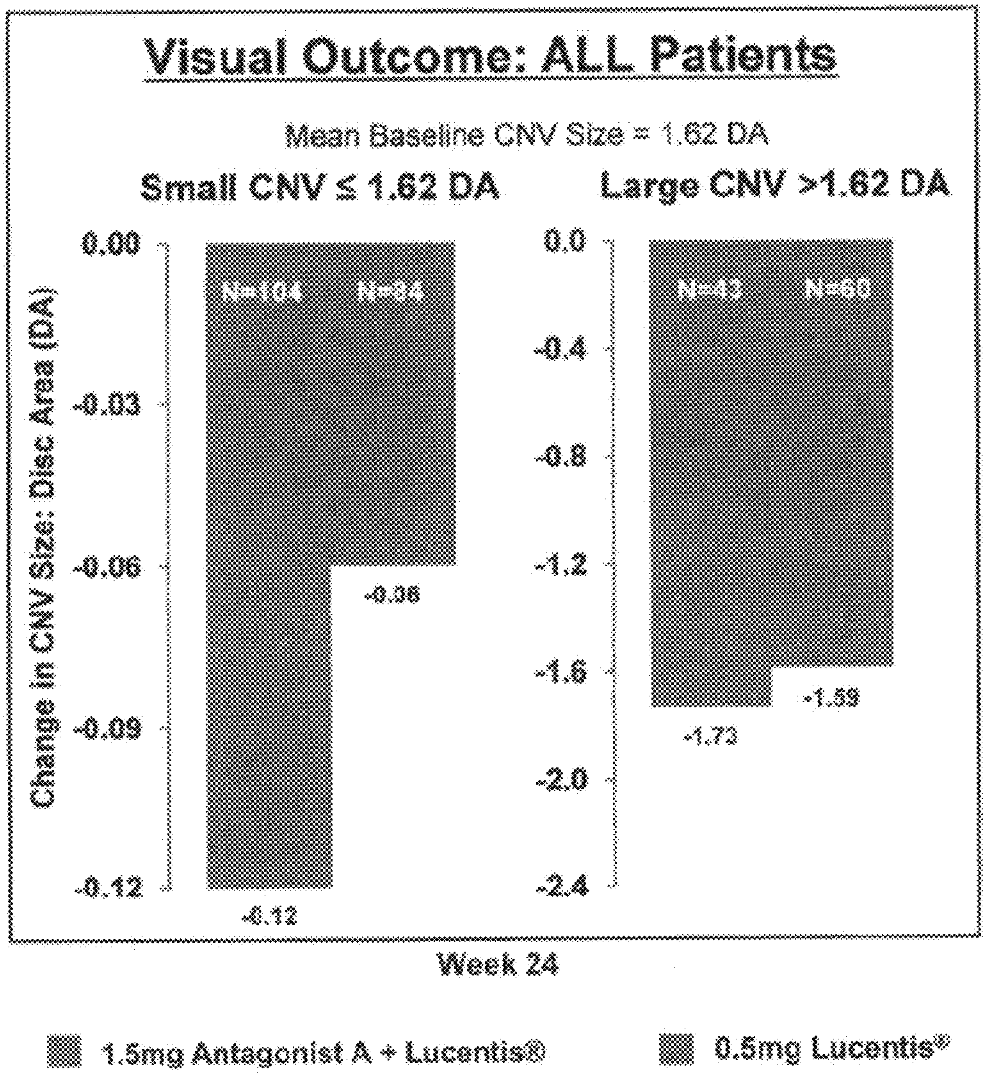
FIGS. 8A and 8B provide bar graphs showing increased reduction in choroidal neovascularization (CNV) lesion size in small and large baseline CNV lesions in wet AMD patients treated with both 0.5 mg of Lucentis® and 1.5 mg of Antagonist A as compared to patients treated with Lucentis® monotherapy (0.5 mg).
Figure 8B:
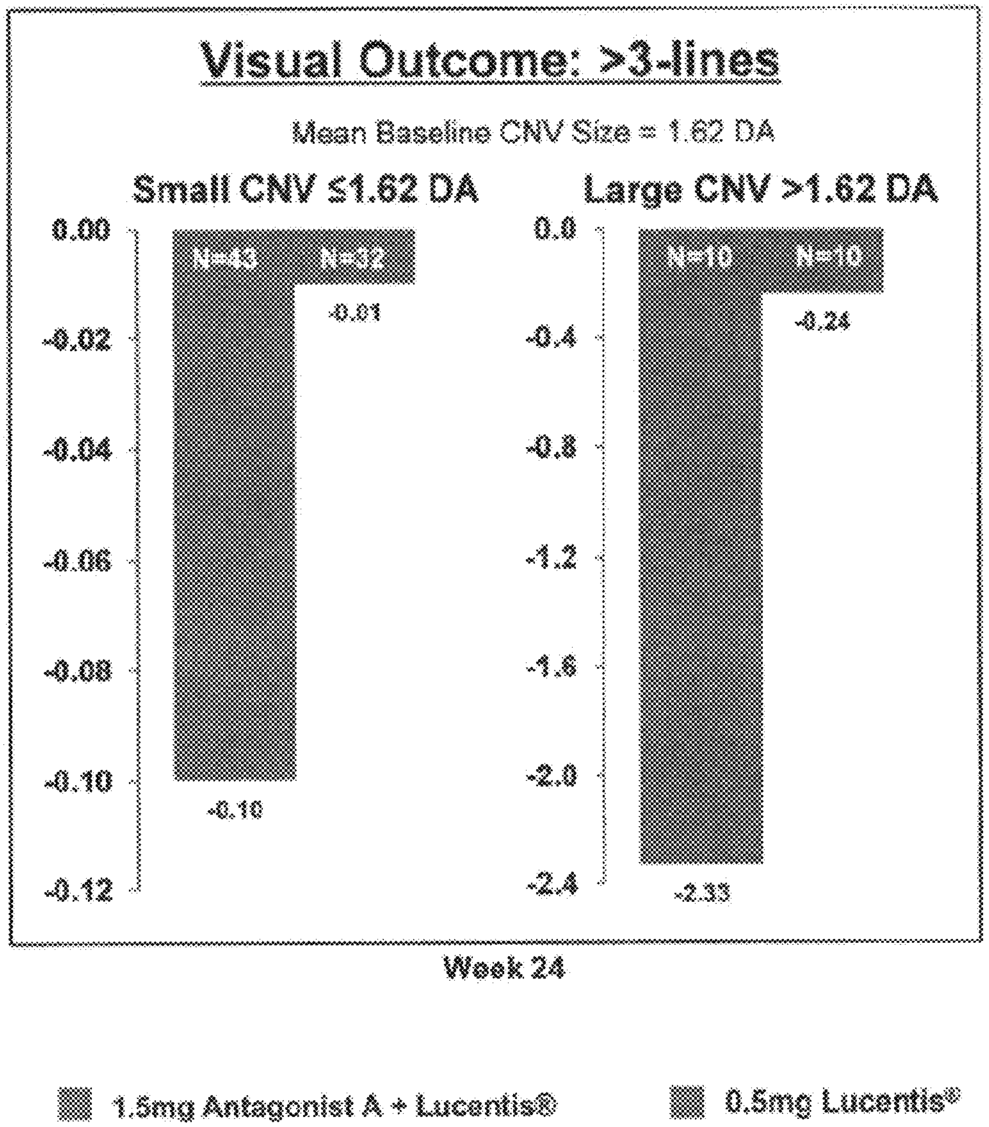

Subjects treated with Lucentis® and 1.5 mg Antagonist A showed improved final visual acuity compared to patients treated with Lucentis® monotherapy. (FIG. 7) Subjects in the Combination Therapy (1.5 mg) group also showed increased reduction in CNV size in small and large baseline CNV as compared to subjects in the Ranibizumab Monotherapy group (FIGS. 8A and 8B).

Combination therapy was well tolerated. There were no events of endophthalmitis, retinal detachment, retinal tear or iatrogenic traumatic cataract after a total of 4431 intravitreal injections (1776 administrations of Antagonist A and 2655 administrations of Lucentis®). As expected, mean intraocular pressure (IOP) increased after each intravitreal injection consistent with a volume effect. However, mean IOP in all arms returned to pre-injection levels at the next visit, including at the end of the study. The systemic safety profile of combination therapy was similar to that of ranibizumab monotherapy.

The results of the trial show statistically significant superior efficacy of the combination treatment with Antagonist A and ranibizumab over Lucentis® (ranibizumab) monotherapy for the treatment of wet AMD.

Example 2: ARC1905 for the Treatment of Wet AMD

Forty-three patients with subfoveal neovascular AMD received six monthly administrations of ARC1905 (0.3 mg/eye, 1 mg/eye or 2 mg/eye) in combination with Lucentis. The mean change in visual acuity at week 24 was an increase of +13.6, +11.7 and +15.3 letters at the doses of 0.3 mg, 1 mg and 2 mg, respectively. Furthermore, 46%, 47% and 60% of patients gained 3 or more lines of visual acuity at the doses of 0.3 mg, 1 mg, and 2 mg, respectively.

Example 3: ARC1905 for the Treatment and Prevention of Dry AMD

Figure 9:
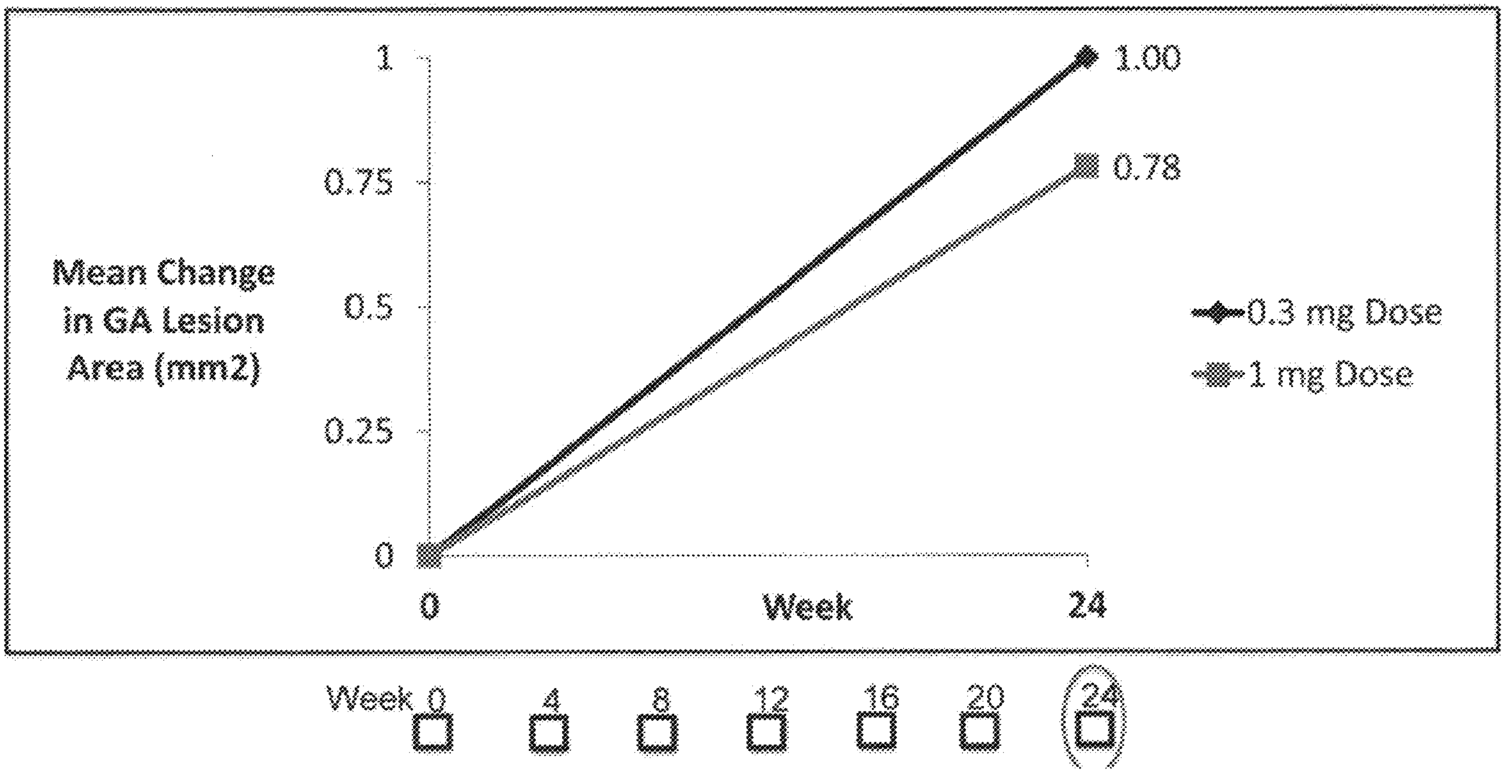
FIG. 9 shows a graph depicting the mean change in geographic atrophy (GA) lesion area in dry AMD patients measured at 24 weeks in patients treated with either a 0.3 mg or 1 mg dose of ARC1905 monthly from weeks 0 to 24 in a phase 2a trial.
Figure 10:
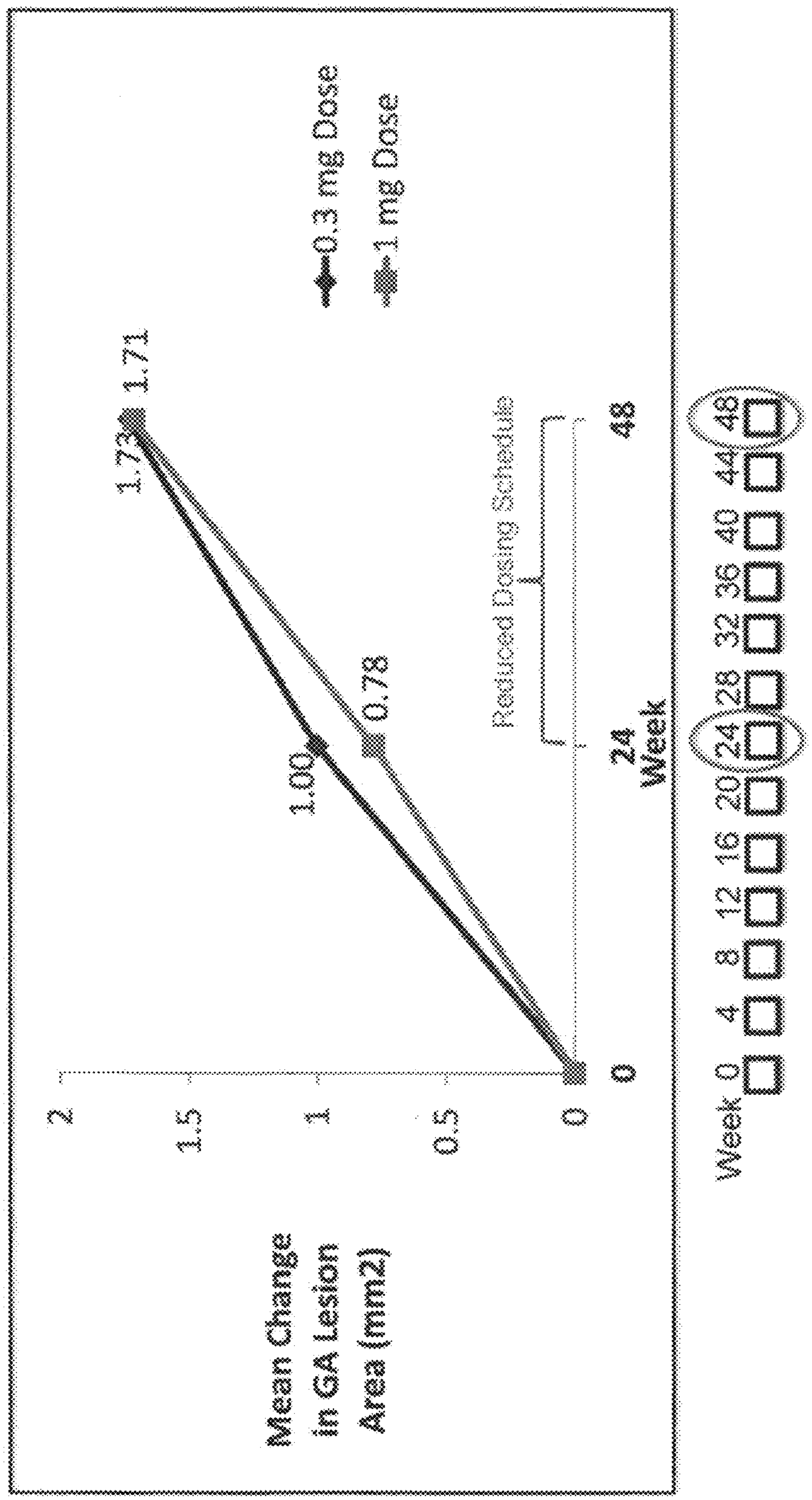
FIG. 10 shows a graph depicting the mean change in GA lesion area in dry AMD patients measured at 24 weeks and 48 weeks in patients treated with either a 0.3 mg or 1 mg dose of ARC1905 monthly from weeks 0 to 48 in a phase 2a trial.

Forty-seven patients with dry AMD were enrolled to receive five intravitreal injections of either 0.3 mg/eye or 1.0 mg/eye of ARC1905 over a 36-week treatment period. FIG. 9 shows the mean change in geographic atrophy (GA) lesion area in dry AMD patients measured at week 24 in patients treated with either 0.3 mg or 1.0 mg doses of ARC1905 at weeks 0, 4, and 8. FIG. 10 shows the mean change in GA lesion in dry AMD patients measured at week 24 and week 48 in patients treated with either 0.3 mg or 1.0 mg doses of ARC1905 at weeks 0, 4, 8, 24, and 36. The results show a dose-dependent reduction in growth of the GA lesion, indicating ARC1905 can slow the progression of GA in non-exudative type AMD patients Example 4: Visual Acuity Testing Using ETDRS Chart Best-corrected visual acuity is measured using standard charts, lighting, and procedures. Best correction is determined by careful refraction at that visit.

Figure 11:
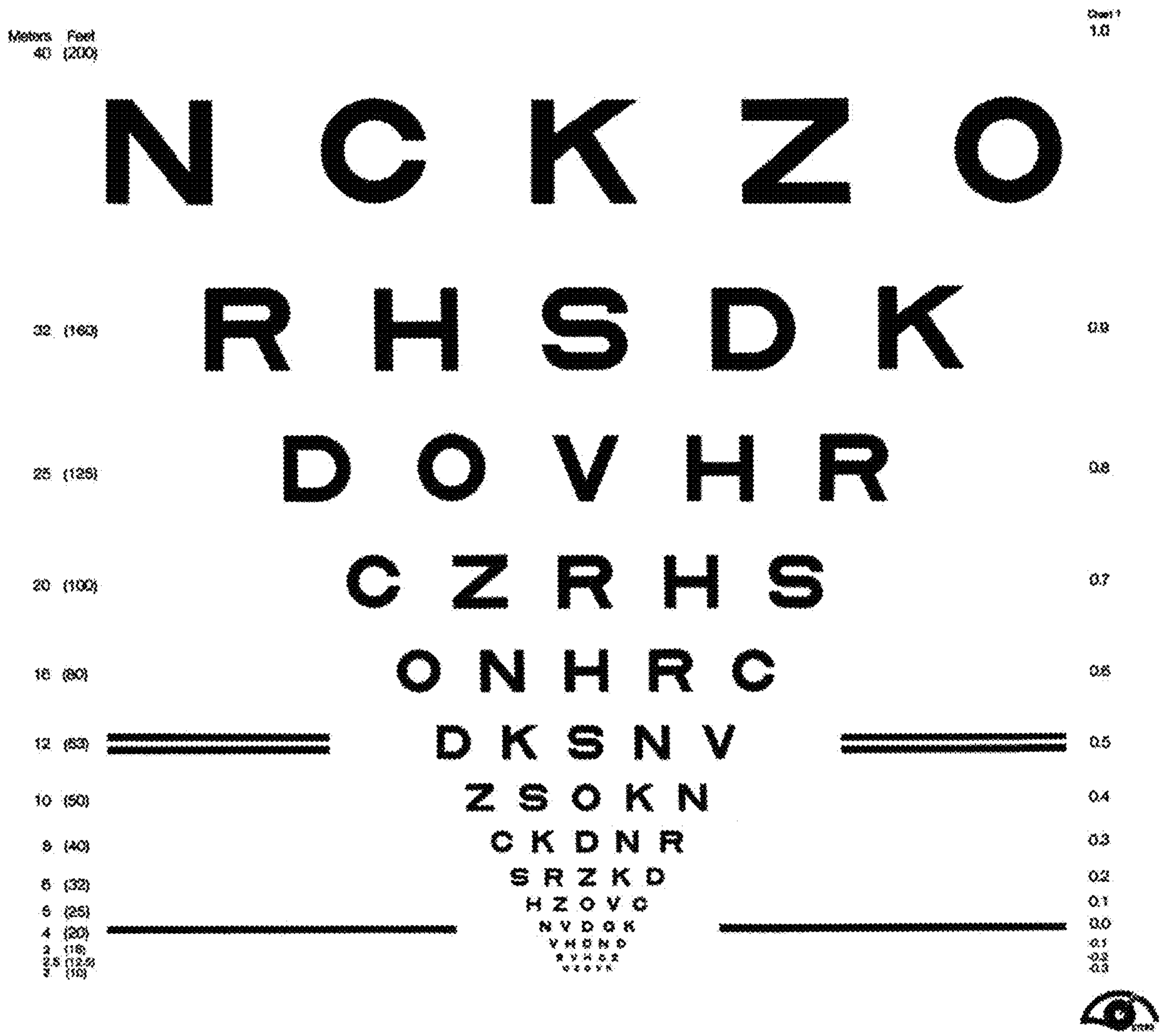
FIG. 11 shows Early Treatment for Diabetic Retinopathy Study ("ETDRS") Chart 1.
Figure 12:
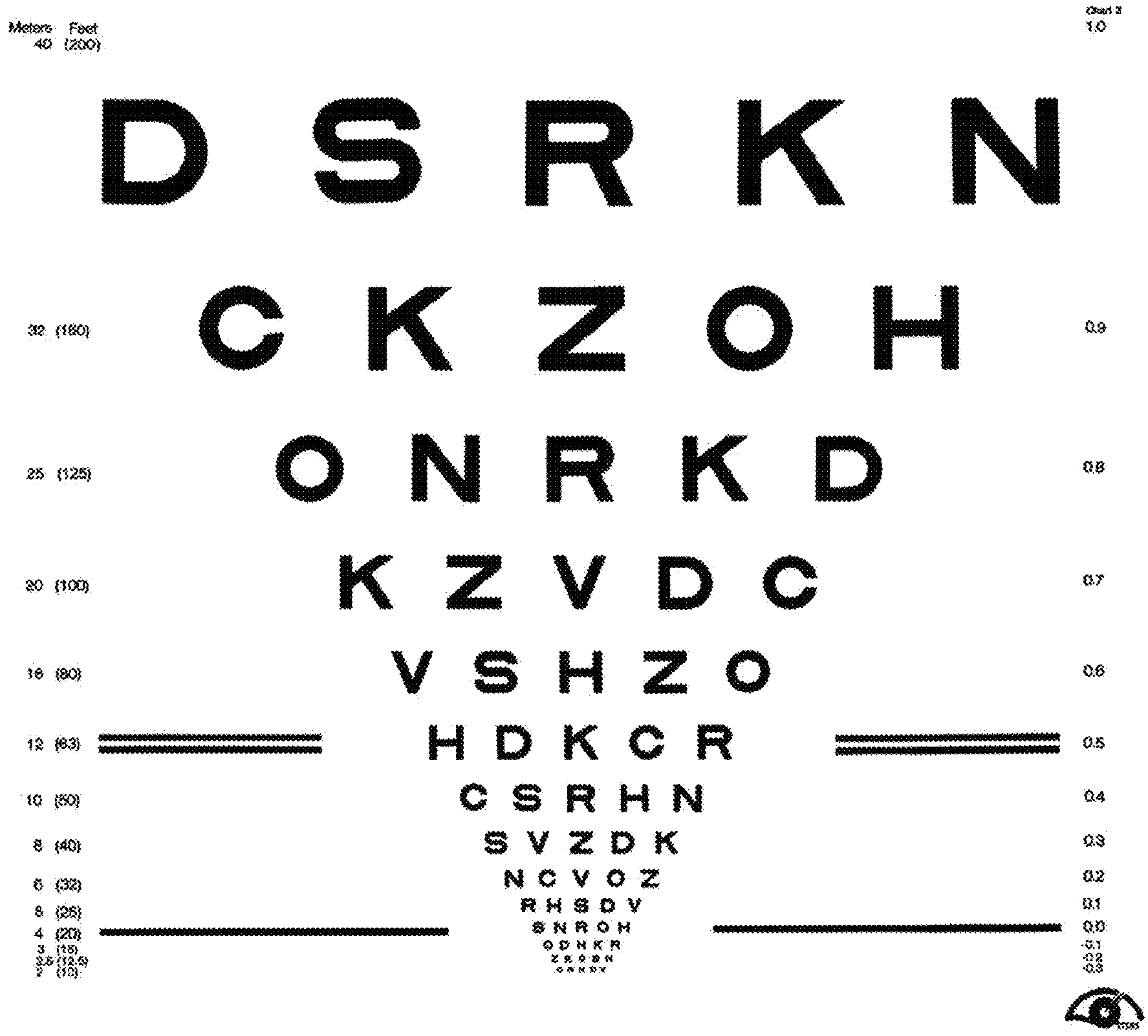
FIG. 12 shows Early Treatment for Diabetic Retinopathy Study ("ETDRS") Chart 2.
Figure 13:
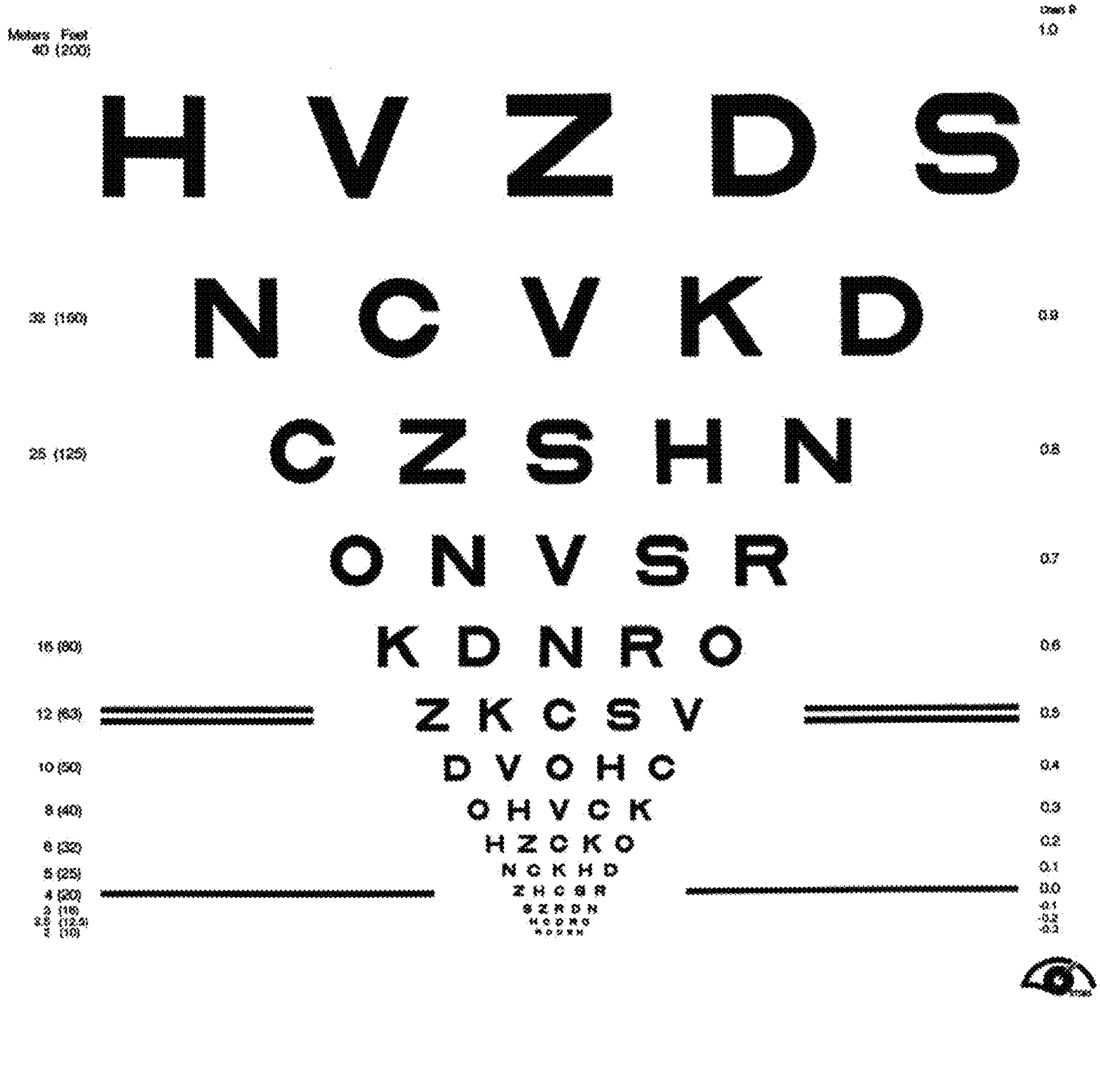
FIG. 13 shows Early Treatment for Diabetic Retinopathy Study ("ETDRS") Chart R.

Chart 1 (FIG. 11) is used for testing the visual acuity of the right eye. Chart 2 (FIG. 12) is used for testing the left eye. Chart R (FIG. 13) is used for testing refraction. Subjects do not see any of the charts before the examination.

A distance of 4 meters is between the subject's eyes and the visual acuity chart. With the box light off, not more than 15 foot-candles of light (161.4 Lux) fall on the center of the chart. To measure the amount of light, the room is set up for visual acuity testing, but with the box light off. The light meter is placed at the fourth line from the top of the chart, with its back against the chart and the reading is taken. If more than one lane is available for testing visual acuity, the visual acuity of an individual subject should be measured in the same lane at each visit. If different lanes are used to test visual acuity, they each meet the same standards.

Retroilluminated ETDRS charts are used. The illuminator box is either wall-mounted or mounted on a stand (available from Lighthouse Low Vision Services). The light box is mounted at a height such that the top of the third row letter is 49±2 inches from the floor.

The visual acuity light box is equipped with two 20-watt fluorescent tubes (available from General Electric Cool Daylight) and a ballast which partially covers the tubes. Because the illumination of fluorescent tubes generally diminishes by 5 percent during the first 100 hours and by another 5 percent during the next 2000 hours, new tubes are kept on for 4 days (96 hours) continuously, and replaced once a year.

A sticker is placed on the back of the light box, indicating the date on which the present tubes were installed. A spare set of burned in bulbs is available.

Each tube is partly covered by a 14-inch fenestrated sleeve, which is open in the back. This serves as a baffle to reduce illumination. Each sleeve is centered on the tube with the opening towards the back.

All eyes are tested at 4 meters first, even if the refraction was performed at 1 meter. The subject is seated comfortably directly in front of the chart so that the eyes remain at the 4 meter distance. Testing begins with the right eye. The subject's left eye is occluded. A folded tissue or eye pad lightly taped over the eye behind the trial frame serves as an effective occluder that allows eccentric fixation without inadvertent use of the covered eye. After testing the right eye, occlusion of the right eye is done before Chart 2 is put up for testing the left eye.

The lens correction from the subjective refraction is in the trial frame worn by the subject.

The subject is asked to read the letters slowly, approximately one letter per second. The subject is told that only one chance is given to read each letter on the chart. If the subject is unsure about the identity of the letter, then the subject is encouraged to guess.

The subject begins by reading the top line of the chart and continue reading every letter on each smaller line, from left to right on each line. The examiner circles every correct letter read and totals each line and the whole column (0 if no letters are correct) on the data collection form. An X is put through letters read incorrectly. Letters, for which no guess was attempted, are not circled. When a subject reaches a level where he/she cannot guess, the examiner may stop the test provided that the subject has made errors on previous guesses, which is a clear indication that the best visual acuity has been obtained.

When a subject cannot read at least 20 letters on the chart at 4.0 meters, the subject is tested at 1.0 meter. The distance from the subject to the chart should be measured again using the rigid one meter stick. The distance is measured from the outer canthus to the center of the fourth letter (right eye) or the second letter (left eye) of the third line of the chart. The spherical correction in the trial frame should be changed by adding +0.75 to correct for the closer test distance. The subject may fixate eccentrically or turn or shake his/her head to improve visual acuity. If this is done, the examiner ensures that the fellow eye remains occluded both centrally and peripherally and that the subject does not move forward in the chair. Particular care should be taken to ensure the subject does not move forward when testing at 1 meter. The subject is reminded to blink.

The examiner does not tell the subject if a letter was identified correctly. The subject may be encouraged by neutral comments, such as “good”, “next”, and “OK”.

The examiner does not stand close to the chart during testing. The examiner's attention is focused on the subject and the data collection form. If the subject has difficulty locating the next line to read, the examiner may go up to the chart and point to the next line to be read, and then moves away from the chart.

When it is possible to measure the visual acuity of the eye at 4.0 meters (i.e., 20 or more letters read at 4 meters), the visual acuity score for that eye is recorded as the number of letters correct plus 30. The subject gets credit for the 30 1M letters even though they did not have to read them. Otherwise, the visual acuity score is the number of letters read correctly at 1.0 meter plus the number, if any, read at 4M. If no letters are read correctly at either 4.0 meters or 1 meter, then the visual acuity score is recorded as 0.

INCORPORATION BY REFERENCE

All publications and patent applications disclosed in this specification are herein incorporated by reference to the same extent as if each individual publication or patent application was specifically and individually indicated to be incorporated by reference.

What is claimed is:

1. A method of treating geographic atrophy in a human subject, the method comprising administering by intravitreal injection, to said subject, 2 mg/eye of a pegylated aptamer;

wherein the aptamer comprises the sequence fCmGfCfCGfCmGmGfUfCfUfC-mAmGmGfCGfCfUmGmAmGfUfCfU mGmAmGfU-fUfUAfCfCfUmGfCmG-3T (SEQ ID NO: 26), wherein fC and fU=2'-fluoro nucleotides, mG and mA=2'-OMe nucleotides, all other nucleotides are 2'-OH, and 3T indicates an inverted deoxythymidine, or a salt thereof;

wherein the pegylated moiety has the following structure:

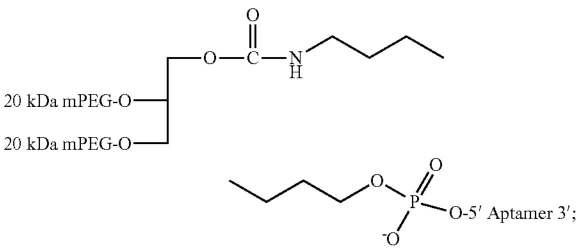

wherein the pegylated aptamer is administered to the subject monthly; and wherein the method slows or inhibits loss of visual acuity in the human subject.

2. The method of claim 1, wherein the pegylated aptamer is administered in an aqueous solution further comprising one or more pH buffering agents and at least one tonicity adjuster.

3. The method of claim 2, where the one or more pH buffering agents comprise dibasic sodium phosphate heptahydrate and monobasic sodium phosphate monohydrate, and the at least one tonicity adjuster comprises sodium chloride.

4. The method according to claim 1, wherein the administration of the aptamer to the subject slows or inhibits the decrease in best corrected visual acuity as compared to a subject who is not administered the aptamer.

5. The method according to claim 1, wherein the administration of the aptamer to the subject increases the best corrected visual acuity as compared to a subject who is not administered the aptamer.

6. The method according to claim 5, wherein the increase is measured between baseline and at least or about 1 month.

7. The method according to claim 5, wherein the increase is measured between baseline and at least or about 6 months.

8. The method according to claim 5, wherein the increase is measured between baseline and at least or about 8 months.

9. The method according to claim 5, wherein the increase is measured between baseline and at least or about 12 months.

10. The method according to claim 5, wherein the best corrected visual acuity is measured using ETDRS letters.

* * * * *

UNITED STATES PATENT AND TRADEMARK OFFICE
CERTIFICATE OF CORRECTION

PATENT NO. : 12,016,875 B2
APPLICATION NO. : 18/132283
DATED : June 25, 2024
INVENTOR(S) : Samir Patel et al.

Page 1 of 1

It is certified that error appears in the above-identified patent and that said Letters Patent is hereby corrected as shown below:

In the Claims

Column 271, Claim 1, the depiction of the moiety as

" 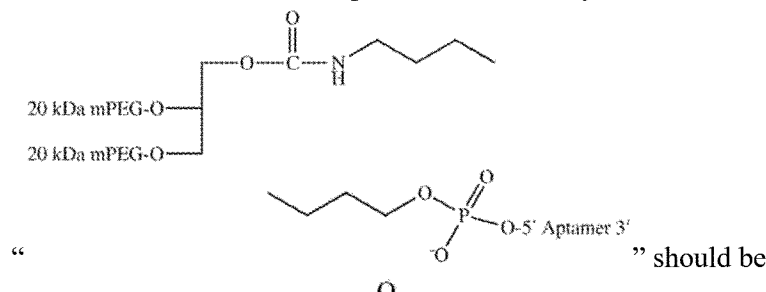 " should be

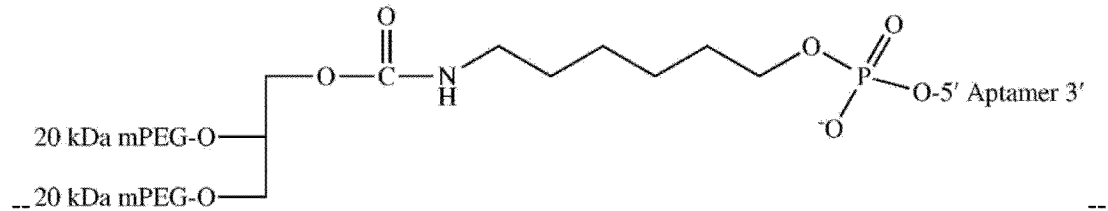 --

Signed and Sealed this
Twenty-ninth Day of October, 2024

Katherine Kelly Vidal
*Director of the United States Patent and Trademark Office*